(12) United States Patent
Ilg et al.

(10) Patent No.: US 10,112,985 B2
(45) Date of Patent: Oct. 30, 2018

(54) TOLL-LIKE RECEPTORS

(71) Applicant: Intervet Inc., Madison, NJ (US)

(72) Inventors: Thomas Simon Ilg, Monheim (DE); Jaap Kool, Münster (DE)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/408,459

(22) PCT Filed: Jun. 27, 2013

(86) PCT No.: PCT/EP2013/063452
§ 371 (c)(1),
(2) Date: Dec. 16, 2014

(87) PCT Pub. No.: WO2014/001422
PCT Pub. Date: Jan. 3, 2014

(65) Prior Publication Data
US 2015/0191523 A1 Jul. 9, 2015

(30) Foreign Application Priority Data

Jun. 28, 2012 (EP) ..................... 12174199

(51) Int. Cl.
| | |
|---|---|
| *C07K 14/705* | (2006.01) |
| *A61K 39/39* | (2006.01) |
| *C12N 15/117* | (2010.01) |
| *G01N 33/50* | (2006.01) |
| *A61K 39/00* | (2006.01) |

(52) U.S. Cl.
CPC ............ *C07K 14/705* (2013.01); *A61K 39/39* (2013.01); *C12N 15/117* (2013.01); *G01N 33/5038* (2013.01); *A61K 2039/55561* (2013.01); *C12N 2310/17* (2013.01); *C12N 2310/315* (2013.01); *G01N 2333/916* (2013.01)

(58) Field of Classification Search
None
See application file for complete search history.

(56) References Cited

U.S. PATENT DOCUMENTS

| | | | |
|---|---|---|---|
| 5,948,677 | A | 9/1999 | Jarvik |
| 9,315,814 | B2 | 4/2016 | Schrier et al. |
| 9,359,602 | B2 | 6/2016 | Schrier et al. |
| 9,364,531 | B2 | 6/2016 | Schrier et al. |
| 2002/0042387 | A1* | 4/2002 | Raz ............... A61K 31/7088 514/44 R |
| 2004/0127682 | A1 | 7/2004 | Neville et al. |
| 2004/0131628 | A1 | 7/2004 | Bratzler et al. |
| 2007/0179101 | A1 | 8/2007 | Kitagawa |
| 2007/0298449 | A1 | 12/2007 | Saito et al. |

FOREIGN PATENT DOCUMENTS

| | | |
|---|---|---|
| CN | 001057286 A | 11/2000 |
| CN | 1271733 * | 11/2000 |
| EP | 2471926 A3 | 7/2012 |
| WO | 200162207 A2 | 8/2001 |
| WO | 2003103708 | 12/2003 |
| WO | WO2004016805 A2 | 2/2004 |
| WO | 2004026888 A2 | 4/2004 |
| WO | 0906372 A1 | 7/2011 |
| WO | WO 2012089800 * | 7/2012 |
| WO | WO 2012/160184 * | 11/2012 |

OTHER PUBLICATIONS

Help Me Under Genetics Gene Therapy https://ghr.nlm.nih.gov/ Gene Therapy, published Jan. 23, 2018, retrieved Jan. 24, 2018.*
Brownlie R. et al, Chicken TLR21 acts as a functional homologue to mammalian TLR9 in the recognition of CpG oligodeoxynucleotides, Molecular Immunology, Sep. 1, 2009, pp. 3163-3170, vol. 46, No. 15, WO.
Dasgupta et al., Structural properties of DNA oligomers containing (GACX)n and (GAXC)n tandem repeats, Biopolymers, Sep. 22, 2011, pp. 155-164, vol. 97, No. 3, WO.
EM_STS:G38864, "TA31 Plasmodium falciparum haploid Plasmodium falciparum STS genomic sequence tagged site", Database EMBL, Jul. 15, 1998, XP-002717668, WO.
Keestra, M et al., Chicken TLR21 is an innate CpG DNA receptor distinct from mammalian TLR9, The Journal of Immunology, Jul. 1, 2010, pp. 460-467, vol. 185, No. 1, WO.
Rachmilewitz et al, Immunostimulatory DNA ameliorates experimental and spontaneous murine colitis, Gastroenterology, May 1, 2002, pp. 1428-1441, vol. 122, No. 5, Elsevier, WO.
Bode, Christian et al, CpG DNA as a vaccine adjuvant, Expert Rev Vaccines, Apr. 2011, pp. 499-511, 10 (4), NZ.
Liang, H et al, Activation of Human B Cells by Phosphorothioate Oligodeoxynucleotides, J. Clin. Invest., 1996, pp. 1119-1129, vol. 98,, JP.
Rachmilewitz, D et al, Immunostimulatory Oligonucleatides Inhibit Colonic Proinflammatory Cytokine Production in Ulcerative Colitis, Inflamm. Bovel Disease, 2006, pp. 339 to 345, vol. 12 No. 5, JP.
Babiuk, L et al, Molecular Approaches to Disease Control, Poultry Science, 2003, pp. 870-875, vol. 82.
Carrington,A et al, A review of CpGs and their relevance to aquaculture, Veterinary Immunology and Immunopathology, 2006, pp. 87-101, vol. 112.
Daubenberger, C, TLR9 agonists as adjuvants for prophylactic and therapeutic vaccines, Current Opinion in Molecular Therapeutics, 2007, pp. 45-52, vol. 9, No. 1.
Dorn, A . et al, Clinical application of CpG-, non-CpG-, and antisense ligodeoxynucleotides as immunomodulators, Current Opinion in Molecular Therapeutics, 2008, pp. 10-20, vol. 10, No. 1.
Fonseca, D et al, Use of CpG oligonucleotides in treatment of asthma and allergic disease, Advanced Drug Delivery Reviews, 2009, pp. 256-262, vol. 61.

(Continued)

*Primary Examiner* — Oluwatosin A Ogunbiyi

(57) ABSTRACT

The present invention relates to toll-like receptors, to cells comprising such toll-like receptors, to methods for the detection of immunostimulatory oligodeoxynucleotides wherein such methods use such toll-like receptors, to immunostimulatory oligodeoxynucleotides detected by use of this method, to the use of such immunostimulatory oligodeoxynucleotides in medicine and to vaccines comprising such immunostimulatory oligodeoxynucleotides.

4 Claims, 32 Drawing Sheets

Figure 1:
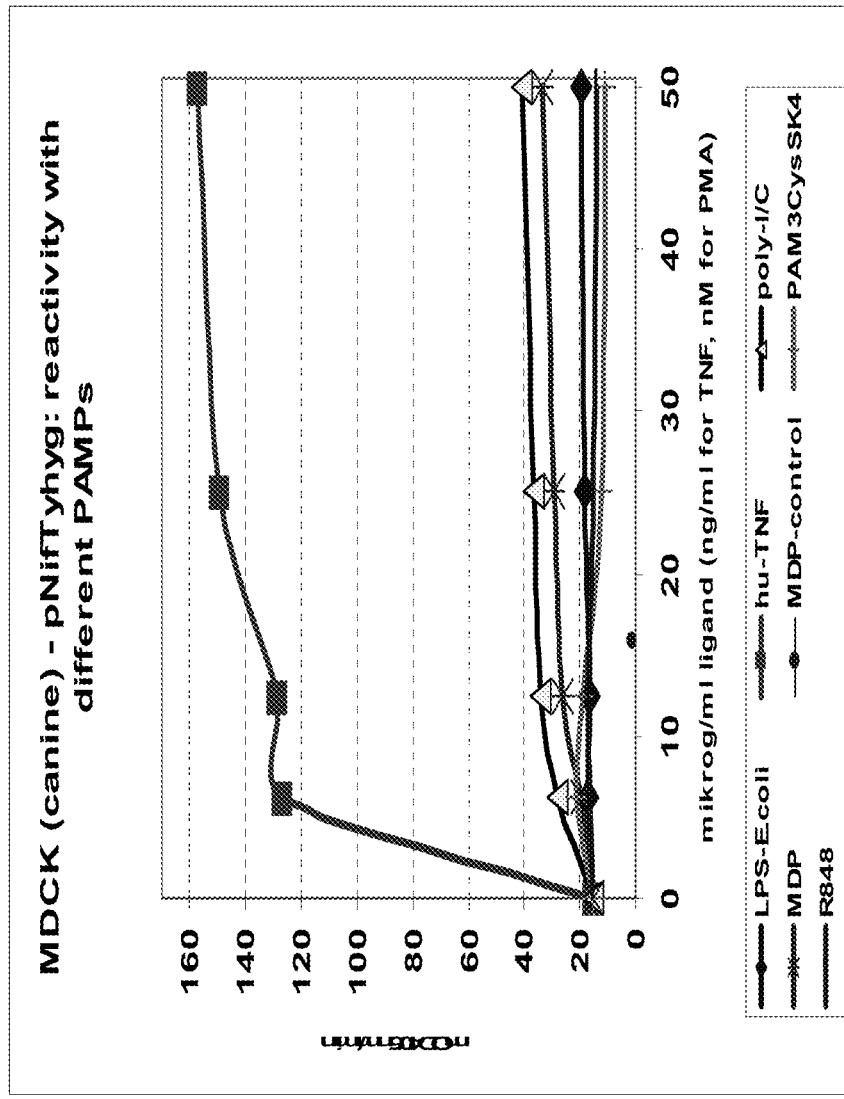

Specification includes a Sequence Listing.

(56) References Cited

OTHER PUBLICATIONS

Griebel, P et al, Bovine toll-like receptor 9: A comparative analysis of molecular structure, function and expression, Veterinary Immunology and Immunopathology, 2005, pp. 11-16, vol. 108, Elsevier.
Hemmi, A Toll-like receptor recognizes bacterial DNA, letters to nature, 2000, pp. 740-745, vol. 408.
Kindrachuk, J et al, Activation and Regulation of Toll-like Receptor 9: CpGs and Beyond, Mini-Reviews in Medicinal Chemistry, 2008, pp. 590-600, vol. 8.
Kline, J, Immunotherapy of asthma using CpG oligodeoxynucleotides, Immunol Res, 2007, pp. 279-286, vol. 39.
Kline, J. et al, Toll-Like Receptor 9 Activation with CpG Oligodeoxynucleotides for Asthma Therapy, Drug News Perspect, 2008, pp. 434-439, vol. 21, No. 8.
Klinman D. et al, CpG oligonucleotides as adjuvants for vaccines targeting infectious diseases, Advanced Drug Delivery Reviews, 2009, pp. 248-255, vol. 61, Elsevier.
Klinman, D. et al, Use of CpG oligodeoxynucleotides as immune adjuvants, Immunological Reviews, 2004, pp. 201-216, vol. 199.
Klinman, D., Adjuvant Activity of CpG Oligodeoxynucleotides, International Reviews of Immunology, 2006, pp. 135-154, vol. 25.
Klinman, D.M., Immunotherapeutic uses of CpG oligodeoxynucleotides, The Journal of Immunology, Apr. 1, 2004, 249-258, vol. 4, No. 4, Nature Pub. Group.
Krieg, A, CpG motifs in Bacterial DNA and Their Immune Effects, Annu. Rev. Immunol., 2002, pp. 709-760, vol. 20.
Krieg, A, Development of TLR9 agonists for cancer therapy, The Journal of Clinical Investigation, 2007, pp. 1184-1194, vol. 117, No. 5.
Krieg, A., Therapeutic potential of Toll-like receptor 9 activation, Nature Reviews Drug Discovery, 2006, pp. 471-484, vol. 5.
Krieg, A.M., Antiinfective applicants of Toll-like Receptor 9 agonists, Proceedings of the American thoracic society, 2007, pp. 289-294, vol. 4.
Krieg, Arthur M., CpG motifs: the active ingredient in bacterial extracts?, Nature Medicine, 2003, pp. 831-835, vol. 9, No. 7.
Medzhitov, CpG DNA: security code for host defense, nature immunology, 2001, pp. 15-16, vol. 2 No. 1, Nature Publishing Group.
Mutiwiri, G. et al, Biological activity of immunostimulatory CpG DNA motifs in domestic animals, Veterinary Immunology and Immunopathology, 2003, pp. 89-103, vol. 91, Elsevier.
Mutwiri, G. et al, Approaches to enhancing immune responses stimulated by CpG oligodeoxynucleotides, Advanced Drug Delivery Reviews, 2009, pp. 225-232, vol. 61, Elsevier.
Singh, M et al, Recent advances in veterinary vaccine adjuvants, International Journal for Parasitology, 2003, pp. 469-478, vol. 33, Elsevier.
Vollmer, J et al, Immunotherapeutic applications of CpG oligodeoxynucleotide TLR9 agonists, Advanced Drug Delivery Reviews, 2009, pp. 195-204, vol. 61.
Vollmer, J, Progress in drug development of immunostimulatory CpG oligodeoxynucleotide ligands for TLR9, Expert Opinion Biol. Ther., 2005, pp. 673-682, vol. 5.
Wagner, H, The immunogenicity of CpG-antigen conjugates, Advanced Drug Delivery Reviews, 2009, pp. 243-247, vol. 61, Elsevier.
Weiner, G., CpG oligodeoxynucleotide-based therapy of lymphoid malignancies, Advanced Drug Delivery Reviews, 2009, pp. 263-267, vol. 61, Elsevier.
Werling, D. et al, Toll-like receptors linking innate and adaptive immune response, Veterinary immunology and Immunopathology, 2003, pp. 1-12, vol. 91, Elsevier.
Wilson, H et al, Immune Mechanisms and Therapeutic Potential of CpG Oligodeoxynucleotides, International Reviews of Immunology, 2006, pp. 183-213, vol. 25.
Wilson, K et al, Lipid-based delivery of CpG oligonucleotides enhances immunotherapeutic efficacy, Advanced Drug Delivery Reviews, 2009, pp. 233-242, vol. 61, Elsevier.

* cited by examiner

TOLL-LIKE RECEPTORS

The present invention relates to hybrid toll-like receptors, to cells comprising such toll-like receptors, to methods for the detection of immunostimulatory oligodeoxynucleotides wherein such methods use such toll-like receptors, to immunostimulatory oligodeoxynucleotides detected by use of this method, to the use of such immunostimulatory oligodeoxynucleotides in medicine and to vaccines comprising such immunostimulatory oligodeoxynucleotides.

During the past two decades, it has emerged in immunological science that the vertebrate immune system possesses mechanisms to detect microbial infection and to trigger rapid immune activation via the receptor-mediated recognition of unique and conserved characteristics of pathogens, the so-called pathogen-associated molecular patterns (PAMPs) interacting with cognate host pathogen recognition receptors (PRRs) (Iwasaki A, Medzhitov R. 2001 and Medzhitov R., 2009).

It is now clear that certain forms of pathogen deoxyribonucleic acid (DNA) are amongst these PAMPs. In 1995 it was reported that non-methylated CpG motifs in bacterial DNA trigger murine B-cell activation (Krieg et al. 1995). This study generated for the first time a link between the specific recognition of bacterial immunostimulatory non-methylated CpG-containing DNA and the previously recognized CpG suppression as well as the widespread CpG methylation in mammalian DNA. The most effective B cell stimulatory non-methylated CpG oligodeoxynucleotide (CpG ODN) was shown to possess the sequence element GACGTT.

The next landmark paper in the field was published by Shizuo Akira's laboratory in Osaka/Japan (Hemmi et al. 2000). By a gene cloning and a targeted gene knockout approach in mice it could be unequivocally shown, that the cellular response in mice to CpG-ODNs is mediated by the toll-like receptor 9 (TLR9). Subsequently it was shown that the CpG-ODNs are agonists for TLR9 signaling predominantly via the NF kappa-B pathway (Medzhitov 2001). In the following decade, quite a number of studies have been published on basic research topics and on general potential immunotherapeutic applications (e.g. reviewed in Krieg 2002, 2003, 2006; Klinman 2004, Vollmer 2005, Wilson et al. 2006, Kindrachuk et al. 2008, Dorn and Kippenberger 2008, Vollmer and Krieg 2009, Wilson et al. 2009). A number of review articles focus on anti-infective applications of CpG-ODNs (Krieg 2007), the use of TLR9 agonists in the treatment of cancer (Krieg 2007, Weiner 2009), TLR9 activation for asthma and allergy treatment (Kline 2007, Kline and Krieg 2008, Fonseca and Kline 2009) and as vaccine adjuvants (Klinman et al. 2004, Klinman 2006, Daubenberger 2007, Wagner 2009, Mutwiri et al. 2009, Klinman et al. 2009).

CpG ODNs have also been described and discussed as immunostimulatory agents and vaccine adjuvants in veterinary applications, particularly in bovines, pigs, sheep, dogs, chicken and fish (Babiuk et al. 2003, Carrington and Secombes 2006, Griebel et al. 2005, Mutwiri et al. 2003, Singh and O'Hagan 2003, Werling and Jungi 2003).

The design of specific CpG ODN's as immune modulators for both human and non-human species has so far been quite random. The reason for this is multi-factorial; first of all there is no knowledge about correlation between immune modulatory CpG motifs for human TLR's and for TLR's in non-human mammalian species. Secondly, there are no in vitro cell-systems comprising a mammalian TLR available, that have a sufficiently low signal to noise level to allow for selective testing of the effects of very low concentrations of CpG ODN's. Moreover, there are no high-throughput screening methods available and even if there were, there is no clear correlation between in vivo versus in vitro efficacy of CpG ODN's as immuno-modulators.

In the PCT Patent Application with Application number PCT/EP2011/074211, unpublished at the filing date of the present invention, the inventors have described an in vitro cell-system that is suitable for reproducible in vitro testing and selection of CpG ODN's as immune modulators for use in poultry. This system is based upon the cloning and heterologous expression of TLR21, the functional homologue of TLR9 in chickens.

In order to develop a comparable system for testing CpG ODN's as immune modulators for mammals, both for human species and for non-human species such as canine, bovine and porcine species, it was decided to use a comparable approach, however now based upon the cloning and expression of i.a. canine, bovine and porcine toll-like receptor TLR9.

To this end, a clonal line of HEK293 cells was used that contains in its genome an integrated version of pNifTy2-SEAP (Invivogen), that provides an NF-κB activation reporter gene assay based on the measurement of secreted alkaline phosphatase (SEAP) production (See Examples section). Such cell lines were shown by the inventors to have broad utility in experiments aiming at stable functional expression of TLR1/2, TLR2/6, TLR3, TLR4, TLR5, TLR7 and TLR8 isolated from various vertebrate (bovine, canine, porcine, chicken) species.

Against this background it was to be expected that expression of bovine, canine and porcine TLR9 should be straightforward, an expectation boosted further by the exceptionally well-functioning HEK293-pNifTy2-SEAP-based functional expression of the chicken TLR9 functional homologue, TLR21.

However, repeated transfection experiments with bovine, canine and porcine TLR9 failed to yield cell lines that could be stimulated with known standard TLR9 agonists, such as 2006-PTO (TCGTCGTTTTGTCGTTTTGTCGTT) SEQ ID NO: 40 or 2007-PTO (TCGTCGTTGTCGTTTTGTCGTT) SEQ ID NO: 41, despite the fact that the selection for plasmid introduction (G418 or hygromycin) worked out successfully. Only in a few experiments, weak signals were initially seen in polyclonal transfectant pools. These signals disappeared upon further cell line cultivation and could not be rescued by single cell cloning. Similar experiments were performed with another NF-κB activation reporter gene containing cell type, the bovine macrophage cell line BOMAC-pNifTy2-SEAP. The outcome was essentially the same as seen previously in HEK293-pNifTy2-SEAP.

The reasons for the unexpected failure of functional expression (as shown by SEAP signal) remained unknown. An attempt to overcome the problem by using 293XL/null cells (InvivoGen), expressing the human anti-apoptotic Bcl-XL gene did also not result in sufficiently high SEAP expression levels.

Thus, there still is a need for selective and sensitive systems for the selection of CpG ODN's having a high immuno-modulatory effect and therefore being effective in low doses in mammals.

It is one of the objectives of the present invention to provide such selective and sensitive CpG ODN selection systems.

It was surprisingly found now that a hybrid toll-like receptor, comprising a Toll-interleukin I receptor-resistance (TIR) domain of poultry TLR21 and a extracellular ligand-binding domain of mammalian TLR9 is capable of overcoming the problem of low functional expression or non-expression as identified above.

TLRs are well-conserved type I transmembrane (TM) proteins composed of an N-terminal signal peptide, an extracellular ligand-binding domain containing leucine rich repeats, a single TM domain, and a cytoplasmic region largely comprised of the Toll-interleukin I receptor-resistance (TIR) domain.

Merely as an example: the extracellular domain of mouseTLR9 spans the region from a.a. 1 to 820, the transmembrane domain spans the region from a.a. 820-838 and the cytoplasmic domain spans the region from a.a. 838 to 1032. The TIR domain spans the region from a.a. 872-1032. (Kajita et al, BBRC 343: 578-584 (2006)).

The compartmentalization of TLR9 and of the poultry homologue TLR21 differs to a certain extent from that of TLR1, 2, 4, 5 and 6 in the sense that the part of TLR9 and 21 referred to as the "extracellular domain" is located in the endolysosome. As a consequence the TM region of TLR9/21 spans the endolysosomal membrane, not the cell's plasma membrane. This aspect and the cell biology of TLR's in general is reviewed by Barton G. M. and Kagan, J. C. in Nature Reviews 9; 535-542 (2009).

Merely as examples of mammalian TLR's, the sequences of bovine, porcine and canine TLR9 are given in SEQ ID NOs: 1, 3 and 5 (nucleic acid sequence) and SEQ ID NOs: 2, 4 and 6 (amino acid sequence) respectively.

It turns out that hybrid TLR's according to the invention, combining the CpG ODN specificity of the extracellular ligand-binding domain of mammalian TLR9 and the signaling properties of Toll-interleukin I receptor-resistance (TIR) domain of poultry TLR21 are accepted by the transfected cell without unacceptable adverse effects and at the same time they are very well suitable for the specific detection of CpG ODN's that are specifically immune stimulatory to mammalian species.

Transfection of e.g. HEK293 cells or MDCK cells with plasmids comprising DNA encoding such hybrid TLR's resulted in stable expression of hybrid TLR's which in turn led to marked NF-κB activation upon stimulation with exogenous CpG ODN's known to be active in mammals, such as 2006-ODN and 2007-ODN.

Thus, a first embodiment of the present invention relates to a hybrid toll-like receptor, characterised in that said hybrid toll-like receptor comprises a Toll-interleukin I receptor-resistance (TIR) domain of poultry TLR21 and a extracellular ligand-binding domain of mammalian TLR9.

The origin of the transmembrane region (TM region) and the non-TIR related part of the cytoplasmic domain is not critical, in the sense that these may independently originate from TLR 9 or TLR21.

In a preferred form of this embodiment, the extracellular ligand-binding domain of mammalian TLR9 is of human, bovine, porcine or canine origin.

Examples of hybrid TLR's according to the invention where the extracellular ligand-binding domain of mammalian TLR9 is of bovine, porcine or canine origin, are given in SEQ ID NOs: 8, 10 and 12 (nucleic acid sequence) and SEQ ID NOs: 9, 11 and 13 (amino acid sequence) respectively.

An "immunostimulatory non-methylated oligodeoxynucleotide" refers to an oligodeoxynucleotide, which contains a non-methylated cytidine-phosphate-guanosine di-nucleotide sequence that stimulates the initiation of signaling cascades leading to activation of transcription factors such as NF-κB or Interferon Regulatory Factor 3 (IRF3). It is this activation that in turn results in the expression of inflammatory cytokines and other cellular activation events. NF-κB binding sites and gene expression influenced by NF-κB are i.a. described by Schindler and Baichwal (1994).

The term oligodeoxynucleotide means a short nucleic acid polymer of deoxynucleotides; i.e. a molecule comprising a multitude of deoxyriboses, linked to a phosphate group and to an exchangeable organic base. Such an organic base is a substituted pyrimidine or a substituted purine. Examples are cytosine and thymine respectively adenine and guanine.

The oligonucleotides according to the invention may comprise modifications. Examples of such modifications are e.g. modifications in the phosphodiester internucleoside bridge located at the 3' and/or 5' end of a nucleoside. Such modifications relate i.a. to the replacement of a phosphodiester by e.g. a phosphorothioate or a phosphorodithioate.

Basically, depending upon the way of synthesis, usual common types of bonds between two nucleotides are: phosphodiester (PDE) bonds and phosphorothioate (PTO) bonds. In order to improve the stability and the immunostimulatory effect of CpG ODN's, the building blocks of synthetic oligodeoxynucleotides may be provided with phosphorothioates, so that they form PTO bonds.

Other modifications are e.g. replacements of a phosphodiester bridge by a dephospho bridge. Examples of dephospho bridges are methylhydroxylamine, formacetal and dimethylenesulfone groups.

Still other modifications are modifications that concern the replacement of a natural nucleoside base by a non-natural nucleoside base such as 5-fluorocytosine, 7-deaza-7-substituted guanine, 7-deaza-8-substituted guanine, 2-thiouracil, dihydrouracil, 5-bromo-cytosine, 6-substituted cytosines or N4-substituted cytosines.

Again other modifications are modifications concerning the replacement of a sugar unit; a β-ribose sugar or a ß-D-2'-ribose sugar unit by a modified sugar unit such as e.g. an L-2'-deoxyribose or 2'-L-arabinose.

A text book giving further insight in oligonucleotides is e.g. "PCR Primer: A Laboratory Manual", Second Edition, 2003, Edited By Carl W. Dieffenbach, *National Institute of Allergy and Infectious Diseases*; Gabriela S. Dreksler, *Uniformed Services University of the Health Sciences*, Cold Spring Harbor Laboratory Press ISBN 978-087969654-2.

For the detection of new CpG ODN's, a system is required that comprises cells that comprise a hybrid TLR according to the invention Thus, a second embodiment of the present invention relates to cells that comprise a hybrid TLR according to the invention.

As mentioned (vide supra), CpG ODN agonists for TLR9 signal predominantly via the NF kappa-B (NF-κB) pathway (Medzhitov 2001).

The detection of the effect of a CpG ODN on the occurrence and the amount of a compound of the (NF-κB) pathway in a cell is therefore indicative for its activity as a PAMP.

Brownlie at al. (2009) describe an NF-κB luciferase based reporter system. Other reporter systems are e.g. based upon IL-8 transcript measurement or cytokine secretion or the detection of NO secretion.

Thus, a preferred form of this embodiment relates to a cell according to the invention, characterised in that said cell comprises a plasmid comprising an NF-κB reporter gene.

Such reporter systems as mentioned above, although useful, have the disadvantage that they are not very sensitive. For a precise determination of the activity of existing and newly developed CpG ODN's, a sensitive detection system is a prerequisite.

The inventors now used a detection system in the present invention, that turned out to be surprisingly sensitive. This system is based upon the use of an enzyme called secreted alkaline phosphatase (SEAP) as a reporter enzyme encoded by the reporter gene. SEAP is a reporter enzyme in mammalian systems (Yang et al., 1997). In this system, SEAP expression is controlled by 5 NF-κB transcription factor binding sites combined with the ELAM promoter (J. Biol. Chem. 1991, Feb. 5; 266(4): 2466-73).

Therefore, a more preferred form of this second embodiment relates to cells according to the invention wherein the reporter gene encodes a secreted alkaline phosphatase (SEAP). The SEAP system is used with para-nitrophenyl-phosphate (pNPP) as a substrate.

Another important improvement over existing systems is the introduction and stable maintenance in cells of the plasmid carrying the reporter gene.

Up till now, all detection systems used transient transfection of cells with the reporter gene. Such transient systems do not allow for a reliable side-by-side comparison of the efficacy of CpG ODN's.

Usually, stable maintenance of a plasmid is obtained by growing the cells under the pressure of one or more selective agents, such as antibiotics for which a resistance gene is present on the plasmid. Loss of the plasmid would then cause the cell that lost the plasmid to die. Remaining viable cells would still harbour the plasmid. Stable means that the plasmid remains present in the cell after several cell division cycles, preferably integrated in the cell genome.

It is due to the introduction and stable maintenance in cells of the reporter gene that now for the first time a reproducible dose/response curve for CpG ODN's can be made. Such curves are essential if a reliable comparison between various CpG ODN's activity is to be made.

Thus, another preferred form of this second embodiment relates to a cell according to the invention that comprises a plasmid encoding an NF-κB reporter gene, which plasmid is stably maintained in the cell. Such cells are very suitable for use in the screening of CpG molecules, more specifically the screening of CpG molecules according to the invention.

The Examples give ample guidance about how to obtain such a cell comprising a plasmid encoding a reporter gene that can be stably maintained in the cell.

Basically, any cell or cell line carrying a hybrid TLR according to the invention that allows introduction and preferably the stable maintenance of a plasmid carrying a NF-κB reporter gene, preferably the SEAP gene as described above is suitable for testing TLR9-specific CpG ODN's.

An example of such a suitable cell line for testing TLR9-specific CpG ODN's is the cell line HEK293 ((ATCC number CRL-1573).

A preferred cell line for testing TLR9-specific CpG ODN's is the cell line Madin Darby canine kidney (ATCC number CCL-34) (MDCK).

Therefore, another preferred form of this second embodiment relates to a cell according to the invention wherein the cell is a HEK293 cell, preferably an MDCK cell.

The methods and cell lines described in detail in the Examples section of the present invention allow for the first time to make a reliable side-by-side comparison between various CpG ODN's for use in mammalian species.

Thus, still another embodiment of the present invention relates to a method for the detection of immunostimulatory oligodeoxynucleotides according to the invention wherein that method comprises the steps of a) contacting an oligodeoxynucleotide with a cell according to the invention, b) detecting the level of product of the reporter gene.

In a preferred form of this method, the product of the reporter gene is SEAP As shown in the Examples below, the hybrid toll-like receptors according to the invention have been used extensively for the identification of new CpG ODN's.

The CpG oligodeoxynucleotides according to the invention are in most cases active in double digit or even sometimes in single digit nanomolar concentrations, both in the in vitro test system and in vivo.

The half-maximal effective concentration (EC50) of an oligodeoxynucleotide is the amount of oligodeoxynucleotide that is necessary to induce an amount of the reporter enzyme SEAP (that produces the colored product absorbing at 405 nm) in the reporter cells that gives a half-maximal absorption change over time.

The Vmax indication given is an indication of the speed with which the chromogenic substrate of SEAP is turned into a colored component with an absorption of 405 nm. A high Vmax indicates that the CpG ODN is capable of rapidly inducing a TLR-reaction.

The following new immunostimulatory non-methylated oligodeoxynucleotides were found to have a low EC50 (double or even single digit nM concentrations) and thus to be very effective already in very low concentrations:

$[gacgtt]_n$ wherein $n \geq 4$

[SEQ ID NO: 214]
$[gacgatcgtc]_n$ wherein $n \geq 3$

[SEQ ID NO: 215]
$[tcgtcgttttcg]_n$ wherein $n \geq 3$

[SEQ ID NO: 216]
$[tcgtcgttgtcgttttgtcgtt]_n$ wherein $n \geq 2$ $(t_x[ttcgtt]t_y)_n$ wherein $n \geq 5$, $x = 0-5$ and $y = 0-5$ $[ttcgtN_1]_n$ wherein $N_1 = t$ or $c$ and wherein $n \geq 5$ $[N_1tcgtc]_n$ wherein $N_1 = t$ or $c$ and wherein $n \geq 5$ $[gN_1cgtt]_n$ wherein $n \geq 4$ and $N_1 = a$ or $t$ $[tcg]_x$ wherein $n \geq 6$ $[tcgN1]_n$ wherein $N1 = c$ or $g$ and $n \geq 6$ $[N1cgt]_n$ wherein $N1 = g$ or $c$ or $a$ or $t$ and $n \geq 6$ $[acga]_n$ wherein $n \geq 6$ It should be kept in mind that all of these new immunostimulatory non-methylated oligodeoxynucleotides are of the phosphorothioate (PTO) type.

Therefore, again another embodiment of the present invention relates to immunostimulatory non-methylated PTO oligodeoxynucleotides having any of the 12 general formulae given above.

It was generally found that the activity of the oligodeoxynucleotides increases when n increases.

This effect is leveling when n increases. Basically, the number n of the backbone structure should therefore be at least the number of n as indicated. Preferably, the upper range of n is n≤100, merely because of the fact that the longer the synthetic sequence the more difficult it is to make.

In practice therefore a more preferable upper range of n is n≤40, even more preferable n≤20.

It is very well possible to link an oligodeoxynucleotide according to the invention to a carrier or hapten, via a reactive chemical group. Such linkage enhances the immunostimulatory effect of the combined molecules.

Mere examples of such components are e.g. digoxigenin, aminohexyl-, Texas red and biotin.

Preferred carriers or haptens are 3'- and 5'-labeled Texas red and 5'-labeled digoxigenin. The linkage of oligodeoxynucleotides to haptens/carriers is well-known in the art.

Thus, a preferred form of this embodiment relates to an immunostimulatory non-methylated PTO oligodeoxynucleotide having one of the 12 general formulae given above wherein said oligodeoxynucleotide is coupled to a carrier or hapten.

Another embodiment of the invention relates to a vector comprising an immunostimulatory non-methylated oligodeoxynucleotide according to the invention. Such a vector can be a nucleic acid molecule such as a plasmid, a virus, a bacteriophage or any other vector used in molecular biology. Merely as an example: a vector comprising an immunostimulatory non-methylated oligodeoxynucleotide can e.g. be a DNA molecule such as a plasmid that can be multiplied in bacteria, into which an immunostimulatory non-methylated oligodeoxynucleotide according to the invention has been cloned. Such a plasmid preferably has an active origin of replication, causing high numbers of the plasmid to be present in the host. Growing such bacteria on a large scale followed by isolation of the plasmids provides an alternative for the synthetic production of the immunostimulatory non-methylated oligodeoxynucleotide according to the invention. It should be kept in mind that this embodiment only applies to immunostimulatory non-methylated oligodeoxynucleotides of the PDE type.

One of the aims of the present invention is to provide new CpG ODN's that can be used as successful immunostimulating components in vaccines that prevent or combat infectious disease together with an antigen component or genetic information encoding an antigen component, and a pharmaceutically acceptable carrier.

In general, the term antigen component refers to a composition of matter that comprises at least one epitope that can induce, stimulate or enhance an immune response when administered to a human or an animal.

The antigen component may be any kind of antigen component but preferably is derived from a micro-organism or virus that in its wild-type form is pathogenic to humans or animals.

The antigen component can be the whole pathogen, preferably in an inactivated or attenuated form, an extract of the pathogen or (an immunogenic part of) an immunogenic protein of the pathogen.

If the antigen component is (an immunogenic part of) an immunogenic protein of the pathogen, that immunogenic protein is preferably expressed in and recovered from in vitro cultured cells.

Therefore, another embodiment relates to a vaccine for preventing or combating infectious disease characterised in that said vaccine comprises an immunostimulating amount of an oligodeoxynucleotide according to the invention and/or a vector according to the invention, an immunogenic amount of an antigen component or genetic information encoding an antigen component, and a pharmaceutically acceptable carrier.

The skilled person will understand that the immunostimulating amount of the oligodeoxynucleotide and the immunogenic amount of the antigen component are strongly interrelated. It is one of the merits of the present invention that new oligodeoxynucleotide are provided that can lower the amount of antigen component that is necessary to prevent or combat infectious disease.

The amount of antigen component that is necessary to prevent or combat infectious disease is referred to as the immunogenic amount of the antigen component.

An immunostimulating amount of the oligodeoxynucleotide is the amount that is capable of decreasing the immunogenic amount of the antigen component, i.e. the amount of the antigen component that is necessary to prevent or combat an infectious disease.

So basically, the wording "immunostimulating amount of the oligodeoxynucleotide" and "immunogenic amount" must be seen in relation to each other.

It goes without saying that, if the vaccine comprises genetic information encoding an antigen component, the amount of antigen component expressed by this genetic information should be enough to prevent or combat infectious disease, i.e.; it must be an immunogenic amount.

The fact that the non-methylated oligodeoxynucleotides according to the invention are immunostimulatory, means that they enhance the immunological efficacy of antigen components in vaccines. For that reason, vaccines according to the invention will in many cases comprise less of the antigen component or the genetic information encoding the antigen component than would be the case if no oligodeoxynucleotides according to the invention would be present.

In some cases an antigen component as such, without the addition of immunostimulatory oligonucleotides, may have such low immunogenic properties that high amounts must be given anyway, albeit without reaching the desired immunogenic level. In such cases, the antigen component can be given in the usual high concentration, however now together with an oligodeoxynucleotide according to the invention in order to so obtain the desired level of immunogenicity.

Thus, the amount of the antigen component or the genetic information encoding the antigen component to be administered with an oligonucleotide according to the invention would as a rule of thumb be equal or below the amount given in the absence of the oligonucleotide. The skilled person involved in the manufacturing of a specific vaccine, would know what amount for that specific vaccine. Also, the Examples give e.g. guidance for the amount of antigen components to be used, e.g. for a rabies vaccine for canine species.

The amount of the oligodeoxynucleotide according to the invention that needs to be administered together with the antigen component or the genetic information encoding the antigen component depends both on the selected oligodeoxynucleotide and the antigen component.

A very suitable amount of oligodeoxynucleotide according to the invention would usually vary between 1 and 100 nanomol. Very good in vivo results have e.g. been obtained with 5-50 μg of oligodeoxynucleotides according to the invention with an average length of 30 deoxynucleotides that were shown to be active in in vitro tests in the nanomolar range.

If an oligodeoxynucleotide is chosen from the group of oligodeoxynucleotides that are active in the picomolar range, the skilled person would realise that amounts below, possibly far below, 1 nanomol, i.e. picomol amounts (e.g. 100-1000 ng), would be worth testing before testing nanomolar amounts. The skilled person should be aware of the fact that there may be an optimal amount for each of the oligodeoxynucleotides according to the invention.

Vaccines according to the invention comprise a pharmaceutically acceptable carrier. The nature of this carrier depends i.a. upon the route of administration. If the administration route is through the oral or intranasal route, the carrier could be as simple as sterile water, a physiological salt solution or a buffer. If injection is the preferred route, the carrier should preferably be isotonic and have pH restrictions that make it suitable for injection. Such carriers however are extensively known in the art.

Vaccines according to the invention may, in addition to the antigen component or the genetic information encoding the antigen component, and an oligodeoxynucleotide according to the invention, comprise an adjuvant. Adjuvants in general are substances that boost the immune response of the host in a non-specific manner.

Many adjuvants are known in the art to be suitable, such as Freund's Complete and Incomplete adjuvant, vitamin E, non-ionic block polymers and polyamines such as dextran sulphate, carbopol and pyran, alum hydroxide. Also frequently used are alumin phosphate, saponins, vegetable oils such as tocopherol and mineral oils. Very efficient adjuvants are oil-in-water emulsions and especially water-in-oil emulsions, further also referred to as oil-in-water adjuvants and water-in-oil adjuvants. Such emulsions are well-known in the art. Thus, preferably, the vaccine comprises a water-in-oil adjuvant.

Preferably the antigen component is, or is derived from a virus or micro-organism that in its wild-type form is pathogenic to humans, porcine, canine or bovine species.

For a large number of pathogens, vaccines are commercially available. These pathogens are listed below.

Thus, more preferably said virus or micro-organism is selected from the group consisting of human papillomavirus, a bacterium causing tuberculosis, diphtheria, pertussis, tetanus, pneumonia or meningitis, measles virus, poliomyelitis virus, hepatitis B virus, *Leptospira, Mycobacterium hyopneumomiae*, Bovine respiratory syncytium virus, Foot-and-mouth disease virus, Bovine Viral Diarrhoea virus, Porcine Respiratory and Reproductive Syndrome virus, canine parvovirus, canine parainfluenza virus, canine coronavirus, canine distemper virus, canine adenovirus, porcine Circovirus 2, Bovine Herpesvirus, rabies virus, classical swine fever virus, equine Herpesvirus, porcine parvovirus, *Escherichia coli, Pasteurella* (i.a. *P. multocida*), *Bordetella* (i.a. *B. bronchiseptica*), Pseudorabies virus, *Erysipelothrix, Haemophilus parasuis*, Bovine parainfluenza virus, *Mannheimia* (i.a. *M. haemolytica*), *Fusobacterium, Lawsonia intracellularis, Streptococcus equi, Chlamidophila, Actinobacillus pleuropneumoniae, Brucella abortus, Dictyocaulis, Toxoplasma gondii, Babesia* (i.a. *B. canis*), *Neospora, Giardia, Sarcocystis* and *Leishmania*.

Again another embodiment of the present invention relates to an immunostimulatory non-methylated oligodeoxynucleotide according to the invention in combination with an immunological amount of an antigen component or genetic information encoding an antigen component, and a pharmaceutically acceptable carrier for use as a medicament.

Still another embodiment of the present invention relates to an immunostimulatory non-methylated oligodeoxynucleotide according to the invention in combination with an immunological amount of an antigen component or genetic information encoding an antigen component, and a pharmaceutically acceptable carrier for use in preventing or combating infectious disease in mammalian species, preferably human, porcine, bovine and canine species.

LEGEND TO THE FIGURES

FIG. 1: MDCK (canine)—pNifTyhyg: reactivity with different PAMPs. Vertical axis: mOD450 nm/min.

Figure 2:
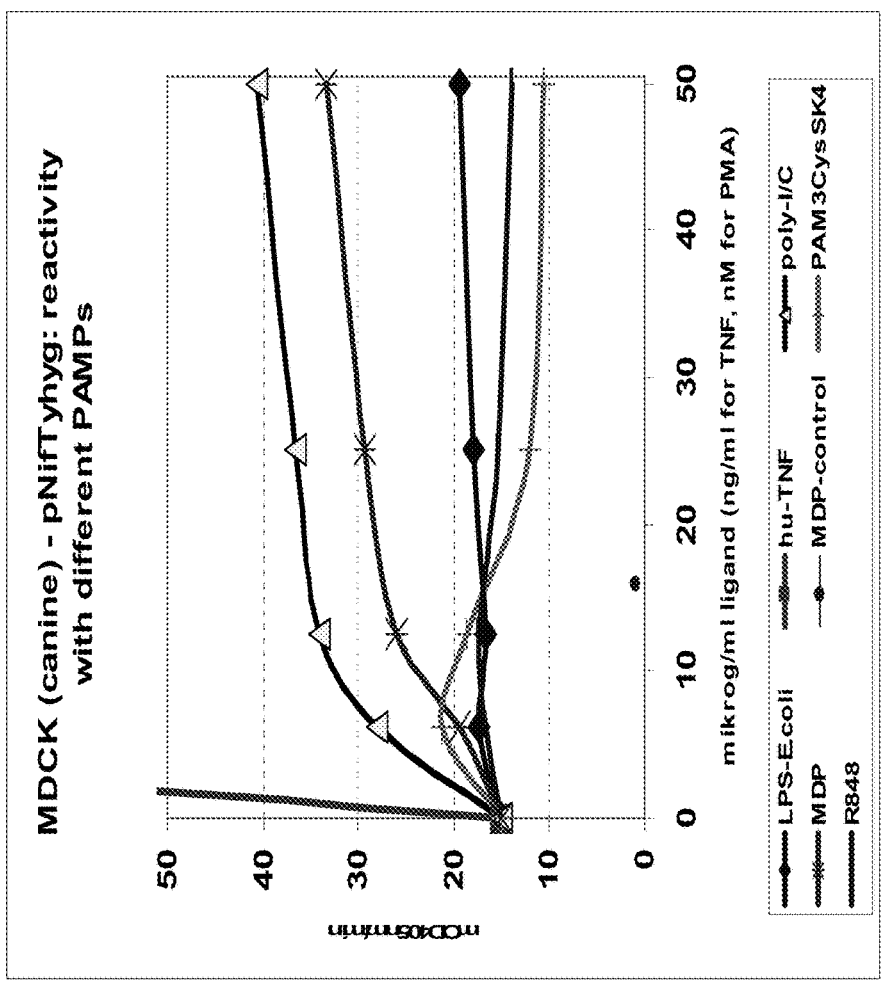

FIG. 2: MDCK (canine)—pNifTyhyg: reactivity with different PAMPs. Vertical axis: mOD450 nm/min.

Figure 3:
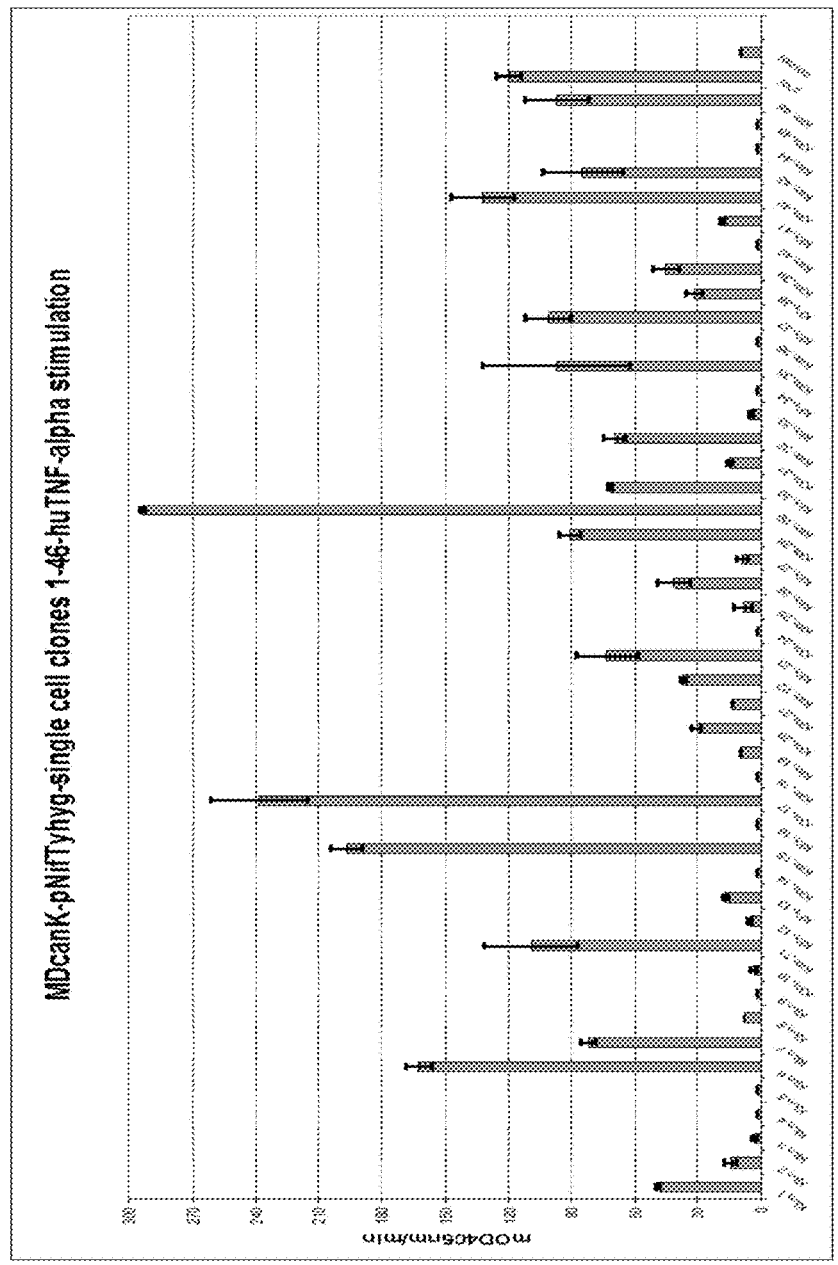
Figure 4:
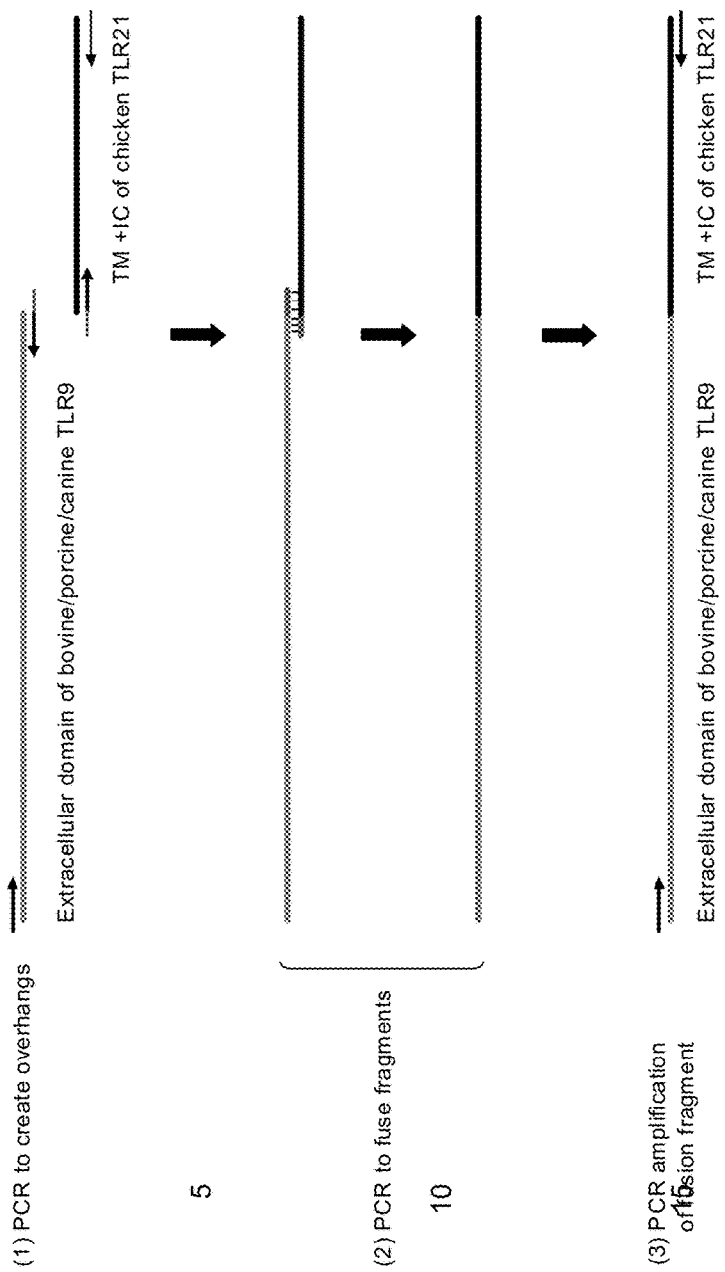

FIG. 3: MDcanK-pNifTyhyg-single cell clones 1-46-huTNF-alpha stimulation. Horizontal axis: from left to right; clone 1 to clone 46, pool and control FIG. 4: PCR "sewing" strategy.

Figure 5:
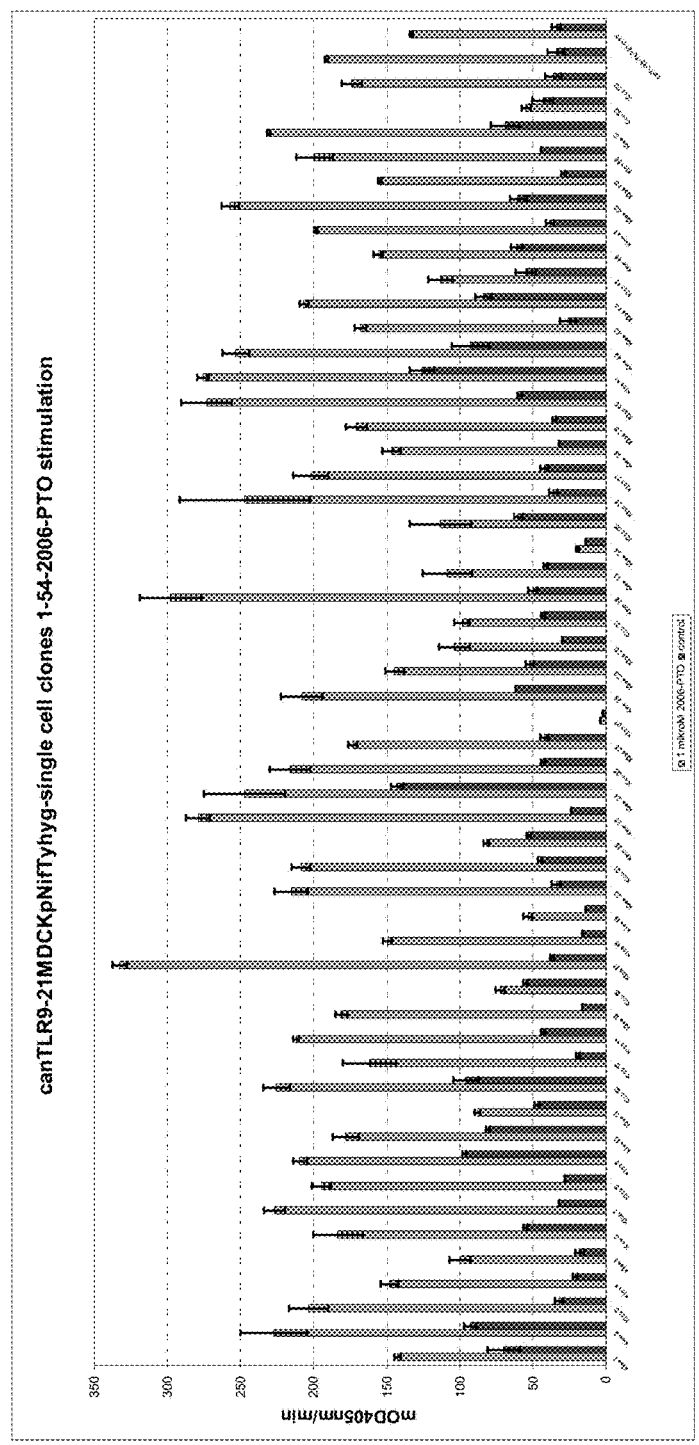

FIG. 5: canTLR9-21MDCKpNifTyhyg-single cell clones 1-54-2006-PTO stimulation. Horizontal axis: from left to right; clone 1 to clone 54, followed by "canTLR9-TLR21-pool" (the polyclonal cell line before single cell cloning). The reactivity is given in pairs of bars: the left bar (gray) is the level of stimulation with 1 microM of 2006-PTO, the right bar (black is the control)

FIG. 6-18: MDCK-pNifTyhyg-pIRESpuro-canTLR9-21fusion: stimulation with several PAMPs as indicated FIG. 19: MDCK-pNifTyhyg-pigTLR9/TLR21-single cell clones 1-75 ODN-2006-PTO stimulation. Horizontal axis: from left to right; clone 1 to clone 75, pool, "canis-TLR9/21-clone17" (dog TLR9-21 fusion clonal cell line (no 17) as a positive control) and "MDCK-pNifTyhyg" (the basal MDCK cell line used for the transfection experiment).

FIG. 20-31: MDCK-pNifTyhyg-pigTLR9/TLR21-fusion, tested with different PAMPs as indicated.

Figure 32:
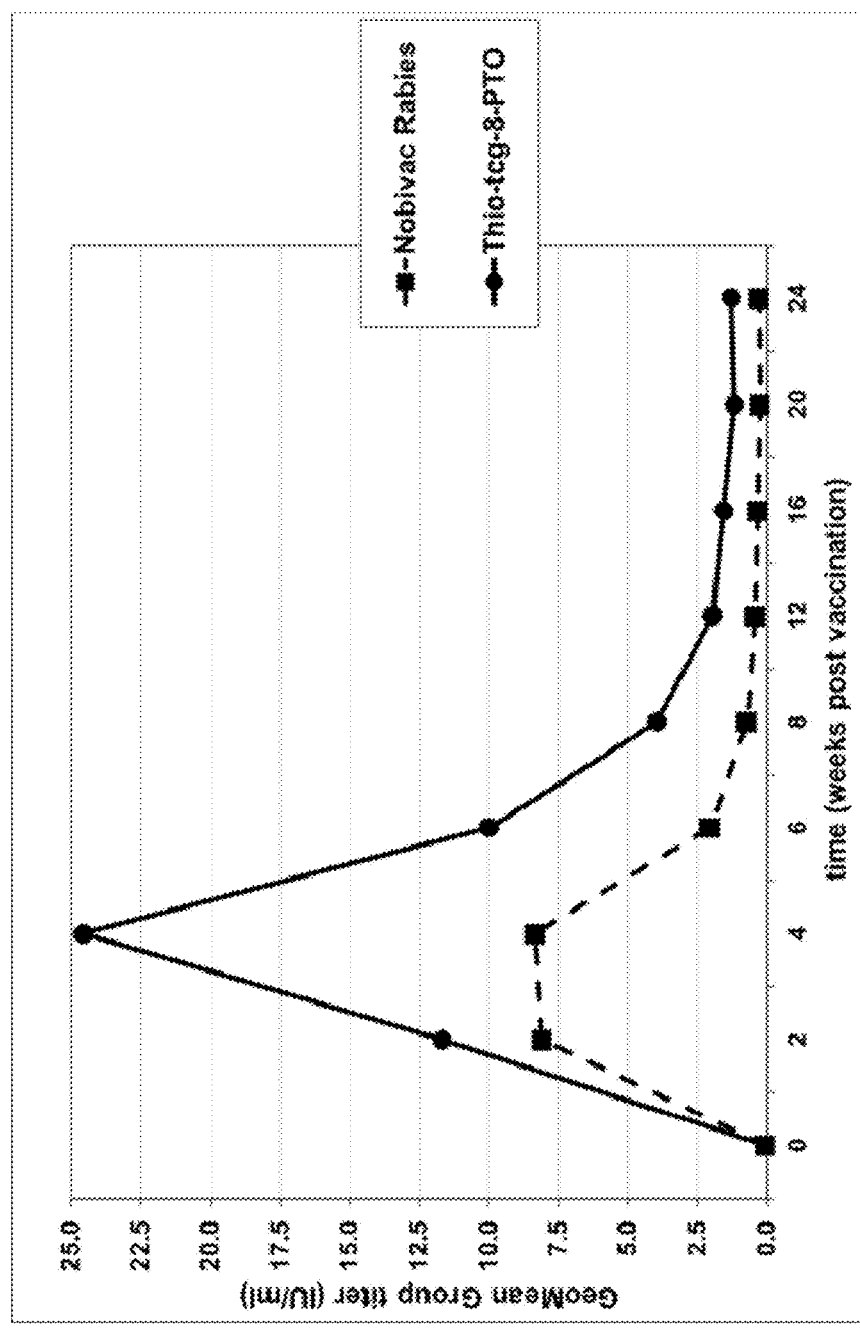

FIG. 32: Antibody titer of Nobivac rabies vaccine with and without hio-tcg-8-PTO as indicated.

LITERATURE REFERENCES

Babiuk L. A., Gomis S., Hecker R., 2003. Molecular approaches to disease control. *Poult. Sci.* 82, 870-875.

Brownlie, R., Zhu J., Allan B., Mutwiri G. K., Babiuk L. A., Potter A., Griebel P., 2009. Chicken TLR21 acts as a functional homologue to mammalian TLR9 in the recognition of CpG oligodeoxynucleotides. *Mol. Immunol.* 46, 3163-3170

Carrington A. C., Secombes C. J., 2006. A review of CpGs and their relevance to aquaculture. *Vet. Immunol. Immunopathol.* 112, 87-101.

Daubenberger C. A., 2007. TLR9 agonists as adjuvants for prophylactic and therapeutic vaccines. *Curr. Opin. Mol. Ther.* 9, 45-52.

Dorn A., Kippenberger S., 2008. Clinical application of CpG-, non-CpG-, and antisense oligodeoxynucleotides as immune modulators. *Curr. Opin. Mol. Ther.* 10, 10-20.

Fonseca D. E., Kline J. N., 2009. Use of CpG oligodeoxynucleotides in treatment of asthma and allergic disease. *Adv. Drug Deliv. Rev.* 61, 256-262.

Graham, F. L., Smiley, J., Russell, W. C., Nairn, R., 1977. Characteristics of a human cell line transformed by DNA from human adenovirus type 5. *J. Gen. Virol.* 36, 59-74.

Griebel P. J., Brownlie R., Manuja A., Nichani A., Mookherjee N., Popowych Y., Mutwiri G., Hecker R., Babiuk L. A., 2005. Bovine toll-like receptor 9: a comparative analysis of molecular structure, function and expression. *Vet. Immunol. Immunopathol.* 108, 11-16.

Hemmi H., Takeuchi O., Kawai T., Kaisho T., Sato S., Sanjo H., Matsumoto M., Hoshino K., Wagner H., Takeda K., Akira S., 2000. A Toll-like receptor recognizes bacterial DNA. *Nature* 408, 740-745.

Iwasaki A, Medzhitov R. Regulation of adaptive immunity by the innate immune system. 2010. Science 327, 291-295.

Keestra A. M., 2008. Molecular dissection of the chicken Toll-like receptor repertoire. PhD thesis (Proefschrift), University of Utrecht, The Netherlands Kline J. N., 2007. Immunotherapy of asthma using CpG oligodeoxynucleotides. *Immunol. Res.* 39, 279-286.

Kline J. N., Krieg A. M., 2008. Toll-like receptor 9 activation with CpG oligodeoxynucleotides for asthma therapy. *Drug News Perspect.* 21, 434-439.

Klinman D. M., 2004. Immunotherapeutic uses of CpG oligodeoxynucleotides. Nat. Rev. Immunol. 4, 249-258.

Klinman D. M, Currie D., Gursel I., Verthelyi D., 2004. Use of CpG oligodeoxynucleotides as immune adjuvants. Immunol. Rev. 199, 201-216.

Klinman D. M., 2006. Adjuvant activity of CpG oligodeoxynucleotides. Int. Rev. Immunol. 25, 135-154.

Klinman D. M., Klaschik S., Sato T., Tross D., 2009. CpG oligodeoxynucleotides as adjuvants for vaccines targeting infectious diseases. *Adv. Drug Deliv. Rev.* 61, 248-255.

Kindrachuk J., Potter J., Wilson H. L., Griebel P., Babiuk L. A., Napper S., 2008. Activation and regulation of toll-like receptor 9: CpGs and beyond. *Mini Rev. Med. Chem.* 8, 590-600.

Krieg A. M., Yi A, K., Matson S., Waldschmidt T, J., Bishop G. A., Teasdale R., Koretzky G. A., Klinman D. M., 1995. CpG motifs in bacterial DNA trigger direct B-cell activation. Nature 374, 546-549.

Krieg A. M., 2002. CpG motifs in bacterial DNA and their immune effects. *Annu. Rev. Immunol.* 20, 709-760.

Krieg A. M., 2003. CpG motifs: the active ingredient in bacterial extracts? *Nat. Med.* 9, 831-835.

Krieg A. M., 2006. Therapeutic potential of Toll-like receptor 9 activation. *Nat. Rev. Drug Discov.* 5, 471-484.

Krieg A. M., 2007a. Anti-infective applications of toll-like receptor 9 agonists. *Proc. Am. Thorac. Soc.* 4, 289-294.

Krieg A. M., 2007b. Development of TLR9 agonists for cancer therapy. *J. Clin. Invest.* 117, 1184-1194.

Linghua Zhang et al., 2007. Vaccination with Newcatle disease vaccine and CpG oligodeoxynucleotides induces specific immunity and protection against Newcastle disease virus in SPF chicken. *Vet. Immun. AndImmunopath.* 115, 216-222.

Medzhitov R., 2001. CpG DNA: security code for host defense. *Nat. Immunol.* 2, 15-16.

Medzhitov R., Approaching the asymptote: 20 years later. 2009. *Immunity* 30, 766-775)

Mutwiri G., van Drunen Littel-van den Hurk S., Babiuk L. A., 2009. Approaches to enhancing immune responses stimulated by CpG oligodeoxynucleotides. *Adv. Drug Deliv. Rev.* 61, 226-232.

Mutwiri G., Pontarollo R., Babiuk S., Griebel P., van Drunen Littel-van den Hurk S., Mena A., Tsang C., Alcon V., Nichani A., Ioannou X., Gomis S., Townsend H., Hecker R., Potter A., Babiuk L. A., 2003. Biological activity of immunostimulatory CpG DNA motifs in domestic animals. *Vet. Immunol. Immunopathol.* 91, 89-103.

Schindler, U., and Baichwal, V. R., 1994. Moll. Cell. Biol. 14: 5820-5831.

Singh M., O'Hagan D. T., 2003. Recent advances in veterinary vaccine adjuvants. *Int. J Parasitol.* 33, 469-478.

Vollmer J., 2005. Progress in drug development of immunostimulatory CpG oligodeoxynucleotide ligands for TLR9. *Expert Opin. Biol. Ther.* 5, 673-682.

Vollmer J., Krieg A. M., 2009. Immunotherapeutic applications of CpG oligodeoxynucleotide TLR9 agonists. *Adv. Drug Deliv. Rev.* 61, 195-204.

Wagner H., 2009. The immunogenicity of CpG-antigen conjugates. *Adv. Drug. Deliv. Rev.* 61, 243-247.

Weiner G. J., 2009. CpG oligodeoxynucleotide-based therapy of lymphoid malignancies. *Adv. Drug Deliv. Rev.* 61, 263-267.

Werling D., Jungi T. W., 2003. TOLL-like receptors linking innate and adaptive immune response. *Vet. Immunol. Immunopathol.* 91, 1-12.

Wilson H. L., Dar A., Napper S. K., Marianela Lopez A., Babiuk L. A., Mutwiri G. K., 2006. Immune mechanisms and therapeutic potential of CpG oligodeoxynucleotides. *Int. Rev. Immunol.* 25, 183-213.

Wilson K. D., de Jong S. D., Tam Y. K., 2009. Lipid-based delivery of CpG oligodeoxynucleotides enhances immunotherapeutic efficacy. *Adv. Drug Deliv. Rev.* 61, 233-242.

Yang, T. T., Sinai, P., Kitts, P. A., Kain, S. R., 1997. Quantification of gene expression with a secreted alkaline phosphatase reporter system. *Biotechniques* 23, 1110-1114.

EXAMPLES

Example 1

Gene Cloning of Bovine Toll-Like Receptor 9 (TLR-9)

Fresh bovine spleen was obtained from a local slaughterhouse as a source of bovine TLR9 messenger RNA (mRNA). Total RNA was prepared from bovine spleen tissue essentially as outlined by Chomczynski and Sacchi (1987) using a commercial kit and its instructions (TRIZOL®, GIBCOBRL). From the bovine spleen total RNA, first strand cDNA was synthesized, essentially as described by the supplier of the reverse transcriptase (-Expand Reverse Transcriptase, Roche). Primer were designed for the polymerase chain reaction (PCR) amplification of bovine TLR9 (Genbank AY859726) from the start codon region to a 3'UTR region downstream of the stop codon (Bov-TLR9-for and Bov-TLR9-rev, see below). However, initial PCR experiments (Expand High Fidelity PCR kit, Roche) using bovine spleen first strand cDNA aiming at the amplification of the full length product (expected: ~3100 bp) proved to be repeatedly negative. Closer inspection of the bovine TLR9 gene indicated a high GC content (~64%). Therefore, it was decided to test a PCR system optimized for this particular problem (Advantage™ GC2, Clontech). The corresponding PCR reaction yielded a weak DNA fragment of the expected size (~3100 bp).

Primer Sequences:

```
Bov-TLR9-for                         [SEQ ID NO: 14]
GGGTACCATGGGCCCCTACTGTGCCCCGCAC Bov-TLR9-rev                         [SEQ ID NO: 15]
GTCTAGAGTCTGTGCTATTCGGCTGTCGTGG
```

Cloning of the PCR fragment into pCR2.1-Topo (Invitrogen) was performed, and four clones were sequenced to identify a PCR error-free version (pCR2.1-Topo-bovineTLR9). By exploiting primer-introduced KpnI and XbaI restriction enzyme sites, the bovine TLR9 insert was excised, agarose gel-purified and subcloned into the KpnI/XbaI-cut mammalian expression vectors pcDNA3.1(neo) and pcDNA3.1(hyg) (both Invitrogen), yielding pcDNA3.1

(neo)-bovineTLR9 and pcDNA3.1(hyg)-bovineTLR9, respectively. The corresponding inserts were resequenced (see below).

pcDNA3.1 Insert Sequence Bovine TLR9 (Primer Sequences Underlined, Start/Stop Codons Highlighted Bold), 3090 bp. [SEQ ID NO: 207]

GGTACC ATGGGCCCCTACTGTGCCCCGCACCCCCTTTCTCTCCTGGTGC
AGGCGGCGGCACTGGCAGCGGCCCTGGCCGAGGGCACCCTGCCTGCCTTC
CTGCCCTGTGAGCTCCAGCCCCATGGTCAGGTGGACTGCAACTGGCTGTT
CCTGAAGTCTGTGCCGCACTTTTCGGCTGGAGCCCCCGGGCCAATGTCA
CCAGCCTCTCCTTAATCTCCAACCGCATCCACCACTTGCATGACTCTGAC
TTCGTCCACCTGTCCAACCTGCGGGTCCTCAACCTCAAGTGGAACTGCCC
GCCGGCCGGCCTCAGCCCCATGCACTTCCCCTGCCGTATGACCATCGAGC
CCAACACCTTCCTGGCTGTGCCCACCCTGGAGGAGCTGAACCTGAGCTAC
AACGGCATCACGACCGTGCCTGCCCTGCCCAGTTCCCTCGTGTCCCTGTC
GCTGAGCCACACCAGCATCCTGGTGCTAGGCCCCACCCACTTCACCGGCC
TGCACGCCCTGCGCTTTCTGTACATGGACGGCAACTGCTACTACATGAAC
CCCTGCCCGCGGGCCCTGGAGGTGGCCCCAGGCGCCCTCCTCGGCCTGGG
CAACCTCACGCACCTGTCGCTCAAGTACAACAACCTCACGGAGGTGCCCC
GCCGCCTGCCCCCCAGCCTGGACACCCTGCTGCTGTCCTACAACCACATT
GTCACCCTGGCACCCGAGGACCTGGCCAACCTGACTGCCCTGCGCGTGCT
TGACGTGGGTGGGAACTGCCGCCGCTGCGACCACGCCCGCAACCCCTGCA
GGGAGTGCCCAAAGAACTTCCCCAAGCTGCACCCTGACACCTTCAGTCAC
CTGAGCCGCCTCGAAGGCCTGGTGTTGAAGGACAGTTCTCTCTACAAACT
AGAGAAAGATTGGTTCCGCGGCCTGGGCAGGCTCCAAGTGCTCGACCTGA
GTGAGAACTTCCTCTATGACTACATCACCAAGACCACCATCTTCAACGAC
CTGACCCAGCTGCGCAGACTCAACCTGTCCTTCAATTACCACAAGAAGGT
GTCCTTCGCCCACCTGCACCTAGCGTCCTCCTTTGGGAGTCTGGTGTCCC
TGGAGAAGCTGGACATGCACGGCATCTTCTTCCGCTCCCTCACCAACATC
ACGCTCCAGTCGCTGACCCGGCTGCCCAAGCTCCAGAGTCTGCATCTGCA
GCTGAACTTCATCAACCAGGCCCAGCTCAGCATCTTTGGGGCCTTCCCGA
GCCTGCTCTTCGTGGACCTGTCGGACAACCGCATCAGCGGAGCCGCGACG
CCAGCGGCCGCCCTGGGGGAGGTGGACAGCAGGGTGGAAGTCTGGCGATT
GCCCAGGGGCCTCGCTCCAGGCCCGCTGGACGCCGTCAGCTCAAAGGACT
TCATGCCAAGCTGCAACCTCAACTTCACCTTGGACCTGTCACGGAACAAC
CTGGTGACAATCCAGCAAGAGATGTTTACCCGCCTCTCCCGCCTCCAGTG
CCTGCGCCTGAGCCACAACAGCATCTCGCAGGCGGTTAATGGCTCCCAGT
TCGTGCCGCTGACCAGCCTGCGAGTGCTCGACCTGTCCCACAACAAGCTG
GACCTGTACCATGGGCGCTCATTCACGGAGCTGCCGCAGCTGGAGGCACT
GGACCTCAGCTACAACAGCCAGCCCTTCAGCATGCAGGGCGTGGGCCACA
ACCTCAGCTTCGTGGCCCAGCTGCCCTCCCTGCGCTACCTCAGCCTTGCG
CACAATGGCATCCACAGCCGCGTGTCACAGAAGCTCAGCAGCGCCCTCGTT

GCGCGCCCTGGACTTCAGCGGCAACTCCCTGAGCCAGATGTGGGCCGAGG
GAGACCTCTATCTCTGCTTTTTCAAAGGCTTGAGGAACCTGGTCCAGCTG
GACCTGTCCGAGAACCATCTGCACACCCTCCTGCCTCGTCACCTGGACAA
CCTGCCCAAGAGCCTGCGGCAGCTGCGTCTCCGGGACAATAACCTGGCCT
TCTTCAACTGGAGCAGCCTGACCGTCCTGCCCCGGCTGGAAGCCCTGGAT
CTGGCAGGAAACCAGCTGAAGGCCCTGAGCAACGGCAGCCTGCCGCCTGG
CATCCGGCTCCAGAAGCTGGACGTGAGCAGCAACAGCATCGGCTTCGTGA
TCCCCGGCTTCTTCGTCCGCGCGACTCGGCTGATAGAGCTTAACCTCAGC
GCCAATGCCCTGAAGACAGTGGATCCCTCCTGGTTCGGTTCCTTAGCAGG
GACCCTGAAAATCCTAGACGTGAGCGCCAACCCGCTCCACTGCGCCTGCG
GGGCGGCCTTTGTGGACTTCCTGCTGGAGAGACAGGAGGCCGTGCCCGGG
CTGTCCAGGCGCGTCACATGTGGCAGTCCGGGCCAGCTCCAGGGCCGCAG
CATCTTCACACAGGACCTGCGCCTCTGCCTGGATGAGACCCTCTCCTTGG
ACTGCTTTGGCCTCTCACTGCTAATGGTGGCGCTGGGCCTGGCAGTGCCC
ATGCTGCACCACCTCTGTGGCTGGGACCTCTGGTACTGCTTCCACCTGTG
TCTGGCCCATTTGCCCCGACGGCGGCGGCAGCGGGGCGAGGACACCCTGC
TCTATGATGCCTTCGTGGTCTTCGACAAGGTGCAGAGTGCAGTGGCTGAT
TGGGTGTACAACGAGCTCCGCGTGCAGCTGGAGGAGCGCCGGGGGCGCCG
GGCGCTCCGCCTCTGCCTGGAGGAGCGAGACTGGCTCCCTGGTAAGACGC
TCTTCGAGAACCTGTGGGCCTCGGTCTACAGCAGCCGCAAGACCATGTTC
GTGCTGGACCACACGGACCGGGTCAGCGGCCTCCTGCGCGCCAGCTTCCT
GCTGGCCCAGCAGCGCCTGTTGGAGGACCGCAAGGACGTCGTAGTGCTGG
TGATCCTGCGCCCCGCCGCCTATCGGTCCCGCTACGTGCGGCTGCGCCAG
CGCCTCTGCCGCCAGAGCGTCCTCCTCTGGCCCCACCAGCCCAGTGGCCA
GGGTAGTTTCTGGGCCAACCTGGGCATAGCCCTGACCAGGGACAACCGTC
ACTTCTATAACCGGAACTTCTGCCGGGGCCCCACGACAGCCGAA TAG
CACAGACTCTAGA

[SEQ ID NO: 2]
MGPYCAPHPLSLLVQAAALAAALAEGTLPAFLPCELQPHGQVDCNWLFLK
SVPHFSAGAPRANVTSLSLISNRIHHLHDSDFVHLSNLRVLNLKWNCPPA
GLSPMHFPCRMTIEPNTFLAVPTLEELNLSYNGITTVPALPSSLVSLSLS
HTSILVLGPTHFTGLHALRFLYMDGNCYYMNPCPRALEVAPGALLGLGNL
THLSLKYNNLTEVPRRLPPSLDTLLLSYNHIVTLAPEDLANLTALRVLDV
GGNCRRCDHARNPCRECPKNFPKLHPDTFSHLSRLEGLVLKDSSLYKLEK
DWFRGLGRLQVLDLSENFLYDYITKTTIFNDLTQLRRLNLSFNYHKKVSF
AHLHLASSFGSLVSLEKLDMHGIFFRSLTNITLQSLTRLPKLQSLHLQLN
FINQAQLSIFGAFPSLLFVDLSDNRISGAATPAAALGEVDSRVEVWRLPR
GLAPGPLDAVSSKDFMPSCNLNFTLDLSRNNLVTIQQEMFTRLSRLQCLR
LSHNSISQAVNGSQFVPLTSLRVLDLSHNKLDLYHGRSFTELPQLEALDL
SYNSQPFSMQGVGHNLSFVAQLPSLRYLSLAHNGIHSRVSQKLSSASLRA
LDFSGNSLSQMWAEGDLYLCFFKGLRNLVQLDLSENHLHTLLPRHLDNLP

-continued
KSLRQLRLRDNNLAFFNWSSLTVLPRLEALDLAGNQLKALSNGSLPPGIR

LQKLDVSSNSIGFVIPGFFVRATRLIELNLSANALKTVDPSWFGSLAGTL

KILDVSANPLHCACGAAFVDFLLERQEAVPGLSRRVTCGSPGQLQGRSIF

TQDLRLCLDETLSLDCFGLSLLMVALGLAVPMLHHLCGWDLWYCFHLCLA

HLPRRRRQRGEDTLLYDAFVVFDKVQSAVADWVYNELRVQLEERRGRRAL

RLCLEERDWLPGKTLFENLWASVYSSRKTMFVLDHTDRVSGLLRASFLLA

QQRLLEDRKDVVVLVILRPAAYRSRYVRLRQRLCRQSVLLWPHQPSGQGS

FWANLGIALTRDNRHFYNRNFCRGPTTAE.

The translated sequence was aligned with 10 bovine TLR9 full length cDNA sequences deposited in Genbank (September 2011, P8-141108-prot-280109.pro Bov-TLR9-NM_183081.pro Bov-rom-TLR9-EF076723.pro Bov-ang-TLR9-EF076724.pro Bov-braf-TLR9-EF076725.pro Bov-brah-TLR9-EF076726.pro Bov-char-TLR9-EF076727.pro Bov-hol-TLR9-EF076728.pro Bov-lim-TLR9-EF076729.pro Bov-pied-TLR9-EF076731.pro Bov-TLR9-AY859726.pro). Alignment (ClustalW; DNAStar) of the 11 bovine TLR9 polypeptide sequences showed polymorphisms at 7 positions. In 5 cases the translated sequence of our TLR9 clone (P8-141108-prot-280109) conformed to the majority polypeptide sequence. In the two other positions, identical residues were found as in the Genbank sequence AY859726.

Therefore, it is concluded that a correct version of bovine TLR9 has been cloned.

Example 2

Gene Cloning of Porcine Toll-Like Receptor 9 (TLR-9)

Fresh porcine spleen was obtained from a local slaughterhouse as a source of porcine TLR9 messenger RNA (mRNA). Total RNA was prepared from porcine spleen tissue essentially as outlined by Chomczynski and Sacchi (1987) using a commercial kit and its instructions (TRIZOL®, GIBCOBRL). From the porcine spleen total RNA, first strand cDNA was synthesized, essentially as described by the supplier of the reverse transcriptase (Expand Reverse Transcriptase, Roche).

Primer were designed for the polymerase chain reaction (PCR) amplification of porcine TLR9 (Genbank NM_213958) from the start codon region to a 3'UTR region downstream of the stop codon (PigTLR9for1 and PigTLR9rev1, see below). However, initial PCR experiments using porcine spleen first strand cDNA aiming at the amplification of the full length product (expected: 3246 bp) proved to be repeatedly negative. Therefore, it was decided to take advantage of a unique Xho I site bisecting the porcine TLR9 gene into two approximately equally sized fragments (1501 bp and 1745 bp, respectively), that were more amenable for a PCR approach. To this end primer were designed upstream of the Xho I site in a forward direction and downstream of the Xho I site in a reverse direction (PigTLR9XhoI-for and PigTLR9XhoI-rev, see below), to give rise to PCR fragments overlapping near the unique Xho I site.

Primer Sequences:

```
PigTLR9for1                          [SEQ ID NO: 16]
GAAGCTTACCATGGGCCCCCGCTGCACCCTGCACCCC PigTLR9rev1                          [SEQ ID NO: 17]
GGCGGCCGCTTACATGCCAGGCTGGGGGGTGGGGTG PigTLR9XhoI-for                      [SEQ ID NO: 18]
GGTGACAATCCAGTCGGAGATGTTTGCTCG

[SEQ ID NO: 19]
GGTCCAGCTTGTTGTGGGACAGGTCCAGC
```

PCR reactions (Expand High Fidelity PCR kit, Roche) were performed with the primer pairs PigTLR9for1/PigTLR9XhoI-rev (for amplification of the 5' gene fragment) and PigTLR9XhoI-for/PigTLR9rev1 (for amplification of the 3' gene fragment). The corresponding PCR products were agarose gel-purified, cloned into pCR2.1-topo (Invitrogen), and three clones each were sequenced to identify PCR error-free versions. By exploiting vector-based and PCR fragment-based XhoI sites, the corresponding 5'- and 3'-PCR fragments were joined to the full length porcine TLR9 gene. From the corresponding construct (pCR2.1-Topo-porcineTLR9) the insert was excised by HindII/NotI digestion, agarose gel-purified and subcloned into the HindIII/NotI-cut mammalian expression vectors pcDNA3.1 (neo) and pcDNA3.1(hyg) (both Invitrogen), yielding pcDNA3.1 (neo)-porcineTLR9 and pcDNA3.1 (hyg)-porcineTLR9, respectively. The corresponding inserts were resequenced (see below).

pcDNA3.1 Insert Sequence Porcine TLR9 (Primer Sequences Underlined, Start/Stop Codons Highlighted Bold, Unique XhoI Site Highlighted) [SEQ ID NO: 208]

<u>GAAGCTTACC</u> ATGGGCCCCCGCTGCACCCTGCACCCCCTTTCTCCTG

GTGCAGGTGACAGCGCTGGCTGCGGCTCTGGCCCAGGGCAGGCTGCCTGC

CTTCCTGCCCTGTGAGCTCCAGCCCCACGGCCTGGTGAACTGCAACTGGC

TCTTCCTGAAGTCCGTGCCCCACTTCTCGGCGGCAGCGCCCGGGCCAAC

GTCACCAGCCTCTCCTTACTCTCCAACCGCATCCACCACCTGCACGACTC

TGACTTCGTCCACCTGTCCAGCCTACGAACTCTCAACCTCAAGTGGAACT

GCCCGCCGGCTGGCCTCAGCCCCATGCACTTCCCCTGCCACATGACCATC

GAGCCCAACACCTTCCTGGCCGTGCCCACCCTGGAGGAGCTGAACCTGAG

CTACAACAGCATCACGACCGTGCCTGCCCTGCCCGACTCCCTCGTGTCCC

TGTCGCTGAGCCGCACCAACATCCTGGTGCTAGACCCCACCCACCTCACT

GGCCTACATGCCCTGCGCTACCTGTACATGGATGGCAACTGCTACTACAA

GAACCCCTGCCAGGGGGCGCTGGAGGTGGTGCCGGGTGCCCTCCTCGGCC

TGGGCAACCTCACACATCTCTCACTCAAGTACAACAATCTCACGGAGGTG

CCCCGCAGCCTGCCCCCCAGCCTGGAGACCCTGCTGTTGTCCTACAACCA

CATTGTCACCCTGACGCCTGAGGACCTGGCCAATCTGACTGCCCTGCGCG

TGCTTGATGTGGGGGGGAACTGCCGCCGCTGTGACCATGCCCGCAACCCC

TGCAGGGAGTGCCCAAAGGACCACCCCAAGCTGCACTCTGACACCTTCAG

CCACCTGAGCCGCCTCGAAGGCCTGGTGTTGAAAGACAGTTCTCTCTACA

ACCTGGACACCAGGTGGTTCCGAGGCCTGGACAGGCTCCAAGTGCTGGAC

CTGAGTGAGAACTTCCTCTACGACTGCATCACCAAGACCACGGCCTTCCA

GGGCCTGGCCCGACTGCGCAGCCTCAACCTGTCCTTCAATTACCACAAGA

AGGTGTCCTTTGCCCACCTGCACCTGGCACCCTCCTTTGGGCACCTCCGG

-continued

```
TCCCTGAAGGAGCTGGACATGCATGGCATCTTCTTCCGCTCGCTCAGTGA
GACCACGCTCCAACCTCTGGTCCAACTGCCTATGCTCCAGACCCTGCGCC
TGCAGATGAACTTCATTAACCAGGCCCAGCTCAGCATCTTTGGGCCTTC
CCTGGCCTGCTGTACGTGGACCTATCGGACAACCGCATCAGCGGAGCTGC
AAGGCCAGTGGCCATTACTAGGGAGGTGGATGGTAGGGAGAGGGTCTGGC
TGCCTTCCAGGAACCTCGCTCCACGTCCACTGGACACTCTCCGCTCAGAG
GACTTCATGCCAAACTGCAAGGCCTTCAGCTTCACCTTGGACCTGTCTCG
GAACAACCTGGTGACAATCCAGTCGGAGATGTTTGCTCGCCTCTCACGCC
TCGAGTGCCTGCGCCTGAGCCACAACAGCATCTCCCAGGCGGTCAATGGC
TCTCAGTTTGTGCCGCTGACCAGCCTGCGGGTGCTGGACCTGTCCCACAA
CAAGCTGGACCTGTATCACGGGCGCTCGTTCACGGAGCTGCCGCGCCTGG
AAGCACTGGACCTCAGCTACAATAGCCAGCCCTTTACCATGCAGGGTGTG
GGCCACAACCTCAGCTTCGTGGCCCAGCTGCCCGCCCTGCGCTACCTCAG
CCTGGCGCACAATGACATCCATAGCCGAGTGTCCCAGCAGCTCTGTAGCG
CCTCACTGTGCGCCCTGGACTTTAGCGGCAACGATCTGAGCCGGATGTGG
GCTGAGGGAGACCTCTATCTCCGCTTCTTCCAAGGCCTAAGAAGCCTAGT
CTGGCTGGACCTGTCCCAGAACCACCTGCACACCCTCCTGCCACGTGCCC
TGGACAACCTCCCCAAAAGCCTGAAGCATCTGCATCTCCGTGACAATAAC
CTGGCCTTCTTCAACTGGAGCAGCCTGACCCTCCTGCCCAAGCTGGAAAC
CCTGGACTTGGCTGGAAACCAGCTGAAGGCCCTAAGCAATGGCAGCCTGC
CATCTGGCACCCAGCTGCGGAGGCTGGACCTCAGTGGCAACAGCATCGGC
TTTGTGAACCCTGGCTTCTTTGCCCTGGCCAAGCAGTTAGAAGAGCTCAA
CCTCAGCGCCAATGCCCTCAAGACAGTGGAGCCCTCCTGGTTTGGCTCGA
TGGTGGGCAACCTGAAAGTCCTAGACGTGAGCGCCAACCCTCTGCACTGT
GCCTGTGGGGCGACCTTCGTGGGCTTCCTGCTGGAGGTACAGGCTGCCGT
GCCTGGGCTGCCCAGCCGCGTCAAGTGTGGCAGTCCGGGGCAGCTCCAGG
GCCATAGCATCTTTGCGCAAGACCTGCGCCTCTGCCTGGATGAGACCCTC
TCGTGGAACTGTTTTGGCATCTCGCTGCTGGCCATGGCCCTGGGCCTGGT
TGTGCCCATGCTGCACCACCTCTGCGGCTGGGACCTCTGGTACTGCTTCC
ACCTGTGCCTGGCCTGGCTGCCCCACCGAGGGCAGCGGCGGGGCGCAGAC
GCCCTGTTCTATGATGCCTTCGTGGTCTTTGACAAAGCTCAGAGTGCTGT
GGCCGACTGGGTGTACAACGAGCTGCGGGTGCAGCTGGAGGAGCGCCGTG
GGCGCCGCGCACTGCGCCTGTGCCTGGAGGAGCGAGACTGGTTACCTGGC
AAGACGCTCTTCGAGAACCTGTGGGCCTCAGTCTACAGCAGCCGCAAGAC
CCTGTTTGTGCTGGCCCACACGGACCGTGTCAGCGGCCTCTTGCGTGCCA
GTTTCCTGCTGGCCCAGCAGCGCCTGCTGGAGGACCGCAAGGACGTTGTA
GTGCTGGTGATCCTGCGCCCCGATGCCTACCGCTCCCGCTACGTGCGGCT
GCGCCAGCGCCTCTGCCGCCAGAGTGTCCTCCTCTGGCCCCACCAGCCC
GTGGGCAGGGCAGCTTCTGGGCCCAGCTGGGCACAGCCCTGACCAGGGAC
AACCACCACTTCTATAACCGGAACTTCTGCCGGGGCCCCACGACAGCCGA
```

-continued
```
ATAGCACTGAGTGACAGCCCAGTTGCCCCAGCCCCCCTGGATTTGCCTCT
CTGCCTGGGGTGCCCCAACCTGCTTTGCTCAGCCACACCACTGCTCTGCT
CCCTGTTCCCCACCCCACCCCCCAGCCTGGCATG
```

[SEQ ID NO: 4]
```
MGPRCTLHPLSLLVQVTALAAALAQGRLPAFLPCELQPHGLVNCNWLFLK
SVPHFSAAAPRANVTSLSLLSNRIHHLHDSDFVHLSSLRTLNLKWNCPPA
GLSPMHFPCHMTIEPNTFLAVPTLEELNLSYNSITTVPALPDSLVSLSLS
RTNILVLDPTHLTGLHALRYLYMDGNCYYKNPCQGALEVVPGALLGLGNL
THLSLKYNNLTEVPRSLPPSLETLLLSYNHIVTLTPEDLANLTALRVLDV
GGNCRRCDHARNPCRECPKDHPKLHSDTFSHLSRLEGLVLKDSSLYNLDT
RWFRGLDRLQVLDLSENFLYDCITKTTAFQGLARLRSLNLSFNYHKKVSF
AHLHLAPSFGHLRSLKELDMHGIFFRSLSETTLQPLVQLPMLQTLRLQMN
FINQAQLSIFGAFPGLLYVDLSDNRISGAARPVAITREVDGRERVWLPSR
NLAPRPLDTLRSEDFMPNCKAFSFTLDLSRNNLVTIQSEMFARLSRLECL
RLSHNSISQAVNGSQFVPLTSLRVLDLSHNKLDLYHGRSFTELPRLEALD
LSYNSQPFTMQGVGHNLSFVAQLPALRYLSLAHNDIHSRVSQQLCSASLC
ALDFSGNDLSRMWAEGDLYLRFFQGLRSLVWLDLSQNHLHTLLPRALDNL
PKSLKHLHLRDNNLAFFNWSSLTLLPKLETLDLAGNQLKALSNGSLPSGT
QLRRLDLSGNSIGFVNPGFFALAKQLEELNLSANALKTVEPSWFGSMVGN
LKVLDVSANPLHCACGATFVGFLLEVQAAVPGLPSRVKCGSPGQLQGHSI
FAQDLRLCLDETLSWNCFGISLLAMALGLVVPMLHHLCGWDLWYCFHLCL
AWLPHRGQRRGADALFYDAFVVFDKAQSAVADWVYNELRVQLEERRGRRA
LRLCLEERDWLPGKTLFENLWASVYSSRKTLFVLAHTDRVSGLLRASFLL
AQQRLLEDRKDVVVLVILRPDAYRSRYVRLRQRLCRQSVLLWPHQPRGQG
SFWAQLGTALTRDNHHFYNRNFCRGPTTAE.
```

The translated sequence was aligned with the four porcine TLR9 full length cDNA sequences deposited in Genbank (September 2011, P1-181109-prot.pro, pig-TLR9-NM_213958.pro, pig-TLR9-AK349013.pro, pig-TLR9-GU 138029.pro, pig-TLR9-AY859728.pro). Alignment (ClustalW; DNAStar) of the five porcine TLR9 polypeptide sequences showed polymorphisms at 9 positions. In each case the translated sequence of our TLR9 clone (P1-181109-prot) conformed to the majority polypeptide sequence, and was identical to the translation of cDNA clone AY859728.

Therefore, it is concluded that a correct version of porine TLR9 has been cloned.

Example 3

Gene Cloning of Canine Toll-Like Receptor 9 (TLR-9)

Total RNA from canine lymph nodes and canine spleen was purchased from Zyagen and was used as source for TLR9 messenger RNA (mRNA). From the canine spleen or lymph node total RNA, first strand cDNA was synthesized, essentially as described by the supplier of the reverse transcriptase (Expand Reverse Transcriptase, Roche).

Primer were designed for the polymerase chain reaction (PCR) amplification of canine TLR9 (Genbank NM_001002998) from the start codon region to the stop codon (Canis-TLR9-for and Canis-TLR9-rev, see below). However, initial PCR experiments using canine lymph node and spleen first strand cDNA aiming at the amplification of the full length product (expected: 3100 bp) proved to be repeatedly negative. Therefore, it was decided to prepare two overlapping TLR9 gene sections, that were more amenable for a PCR approach, in preparation for a PCR overlap extension approach. To this end primers were designed to yield a 5'-PCR canine TLR9 product with ~1600 bp (Canis-TLR9-for and CanTLR9olr, see below), and a 3'-PCR canine TLR9 product with ~1700 bp (CanTLR9olf and Canis-TLR9-rev).

Primer Sequences:

```
Canis-TLR9-for
                                           [SEQ ID NO: 20]
GAAGCTTACCATGGGCCCCTGCCGTGGCGCCCTGCA Canis-TLR9-rev
                                           [SEQ ID NO: 21]
GTCTAGATGATCAGGCTGTCGTGGGGCCCCGGCAGA CanTLR9olf
                                           [SEQ ID NO: 22]
TCACCTTGGACCTGTCTCGGAACAACC CanTLR9olr
                                           [SEQ ID NO: 23]
ACAGGTCCAGCTTGTTATGGGACAGG
```

PCR reactions (Expand High Fidelity PCR kit, Roche) were performed, the corresponding PCR products were agarose gel-purified, cloned into pCR2.1-Topo (Invitrogen), and three clones each were sequenced to identify PCR error-free versions, by comparing their translation products to each other, and to the database sequences NM_00102998 and AY859723. These (pCR2.1-Topo-canTLR9-Nterm and pCR2.1-Topo-canTLR9-Cterm) were then used to join the 5' and the 3' region of the canine TLR9 gene by an overlap extension approach. To this end inserts of pCR2.1-Topo-canTLR9-Nterm (primer: Canis-TLR9-for and CanTLR9olr) and pCR2.1-Topo-canTLR9-Cterm (primer: CanTLR9olf and Canis-TLR9-rev) were PCR amplified with only 9 cycles and a proof-reading polymerase (Phusion® Hot Start High-Fidelity DNA Polymerase, Thermo Scientific). The resulting PCR product were agarose gel purified, and then used combined in an overlap extension-PCR combination using the primer Canis-TLR9-for and Canis-TLR9-rev. The resulting ~3100 bp PCR product was agarose gel purified and cloned into pCRBlunt-II (Invitrogen). Four independent clones were sequenced and one clone was chosen for further processing (pCR2.1-Topo-canineTLR9).

From this construct the insert was excised by HindIII/XbaI digestion, agarose gel-purified and subcloned into the HindIII/XbaI-cut mammalian expression vectors pcDNA3.1 (neo) and pcDNA3.1(hyg) (both Invitrogen), yielding pcDNA3.1 (neo)-canineTLR9 and pcDNA3.1(hyg)-canineTLR9, respectively. The corresponding inserts were resequenced (see below).

pcDNA3.1 Insert Sequence Canine TLR9 (Primer Sequences Underlined, Start/Stop Codons Highlighted Bold) [SEQ ID NO: 209]

```
AAGCTTACC ATGGGCCCCTGCCGTGGCGCCCTGCACCCCTGTCTCTCC

TGGTGCAGGCTGCCGCGCTAGCCCTGGCCCTGGCCCAGGGCACCCTGCCT

GCCTTCCTGCCCTGTGAGCTCCAGCCCCATGGCCTGGTGAACTGCAACTG

GCTGTTCCTCAAGTCCGTGCCCCGCTTCTCGGCAGCTGCACCCCGCGGTA

ACGTCACCAGCCTTTCCTTGTACTCCAACCGCATCCACCACCTCCATGAC

TATGACTTTGTCCACTTCGTCCACCTGCGGCGTCTCAATCTCAAGTGGAA

CTGCCCGCCCGCCAGCCTCAGCCCCATGCACTTTCCCTGTCACATGACCA

TTGAGCCCAACACCTTCCTGGCTGTGCCCACCCTAGAGGACCTGAATCTG

AGCTATAACAGCATCACGACTGTGCCCGCCCTGCCCAGTTCGCTTGTGTC

CCTGTCCCTGAGCCGCACCAACATCCTGGTGCTGGACCCTGCCACCCTGG

CAGGCCTTTATGCCCTGCGCTTCCTGTTCCTGGATGGCAACTGCTACTAC

AAGAACCCCTGCCAGCAGGCCCTGCAGGTGGCCCCAGGTGCCCTCCTGGG

CCTGGGCAACCTCACACACCTGTCACTCAAGTACAACAACCTCACCGTGG

TGCCGCGGGGCCTGCCCCCCAGCCTGGAGTACCTGCTCTTGTCCTACAAC

CACATCATCACCCTGGCACCTGAGGACCTGGCCAATCTGACTGCCCTGCG

TGTCCTCGATGTGGGTGGGAACTGTCGCCGCTGTGACCATGCCCGTAACC

CCTGCAGGGAGTGCCCCAAGGGCTTCCCCCAGCTGCACCCCAACACCTTC

GGCCACCTGAGCCACCTCGAAGGCCTGGTGTTGAGGGACAGCTCTCTCTA

CAGCCTGGACCCCAGGTGGTTCCATGGCCTGGGCAACCTCATGGTGCTGG

ACCTGAGTGAGAACTTCCTGTATGACTGCATCACCAAAACCAAAGCCTTC

TACGGCCTGGCCCGGCTGCGCAGACTCAACCTGTCCTTCAATTATCATAA

GAAGGTGTCCTTTGCCCACCTGCATCTGGCATCCTCCTTCGGGAGCCTAC

TGTCCCTGCAGGAGCTGGACATACATGGCATCTTCTTCCGCTCGCTCAGC

GAGACCACGCTCCAGTCGCTGGCCCACCTGCCCATGCTCCAGCGTCTGCA

TCTGCAGTTGAACTTTATCAGCCAGGCCCAGCTCAGCATCTTCGGCGCCT

TCCCTGGCCTGCGGTACGTGGACTTGTCAGACAACCGCATCAGTGGAGCT

GCAGAGCCCGCGGCTGCCACAGGGGAGGTAGAGGCGGACTGTGGGGAGAG

AGTCTGGCCACAGTCCCGGGACCTTGCTCTGGGCACACTGGGCACCCCCG

GCTCAGAGGCCTTCATGCCGAGCTGCAGGACCCTCAACTTCACCTTGGAC

CTGTCTCGGAACAACCTAGTGACTGTTCAGCCGGAGATGTTTGTCCGGCT

GGCGCGCCTCCAGTGCCTGGGCCTGAGCCACAACAGCATCTCGCAGGCGG

TCAATGGCTCGCAGTTCGTGCCTCTGAGCAACCTGCGGGTGCTGGACCTG

TCCCATAACAAGCTGGACCTGTACCACGGGCGCTCGTTCACGGAGCTGCC

GCGGCTGGAGGCCTTGGACCTCAGCTACAACAGCCAGCCCTTCAGCATGC

GGGGCGTGGGCCACAATCTCAGCTTTGTGGCACAGCTGCCAGCCCTGCGC

TACCTCAGCCTGGCGCACAATGGCATCCACAGCCGCGTGTCCCAGCAGCT

CCGCAGCGCCTCGCTCCGGGCCCTGGACTTCAGTGGCAATACCCTGAGCC

AGATGTGGGCCGAGGGAGACCTCTATCTCCGCTTCTTCCAAGGCCTGAGA

AGCCTGGTTCAGCTGGACCTGTCCCAGAATCGCCTGCATACCCTCCTGCC

ACGCAACCTGGACAACCTCCCCAAGAGCCTGCGGCTCCTGCGGCTCCGTG

ACAATTACCTGGCTTTCTTCAACTGGAGCAGCCTGGCCCTCCTACCCAAG

CTGGAAGCCCTGGACCTGGCGGGAAACCAGCTGAAGGCCCTGAGCAATGG

CAGCTTGCCCAACGGCACCCAGCTCCAGAGGCTGGACCTCAGCGGCAACA

GCATCGGCTTCGTGGTCCCCGGCTTTTTTGCCCTGGCCGTGAGGCTTCGA
```

-continued

```
GAGCTCAACCTCAGCGCCAACGCCCTCAAGACGGTGGAGCCCTCCTGGTT

TGGTTCCCTGGCGGGTGCCCTGAAAGTCCTAGACGTGACCGCCAACCCCT

TGCATTGCGCTTGCGGCGCAACCTTCGTGGACTTCTTGCTGGAGGTGCAG

GCTGCGGTGCCCGGCCTGCCTAGCCGTGTCAAGTGCGGCAGCCCGGGCCA

GCTCCAGGGCCGCAGCATCTTCGCACAGGACCTGCGCCTCTGCCTGGACG

AAGCGCTCTCCTGGGTCTGTTTCAGCCTCTCGCTGCTGGCTGTGGCCCTG

AGCCTGGCTGTGCCCATGCTGCACCAGCTCTGTGGCTGGGACCTCTGGTA

CTGCTTCCACCTGTGCCTGGCCTGGCTGCCCCGGCGGGGCGGCGGCGGG

GTGTGGATGCCCTGGCCTACGACGCCTTCGTGGTCTTCGACAAGGCGCAG

AGCTCGGTGGCGGACTGGGTGTACAATGAGCTGCGGGTACAGCTAGAGGA

GCGCCGTGGGCGCCGGGCGCTACGCCTGTGTCTGGAGGAACGTGACTGGG

TACCCGGCAAAACCCTCTTCGAGAACCTCTGGGCCTCAGTTTACAGCAGC

CGCAAGACGCTGTTTGTGCTGGCCCGCACGGACAGAGTCAGCGGCCTCCT

GCGTGCCAGCTTCCTGCTGGCCCAACAGCGCCTGCTGGAGGACCGCAAGG

ACGTCGTGGTGCTGGTGATCCTGTGCCCCGACGCCCACCGCTCCCGCTAT

GTGCGGCTGCGCCAGCGCCTCTGCCGCCAGAGTGTCCTCCTCTGGCCCCA

CCAGCCCAGTGGCCAGCGCAGCTTCTGGGCCCAGCTGGGCACGGCCCTGA

CCAGGGACAACCGCCACTTCTACAACCAGAACTTCTGCCGGGGCCCCACG

ACAGCC TGATCATCTA
```

[SEQ ID NO: 6]
```
MGPCRGALHPLSLLVQAAALALALAQGTLPAFLPCELQPHGLVNCNWLFL

KSVPRFSAAAPRGNVTSLSLYSNRIHHLHDYDFVHFVHLRRLNLKWNCPP

ASLSPMHFPCHMTIEPNTFLAVPTLEDLNLSYNSITTVPALPSSLVSLSL

SRTNILVLDPATLAGLYALRFLFLDGNCYYKNPCQQALQVAPGALLGLGN

LTHLSLKYNNLTVVPRGLPPSLEYLLLSYNHIITLAPEDLANLTALRVLD

VGGNCRRCDHARNPCRECPKGFPQLHPNTFGHLSHLEGLVLRDSSLYSLD

PRWFHGLGNLMVLDLSENFLYDCITKTKAFYGLARLRRLNLSFNYHKKVS

FAHLHLASSFGSLLSLQELDIHGIFFRSLSETTLQSLAHLPMLQRLHLQL

NFISQAQLSIFGAFPGLRYVDLSDNRISGAAEPAAATGEVEADCGERVWP

QSRDLALGTLGTPGSEAFMPSCRTLNFTLDLSRNNLVTVQPEMFVRLARL

QCLGLSHNSISQAVNGSQFVPLSNLRVLDLSHNKLDLYHGRSFTELPRLE

ALDLSYNSQPFSMRGVGHNLSFVAQLPALRYLSLAHNGIHSRVSQQLRSA

SLRALDFSGNTLSQMWAEGDLYLRFFQGLRSLVQLDLSQNRLHTLLPRNL

DNLPKSLRLLRLRDNYLAFFNWSSLALLPKLEALDLAGNQLKALSNGSLP

NGTQLQRLDLSGNSIGFVVPGFFALAVRLRELNLSANALKTVEPSWFGSL

AGALKVLDVTANPLHCACGATFVDFLLEVQAAVPGLPSRVKCGSPGQLQG

RSIFAQDLRLCLDEALSWVCFSLSLLAVALSLAVPMLHQLCGWDLWYCFH

LCLAWLPRRGRRRGVDALAYDAFVVFDKAQSSVADWVYNELRVQLEERRG

RRALRLCLEERDWVPGKTLFENLWASVYSSRKTLFVLARTDRVSGLLRAS

FLLAQQRLLEDRKDVVVLVILCPDAHRSRYVRLRQRLCRQSVLLWPHQPS

GQRSFWAQLGTALTRDNRHFYNQNFCRGPTTA.
```

The translated sequence was aligned with the two canine TLR9 full length cDNA sequences deposited in Genbank (September 2011, P1-010709-prot.pro, TLR-9-NM_001002998.pro, TLR-9-AY859723.pro). Alignment (ClustalW; DNAStar) of the three canine TLR9 polypeptide sequences showed polymorphisms at 8 positions. Except for one position (T459 in our sequence, P459 in the two database sequences) all polymorphic positions in our TLR9 clone (P1-010709-prot) conformed to either NM_00102998 or AY859723. T459 has been confirmed in four independent PCR products from dog lymph node and spleen cDNA suggesting that this corresponds to the genotype of the donor dog.

Therefore, it is concluded that a correct version of canine TLR9 has been cloned.

Example 4

Madine-Darby Canine Kidney Cells as NF-κB Activation Reporter Cells

Madine-Darby canine kidney (MDCK) cells were obtained from ATCC that were maintained in MEM, 1× non-essential amino acids, 8% (v/v) iFCS. Testing of spent growth medium for presence of secreted alkaline phosphatase activity was negative, a prerequisite for the use of this cell line in reporter gene assays.

As a first step, it was planned to transfect the MDCK cells with pNifTy2-SEAP (Invivogen), a plasmid containing a secreted alkaline phosphatase (SEAP) reporter gene under the control of NF-κB binding sites, and a zeocin resistance gene as selection marker. The inventor's studies showed, however, that MDCK cells are largely resistant to zeocin (up to the mg/ml range) precluding the use of pNifTy2-SEAP. Therefore, it was decided to generate 'pNifTy-hyg-SEAP' by replacing the CMV promoter region and parts of the polylinker (Nru I/Xba I digest of the plasmid and agarose gel isolation of the large fragment) in pcDNA3.1(hyg) by the Swa I/NheI fragment containing the NF-κB binding sites and the SEAP gene of pNifTy2-SEAP. Thereby, presence of the reporter gene cassette could now be selected for by addition of hygromycin to the medium, a cytostatic that is effective on MDCK cell.

MDCK cells were transfected with pNifTy-hyg-SEAP, selection pressure was applied (300 μg/ml hygromycin) and a resistant line was selected by repeated subculture in selection medium. The selected cell line was tested for SEAP induction by human tumor necrosis factor (huTNF-α, →positive control for proper functioning of the NF-κB pathway and reporter gene activation) as well as by a selection of pathogen-associated molecular patterns (PAMPs, such as E. coli lipopolysaccharide (LPS, TLR4), poly-I/polyC (double-stranded RNA, TLR3), muramyl dipeptide (MDP, NOD2), PAM$_3$CysSK$_4$ (a synthetic lipopeptide, TLR1/2), and R-848 (a low molecular weight agonist of TLR7). The results are shown in FIGS. 1 and 2 (FIG. 2 is a y-axis expansion of FIG. 1).

huTNF-α potently induces SEAP production in a polyclonal MDCK-pNifTy-hyg-SEAP cell line, a second prerequisite for the use of this cell line in reporter gene assays. PAMPs addressing 5 different pattern recognition receptors feeding into the NF-κB pathway showed low or no SEAP induction, which suggests that our MDCK-pNifTy-hyg-SEAP cell line expresses none or very few copies of the corresponding receptors, a third prerequisite for the use of this cell line in reporter gene assays. The highest background (albeit still very low) was seen with dsRNA, followed by MDP, while LPS, PAM₃CysSK₄ and R-848 showed virtually none.

These results prompted the inventors to perform single cell cloning of the MDCK-pNifTy-hyg-SEAP cell line, to stabilize the properties seen in the polyclonal line and to identify a superior clone. 46 clones were selected by limiting dilution in 96 well plates, and following expansion, they were stimulated with huTNF-α to identify the clones with the highest NF-κB-induced SEAP production capacity (see FIG. 3).

Example 5

Generation of Canine, Porcine and Bovine TLR9-21 Fusion Constructs and Subcloning into Expression Vector pIRES-Puro.

A fusion construct encoding the extracellular domain of bovine TLR9 and intracellular domain of chicken TLR21 was created using a "PCR-sewing" protocol.

"PCR-sewing" entails three steps (see FIG. 4): first, complementary sequences are added by PCR to DNA fragments that should be fused into one construct. Secondly, the two fragments having complementary sequences are combined in a PCR-reaction without addition of primers. The complementary sequences enable the fragments to anneal and prime the elongation reaction by DNA polymerase. In the third PCR step, primers annealing to the 5' and 3' end of the chimeric molecule are added to amplify the fusion molecule.

The sequence encoding the extracellular domain of bovine TLR9 was amplified from the pcDNA3.1(neo)-bovine TLR9 construct (section 1) by PCR, the sequence encoding the transmembrane and intracellular domain of chicken TLR21 was amplified from pcDNA3.1(neo)-chicken TLR21 (sequences below). Complementary sequences were added to the 3' end of the extracellular (TLR9) fragment and the 5' end of the TLR21 fragment using primers with a 5' overhang (sequences below) by PCR. Expand High Fidelity PCR kit (Roche) was used for all PCRs.

pcDNA3.1 (Neo)-Chicken TLR21 Insert Sequence, Start/Stop Codons Highlighted Bold. [SEQ ID NO: 210]

AAGCTTACCATGATGGAGACAGCGGAGAAGGCATGGCCCAGCACCAGGAT

GTGCCCCTCCCACTGCTGTCCACTCTGGCTGCTGCTGCTGGTGACAGTGA

CACTGATGCCGATGGTGCACCCGTATGGCTTTCGCAACTGCATTGAGGAT

GTCAAGGCACCTTTGTACTTCCGCTGCATCCAGCGCTTCCTGCAGTCGCC

GGCCCTGGCAGTGTCTGACCTGCCACCACATGCCATCGCGCTCAATCTGT

CATACAACAAAATGCGCTGCCTGCAGCCCTCTGCCTTTGCCCACCTGACA

CAGCTGCATACCCTGGACCTGACCTACAACCTCCTGGAGACCCTCTCCCC

TGGTGCCTTCAATGGGCTGGGTGTGCTGGTGGTGCTGGACCTGTCTCACA

ACAAGCTGACCACACTTGCTGAAGGGGTGTTCAACAGCTTGGGCAACCTG

TCCTCGCTGCAGGTACAACATAACCCCCTCAGCACGGTGTCACCAAGTGC

TCTGCTACCCCTGGTCAACCTGCGCCGCCTGTCTCTACGGGGCGGGCGGC

TGAATGGGTTGGGGGCAGTGGCAGTGGCAGTGCAGGGCTTGGCACAGCTG

GAGCTGTTGGACCTATGTGAAAACAACCTGACAACGCTGGGGCCAGGCCC

ACCGCTACCCGCCTCGCTGCTCACCCTGCAGCTGTGCAACAACTCGCTGA

GGGAGTTAGCGGGGGGCAGCCCGGAGATGCTATGGCACGTGAAGATACTC

GACCTCTCCTACAACAGTATCTCACAGGCGGAGGTCTTCACCCAGCTCCA

CCTGCGCAACATCAGCCTGCTCCACCTGATCGGCAACCCCTTGGATGTCT

TCCACCTGTTGGACATCTCTGACATCCAACCTCGCAGCCTGGATTTCTCT

GGGTTGGTGCTGGGGGCTCAGGGGCTGGATAAGGTGTGCCTGAGGCTGCA

GGGTCCCCAGGCCTTGCGGCGGCTGCAGCTACAACGCAACGGGCTGAAGG

TGCTGCATTGTAATGCACTGCAGTTGTGTCCTGTGCTGAGAGAGCTGGAC

CTGTCCTGGAACCGGCTACAGCACGTGGGCTGTGCCGGCCGGCTGCTGGG

CAAGAAGCAGCGGGAGAAGCTGGAAGTGCTGACAGTGGAACACAACCTGC

TGAAGAAACTGCCGTCTTGCCTGGGGGCCCAGGTGCTGCCTCGGCTGTAC

AACATTTCCTTCCGCTTTAACCGCATCCTGACTGTTGGGCCCCAAGCCTT

TGCCTACGCCCCGCCCTGCAGGTGTTGTGGCTCAATATTAACAGCCTGG

TGTGGCTGGACAGGCAGGCACTGTGGAGGCTGCACAACCTGACAGAGCTG

CGCCTGGACAACAACCTGCTGACCGACCTCTATCACAACTCCTTCATTGA

CCTCCACAGACTGCGCACCCTCAACCTGCGCAACAACCGTGTCTCCGTCC

TCTTCTCTGGTGTCTTCCAGGGGCTGGCTGAGCTGCAGACGCTGGATTTA

GGGGGCAACAACTTGCGCCACCTGACTGCACAGTCACTGCAGGGGCTGCC

CAAACTGCGCAGGCTGTACCTGGACCGCAACAGATTGCTGGAGGTGAGCA

GCACTGTGTTCGCCCCAGTGCAGGCTACCCTGGGGGTGCTGGACCTGCGG

GCCAACAACCTGCAGTACATCTCACAGTGGCTGCGCAAGCCGCCACCCTT

CCGCAACCTGAGCAGCCTGTACGACCTGAAGCTGCAGGCGCAGCAGCCCT

ATGGACTGAAGATGCTGCCTCACTACTTCTTCCAGGGCTTGGTGAGGCTG

CAGCAGCTGTCGCTGTCACAGAACATGCTGCGGTCCATCCCACCGGATGT

CTTCGAGGACTTGGGCCAGCTGCGCTCCCTGGCATTGGCTGACAGCAGCA

ATGGGCTGCATGACCTGCCTGACGGCATCTTCAGAAACCTGGGCAACCTG

CGGTTCCTGGACCTGGAGAATGCAGGGCTGCACTCGCTCACTCTGGAAG

TCTTCGGCAATCTCAGCCGGCTGCAGGTGCTGCACTTGGCCAGAAACGA

GCTGAAGACCTTCAATGACAGCGTTGCCAGCCGGCTGTCCTCCTTGCGC

TACCTGGACCTGCGCAAGTGTCCGCTCAGCTGCACCTGTGACAACATGT

GGCTGCAGGGCTGGCTGAACAACAGCCGTGTGCAGGTTGTCTACCCCTA

CAACTACACCTGTGGCTCACAGCACAATGCCTACATCCACAGCTTTGAC

ACACACGTCTGCTTCCTGGACCTGGGGCTCTATCTCTTTGCTGGGACTG

CACCGGCAGTGCTGCTGCTGCTGGTGGTGCCGGTGGTGTACCACCGCGCC

TACTGGAGGCTGAAGTACCACTGGTACCTTCTGCGGTGCTGGGTCAACCA

GCGGTGGCGGCGGGAGGAAAAGTGCTACCTCTATGACAGCTTTGTGTCCT

ACAATTCAGCTGATGAAAGTTGGGTGTTGCAGAAGCTGGTGCCTGAGCTG

GAGCACGGTGCCTTCCGCCTCTGCTTGCACCACCGCGACTTCCAGCCGGG

CCGCAGCATCATTGACAACATTGTGGATGCTGTCTACAACAGCCGGAAGA

CGGTGTGCGTGGTGAGCCGCAGCTACCTGCGCAGCGAGTGGTGCTCTCTA

GAGGTGCAGTTGGCCAGCTACCGGCTGTTGGATGAGCGGCGTGACATCCT

```
GGTACTGGTGCTGCTGGAGGACGTGGGTGATGCTGAGCTGTCTGCCTACC

ACCGCATGCGGCGGGTGCTGCTGCGGCGCACCTACCTGCGCTGGCCTCTT

GACCCCGCAGCTCAGCCGCTCTTTTGGGCACGGCTGAAGAGGGCACTGAG

GTGGGGAGAGGGAGGAGAGGAGGAGGAAGAAGAAGGTTTGGGTGGAGGGA

CGGGAAGGCCCAGGGAAGGAGACAAACAGATGTAGCGGCCGC
```

Primers for Bovine TLR9 (Extracellular Domain):

cowT9-chT21 5'Eco:
[SEQ ID NO: 24]
GCGGATATCACCATGGGCCCCTACTGTGC cowT9-chT21fusRV:
[SEQ ID NO: 25]
ATAGAGCCCCAGGTCCAGGAAGCAGAGGCGCAGGTCCTGTGT Primers for Chicken TLR21 (Transmembrane and Intracellular Domain):

cowT9-chT21fusFW:
[SEQ ID NO: 26]
ACACAGGACCTGCGCCTCTGCTTCCTGGACCTGGGGCTCTAT cowT9-chT21 3' Eco:
[SEQ ID NO: 27]
GCGGAATTCCTACATCTGTTTGTCTCCTT.

The fusion product was cloned into pCRII-TOPO (Invitrogen) and one (1) clone was sequenced to examine if the sequence was PCR error-free. The sequence contained one (1) coding mutation which was corrected using the Quik Change II XL site directed mutagenesis kit from Stratagene and primers:
Mutagenesis Primers:

18-CowT9-chT21:
[SEQ ID NO: 28]
CCAAGACCACCATCTTCAACGACCTGACCCAGCTGCGCAGACTCAACC

19-CowT9-chT21:
[SEQ ID NO: 29]
GGTTGAGTCTGCGCAGCTGGGTCAGGTCGTTGAAGATGGTGGTCTTGG

After the mutagenesis procedure, multiple (5) clones were sequenced to examine if site-directed mutagenesis had been successful and did not introduce new mutations. A correct clone was used to reclone the fusion construct into pIRESpuro3 (Clontech) using the primer-introduced EcoRI and EcoRV sites. The fusion construct in the resulting vector (pIRESpuro-bovTLR9-21) was resequenced (see below).
pIRESpuro-bovTLR9-21 Insert Sequence, (Partial) Primer Sequence Underlined, TLR21 (Coding) Sequences in Italics, Start/Stop Codons Highlighted Bold. [SEQ ID NO: 211]

```
GATATCACCATGGGCCCCTACTGTGCCCCGCACCCCCTTTCTCTCCTGGTGCAGGCGGCGGCACTGGCAGC

GGCCCTGGCCGAGGGCACCCTGCCTGCCTTCCTGCCCTGTGAGCTCCAGCCCCATGGTCAGGTGGACTGCA

ACTGGCTGTTCCTGAAGTCTGTGCCGCACTTTTCGGCTGGAGCCCCCGGGCCAATGTCACCAGCCTCTCC

TTAATCTCCAACCGCATCCACCACTTGCATGACTCTGACTTCGTCCACCTGTCCAACCTGCGGGTCCTCAA

CCTCAAGTGGAACTGCCCGCCGGCCGGCCTCAGCCCCATGCACTTCCCCTGCCGTATGACCATCGAGCCCA

ACACCTTCCTGGCTGTGCCCACCCTGGAGGAGCTGAACCTGAGCTACAACGGCATCACGACCGTGCCTGCC

CTGCCCAGTTCCCTCGTGTCCCTGTCGCTGAGCCACACCAGCATCCTGGTGCTAGGCCCCACCCACTTCAC

CGGCCTGCACGCCCTGCGCTTTCTGTACATGGACGGCAACTGCTACTACATGAACCCCTGCCCGCGGGCCC

TGGAGGTGGCCCCAGGCGCCCTCCTCGGCCTGGGCAACCTCACGCACCTGTCGCTCAAGTACAACAACCTC

ACGGAGGTGCCCCGCCGCCTGCCCCCCAGCCTGGACACCCTGCTGCTGTCCTACAACCACATTGTCACCCT

GGCACCCGAGGACCTGGCCAACCTGACTGCCCTGCGCGTGCTTGACGTGGGTGGGAACTGCCGCCGCTGCG

ACCACGCCCGCAACCCCTGCAGGGAGTGCCCAAAGAACTTCCCCAAGCTGCACCCTGACACCTTCAGTCAC

CTGAGCCGCCTCGAAGGCCTGGTGTTGAAGGACAGTTCTCTCTACAAACTAGAGAAAGATTGGTTCCGCGG

CCTGGGCAGGCTCCAAGTGCTCGACCTGAGTGAGAACTTCCTCTATGACTACATCACCAAGACCACCATCT

TCAACGACCTGACCCAGCTGCGCAGACTCAACCTGTCCTTCAATTACCACAAGAAGGTGTCCTTCGCCCAC

CTGCACCTAGCGTCCTCCTTTGGGAGTCTGGTGTCCCTGGAGAAGCTGGACATGCACGGCATCTTCTTCCG

CTCCCTCACCAACATCACGCTCCAGTCGCTGACCCGGCTGCCCAAGCTCCAGAGTCTGCATCTGCAGCTGA

ACTTCATCAACCAGGCCCAGCTCAGCATCTTTGGGGCCTTCCCGAGCCTGCTCTTCGTGGACCTGTCGGAC

AACCGCATCAGCGGAGCCGCGACGCCAGCGGCCGCCCTGGGGGAGGTGGACAGCAGGGTGGAAGTCTGGCG

ATTGCCCAGGGGCCTCGCTCCAGGCCCGCTGGACGCCGTCAGCTCAAAGGACTTCATGCCAAGCTGCAACC

TCAACTTCACCTTGGACCTGTCACGGAACAACCTGGTGACAATCCAGCAAGAGATGTTTACCCGCCTCTCC

CGCCTCCAGTGCCTGCGCCTGAGCCACAACAGCATCTCGCAGGCGGTTAATGGCTCCCAGTTCGTGCCGCT
```

-continued

```
GACCAGCCTGCGAGTGCTCGACCTGTCCCACAACAAGCTGGACCTGTACCATGGGCGCTCATTCACGGAGC

TGCCGCAGCTGGAGGCACTGGACCTCAGCTACAACAGCCAGCCCTTCAGCATGCAGGGCGTGGGCCACAAC

CTCAGCTTCGTGGCCCAGCTGCCCTCCCTGCGCTACCTCAGCCTTGCGCACAATGGCATCCACAGCCGCGT

GTCACAGAAGCTCAGCAGCGCCTCGTTGCGCGCCCTGGACTTCAGCGGCAACTCCCTGAGCCAGATGTGGG

CCGAGGGAGACCTCTATCTCTGCTTTTTCAAAGGCTTGAGGAACCTGGTCCAGCTGGACCTGTCCGAGAAC

CATCTGCACACCCTCCTGCCTCGTCACCTGGACAACCTGCCCAAGAGCCTGCGGCAGCTGCGTCTCCGGGA

CAATAACCTGGCCTTCTTCAACTGGAGCAGCCTGACCGTCCTGCCCCGGCTGGAAGCCCTGGATCTGGCAG

GAAACCAGCTGAAGGCCCTGAGCAACGGCAGCCTGCCGCCTGGCATCCGGCTCCAGAAGCTGGACGTGAGC

AGCAACAGCATCGGCTTCGTGATCCCCGGCTTCTTCGTCCGCGCGACTCGGCTGATAGAGCTTAACCTCAG

CGCCAATGCCCTGAAGACAGTGGATCCCTCCTGGTTCGGTTCCTTAGCAGGGACCCTGAAAATCCTAGACG

TGAGCGCCAACCCGCTCCACTGCGCCTGCGGGCGGCCTTTGTGGACTTCCTGCTGGAGAGACAGGAGGCC

GTGCCCGGGCTGTCCAGGCGCGTCACATGTGGCAGTCCGGGCCAGCTCCAGGGCCGCAGCATCTTCACACA

GGACCTGCGCCTCTGCTTCCTGGACCTGGGGCTCTATCTCTTTGCTGGGACTGCACCGGCAGTGCTGCTGC

TGCTGGTGGTGCCGGTGGTGTACCACCGCGCCTACTGGAGGCTGAAGTACCACTGGTACCTTCTGCGGTGC

TGGGTCAACCAGCGGTGGCGGCGGGAGGAAAAGTGCTACCTCTATGACAGCTTTGTGTCCTACAATTCAGC

TGATGAAAGTTGGGTGTTGCAGAAGCTGGTGCCTGAGCTGGAGCACGGTGCCTTCCGCCTCTGCTTGCACC

ACCGCGACTTCCAGCCGGGCCGCAGCATCATTGACAACATTGTGGATGCTGTCTACAACAGCCGGAAGACG

GTGTGCGTGGTGAGCCGCAGCTACCTGCGCAGCGAGTGGTGCTCTCTAGAGGTGCAGTTGGCCAGCTACCG

GCTGTTGGATGAGCGGCGTGACATCCTGGTACTGGTGCTGCTGGAGGACGTGGGTGATGCTGAGCTGTCTG

CCTACCACCGCATGCGGCGGGTGCTGCTGCGGCGCACCTACCTGCGCTGGCCTCTTGACCCCGCAGCTCAG

CCGCTCTTTTGGGCACGGCTGAAGAGGGCACTGAGGTGGGGAGAGGGAGGAGAGGAGGAGGAAGAAGAAGG

TTTGGGTGGAGGGACGGGAAGGCCCAGGGAAGGAGACAAACAGATGTAGGAATTC
```

[SEQ ID NO: 9]

MGPYCAPHPLSLLVQAAALAAALAEGTLPAFLPCELQPHGQVDCNWLFLKSVPHFSAGAPRANVTSLSLIS

NRIHHLHDSDFVHLSNLRVLNLKWNCPPAGLSPMHFPCRMTIEPNTFLAVPTLEELNLSYNGITTVPALPS

SLVSLSLSHTSILVLGPTHFTGLHALRFLYMDGNCYYMNPCPRALEVAPGALLGLGNLTHLSLKYNNLTEV

PRRLPPSLDTLLLSYNHIVTLAPEDLANLTALRVLDVGGNCRRCDHARNPCRECPKNFPKLHPDTFSHLSR

LEGLVLKDSSLYKLEKDWFRGLGRLQVLDLSENFLYDYITKTTIFNDLTQLRRLNLSFNYHKKVSFAHLHL

ASSFGSLVSLEKLDMHGIFFRSLTNITLQSLTRLPKLQSLHLQLNFINQAQLSIFGAFPSLLFVDLSDNRI

SGAATPAAALGEVDSRVEVWRLPRGLAPGPLDAVSSKDFMPSCNLNFTLDLSRNNLVTIQQEMFTRLSRLQ

CLRLSHNSISQAVNGSQFVPLTSLRVLDLSHNKLDLYHGRSFTELPQLEALDLSYNSQPFSMQGVGHNLSF

VAQLPSLRYLSLAHNGIHSRVSQKLSSASLRALDFSGNSLSQMWAEGDLYLCFFKGLRNLVQLDLSENHLH

TLLPRHLDNLPKSLRQLRLRDNNLAFFNWSSLTVLPRLEALDLAGNQLKALSNGSLPPGIRLQKLDVSSNS

IGFVIPGFFVRATRLIELNLSANALKTVDPSWFGSLAGTLKILDVSANPLHCACGAAFVDFLLERQEAVPG

LSRRVTCGSPGQLQGRSIFTQDLRLC*FLDLGLYLFAGTAPAVLLLLVVPVVYHRAYWRLKYHWYLLRCWVN*

*QRWRREEKCYLYDSFVSYNSADESWVLQKLVPELEHGAFRLCLHHRDFQPGRSIIDNIVDAVYNSRKTVCV*

*VSRSYLRSEWCSLEVQLASYRLLDERRDILVLVLLEDVGDAELSAYHRMRRVLLRRTYLRWPLDPAAQPLF*

*WARLKRALRWGEGGEEEEEEGLGGGTGRPREGDKQM*

Cloning of a Fusion Construct of the Extracellular Domain of Porcine TLR9 and the Transmembrane and Intracellular Domain of Chicken TLR21.

A fusion construct encoding the extracellular domain of porcine TLR9 and intracellular domain of chicken TLR21 was created using the "PCR-sewing" protocol as described above.

The sequence encoding the extracellular domain of porcine TLR9 from the pcDNA3.1(neo)-porcine TLR9 construct (described in Example 2) was amplified by PCR as well as the sequence encoding the transmembrane and intracellular domain of chicken TLR21 from pcDNA3.1 (neo)-chicken TLR21 (sequences above). Complementary sequences were added to the 3' end of the extracellular (TLR9) fragment and the 5' end of the TLR21 fragment using primers with a 5' overhang (sequences below) by PCR. Expand High Fidelity PCR kit (Roche) was used for all PCRs.

Primers for Porcine TLR9 (Extracellular Domain):

```
piT9-chT21 5' E:
                                       [SEQ ID NO: 30]
GCGGAATTCCACCATGGGCCCCCGCTGCAC
```

```
pigT9-chT21fusRV:
                                       [SEQ ID NO: 31]
ATAGAGCCCCAGGTCCAGGAAGCAGAGGCGCAGGTCTTGCGC
```

Primers for Chicken TLR21 (Transmembrane and Intracellular Domain):

```
pigT9-chT21fusFW:
                                       [SEQ ID NO: 32]
GCGCAAGACCTGCGCCTCTGCTTCCTGGACCTGGGGCTCTAT
```

```
pig/dogT9-chT21-:
                                       [SEQ ID NO: 33]
GCGGCGGCCGCCTACATCTGTTTGTCTCCTT
```

The fusion product was cloned into pCRII-TOPO (Invitrogen) and one (1) clone was sequenced to examine if the sequence was PCR error-free. This clone was correct and was used to reclone the fusion construct into pIRESpuro3 (Clontech) using primer-introduced EcoRI and NotI sites. The 5' and 3' ligation site of the fusion construct in pIRESpuro3 were sequenced to check the correct insertion of the fragment in the plasmid. The correct, resulting vector is pIRESpuro-porTLR9-21 (sequences below).

pIRESpuro-porTLR9-21 Insert Sequence, (Partial) Primer Sequence Underlined, TLR21 (Coding) Sequences in Italics, Start/Stop Codons Highlighted Bold. [SEQ ID NO: 212]

```
GAATTCCACCATGGGCCCCCGCTGCACCCTGCACCCCCTTTCTCTCCTGGTGCAGGTGACAGCGCTGGCTG
CGGCTCTGGCCCAGGGCAGGCTGCCTGCCTTCCTGCCCTGTGAGCTCCAGCCCCACGGCCTGGTGAACTGC
AACTGGCTCTTCCTGAAGTCCGTGCCCCACTTCTCGGCGGCAGCGCCCGGGCCAACGTCACCAGCCTCTC
CTTACTCTCCAACCGCATCCACCACCTGCACGACTCTGACTTCGTCCACCTGTCCAGCCTACGAACTCTCA
ACCTCAAGTGGAACTGCCCGCCGGCTGGCCTCAGCCCCATGCACTTCCCCTGCCACATGACCATCGAGCCC
AACACCTTCCTGGCCGTGCCCACCCTGGAGGAGCTGAACCTGAGCTACAACAGCATCACGACCGTGCCTGC
CCTGCCCGACTCCCTCGTGTCCCTGTCGCTGAGCCGCACCAACATCCTGGTGCTAGACCCCACCCACCCTCA
CTGGCCTACATGCCCTGCGCTACCTGTACATGGATGGCAACTGCTACTACAAGAACCCCTGCCAGGGGCG
CTGGAGGTGGTGCCGGGTGCCCTCCTCGGCCTGGGCAACCTCACACATCTCTCACTCAAGTACAACAATCT
CACGGAGGTGCCCCGCAGCCTGCCCCCCAGCCTGGAGACCCTGCTGTTGTCCTACAACCACATTGTCACCC
TGACGCCTGAGGACCTGGCCAATCTGACTGCCCTGCGCGTGCTTGATGTGGGGGGGAACTGCCGCCGCTGT
GACCATGCCCGCAACCCCTGCAGGAGTGCCCAAAGGACCACCCCAAGCTGCACTCTGACACCTTCAGCCA
CCTGAGCCGCCTCGAAGGCCTGGTGTTGAAAGACAGTTCTCTCTACAACCTGGACACCAGGTGGTTCCGAG
GCCTGGACAGGCTCCAAGTGCTGGACCTGAGTGAGAACTTCCTCTACGACTGCATCACCAAGACCACGGCC
TTCCAGGGCCTGGCCCGACTGCGCAGCCTCAACCTGTCCTTCAATTACCACAAGAAGGTGTCCTTTGCCCA
CCTGCACCTGGCACCCTCCTTTGGGCACCTCCGGTCCCTGAAGGAGCTGGACATGCATGGCATCTTCTTCC
GCTCGCTCAGTGAGACCACGCTCCAACCTCTGGTCCAACTGCCTATGCTCCAGACCCTGCGCCTGCAGATG
AACTTCATTAACCAGGCCCAGCTCAGCATCTTTGGGGCCTTCCCTGGCCTGCTGTACGTGGACCTATCGGA
CAACCGCATCAGCGGAGCTGCAAGGCCAGTGGCCATTACTAGGGAGGTGGATGGTAGGGAGAGGGTCTGGC
TGCCTTCCAGGAACCTCGCTCCACGTCCACTGGACACTCTCCGCTCAGAGGACTTCATGCCAAACTGCAAG
GCCTTCAGCTTCACCTTGGACCTGTCTCGGAACAACCTGGTGACAATCCAGTCGGAGATGTTTGCTCGCCT
CTCACGCCTCGAGTGCCTGCGCCTGAGCCACAACAGCATCTCCCAGGCGGTCAATGGCTCTCAGTTTGTGC
CGCTGACCAGCCTGCGGGTGCTGGACCTGTCCCACAACAAGCTGGACCTGTATCACGGGCGCTCGTTCACG
GAGCTGCCGCGCCTGGAAGCACTGGACCTCAGCTACAATAGCCAGCCCTTTACCATGCAGGGTGTGGGCCA
```

-continued

```
CAACCTCAGCTTCGTGGCCCAGCTGCCCGCCCTGCGCTACCTCAGCCTGGCGCACAATGACATCCATAGCC

GAGTGTCCCAGCAGCTCTGTAGCGCCTCACTGTGCGCCCTGGACTTTAGCGGCAACGATCTGAGCCGGATG

TGGGCTGAGGGAGACCTCTATCTCCGCTTCTTCCAAGGCCTAAGAAGCCTAGTCTGGCTGGACCTGTCCCA

GAACCACCTGCACACCCTCCTGCCACGTGCCCTGGACAACCTCCCCAAAAGCCTGAAGCATCTGCATCTCC

GTGACAATAACCTGGCCTTCTTCAACTGGAGCAGCCTGACCCTCCTGCCCAAGCTGGAAACCCTGGACTTG

GCTGGAAACCAGCTGAAGGCCCTAAGCAATGGCAGCCTGCCATCTGGCACCCAGCTGCGGAGGCTGGACCT

CAGTGGCAACAGCATCGGCTTTGTGAACCCTGGCTTCTTTGCCCTGGCCAAGCAGTTAGAAGAGCTCAACC

TCAGCGCCAATGCCCTCAAGACAGTGGAGCCCTCCTGGTTTGGCTCGATGGTGGGCAACCTGAAAGTCCTA

GACGTGAGCGCCAACCCTCTGCACTGTGCCTGTGGGCGACCTTCGTGGGCTTCCTGCTGGAGGTACAGGC

TGCCGTGCCTGGGCTGCCCAGCCGCGTCAAGTGTGGCAGTCCGGGGCAGCTCCAGGGCCATAGCATCTTTG

CGCAAGACCTGCGCCTCTGCTTCCTGGACCTGGGGCTCTATCTCTTTGCTGGGACTGCACCGGCAGTGCTG

CTGCTGCTGGTGGTGCCGGTGGTGTACCACCGCGCCTACTGGAGGCTGAAGTACCACTGGTACCTTCTGCG

GTGCTGGGTCAACCAGCGGTGGCGGCGGGAGGAAAAGTGCTACCTCTATGACAGCTTTGTGTCCTACAATT

CAGCTGATGAAAGTTGGGTGTTGCAGAAGCTGGTGCCTGAGCTGGAGCACGGTGCCTTCCGCCTCTGCTTG

CACCACCGCGACTTCCAGCCGGGCCGCAGCATCATTGACAACATTGTGGATGCTGTCTACAACAGCCGGAA

GACGGTGTGCGTGGTGAGCCGCAGCTACCTGCGCAGCGAGTGGTGCTCTCTAGAGGTGCAGTTGGCCAGCT

ACCGGCTGTTGGATGAGCGGCGTGACATCCTGGTACTGGTGCTGCTGGAGGACGTGGGTGATGCTGAGCTG

TCTGCCTACCACCGCATGCGGCGGGTGCTGCTGCGGCGCACCTACCTGCGCTGGCCTCTTGACCCCGCAGC

TCAGCCGCTCTTTTGGGCACGGCTGAAGAGGGCACTGAGGTGGGGAGAGGGAGGAGAGGAGGAGGAAGAAG

AAGGTTTGGGTGGAGGGACGGGAAGGCCCAGGGAAGGAGACAAACAGATGTAGGCGGCCGC
```

[SEQ ID NO: 11]

MGPRCTLHPLSLLVQVTALAAALAQGRLPAFLPCELQPHGLVNCNWLFLKSVPHFSAAAPRANVTSLSLLS

NRIHHLHDSDFVHLSSLRTLNLKWNCPPAGLSPMHFPCHMTIEPNTFLAVPTLEELNLSYNSITTVPALPD

SLVSLSLSRTNILVLDPTHLTGLHALRYLYMDGNCYYKNPCQGALEVVPGALLGLGNLTHLSLKYNNLTEV

PRSLPPSLETLLLSYNHIVTLTPEDLANLTALRVLDVGGNCRRCDHARNPCRECPKDHPKLHSDTFSHLSR

LEGLVLKDSSLYNLDTRWFRGLDRLQVLDLSENFLYDCITKTTAFQGLARLRSLNLSFNYHKKVSFAHLHL

APSFGHLRSLKELDMHGIFFRSLSETTLQPLVQLPMLQTLRLQMNFINQAQLSIFGAFPGLLYVDLSDNRI

SGAARPVAITREVDGRERVWLPSRNLAPRPLDTLRSEDFMPNCKAFSFTLDLSRNNLVTIQSEMFARLSRL

ECLRLSHNSISQAVNGSQFVPLTSLRVLDLSHNKLDLYHGRSFTELPRLEALDLSYNSQPFTMQGVGHNLS

FVAQLPALRYLSLAHNDIHSRVSQQLCSASLCALDFSGNDLSRMWAEGDLYLRFFQGLRSLVWLDLSQNHL

HTLLPRALDNLPKSLKHLHLRDNNLAFFNWSSLTLLPKLETLDLAGNQLKALSNGSLPSGTQLRRLDLSGN

SIGFVNPGFFALAKQLEELNLSANALKTVEPSWFGSMVGNLKVLDVSANPLHCACGATFVGFLLEVQAAVP

GLPSRVKCGSPGQLQGHSIFAQDLRLCFLDLGLYLFAGTAPAVLLLLVVPVVYHRAYWRLKYHWYLLRCWV

NQRWRREEKCYLYDSFVSYNSADESWVLQKLVPELEHGAFRLCLHHRDFQPGRSIIDNIVDAVYNSRKTVC

VVSRSYLRSEWCSLEVQLASYRLLDERRDILVLVLLEDVGDAELSAYHRMRRVLLRRTYLRWPLDPAAQPL

FWARLKRALRWGEGGEEEEEEGLGGGTGRPREGDKQM

Cloning of a Fusion Construct of the Extracellular Domain of Canine TLR9 and the Transmembrane and Intracellular Domain of Chicken TLR21.

A fusion construct encoding the extracellular domain of canine TLR9 and intracellular domain of chicken TLR21 was created using the "PCR-sewing" protocol as described above.

The sequence encoding the extracellular domain of canine TLR9 from the pcDNA3.1(neo)-canine TLR9 construct (described in example 3) was amplified by PCR as well as the sequence encoding the transmembrane and intracellular domain of chicken TLR21 from pcDNA3.1(neo)-chicken TLR21 (sequences above). Complementary sequences were added to the 3' end of the extracellular (TLR9) fragment and the 5' end of the TLR21 fragment using primers with a 5' overhang (sequences below) by PCR. Expand High Fidelity PCR kit (Roche) was used for all PCRs.
Primers for Canine TLR9 (Extracellular Domain):

```
doT9-chT21 5' E:
                                        [SEQ ID NO: 34]
GCGGAATTCCACCATGGGCCCCTGCCGTGG dogT9-chT21fusRV:
                                        [SEQ ID NO: 35]
ATAGAGCCCCAGGTCCAGGAAGCAGAGGCGCAGGTCCTGTGC
```

Primers for Chicken TLR21 (Transmembrane and Intracellular Domain):

```
dogT9-chT21fusFW:
                                        [SEQ ID NO: 36]
GCACAGGACCTGCGCCTCTGCTTCCTGGACCTGGGGCTCTAT pig/dogT9-chT21-:
                                        [SEQ ID NO: 37]
GCGGCGGCCGCCTACATCTGTTTGTCTCCTT
```

The fusion product was cloned into pCRII-TOPO (Invitrogen) and one clone was sequenced to examine if the sequence was PCR error-free. The sequence contained one coding and one silent mutation. The coding mutation was corrected using the Quik Change II XL site directed mutagenesis kit (Stratagene) and primers:
Mutagenesis Primers:

```
dT9-chT21mt FW:
                                        [SEQ ID NO: 38]
GCAGGCTGCCGCGCTAGCCCTGGCCCTGGCCCAGGGC dT9-chT21mt RV:
                                        [SEQ ID NO: 39]
GCCCTGGGCCAGGGCCAGGGCTAGCGCGGCAGCCTGC
```

After the mutagenesis procedure, multiple (8) clones were sequenced to examine if site-directed mutagenesis had been successful. One clone contained the corrected nucleotide. This clone was used to reclone the fusion construct into pIRESpuro3 (Clontech) using the primer-introduced EcoRI and the EcoRI site present in pCRII-TOPO. The resulting vector (pIRESpuro-canTLR9-21) was completely sequenced. Sequencing identified two silent mutations which do not affect the amino acid sequence. Therefore it was concluded that this clone could be used for further applications.
pIRESpuro-canTLR9-21 Insert Sequence, (Partial) Primer Sequence Underlined, TLR21 (Coding) Sequences in Italics, Start/Stop Codons Highlighted Bold. [SEQ ID NO: 213]

```
GAATCCACCATGGGCCCCTGCCGTGGCGCCCTGCACCCCCTGTCTCTCCTGGTGCAGGCTGCCGCGCTAGC

CCTGGCCCTGGCCCAGGGCACCCTGCCTGCCTTCCTGCCCTGTGAGCTCCAGCCCCATGGCCTGGTGAACT

GCAACTGGCTGTTCCTCAAGTCCGTGCCCCGCTTCTCGGCAGCTGCACCCCGCGGTAACGTCACCAGCCTT

TCCTTGTACTCCAACCGCATCCACCACCTCCATGACTATGACTTTGTCCACTTCGTCCACCTGCGGCGTCT

CAATCTCAAGTGGAACTGCCCGCCCGCCAGCCTCAGCCCCATGCACTTTCCCTGTCACATGACCATTGAGC

CCAACACCTTCCTGGCTGTGCCCACCCTAGAGGACCTGAATCTGAGCTATAACAGCATCACGACTGTGCCC

GCCCTGCCCAGTTCGCTTGTGTCCCTGTCCCTGAGCCGCACCAACATCCTGGTGCTGGACCCTGCCACCCT

GGCAGGCCTTTATGCCCTGCGCTTCCTGTTCCTGGATGGCAACTGCTACTACAAGAACCCCTGCCAGCAGG

CCCTGCAGGTGGCCCCAGGTGCCCTCCTGGGCCTGGGCAACCTCACACACCTGTCACTCAAGTACAACAAC

CTCACCGTGGTGCCGCGGGGCCTGCCCCCCAGCCTGGAGTACCTGCTCTTGTCCTACAACCACATCATCAC

CCTGGCACCTGAGGACCTGGCCAATCTGACTGCCCTGCGTGTCCTCGATGTGGGTGGGAACTGTCGCCGCT

GTGACCATGCCCGTAACCCCTGCAGGGAGTGCCCCAAGGGCTTCCCCCAGCTGCACCCCAACACCTTCGGC

CACCTGAGCCACCTCGAAGGCCTGGTGTTGAGGGACAGCTCTCTCTACAGCCTGGACCCCAGGTGGTTCCA

TGGCCTGGGCAACCTCATGGTGCTGGACCTGAGTGAGAACTTCCTGTATGACTGCATCACCAAAACCAAAG

CCTTCTACGGCCTGGCCCGGCTGCGCAGACTCAACCTGTCCTTCAATTATCATAAGAAGGTGTCCTTTGCC

CACCTGCATCTGGCATCCTCCTTCGGGAGCCTACTGTCCCTGCAGGAGCTGGACATACATGGCATCTTCTT

CCGCTCGCTCAGCGAGACCACGCTCCAGTCGCTGGCCCACCTGCCCATGCTCCAGCGTCTGCATCTGCAGT

TGAACTTTATCAGCCAGGCCCAGCTCAGCATCTTCGGCGCCTTCCCTGGCCTGCGGTACGTGGACTTGTCA

GACAACCGCATCAGTGGAGCTGCAGAGCCCGCGGCTGCCACAGGGGAGGTAGAGGCGGACTGTGGGGAGAG

AGTCTGGCCACAGTCCCGGGACCTTGCTCTGGGCACACTGGGCACCCCCGGCTCAGAGGCCTTCATGCCGA

GCTGCAGGACCCTCAACTTCACCTTGGACCTGTCTCGGAACAACCTAGTGACTGTTCAGCCAGAGATGTTT

GTCCGGCTGGCGCGCCTCCAGTGCCTGGGCCTGAGCCACAACAGCATCTCGCAGGCGGTCAATGGCTCGCA

GTTCGTGCCTCTGAGCAACCTGCGGGTGCTGGACCTGTCCCATAACAAGCTGGACCTGTACCACGGGCGCT

CGTTCACGGAGCTGCCGCGGCTGGAGGCCTTGGACCTCAGCTACAACAGCCAGCCCTTCAGCATGCGGGGC
```

-continued

```
GTGGGCCACAATCTCAGCTTTGTGGCACAGCTGCCAGCCCTGCGCTACCTCAGCCTGGCGCACAATGGCAT

CCACAGCCGCGTGTCCCAGCAGCTCCGCAGCGCCTCGCTCCGGGCCCTGGACTTCAGTGGCAATACCCTGA

GCCAGATGTGGGCCGAGGGAGACCTCTATCTCCGCTTCTTCCAAGGCCTGAGAAGCCTGGTTCAGCTGGAC

CTGTCCCAGAATCGCCTGCATACCCTCCTGCCACGCAACCTGGACAACCTCCCCAAGAGCCTGCGGCTCCT

GCGGCTCCGTGACAATTACCTGGCTTTCTTCAACTGGAGCAGCCTGGCCCTCCTACCCAAGCTGGAAGCCC

TGGACCTGGCGGGAAACCAGCTGAAGGCCCTGAGCAATGGCAGCTTGCCCAACGGCACCCAGCTCCAGAGG

CTGGACCTCAGCGGCAACAGCATCGGCTTCGTGGTCCCCGGCTTTTTTGCCCTGGCCGTGAGGCTTCGAGA

GCTCAACCTCAGCGCCAACGCCCTCAAGACGGTGGAGCCCTCCTGGTTTGGTTCCCTGGCGGGTGCCCTGA

AAGTCCTAGACGTGACCGCCAACCCCTTGCATTGCGCTTGCGGCGCAACCTTCGTGGACTTCTTGCTGGAG

GTGCAGGCTGCGGTGCCCGGCCTGCCTAGCCGTGTCAAGTGCGGCAGCCCGGGCCAGCTCCAGGGCCGCAG

CATCTTCGCACAGGACCTGCGCCTCTGCTTCCTGGACCTGGGGCTCTATCTCTTTGCTGGGACTGCACCGG

CAGTGCTGCTGCTGGTGGTGCCGGTGGTGTACCACCGCGCCTACTGGAGGCTGAAGTACCACTGGTAC

CTTCTGCGGTGCTGGGTCAACCAGCGGTGGCGGCGGGAGGAAAAGTGCTACCTCTATGACAGCTTTGTGTC

CTACAATTCAGCTGATGAAAGTTGGGTGTTGCAGAAGCTGGTGCCTGAGCTGGAGCACGGTGCCTTCCGCC

TCTGCTTGCACCACCGCGACTTCCAGCCGGGCCGAGCATCATTGACAACATTGTGGATGCTGTCTACAAC

AGCCGGAAGACGGTGTGCGTGGTAAGCCGCAGCTACCTGCGCAGCGAGTGGTGCTCTCTAGAGGTGCAGTT

GGCCAGCTACCGGCTGTTGGATGAGCGGCGTGACATCCTGGTACTGGTGCTGCTGGAGGACGTGGGTGATG

CTGAGCTGTCTGCCTACCACCGCATGCGGCGGGTGCTGCTGCGGCGCACCTACCTGCGCTGGCCTCTTGAC

CCCGCAGCTCAGCCGCTCTTTTGGGCACGGCTGAAGAGGGCACTGAGGTGGGGAGAGGGAGGAGAGGAGGA

GGAAGAAGAAGGTTTGGGTGGAGGGACGGGAAGGCCCAGGGAAGGAGACAAACAGATGTAGGCGGCCGC
```

[SEQ ID NO: 217]

```
MGPCRGALHPLSLLVQAAALALALAQGTLPAFLPCELQPHGLVNCNWLFLKSVPRFSAAAPRGNVTSLSLY

SNRIHHLHDYDFVHFVHLRRLNLKWNCPPASLSPMHFPCHMTIEPNTFLAVPTLEDLNLSYNSITTVPALP

SSLVSLSLSRTNILVLDPATLAGLYALRFLFLDGNCYYKNPCQQALVAPGALLGLGNLTHLSLKYNNLTV

VPRGLPPSLEYLLLSYNHIITLAPEDLANLTALRVLDVGGNCRRCDHARNPCRECPKGFPQLHPNTFGHLS

HLEGLVLRDSSLYSLDPRWFHGLGNLMVLDLSENFLYDCITKTKAFYGLARLRRLNLSFNYHKKVSFAHLH

LASSFGSLLSLQELDIHGIFFRSLSETTLQSLAHLPMLQRLHLQLNFISQAQLSIFGAFPGLRYVDLSDNR

ISGAAEPAAATGEVEADCGERVWPQSRDLALGTLGTPGSEAFMPSCRTLNFTLDLSRNNLVTVQPEMFVRL

ARLQCLGLSHNSISQAVNGSQFVPLSNLRVLDLSHNKLDLYHGRSFTELPRLEALDLSYNSQPFSMRGVGH

NLSFVAQLPALRYLSLAHNGIHSRVSQQLRSASLRALDFSGNTLSQMWAEGDLYLRFFQGLRSLVQLDLSQ

NRLHTLLPRNLDNLPKSLRLLRLRDNYLAFFNWSSLALLPKLEALDLAGNQLKALSNGSLPNGTQLQRLDL

SGNSIGFVVPGFFALAVRLRELNLSANALKTVEPSWFGSLAGALKVLDVTANPLHCACGATFVDFLLEVQA

AVPGLPSRVKCGSPGQLQGRSIFAQDLRLCFLDLGLYLFAGTAPAVLLLLVVPVVYHRAYWRLKYHWYLLR

CWVNQRWRREEKCYLYDSFVSYNSADESWVLQKLVPELEHGAFRLCLHHRDFQPGRSIIDNIVDAVYNSRK

TVCVVSRSYLRSEWCSLEVQLASYRLLDERRDILVLVLLEDVGDAELSAYHRMRRVLLRRTYLRWPLDPAA

QPLFWARLKRALRWGEGGEEEEEGLGGGTGRPREGDKQM
```

Example 6

Transfection of MDCK-pNifTyhyg-SEAP with Canine TLR9-21 Fusion Constructs a) Transfection and Selection of Clones To investigate the potential of MDCK-pNifTyhyg-SEAK-clone 15 for the expression and detection of TLR9-21 fusion constructs, this clonal cell line was transfected with pIRES-puro-canineTLR9-21. Transfectants were selected by repeated passage with medium supplemented with 300 µg/ml hygromycin and 8 µg/ml puromycin. Testing of the resulting polyclonal cell line with the standard oligonucleotide ODN-2006-PTO indicated induction of SEAP secretion. Single cell cloning was performed and 54 clones were expanded for further testing with ODN-2006-PTO (see graph below). A large number of clones were identified that showed induction of massive amounts of SEAP. Four clones with the best signal-to-noise ratio (No 17, 23, 32 and 40) were chosen for expansion and to generate frozen stabilates. After retesting, clone No 17 was selected for further experiments (See FIG. 5).

b) MDCK-pNifTyhyg-SEAP-pIRESpuro-canTLR9-21-Clone 17: Testing of the Stimulatory Activity of Oligonucleotides Experiment 1:

A series of phosphorothioate oligonucleotides (PTO-ODNs, thio5-4 up to thio 5-10) was tested, together with the standard oligonucleotides from human medicine, 2006-PTO and 2007-PTO

| | | EC$_{50}$ (nM) | V$_{max}$ (mOD/min/ 20 ul) |
|---|---|---|---|
| 2006-PTO | tcgtcgttttgtcgtttt-gtcgtt SEQ ID NO: 40 | 6.3 | 311 |
| 2007-PTO | tcgtcgttgtcgttttgtcgtt SEQ ID NO: 41 | 8.6 | 325 |
| thio5-4 | gtcgtcgtcgtc SEQ ID NO: 44 | >250 | n.d. |
| thio5-5 | gtcgtcgtcgtcgtc SEQ ID NO: 45 | 80.6 | 348 |
| thio5-6 | gtcgtcgtcgtcgtcgtc SEQ ID NO: 46 | 23.6 | 319 |
| thio5-7 | gtcgtcgtcgtcgtcgtcgtc SEQ ID NO: 47 | 7.2 | 300 |
| thio5-8 | gtcgtcgtcgtcgtcgtcgtcgtc SEQ ID NO: 48 | 7.8 | 308 |
| thio5-10 | gtcgtcgtcgtcgtcgtcgtcgtc gtcgtc SEQ ID NO: 49 | 4.3 | 296 |

Figure 6:
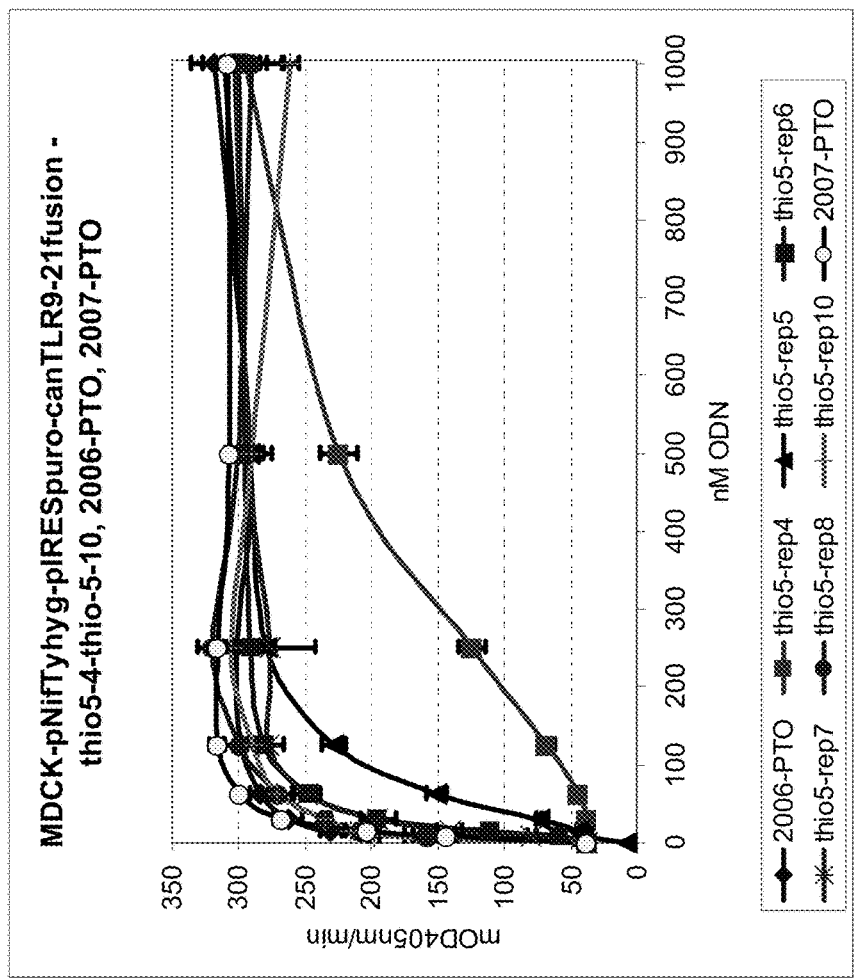

From this experiments, it can be deduced that the pIRE-Spuro-canTLR9-21-expressing MDCK-pNifTyhyg cell line that was generated is capable of defining different potencies via the calculation of EC$_{50}$ values (see FIG. 6).

It can be shown that for immunostimulatory ODNs, with structure elements such as gtcgtc, the number of cg elements is important: 9>7>6>5>>4>>3 (see table above). This experiment also immediately outlines the potential of this cell line for generation of structure-activity relationships (SAR) and lead optimization of immunostimulatory ODNs.

It was also shown that PTO-ODNs (2006-PTO and 2007-PTO) known from human research are highly potent on the canine TLR9-21 fusion protein, but at least one candidate (thio5-10) of the inventor's initial 'lead optimization' proved to be as potent or slightly more potent on canine TLR9-21 fusion that these human standard ODNs.

Figure 7:
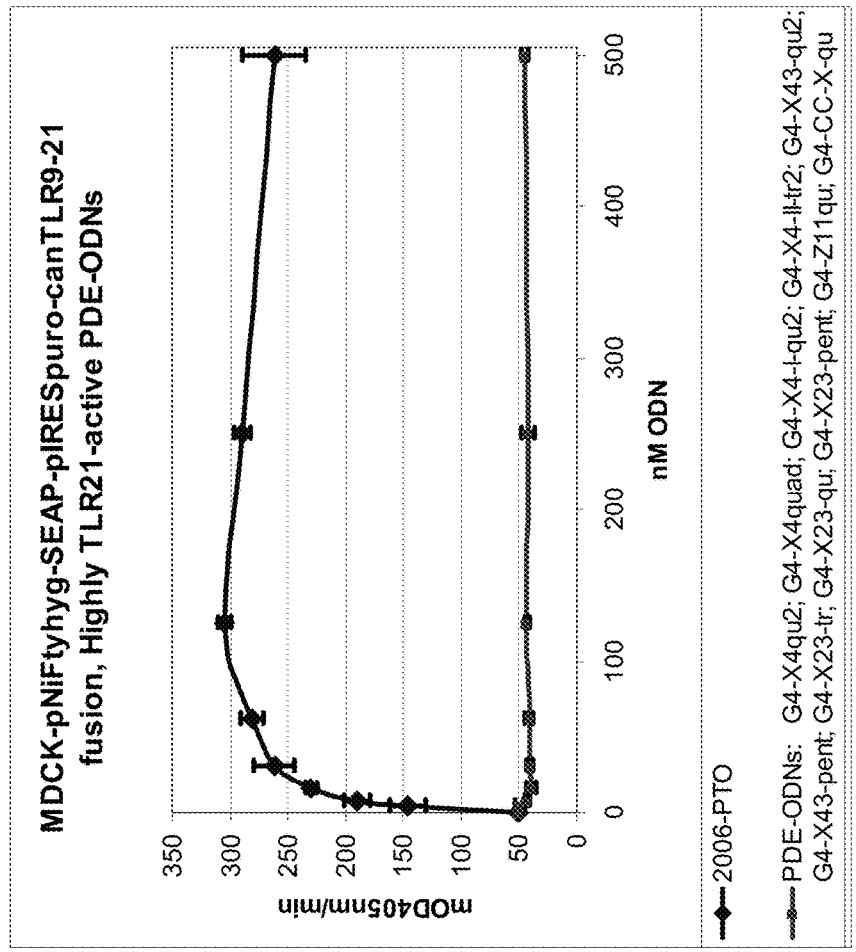
Figure 8:
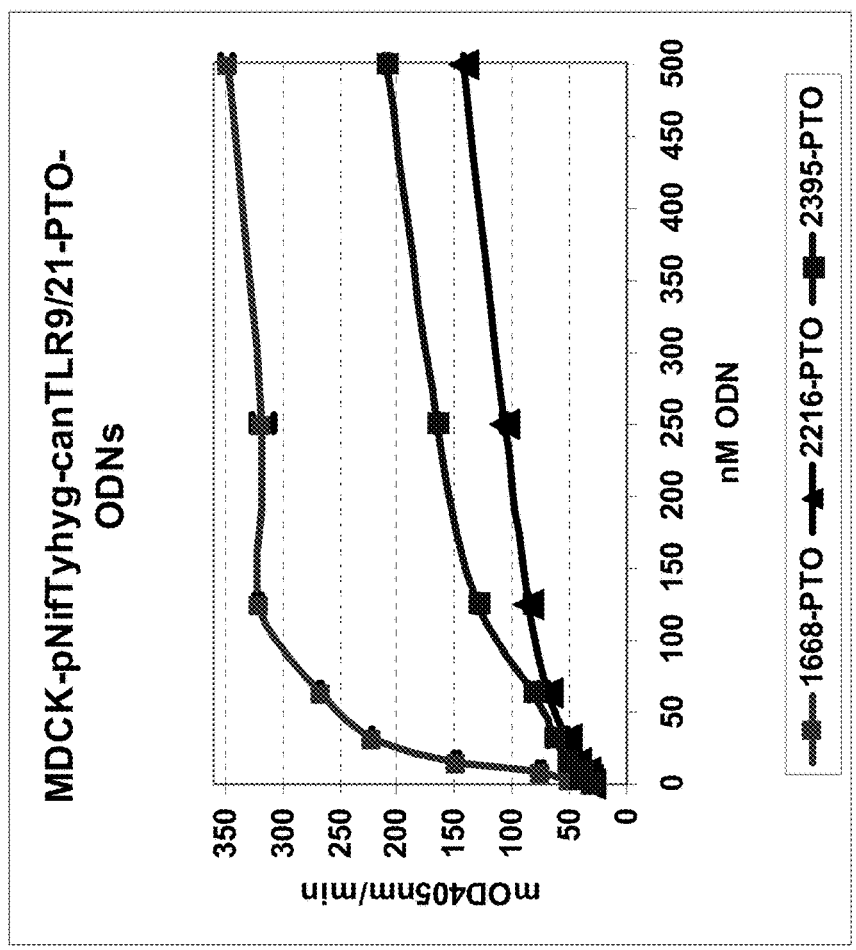
Figure 9:
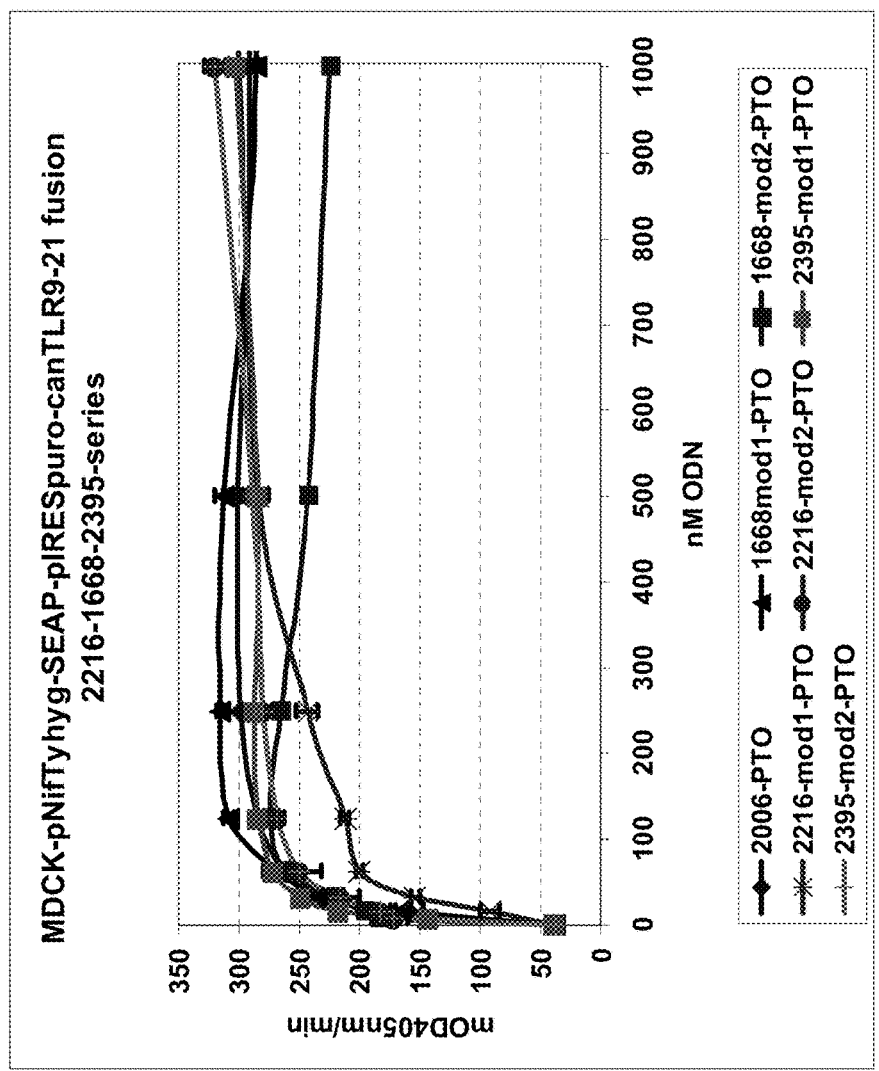
Figure 10:
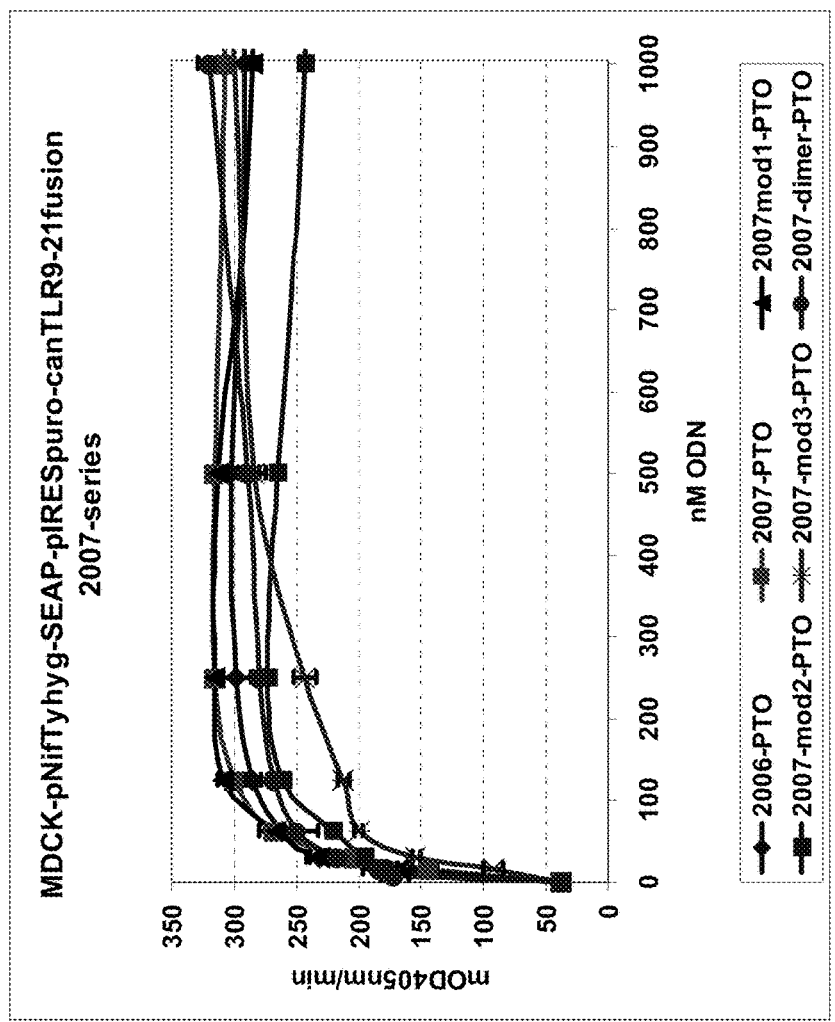
Figure 11:
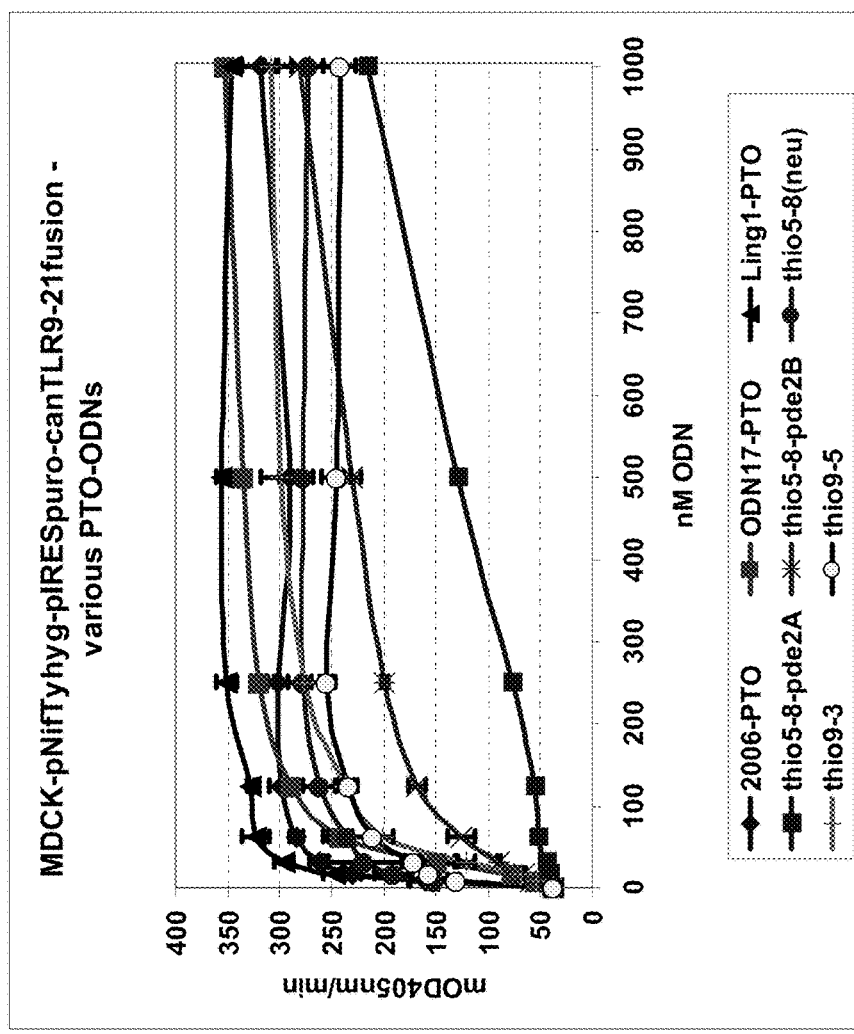

Experiment 2:

A series of phosphodiester oligonucleotides (10 PDE-ODNs), that had proven to be highly potent on chicken TLR21 (the donor of the fusion part) were tested on canine TLR9-21 fusion, together with the standard oligonucleotide from human medicine, 2006-PTO (see FIG. 7).

Result:

None of the 10 PDE-ODNs showed any SEAP-inducing activity in the test range (500 nM-3.9 nM), while 2006-PTO showed an EC$_{50}$ of ~4 nM, the expected range for this ODN.

Interpretation:

the recognition of ODNs is dictated by the N-terminal fusion portion (in this case canine TLR9). There is a dramatic species specificity of PDE-ODN recognition, since the tested ODNs show single digit nM or even pM EC$_{50}$ values on chicken TLR21, while 2006-PTO is less potent on this receptor (31 nM) than on canine TLR9-21 fusion.

Experiment 3:

Here an experiment was performed on PTO-ODNs that have been used in the literature in the human and mouse context: 1668-PTO, 2216-PTO and 2395-PTO.

| | | EC$_{50}$ (nM) | V$_{max}$ (mOD/min/ 20 ul) |
|---|---|---|---|
| 1668-PTO | tccatgacgttcctgatgct SEQ ID NO: 50 | 22.5 | 363 |
| 2216-PTO | ggggacgatcgtcggggg SEQ ID NO: 51 | 30.6 | 161 |
| 2395-PTO | tcgtcgttttcggcgcgcgccg SEQ ID NO: 52 | 47.1 | 201 |

All three PTO-ODNs are active on canine TLR9-21 fusion with double digit nM EC$_{50}$ values. However, with respect to maximally attainable stimulation of SEAP production (V$_{max}$) the potency order is 1668 >2395 >2216 (see FIG. 8). Remarkable, testing of the same ODNs on chicken TLR21 shows that 2216-PTO is inactive, 1668-PTO has an EC$_{50}$ of ~1000 nM, and only 2395-PTO has some potency in showing an EC$_{50}$ of 39.4 nM.

Experiment 4:

A 'lead optimization' was attempted based on what could possibly be active elements form the published oligonucleotides 1668-PTO, 2216-PTO and 2395-PTO. These active elements are underlined and/or in Italic in the parental ODN and then arranged in repeats in the mod1/2 ODNs:

| | | EC$_{50}$ (nM) | V$_{max}$ (mOD/ min/ 20 ul) |
|---|---|---|---|
| 2006-PTO | tcgtcgttttgtcgttttgtcgtt SEQ ID NO: 53 | 6.3 | 311 |
| 1668-PTO | tccat*gacgtt*cctgatgct SEQ ID NO: 54 | 22.5 | 363 |
| 1668-mod1 | gacgttgacgttgacgttgacgtt SEQ ID NO: 555 | 5.7 | 312 |
| 1668-mod2 | tgacgttctgacgttctgacgttctgacgttc SEQ ID NO: 56 | 4.9 | 273 |
| 2216-PTO | ggggg*acgatcgtc*ggggg SEQ ID NO: 57 | 30.6 | 161 |
| 2216-mod1 | gacgatcgtcgacgatcgtc SEQ ID NO: 58 | 19.0 | 309 |
| 2216-mod2 | gacgatcgtcgacgatcgtcgacgatcgtc SEQ ID NO: 59 | 7.9 | 293 |
| 2395-PTO | tcgtcgttttcggcgcgcgccg SEQ ID NO: 60 | 47.1 | 201 |
| 2395-mod1 | tcgtcgttttcgtcgtcgttttcg SEQ ID NO: 61 | 7.1 | 299 |

| | | $EC_{50}$ (nM) | $V_{max}$ (mOD/ min/ 20 ul) |
|---|---|---|---|
| 2395-mod2 | tcgtcgttttcgtcgtcgttttcgtcgtcg ttttcg SEQ ID NO: 62 | 3.7 | 258 |

Based on the $EC_{50}$ values the 'lead optimization' has proven to be successful. In all three cases, the mod1/2 PTO-ODN versions were more potent than their parental PTO ODN. In the case of 2216-PTO and 2395-PTO in addition a significant increase in $V_{max}$ was visible. Five out of six newly designed PTO-ODNs are within the activity region of the paradigmal 2006-PTO (see FIG. 9).

Experiment 5:

A 'lead optimization' based on possible active elements was tried for the published oligonucleotide 2007-PTO.

| | | $EC_{50}$ (nM) | $V_{max}$ (mOD/ min/ 20 ul) |
|---|---|---|---|
| 2006-PTO | tcgtcgttttgtcgttttgtcgtt SEQ ID NO: 63 | 6.3 | 311 |
| 2007-PTO | tcgtcgttgtcgttttgtcgtt SEQ ID NO: 64 | 8.6 | 325 |
| 2007-mod1 | tcgtcgttgtcgttttgtcgttgtcgtt SEQ ID NO: 65 | 6.0 | 299 |
| 2007-mod2 | tcgtcgtcgtcgttgtcgttttgtcgtt SEQ ID NO: 66 | 6.1 | 306 |
| 2007-mod3 | tcgtcgtcgtcgttgtcgttttgtcgtt gtcgtt SEQ ID NO: 67 | 6.6 | 295 |
| 2007-dimer | tcgtcgttgtcgttttgtcgtttcgtcg ttgtcgttttgtcgtt SEQ ID NO: 68 | 4.1 | 293 |

The addition of cg-containing elements to the 5'-end or 3'-end or both, as well as dimerization of 2007-PTO did not lead to an improvement of activity (both with respect to $EC_{50}$ and $V_{max}$), but neither did it lead to a loss of activity. The single digit nanomolar activity is preserved. None of the listed ODNs has been reported in the literature so far (see FIG. 10).

Experiment 6:

Here two PTO-ODNs were tested that are mentioned in the literature (ODN-17 and ODN-Ling 1). Also was tested the impact of replacement of the complete (thio5-8pde2A) and partial (thio5-8pde2B) phosphorothioate bonds of the CpG elements in thio5-8. Furthermore, multimers of the immunomodulatoy element -ttcgtc- were tested.

| | | $EC_{50}$ (nM) | $V_{max}$ (mOD/ min/ 20 ul) |
|---|---|---|---|
| 2006-PTO | tcgtcgttttgtcgttttgtcgtt SEQ ID NO: 69 | 6.3 | 311 |
| thio5-8 | gtcgtcgtcgtcgtcgtcgtc SEQ ID NO: 70 | 7.0 | 276 |
| thio5-8pde2A | gtCGtCGtCGtCGtCGtCGtCGtCGtc SEQ ID NO: 71 | >100 | n.d. |
| thio5-8pde2B | gtCGtcgtCGtcgtCGtcgtCGtc SEQ ID NO: 72 | 61.0 | 268 |
| thio9-3 | ttcgtcttcgtcttcgtc SEQ ID NO: 73 | 47.0 | 327 |
| thio9-5 | ttcgtcttcgtcttcgtcttcgtc ttcgtc SEQ ID NO: 74 | 8.9 | 248 |
| ODN-17 | gtcgttgtcgttgtcgtt SEQ ID NO: 75 | 43.4 | 374 |
| ODN-Ling1 | tcgacgtttgacgtttgacgtt SEQ ID NO: 76 | 8.2 | 359 |

It has been reported in the literature that replacement of PTO by PDE bonds within the CpG elements sometimes boosts stimulatory activity of PTO-ODNs. This idea was tested with thio5-8. In the inventor's hands the PDE-modified versions were far less active on canine TLR9-21 fusion than the parental 'PTO-only' ODN. They have identified one further novel PTO-ODN being similarly active on canine TLR9-21 fusion as 2006-PTO: thio9-5. Furthermore Ling1-PTO proved to be a potent PTO-ODN (see FIG. 11).

Experiment 7:

Here some PTO versions of PDE oligonucleotides were tested, that proved to be highly active on chicken TLR21, when combined with 5'- and 3'dG runs. The PTO versions, however, lack the 5'- and 3'dG runs (therefore minus G, 'mG')

| | | $EC_{50}$ (nM) | $V_{max}$ (mOD/ min/ 20 ul) |
|---|---|---|---|
| 2006-PTO | tcgtcgttttgtcgt tttgtcgtt SEQ ID NO: 77 | 6.3 | 311 |
| X4qu-PTOmG | ttcgttttcgttttc gttttcgtt SEQ ID NO: 78 | 12.2 | 328 |
| X4pe-PTOmG | ttcgttttcgttttc gttttcgttttcgtt SEQ ID NO: 79 | 5.3 | 313 |
| X4-I-tr-PTOmG | tttcgttttttcgtt ttttcgttt SEQ ID NO: 80 | 10.1 | 332 |
| X4-I-qu-PTOmG | tttcgttttttcgttt tttcgttttttcgttt SEQ ID NO: 81 | 6.2 | 262 |
| X4-II-tr-PTOmG | ttttcgttttttttcg ttttttcgtttt SEQ ID NO: 82 | 11.2 | 299 |

Figure 12:
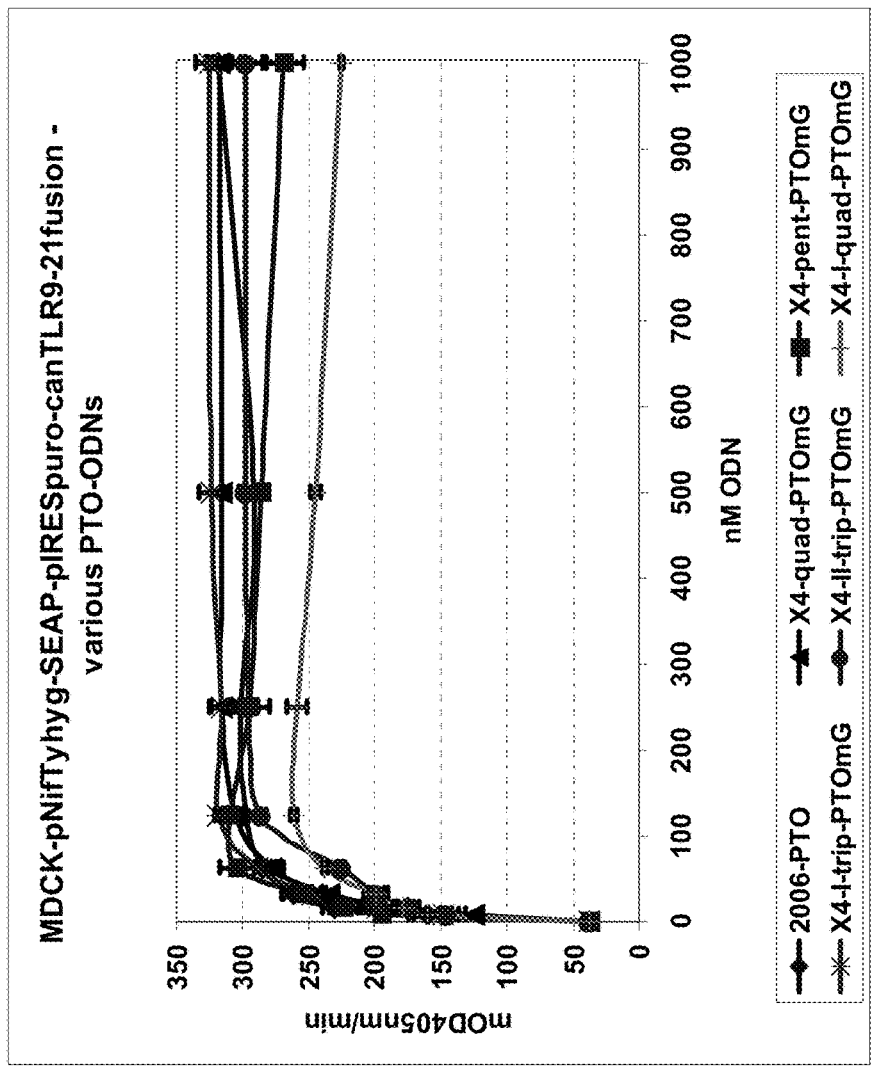
Figure 13:
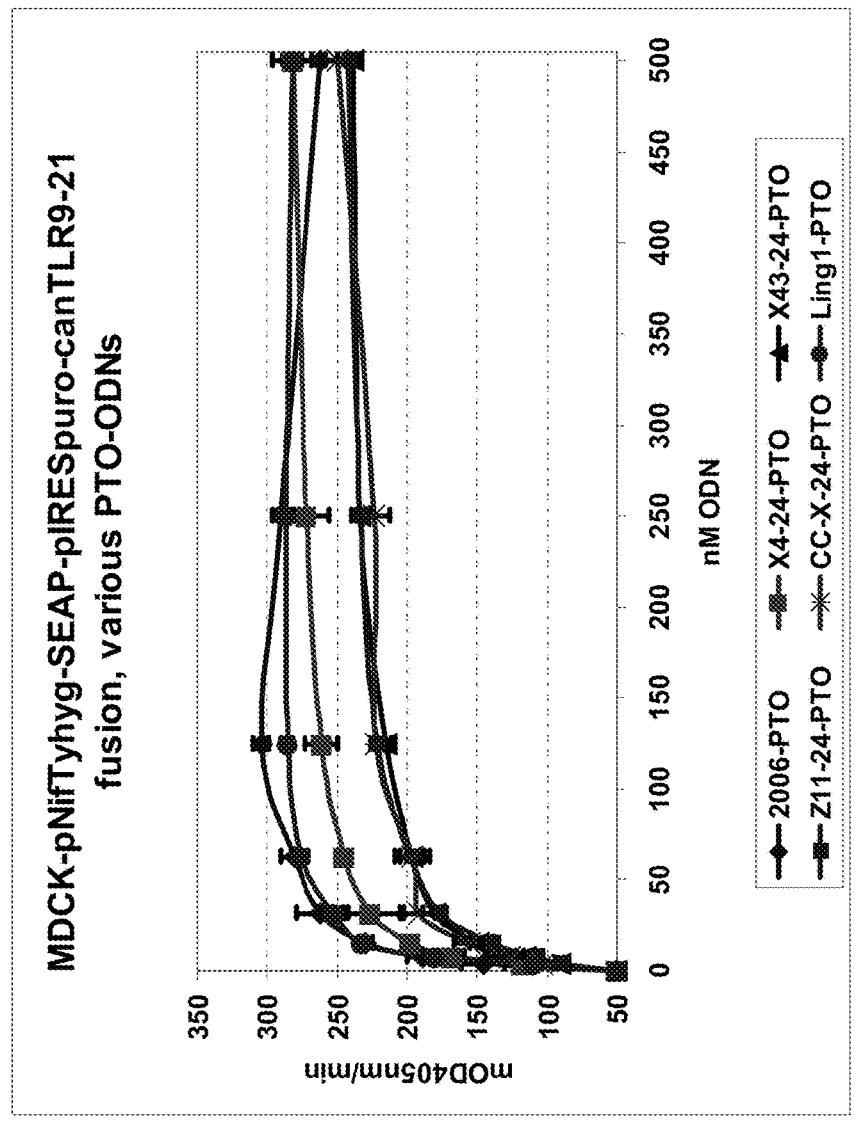
Figure 14:
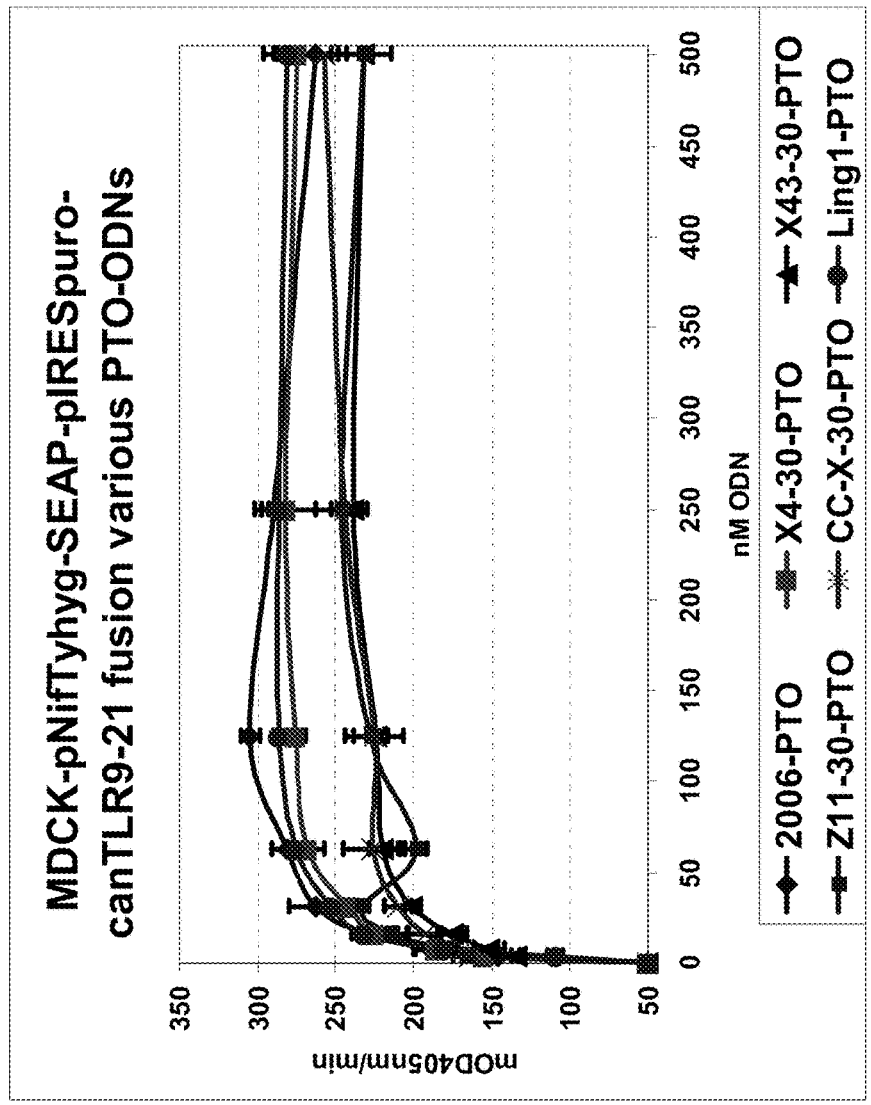
Figure 15:
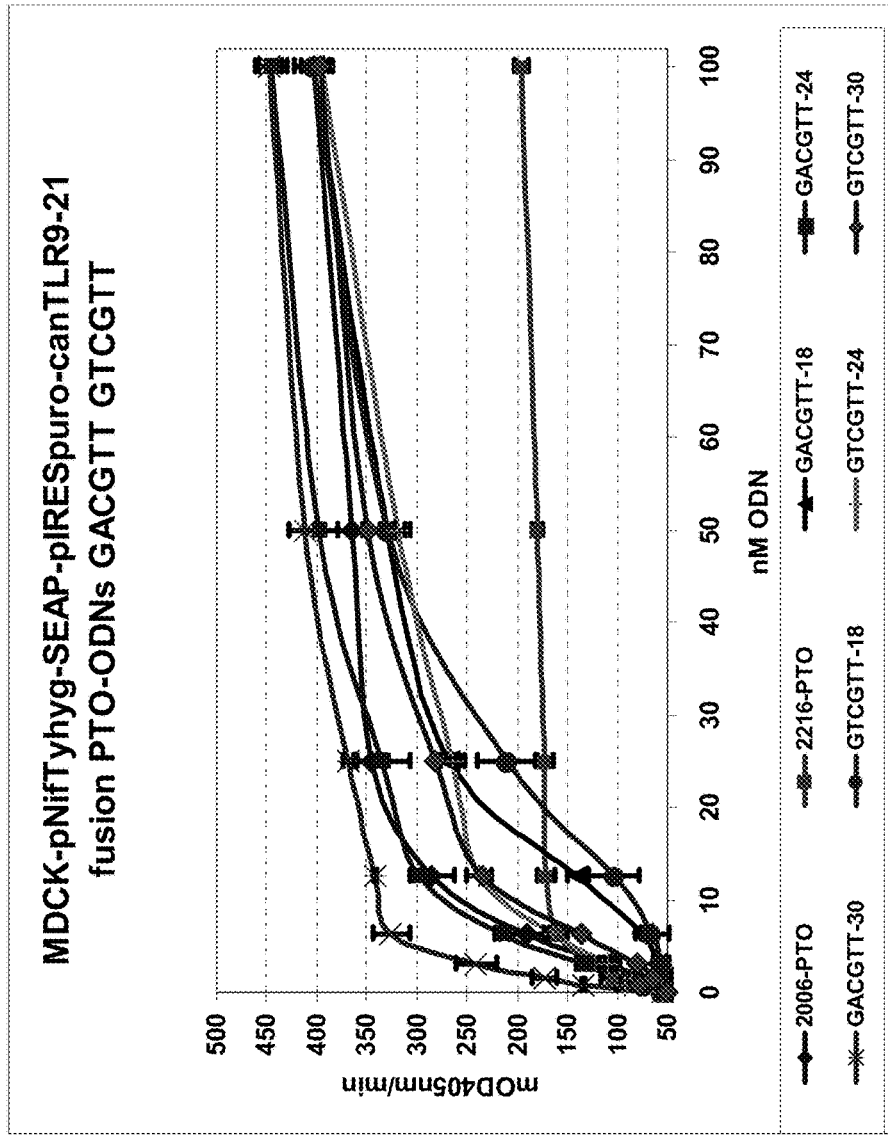

All tested ODNs proved to be highly potent with $EC_{50}$ and $V_{max}$ values identical or close to the standard PTO-ODN 2006 (see FIG. 12).

Experiment 8:

Further series of PTO-ODNs based on the active elements (chicken TLR21) of ODNs X4, X43, Z11 and CC-X were tested for their potency on canine TLR9-21 fusion

| | | EC$_{50}$ (nM) | V$_{max}$ (mOD/ min/20 ul) |
|---|---|---|---|
| 2006-PTO | tcgtcgttttgtcgttttgtcgtt SEQ ID NO: 83 | 4.0 | 292 |
| X4-24-PTO | ttcgttttcgttttcgttttcgtt SEQ ID NO: 84 | 5.4 | 274 |
| X43-24-PTO | ttcgtcttcgtcttcgtcttcgtc SEQ ID NO: 85 | 7.8 | 233 |
| Z11-24-PTO | ctcgtcctcgtcctcgtcctcgtc SEQ ID NO: 86 | 9.0 | 237 |
| CC-X-24-PTO | ttcgccttcgccttcgccttcgcc SEQ ID NO: 87 | 10.5 | 235 |
| X4-30-PTO | ttcgttttcgttttcgttttcgtt ttcgtt SEQ ID NO: 88 | 3.6 | 280 |
| X43-30-PTO | ttcgtcttcgtcttcgtcttcgtc ttcgtc SEQ ID NO: 89 | 3.6 | 231 |
| Z11-30-PTO | ctcgtcctcgtcctcgtcctcgtc ctcgtc SEQ ID NO: 90 | 1.9 | 238 |
| CC-X-30-PTO | ttcgccttcgccttcgccttcgcc ttcgcc SEQ ID NO: 91 | 1.9 | 242 |
| ODN-Ling1 | tcgacgtttgacgtttgacgtt SEQ ID NO: 92 | 5.3 | 295 |

All new PTO-oligonucleotides have high stimulatory activity (EC$_{50}$ in the single digit nanomolar range) and comparable V$_{max}$ on canine TLR9-21, in the case of Z11-30-PTO and CC-X-30-PTO with EC$_{50}$s below 2 nM. None of these PTO-ODNs has been mentioned yet in relation to their use in dogs (see FIGS. 13 and 14).

Experiment 9:

In this experiment repeats of the frequently used immunostimulatory elements gacgtt and gtcgtt were tested for their potency on canine TLR9-21 fusion.

| | | EC$_{50}$ (nM) | V$_{max}$ (mOD/ min/20 ul) |
|---|---|---|---|
| 2006-PTO | tcgtcgttttgtcgttttgtcgtt SEQ ID NO: 93 | 7.1 | 431 |
| GACGTT-18-PTO | gacgttgacgttgacgtt SEQ ID NO: 94 | 16.1 | 450 |
| GACGTT-24-PTO | gacgttgacgttgacgttgacgtt SEQ ID NO: 95 | 6.8 | 456 |
| GACGTT-30-PTO | gacgttgacgttgacgttgacgtt gacgtt SEQ ID NO: 96 | 1.9 | 419 |
| GTCGTT-18-PTO | gtcgttgtcgttgtcgtt SEQ ID NO: 97 | 12.4 | 397 |
| GTCGTT-24-PTO | gtcgttgtcgttgtcgttgtcgtt SEQ ID NO: 98 | 5.9 | 369 |
| GTCGTT-30-PTO | gtcgttgtcgttgtcgttgtcgtt gtcgtt SEQ ID NO: 99 | 9.3 | 416 |

| | | EC$_{50}$ (nM) | V$_{max}$ (mOD/ min/20 ul) |
|---|---|---|---|
| 2216-PTO | ggggacgatcgtcgggggg SEQ ID NO: 100 | 1.2 | 187 |

In the case of the repeat element gacgtt, the experiment demonstrates that repeat number matters. The pentamer reaches an EC$_{50}$ below 2 nM. Somewhat unexplained is the low EC$_{50}$ of this new batch of 2216-PTO. However, the V$_{max}$ value is clearly lower than for all other ODNs tested (see FIG. 15).

Experiment 10:

In this experiment repeats of triplet and quadruplet elements were tested for their potency on canine TLR9-21 fusion.

| | | EC$_{50}$ (nM) | V$_{max}$ (mOD/ min/20 ul) |
|---|---|---|---|
| 2006-PTO | tcgtcgttttgtcgttttgtcgtt SEQ ID NO: 101 | 4.0 | 292 |
| Thio-ACG-8 | acgacgacgacgacgacgacgacg SEQ ID NO: 102 | inactive | |
| Thio-TCG-8 | tcgtcgtcgtcgtcgtcgtcgtcg SEQ ID NO: 103 | 2.1 | 246 |
| Thio-TCGT-6 | tcgttcgttcgttcgttcgttcgt SEQ ID NO: 104 | 7.2 | 256 |
| Thio-TCGC-6 | tcgctcgctcgctcgctcgctcgc SEQ ID NO: 105 | 3.0 | 238 |
| Thio-TCGA-6 | tcgatcgatcgatcgatcgatcga SEQ ID NO: 106 | 12.4 | 302 |
| Thio-TCGG-6 | tcggtcggtcggtcggtcggtcgg SEQ ID NO: 107 | 4.0 | 226 |
| Thio-CCGT-6 | ccgtccgtccgtccgtccgtccgt SEQ ID NO: 108 | 2.2 | 131 |
| Thio-ACGT-6 | acgtacgtacgtacgtacgtacgt SEQ ID NO: 109 | 5.9 | 266 |
| Thio-GCGT-6 | gcgtgcgtgcgtgcgtgcgtgcgt SEQ ID NO: 110 | 4.9 | 194 |
| Thio-ACGA-6 | acgaacgaacgaacgaacgaacga SEQ ID NO: 111 | 5.1 | 282 |
| Thio-CCGC-6 | ccgccgccgccgccgccgccgccgc SEQ ID NO: 112 | poorly active* | |
| Thio-GCGC-6 | gcgcgcgcgcgcgcgcgcgcgcgc SEQ ID NO: 113 | poorly active* | |
| Thio-GCGG-6 | gcgggcgggcgggcgggcgggcgg SEQ ID NO: 114 | poorly active* | |

*EC$_{50}$ and V$_{max}$ calculations not possible due to poor activity

It is remarkable that while TCG-8 is highly active, ACG-8 does not show any stimulation of canine TLR9-21 fusion. In this study, the 'SAR' of PTO-ODN TCGT-6 was investigated in detail; the 5'T and then the 3'T was replaced with all other bases. Unexpectedly, all the derivatives proved to be highly active with respect to EC$_{50}$, no dramatic loss of activity could be seen. With respect to V$_a$, a major loss of potency was seen for CCGT-6, a minor one for GCGT-6. The G/C-only containing PTO-ODNs were only marginally active in this assay.

Figure 16:
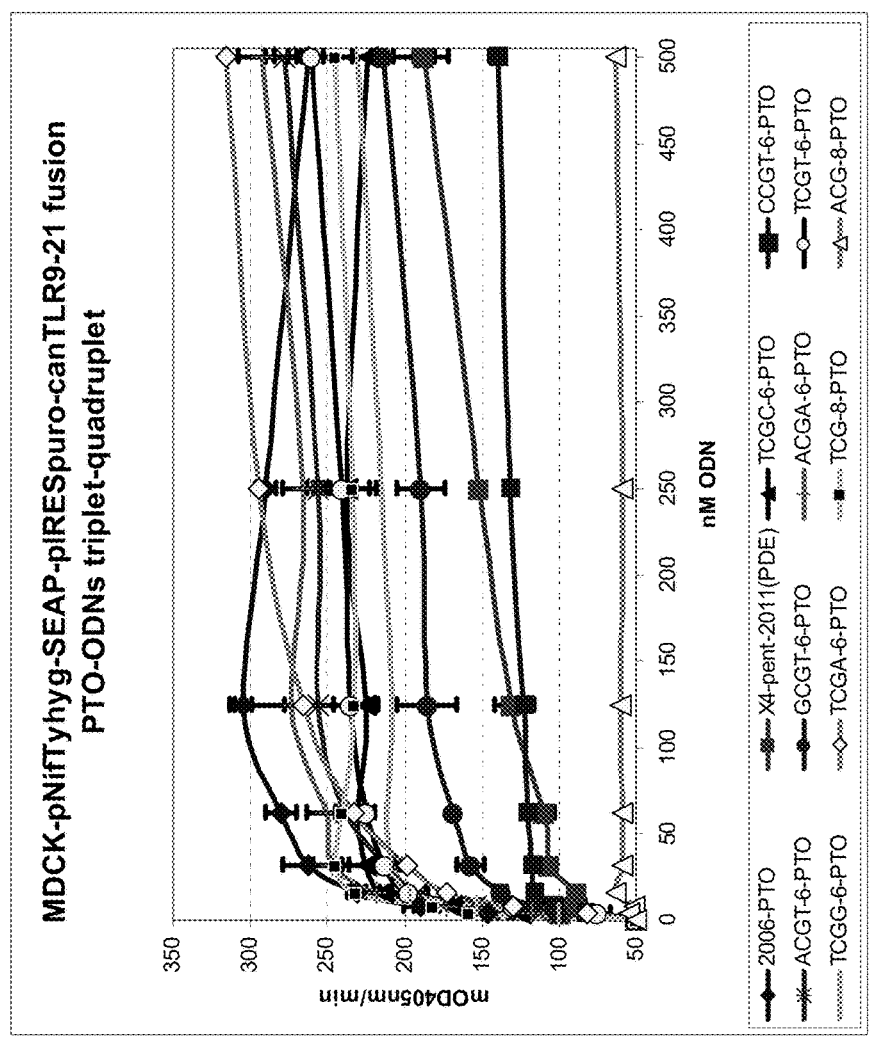
Figure 17:
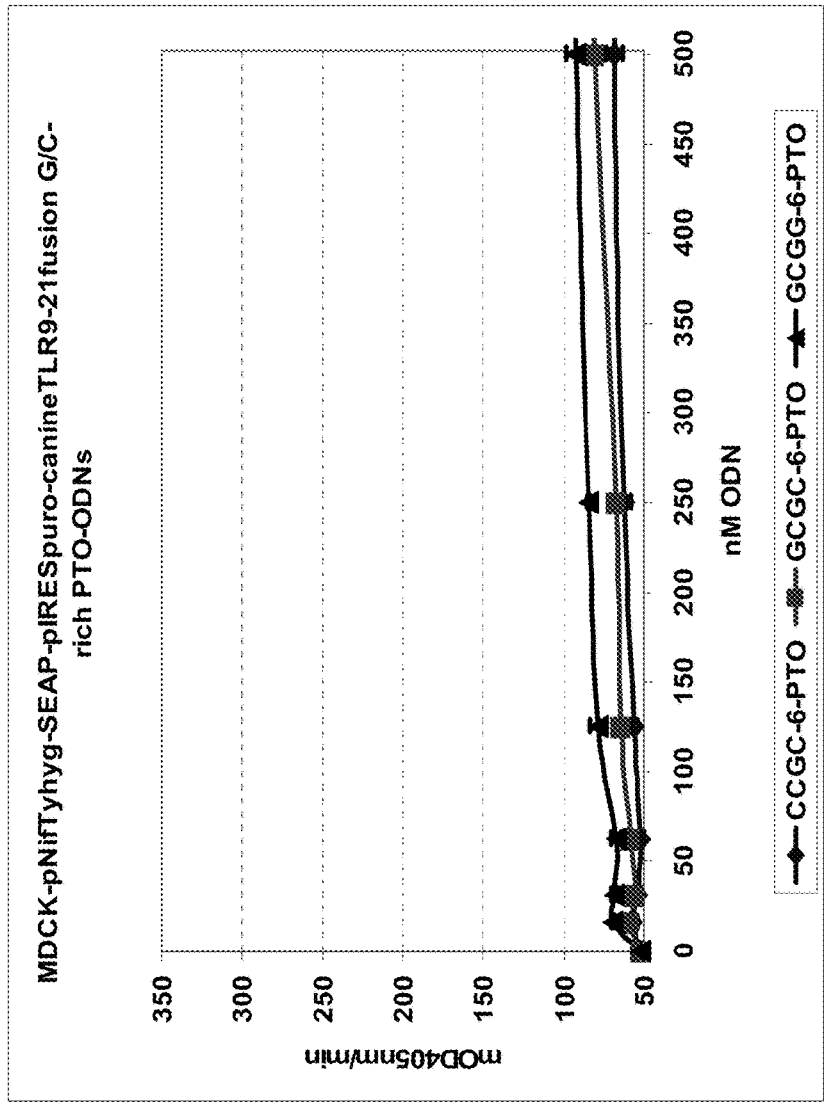

This is the determination of a comprehensive structure-activity relationship for canTLR9-21 based on hexamers of tetranucleotide motifs (see FIGS. 16 and 17).

Figure 18:
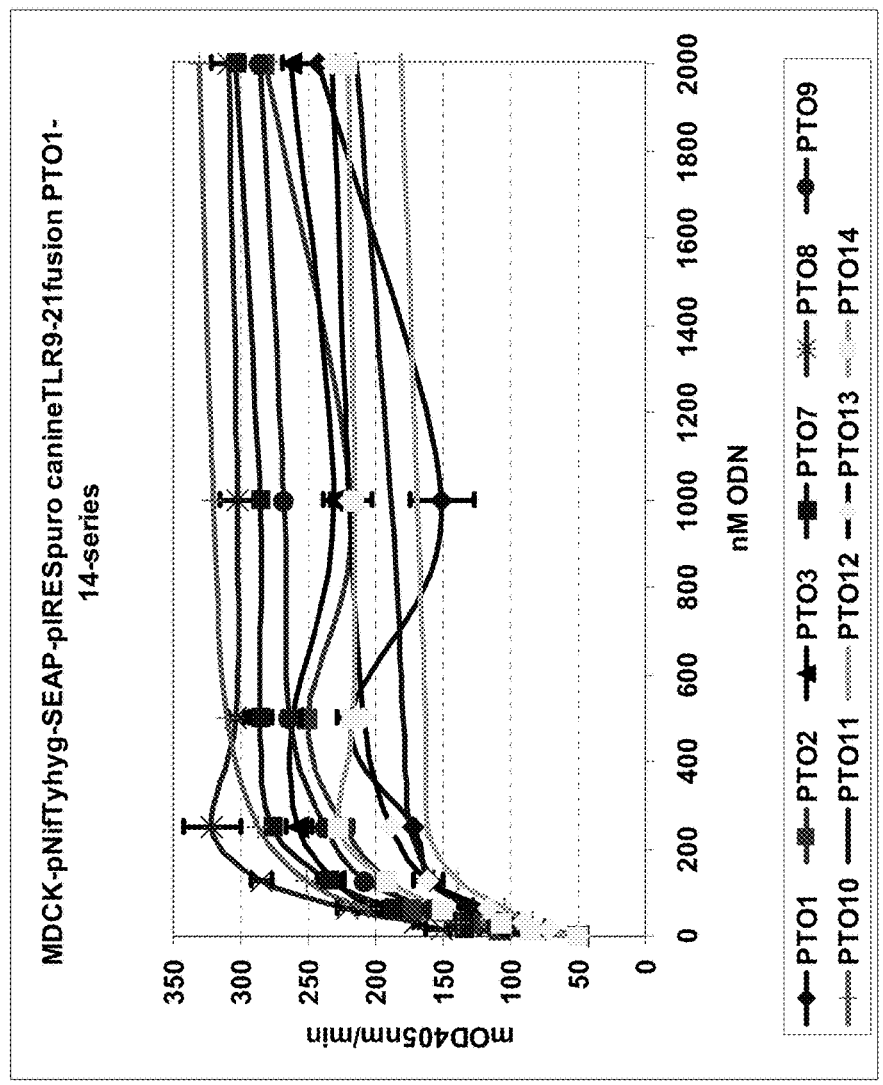
Figure 19:
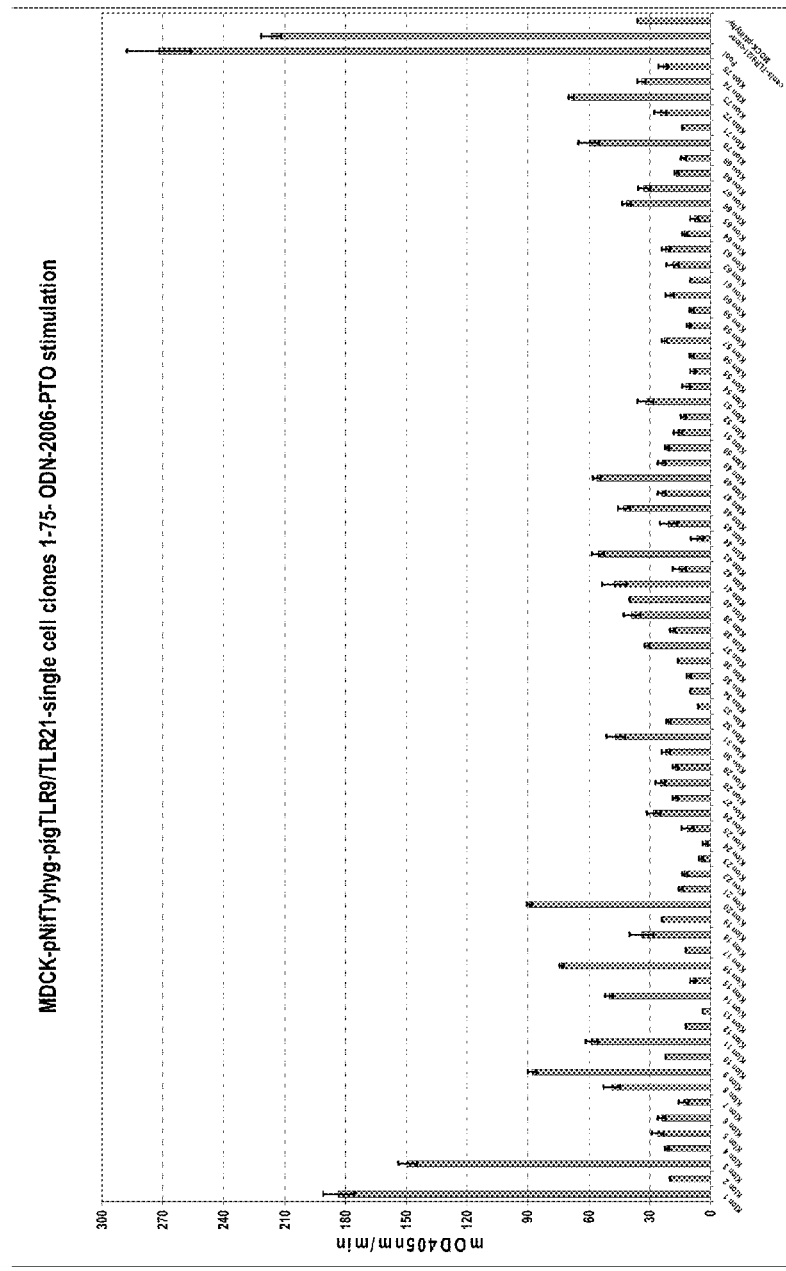
Figure 20:
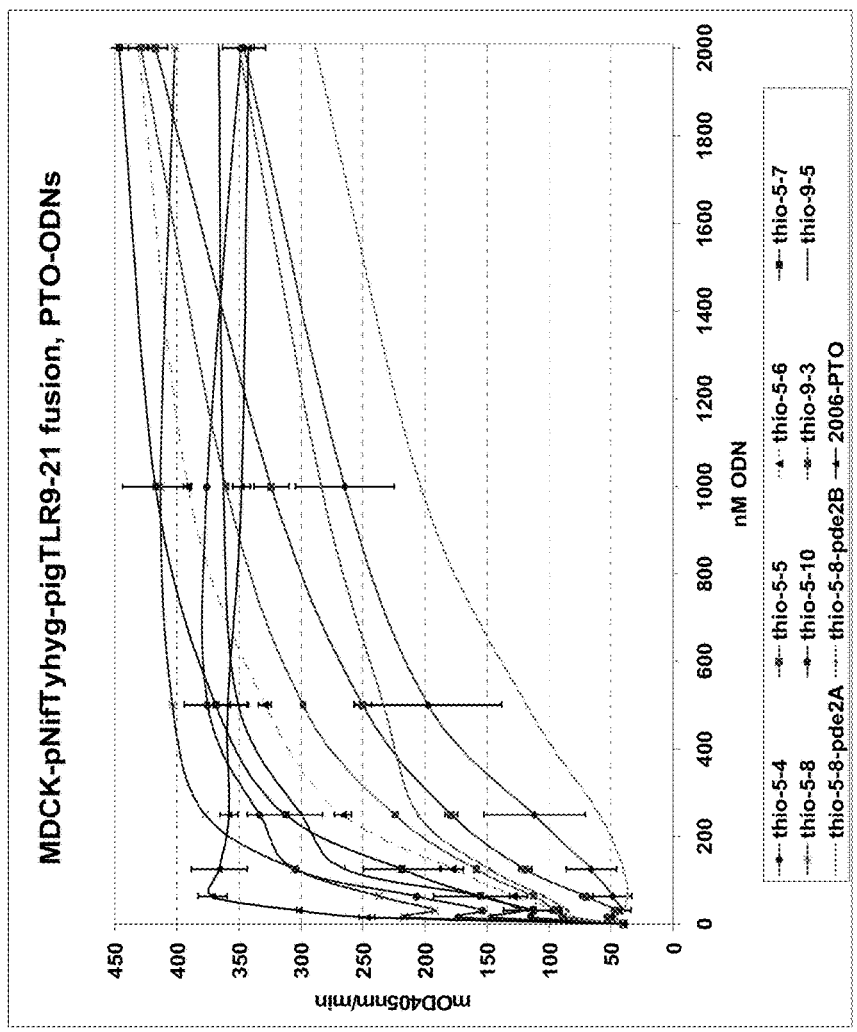
Figure 21:
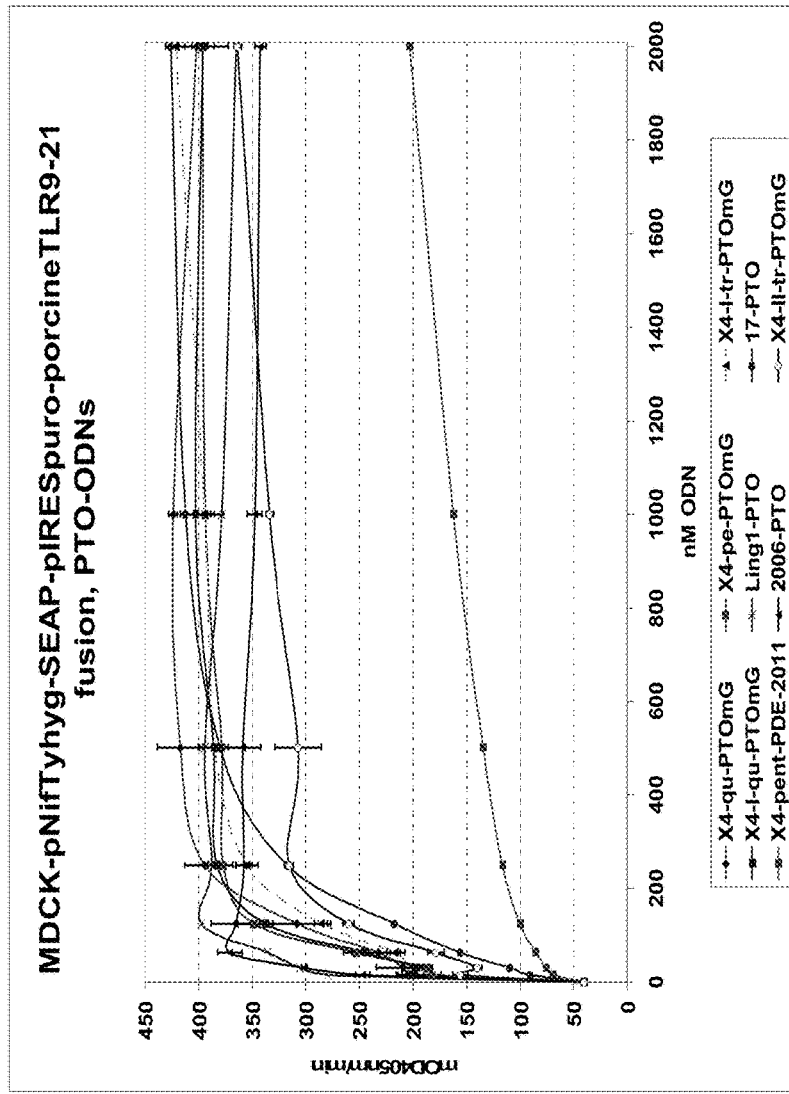

Experiment 11:

In this experiment combinations of immunomodulatory hexamer and tetramer sequences elements were tested for their potency on canine TLR9-21 fusion (see FIG. 18).

| | | $EC_{50}$ (nM) | $V_{max}$ (mOD/min/20 ul) |
|---|---|---|---|
| PTO1 | gtcgtcgtcgtcgtcgtcgtc SEQ ID NO: 115 | 38.2 | 226 |
| PTO2 | gtcgttgtcgttgtcgttgtcgtt SEQ ID NO: 116 | 27.8 | 253 |
| PTO3 | gacgttgacgttgacgttgacgtt SEQ ID NO: 117 | 23.6 | 265 |
| PTO7 | gtcgttgtcgacgtcgttgtcgac SEQ ID NO: 118 | 29.4 | 299 |
| PTO8 | gacgttgtcgttgacgttgtcgtt SEQ ID NO: 119 | 21.7 | 319 |
| PTO9 | tcgtgtcgtttcgtgtcgtttcgt SEQ ID NO: 120 | 47.2 | 286 |
| PTO10 | tcgtgacgtttcgtgacgtttcgt SEQ ID NO: 121 | 41.0 | 335 |
| PTO11 | gtcgtttcgtgtcgtttcgtgtcgtt SEQ ID NO: 122 | 33.9 | 201 |
| PTO12 | gacgtttcgtgacgtttcgtgacgtt SEQ ID NO: 123 | 32.2 | 177 |
| PTP13 | gtcgttgtcgtcgtcgttgtcgtc SEQ ID NO: 124 | 49.7 | 230 |
| PTO14 | gacgttgtcgtcgacgttgtcgtc SEQ ID NO: 125 | 30.2 | 231 |

Conclusion it is shown that MDCK-pNifTyhyg-SEAP-pIRESpuro-canTLR9-21 is a unique screening tool for the identification of canine TLR9 ligands. A number of novel active ODNs has been identified.

Example 7

Transfection of MDCK-pNifTyhyg-SEAP with Porcine TLR9-21 Fusion Constructs
a) Transfection and Selection of Clones MDCK-pNifTyhyg-SEAK-clone 15 was transfected with pIRES-puro-porcineTLR9-21. Transfectants were selected by repeated passage with medium supplemented with 300 µg/ml hygromycin and 8 µg/ml puromycin. Testing of the resulting polyclonal cell line with the standard oligonucleotide ODN-2006-PTO indicated induction of SEAP secretion. Single cell cloning was performed and 75 clones were expanded for further testing with ODN-2006-PTO. A large number of clones were identified that showed induction of SEAP. A number of clones with the best signal-to-noise ratio were chosen for expansion and to generate frozen stabilates. After retesting, clone No 20 was selected for further experiments (see FIG. 19).

b) MDCK-pNifTyhyg-SEAP-pIRESpuro-Porcine TLR9-21-Clone 20: Testing of the Stimulatory Activity of Oligonucleotides Experiment 1:

A series of phosphorothioate oligonucleotides (PTO-ODNs, thio5-4 up to thio 5-10, thio9-3 and thio9-5) was tested, together with the standard oligonucleotides from human medicine, 2006-PTO

| | | $EC_{50}$ (nM) | $V_{max}$ (mOD/min/20 ul) |
|---|---|---|---|
| 2006-PTO | tcgtcgttttgtcgttttgtcgtt SEQ ID NO: 126 | 6.1 | 365 |
| thio5-4 | gtcgtcgtcgtc SEQ ID NO: 127 | 673 | 458 |
| thio5-5 | gtcgtcgtcgtcgtc SEQ ID NO: 128 | 436 | 489 |
| thio5-6 | gtcgtcgtcgtcgtcgtc SEQ ID NO: 129 | 175 | 459 |
| thio5-7 | gtcgtcgtcgtcgtcgtcgtc SEQ ID NO: 130 | 127 | 470 |
| thio5-8 | gtcgtcgtcgtcgtcgtcgtcgtc SEQ ID NO: 131 | 43.2 | 426 |
| thio5-10 | gtcgtcgtcgtcgtcgtcgtcgtcgtcgtc SEQ ID NO: 132 | 45.4 | 388 |
| thio5-8(II) | gtcgtcgtcgtcgtcgtcgtcgtc SEQ ID NO: 133 | 54.9 | 440 |
| thio5-8pde2A | gtCGtCGtCGtCGtCGtCGtCGtc SEQ ID NO: 134 | 1810 | 553 |
| thio5-8pde2B | gtCGtcgtCGtcgtCGtcgtCGtc SEQ ID NO: 135 | 159 | 343 |
| thio9-3 | ttcgtcttcgtcttcgtc SEQ ID NO: 136 | 217 | 214 |
| thio9-5 | ttcgtcttcgtcttcgtcttcgtcttcgtc SEQ ID NO: 137 | 73.9 | 390 |

From this experiments, it can be deduced that the pIRE-Spuro-porcineTLR9-21-expressing MDCK-pNifTyhyg cell line that was generated is capable of defining different potencies via the calculation of $EC_{50}$ values.

It is shown that for immunostimulatory ODNs, with structure elements such as gtcgtc, the number of cg elements is important: 9-7>6>5>4>3 (see table above). This experiment also immediately outlines the potential of this cell line for generation of structure-activity relationships (SAR) and lead optimization of immunostimulatory ODNs.

It was also shows that 2006-PTO known from human research are highly potent on the porcine TLR9-21 fusion protein. Furthermore, the impact of replacement of the complete (thio5-8pde2A) and partial (thio5-8pde2B) phosphorothioate bonds of the CpG elements in thio5-8 was tested. In the inventor's hands the PDE-modified versions were far less active on porcine TLR9-21 fusion than the parental 'PTO-only' ODN. Finally, thio9-3 and thio9-5, which are trimers and tetramers of the motif ttcgtc, respectively were tested. (Results, see FIG. 20).

Experiment 2:

Here some PTO versions of PDE oligonucleotides were tested that proved to be highly active on chicken TLR21, when combined with 5'- and 3' dG runs. The PTO versions, however, lack the 5'- and 3' dG runs (therefore minus G, 'mG')

| | | EC$_{50}$ (nM) | V$_{max}$ (mOD/ min/20 ul) |
|---|---|---|---|
| 2006-PTO | tcgtcgttttgtcgttttgtcgtt SEQ ID NO: 138 | 6.1 | 365 |
| X4qu-PTOmG | ttcgttttcgttttcgttttcgtt SEQ ID NO: 139 | 42.1 | 434 |
| X4pe-PTOmG | ttcgttttcgttttcgttttcgtt ttcgtt SEQ ID NO: 140 | 34.3 | 413 |
| X4-I-tr-PTOmG | tttcgttttttcgttttttcgttt SEQ ID NO: 141 | 46.9 | 419 |
| X4-I-qu-PTOmG | tttcgttttttcgttttttcgttt tttcgttt SEQ ID NO: 142 | 35.8 | 417 |
| X4-II-tr-PTOmG | ttttcgtttttttcgtttttttt cgtttt SEQ ID NO: 143 | 35.5 | 345 |
| ODN-17-PTO | gtcgttgtcgttgtcgtt SEQ ID NO: 144 | 119 | 459 |
| ODN-Ling1-PTO | tcgacgtttgacgtttgacgtt SEQ ID NO: 145 | 8.1 | 391 |
| X4-pent-PDE | GGGGGGGTTCGTTTTCGTTTTCGTT TTCGTTTTCGTTGGGGG SEQ ID NO: 146 | >500 | |

Furthermore, two PTO-ODNs from published reports (ODN17 and ODN-Ling1) were tested. While the X4-X4-I- and X4-II-PTO-derivatives all proved to be potently active with EC50 values between 30 and 50 nM, X4-pent-PDE, which is highly potent on chicken TLR21 proved to be a poor stimulator, both with respect to EC$_{50}$ and prospective V$_{max}$. Interestingly, while ODN-17-PTO (a gtcgtt triplett) had an EC50 above 100 nM, ODN-Ling1-PTO proved to be as active as 2006-PTO (see FIG. 21).

Experiment 3:
In this experiment repeats of triplet and quadruplet elements were tested for their potency on porcine TLR9-21 fusion.

| | | EC$_{50}$ (nM) | V$_{max}$ (mOD/ min/20 ul) |
|---|---|---|---|
| 2006-PTO | tcgtcgttttgtcgttttgtcgtt SEQ ID NO: 101 | 6.1 | 365 |
| Thio-ACG-8 | acgacgacgacgacgacgacg SEQ ID NO: 102 | poorly active* | |
| Thio-TCG-8 | tcgtcgtcgtcgtcgtcgtcg SEQ ID NO: 103 | 61.8 | 246 |
| Thio-TCGT-6 | tcgttcgttcgttcgttcgttcgt SEQ ID NO: 104 | 3.7 | 256 |
| Thio-TCGC-6 | tcgctcgctcgctcgctcgctcgc SEQ ID NO: 105 | 50.9 | 238 |
| Thio-TCGA-6 | tcgatcgatcgatcgatcgatcga SEQ ID NO: 106 | 104.9 | 302 |
| Thio-TCGG-6 | tcggtcggtcggtcggtcggtcgg SEQ ID NO: 107 | 56.0 | 226 |
| Thio-CCGT-6 | ccgtccgtccgtccgtccgtccgt SEQ ID NO: 108 | 568.0 | 131 |
| Thio-ACGT-6 | acgtacgtacgtacgtacgtacgt SEQ ID NO: 109 | 163.2 | 266 |
| Thio-GCGT-6 | gcgtgcgtgcgtgcgtgcgtgcgt SEQ ID NO: 110 | 85.1 | 194 |
| Thio-ACGA-6 | acgaacgaacgaacgaacgaacga SEQ ID NO: 111 | 72.1 | 282 |
| Thio-CCGC-6 | ccgcccgcccgcccgcccgcccgc SEQ ID NO: 112 | poorly active* | |
| Thio-GCGC-6 | gcgcgcgcgcgcgcgcgcgcgcgc SEQ ID NO: 113 | poorly active* | |
| Thio-GCGG-6 | gcgggcgggcgggcgggcgggcgg SEQ ID NO: 114 | poorly active* | |

*EC$_{50}$ and V$_{max}$ calculations not possible due to poor activity

ACG-8 does not show only minor stimulation of porcine TLR9-21 fusion, while TCG-8 has an EC50 of ~62 nM. In this study, the 'SAR' of PTO-ODN TCGT-6 was investigated in detail; the 5'T and then the 3'T was replaced with all other bases. It turned out that with respect to EC$_{50}$, TCGT-6 was clearly the best derivative, performing even better than the standard 2006-PTO. Like for canTLR9-21, with respect to V$_{max}$, a major loss of potency on porcineTLR9-21 was seen for CCGT-6, a minor one for GCGT-6. The G/C-only containing PTO-ODNs were only marginally active in this assay, with GCGC-6 being the best one.

Figure 22:
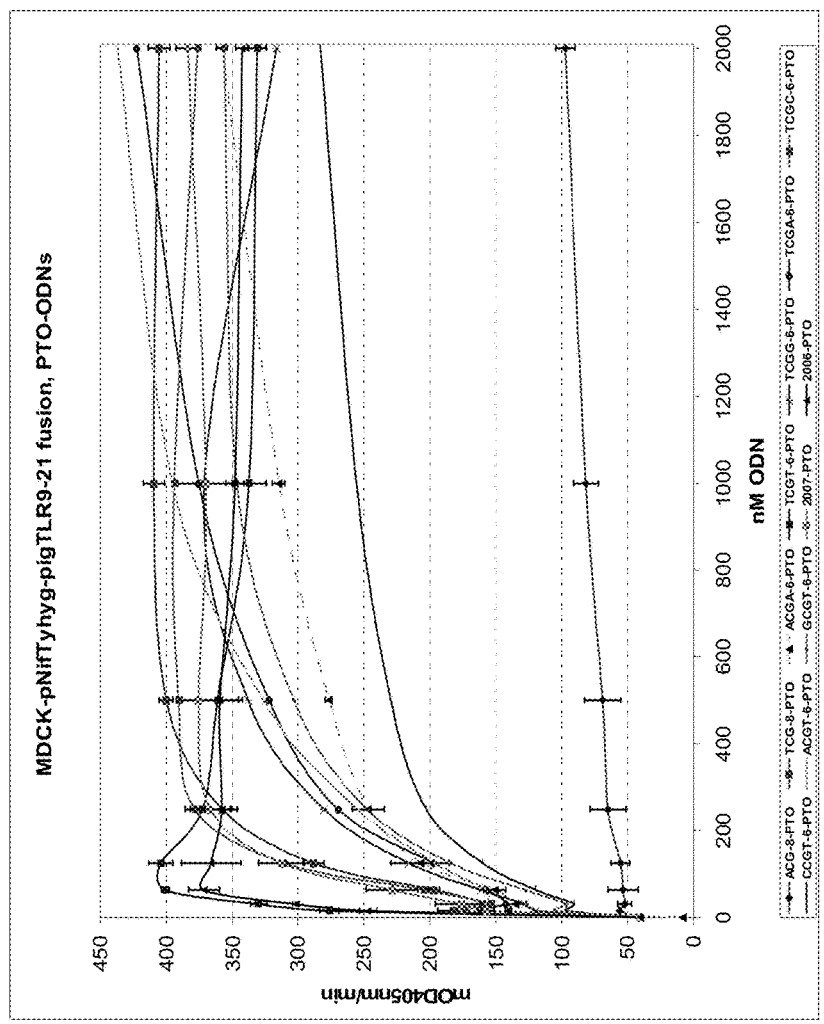
Figure 23:
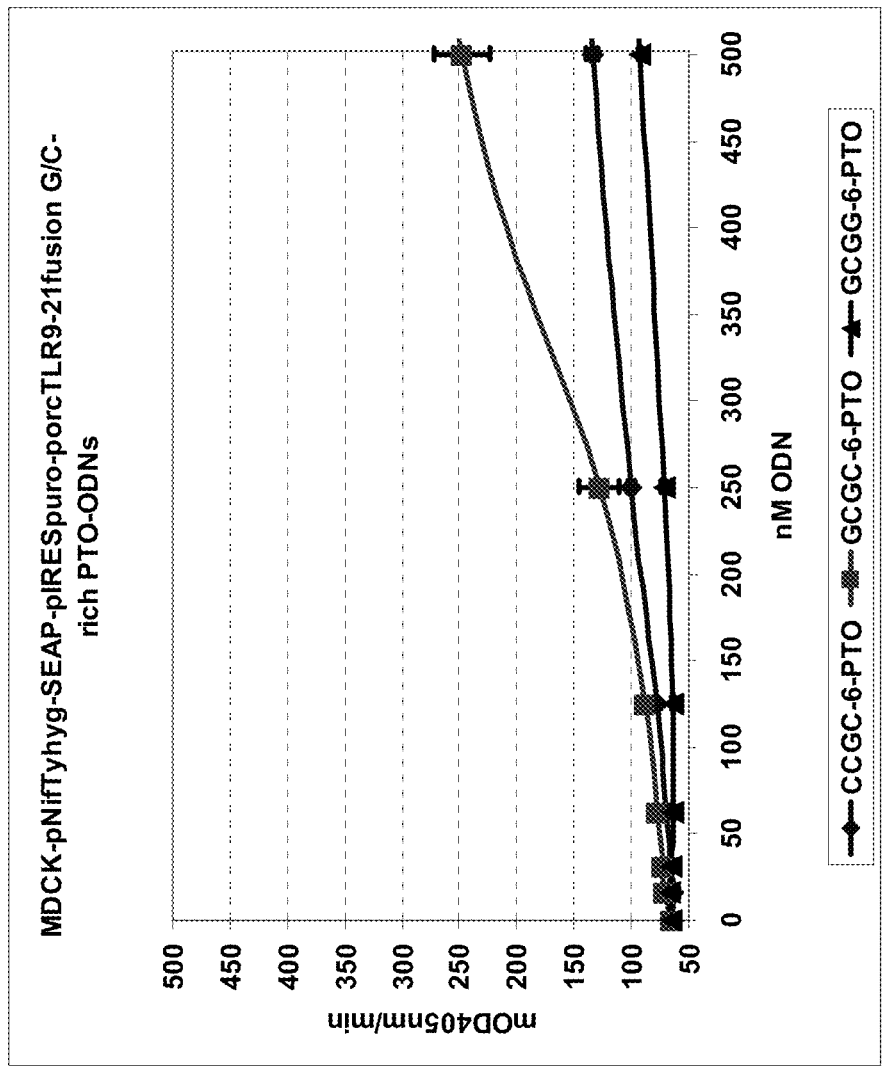

This is the determination of a comprehensive structure-activity relationship for porcineTLR9-21 based on hexamers of tetranucleotide motifs (see FIGS. 22 and 23).

Experiment 4:
Here a lead optimization was attempted based upon possibly active elements form the published oligonucleotides 1668-PTO, 2216-PTO and 2395-PTO. These 'active elements' are underlined and/or in Italic in the parental ODN and then arranged in repeats in the mod1/2 ODNs:

| | | EC$_{50}$ (nM) | V$_{max}$ (mOD/ min/20 ul) |
|---|---|---|---|
| 2006-PTO | tcgtcgttttgtcgttttgtcgtt SEQ ID NO: 40 | 6.7 | 410 |
| 2007-PTO | tcgtcgttttgtcgttttgtcgtt SEQ ID NO: 41 | 27.3 | 376 |
| 1668-PTO | tcca*tgacgtt*cctgatgct SEQ ID NO: 54 | 17.0 | 388 |
| 1668-mod1 | gacgttgacgttgacgttgacgtt SEQ ID NO: 55 | 10.0 | 457 |
| 1668-mod2 | tgacgttctgacgttctgacgttc tgacgttc SEQ ID NO: 56 | 16.5 | 434 |
| 2216-PTO | gggg*gacgatcgt*cggggg SEQ ID NO: 57 | 249.0 | 361 |
| 2216-mod1 | gacgatcgtcgacgatcgtc SEQ ID NO: 58 | 53.1 | 447 |
| 2216-mod2 | gacgatcgtcgacgatcgtcgacg atcgtc SEQ ID NO: 59 | 19.0 | 448 |

-continued

|  |  | EC$_{50}$ (nM) | V$_{max}$ (mOD/ min/20 ul) |
|---|---|---|---|
| 2395-PTO | tcgtcgttttcggcgcgccg SEQ ID NO: 60 | 16.7 | 301 |
| 2395-mod1 | tcgtcgttttcgtcgtcgttttcg SEQ ID NO: 61 | 15.1 | 391 |
| 2395-mod2 | tcgtcgttttcgtcgtcgttttcg tcgtcgttttcg SEQ ID NO: 62 | 12.3 | 407 |

Figure 24:
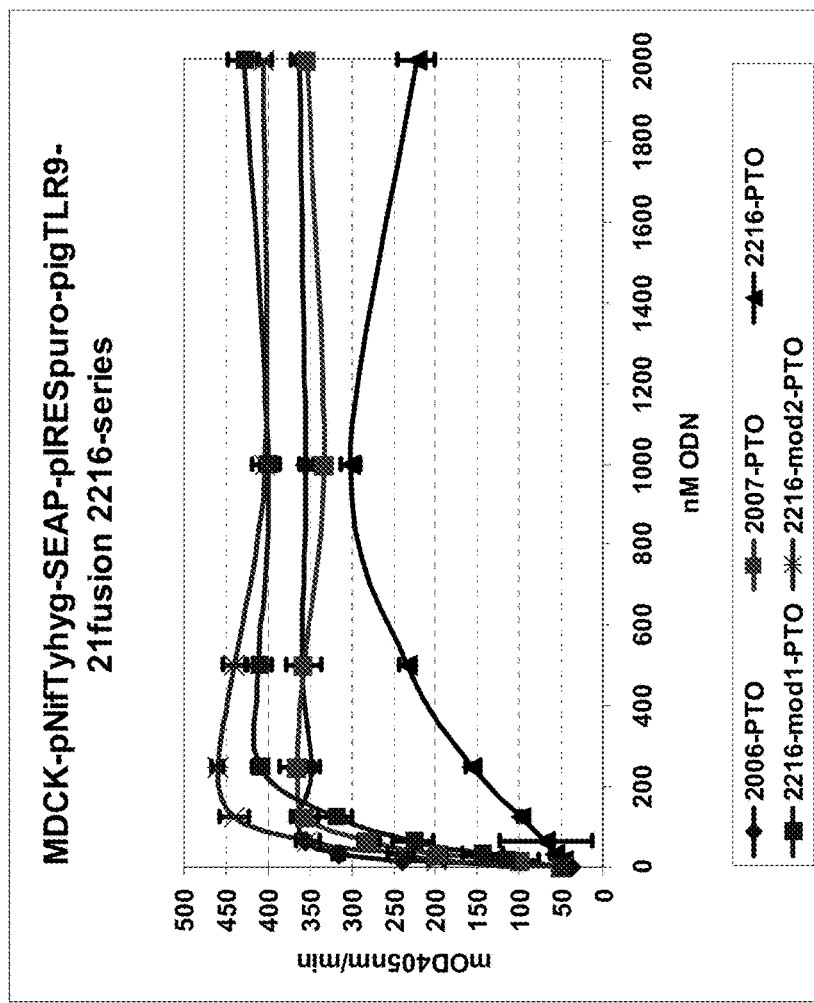
Figure 25:
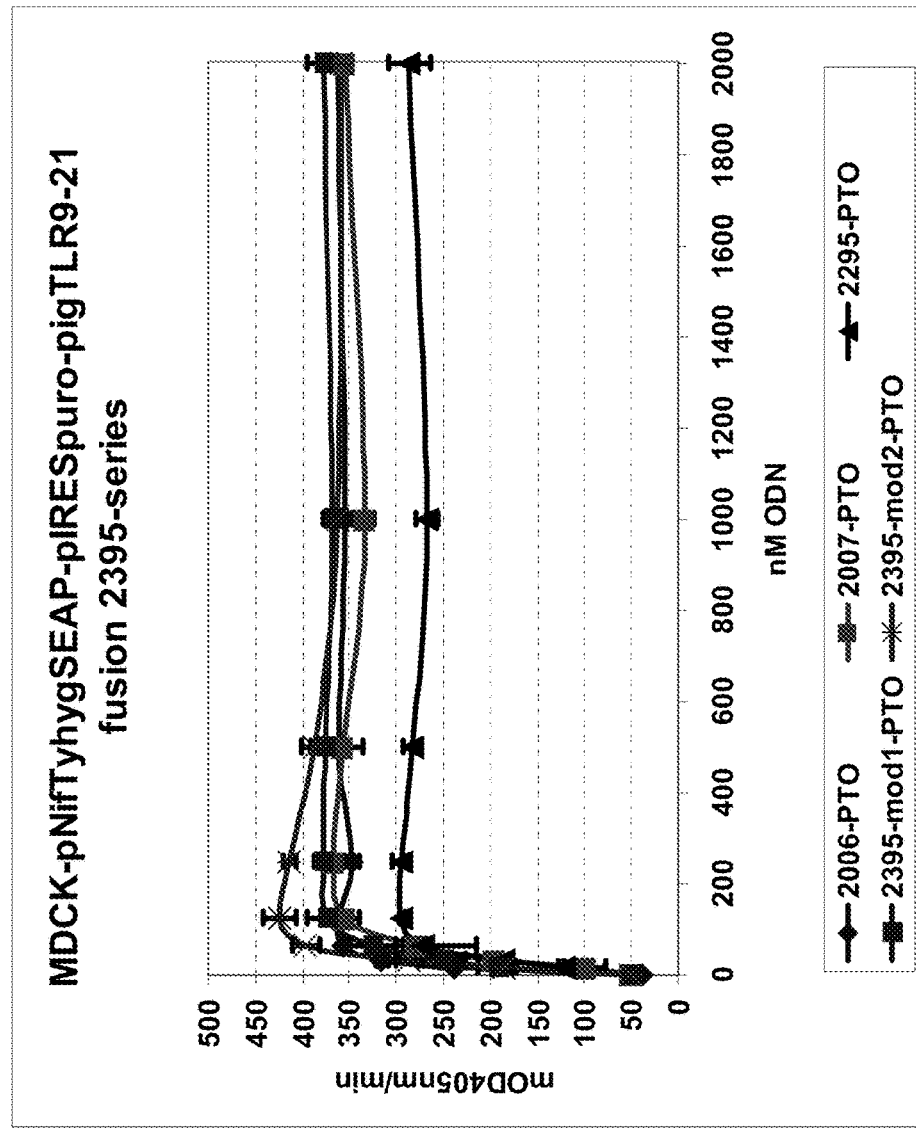
Figure 26:
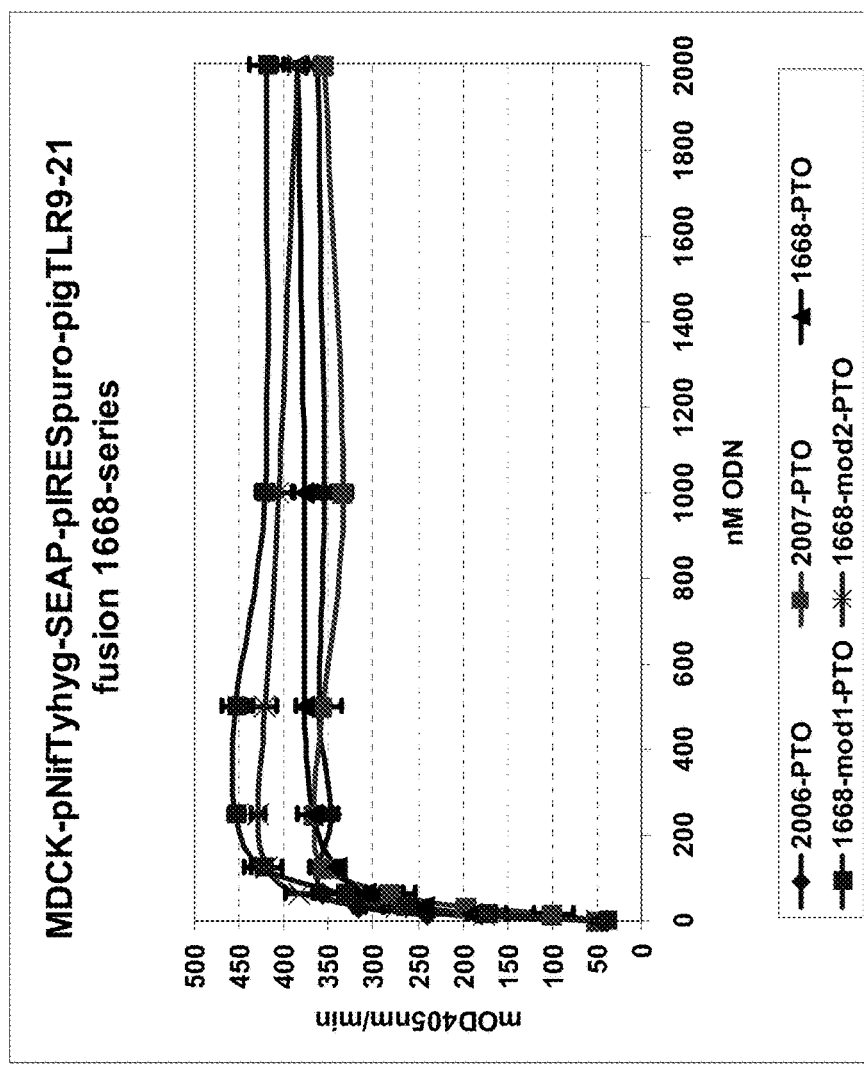

Results: see FIGS. 24, 25 and 26.

Experiment 5:

In this experiment repeats of the frequently used immunostimulatory elements gacgtt and gtcgtt were tested for their potency on porcine TLR9-21 fusion.

|  |  | EC$_{50}$ (nM) | V$_{max}$ (mOD/ min/20 ul) |
|---|---|---|---|
| 2006-PTO | tcgtcgttttgtcgttttgt cgtt SEQ ID NO: 40 | 6.7 | 410 |
| GACGTT-18-PTO | gacgttgacgttgacgtt SEQ ID NO: 55 | 60.2 | 405 |
| GACGTT-24-PTO | gacgttgacgttgacgttgac gtt SEQ ID NO: 95 | 34.0 | 421 |
| GACGTT-30-PTO | gacgttgacgttgacgttgac gttgacgtt SEQ ID NO: 96 | 30.2 | 399 |
| GTCGTT-18-PTO | gtcgttgtcgttgtcgtt SEQ ID NO: 97 | 34.6 | 325 |
| GTCGTT-24-PTO | gtcgttgtcgttgtcgttgtc gtt SEQ ID NO: 98 | 20.0 | 354 |
| GTCGTT-30-PTO | gtcgttgtcgttgtcgttgtc gttgtcgtt SEQ ID NO: 99 | 21.6 | 347 |
| X4-pent-PDE | GGGGGGGTTCGTTTTCGTTTTC GTTTTCGTTTTCGTTGGGGG SEQ ID NO: 146 | >500 | — |

Figure 27:
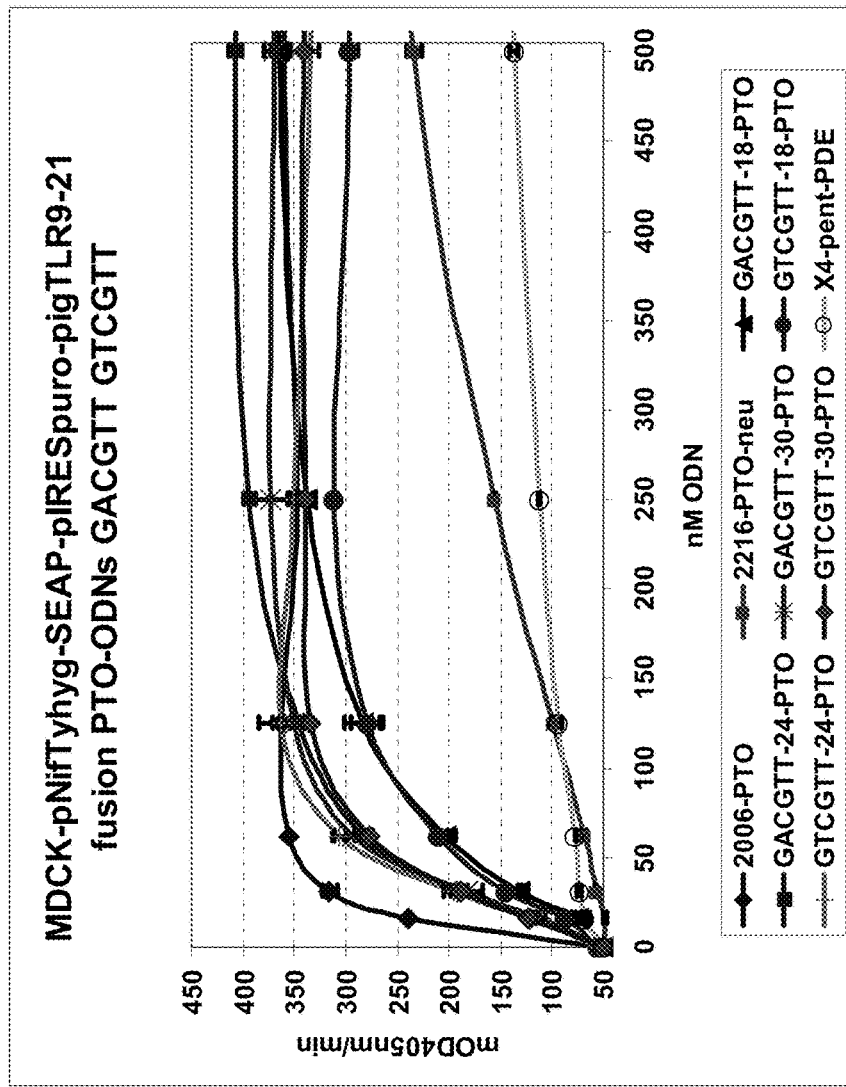

Results: see FIG. 27.

Experiment 6:

Here a 'lead optimization' was attempted based upon possible active elements form the published oligonucleotide 2007-PTO.

|  |  | EC$_{50}$ (nM) | V$_{max}$ (mOD/ min/20 ul) |
|---|---|---|---|
| 2006-PTO | tcgtcgttttgtcgtttt- gtcgtt SEQ ID NO: 63 | 6.7 | 410 |
| 2007-PTO | tcgtcgttgtcgtttgtcgtt SEQ ID NO: 64 | 27.3 | 378 |
| 2007-mod1 | tcgtcgttgtcgttttgtcgtt gtcgtt SEQ ID NO: 65 | 32.7 | 439 |
| 2007-mod2 | tcgtcgtcgtcgttgtcgtttt gtcgtt SEQ ID NO: 66 | 28.5 | 436 |
| 2007-mod3 | tcgtcgtcgtcgttgtcgtttt gtcgttgtcgtt SEQ ID NO: 67 | 31.7 | 425 |
| 2007-dimer | tcgtcgttgtcgttttgtcgtt tcgtcgttgtcgttttgtcgtt SEQ ID NO: 68 | 8.9 | 351 |

Figure 28:
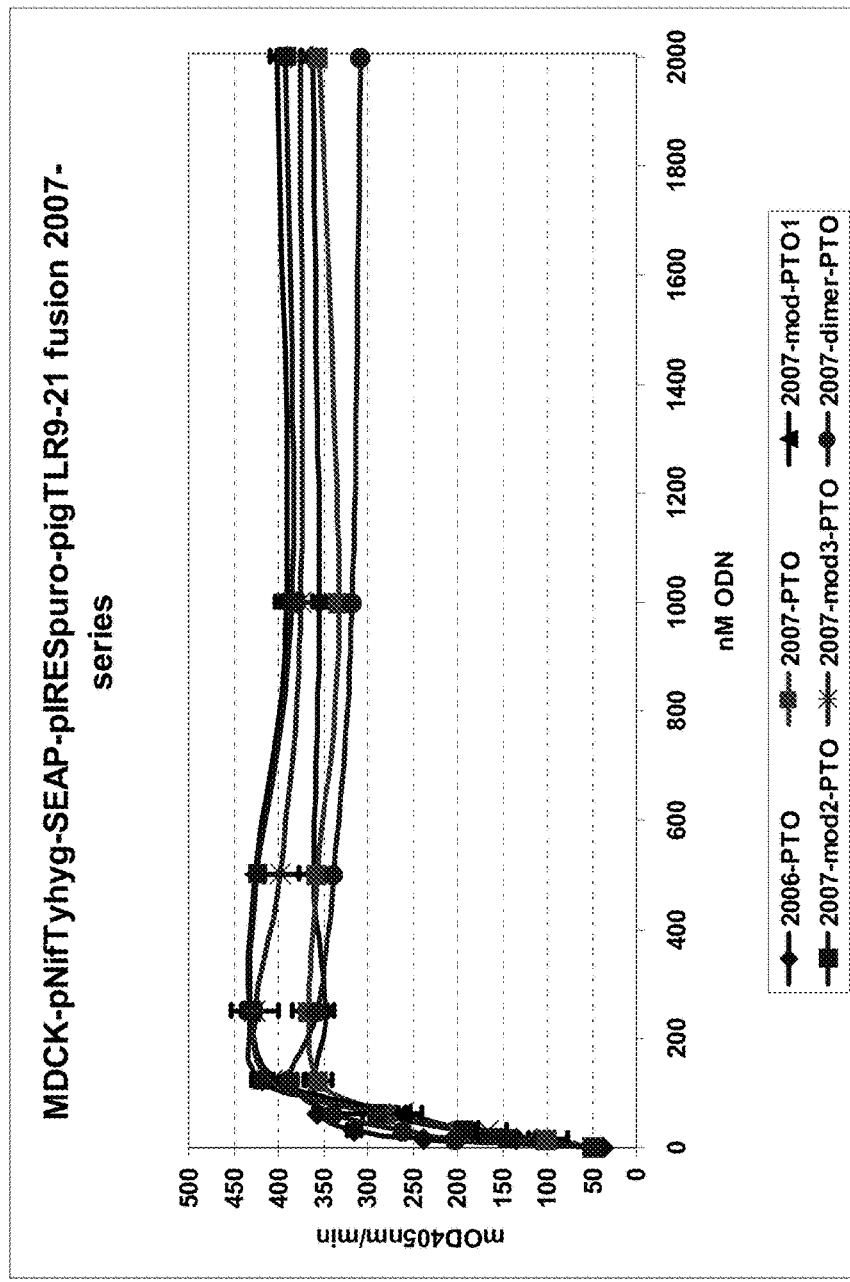
Figure 29:
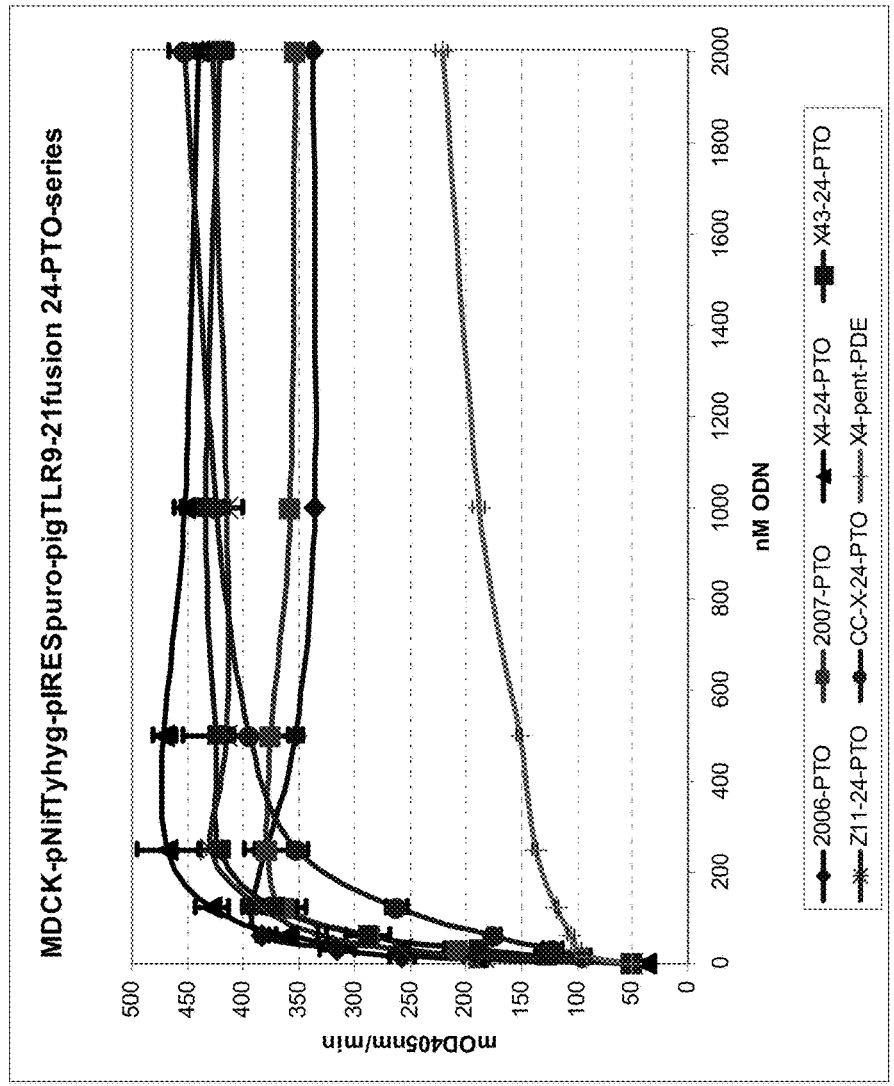
Figure 30:
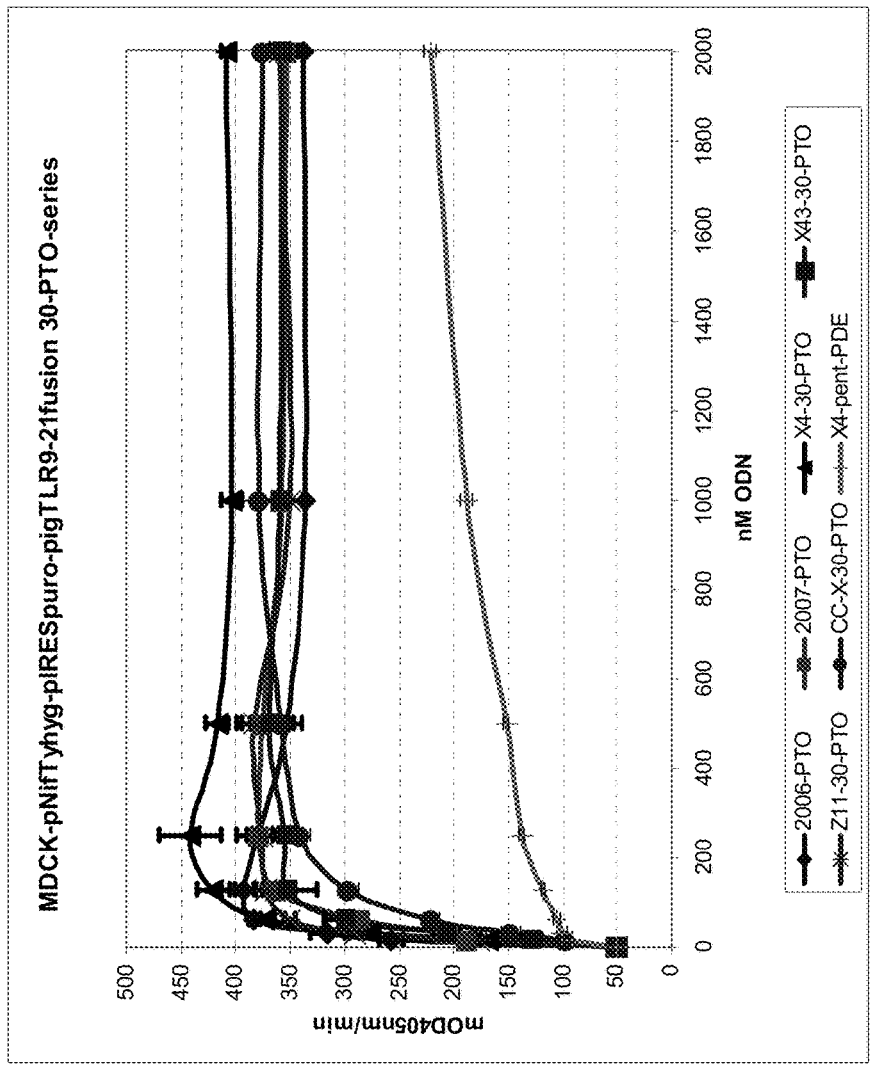

Results: see FIG. 28.

Experiment 7:

Further series of PTO-ODNs based on the active elements (chicken TLR21) of ODNs X4, X43, Z11 and CC-X were tested for their potency on porcine TLR9-21 fusion

|  |  | EC$_{50}$ (nM) | V$_{max}$ (mOD/ min/20 ul) |
|---|---|---|---|
| 2006-PTO | tcgtcgttttgtcgttttgtcgtt SEQ ID NO: 63 | 5.1 | 369 |
| X4-24-PTO | ttcgttttcgttttcgttttcgtt SEQ ID NO: 78 | 22.5 | 479 |
| X43-24-PTO | ttcgtcttcgtcttcgtcttcgtc SEQ ID NO: 74 | 36.9 | 454 |
| Z11-24-PTO | ctcgtcctcgtcctcgtcctcgtc SEQ ID NO: 86 | 20.8 | 498 |
| CC-X-24-PTO | ttcgccttcgccttcgccttcgcc SEQ ID NO: 87 | 92.2 | 469 |
| X4-30-PTO | ttcgttttcgttttcgttttcgtt ttcgtt SEQ ID NO: 88 | 24.4 | 447 |
| X43-30-PTO | ttcgtcttcgtcttcgtcttcgtc ttcgtc SEQ ID NO: 89 | 23.9 | 383 |
| Z11-30-PTO | ctcgtcctcgtcctcgtcctcgtc ctcgtc SEQ ID NO: 90 | 12.6 | 385 |
| CC-X-30-PTO | ttcgccttcgccttcgccttcgcc ttcgcc SEQ ID NO: 91 | 47.3 | 395 |

Most new PTO-oligonucleotides have high stimulatory activity (EC$_{50}$ in the single digit nanomolar range) and comparable V$_{ma}$, on porcine TLR9-21. Particularly potent appears to be the motif of Z11 (ctcgtc). None of these PTO-ODNs has been mentioned yet in the context porcine (see FIGS. 29 and 30).

Experiment 8:

In this experiment combinations of immunomodulatory hexamer and tetramer sequences elements were tested for their potency on porcine TLR9-21 fusion.

|  |  | EC$_{50}$ (nM) | V$_{max}$ (mOD/ min/20 ul) |
|---|---|---|---|
| PTO1 | gtcgtcgtcgtcgtcgtcgtc SEQ ID NO: 115 | 55.9 | 499 |

| | | EC$_{50}$ (nM) | V$_{max}$ (mOD/min/20 ul) |
|---|---|---|---|
| PTO2 | gtcgttgtcgttgtcgttgtcgtt SEQ ID NO: 116 | 28.0 | 472 |
| PTO3 | gacgttgacgttgacgttgacgtt SEQ ID NO: 117 | 49.1 | 503 |
| PTO7 | gtcgttgtcgacgtcgttgtcgac SEQ ID NO: 118 | 23.7 | 460 |
| PTO8 | gacgttgtcgttgacgttgtcgtt SEQ ID NO: 119 | 38.5 | 442 |
| PTO9 | tcgtgtcgtttcgtgtcgtttcgt SEQ ID NO: 120 | 35.6 | 460 |
| PTO10 | tcgtgacgtttcgtgacgtttcgt SEQ ID NO: 121 | 22.4 | 427 |
| PTO11 | gtcgtttcgtgtcgtttcgtgtcgtt SEQ ID NO: 122 | 38.8 | 438 |
| PTO12 | gacgtttcgtgacgtttcgtgacgtt SEQ ID NO: 123 | 63.8 | 469 |
| PTP13 | gtcgttgtcgtcgtcgttgtcgtc SEQ ID NO: 124 | 45.9 | 456 |
| PTO14 | gacgttgtcgtcgacgttgtcgtc SEQ ID NO: 125 | 42.4 | 479 |

Figure 31:
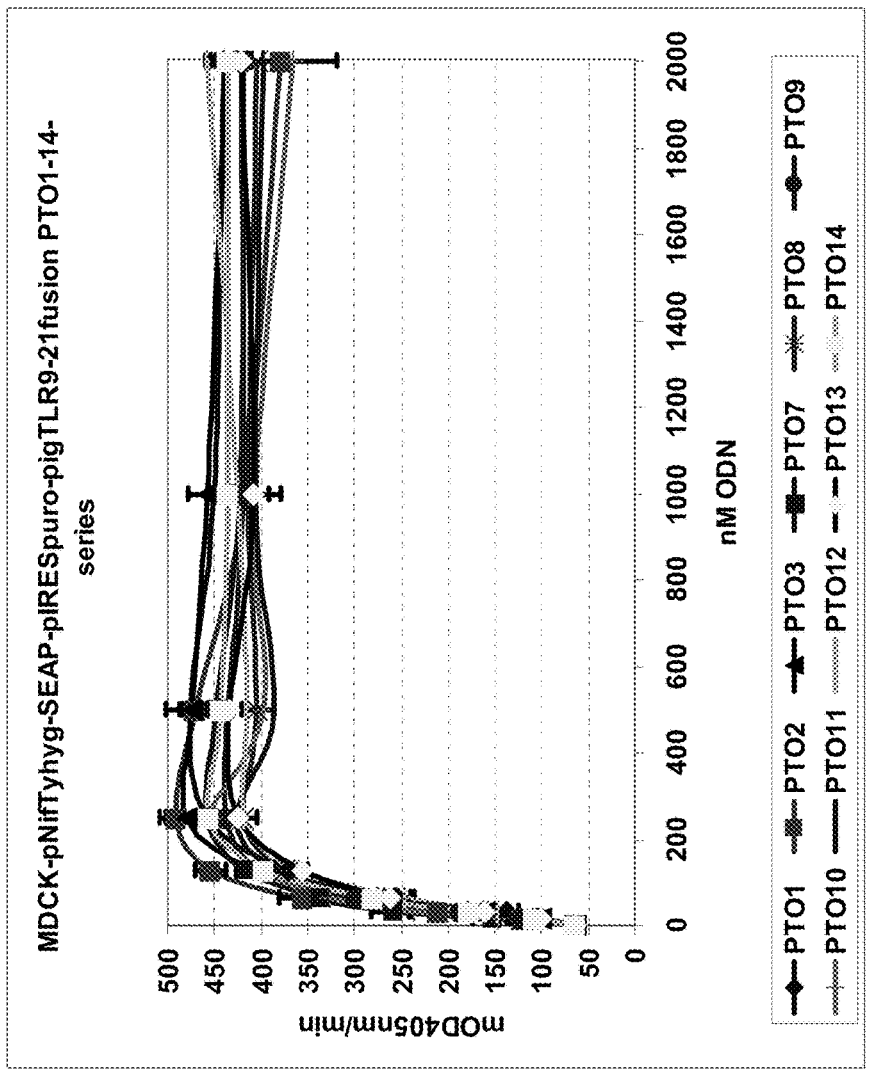

In this experiment, various combinations of gtcgtc-, gtcgtt-, gtcgac- and tcgt-containing PTO-ODNs proved to be of similar double digit nanomolar potency on porcine TLR9-21 (see FIG. 31).

Example 8

Experimental Design

Two groups of five (N=5) Beagle puppies of 3-4 months of age, not vaccinated against Rabies, of which the bitches were not vaccinated the past 12 month against Rabies were used. The puppies were vaccinated with 1 ml of the respective vaccine compositions. Immediately before vaccination (T=0) and at T=2, T=4, T=6, T=8, T=12, T=16, T=20 and T=24 weeks post vaccination, blood samples were taken and the antibody titers against Rabies virus were determined.

Groups and Vaccination

| Group | N = | Vaccine | Dose volume | Immunostimulator Supplement | Concentration |
|---|---|---|---|---|---|
| 1 | 5 | Nobivac ® Rabies | 1 ml | — | — |
| 2 | 5 | Nobivac ® Rabies | 1 ml | Thio-tcg-8-PTO | 5 µg/1 dose |

Vaccine

Nobivac® Rabies

Formulation: commercially available vaccine

Presentation: 10 ml flacons

Supplier: Intervet International BV, Boxmeer, The Netherlands

Dosage and Administration

The puppies were vaccinated subcutaneously (s.c.) in the neck with 1 ml of Nobivac® Rabies vaccine with (group 2) or without (group 1) the addition of 5 µg Thio-tcg-8-PTO (TCGTCGTCGTCGTCGTCGTCGTCG) [SEQ ID NO: 103] per 1 ml.

Induction of Antibodies

Directly before vaccination (T=0) and at T=2, T=4, T=6, T=8, T=12, T=16, T=20 and T=24 weeks post vaccination, blood samples were taken from each puppy. Blood samples were allowed to clot over night at 2-8° C. After centrifugation the serum was transferred into appropriate containers and stored at −20° C. until analysis. The antibody titer against Rabies in the serum was determined using the Rapid Fluorescent Focus Inhibition Test (RFFIT) which is a virus neutralization test.

Rapid Fluorescent Focus Inhibition Test (RFFIT)

RFFIT has been internationally recognized as the standard in vitro test for quantifying the presence of Rabies neutralizing antibodies. Serial 3-fold dilutions of the sera to be examined were made and mixed with an equal volume of a Rabies virus-suspension containing a standard dose (according to WHO/PHEUR with a titer between 30-300 Focus Forming Units (FFU)). The sera/virus mixture were incubated at 37° C. and 5% $CO_2$ for 90 minutes. To grow non-neutralized virus after a pre-incubation period, susceptible cells (BHK cells) were added into the mixture and incubated for 24 hour at 37° C. and 5% $CO_2$ to form a monolayer. After incubation and Rabies virus specific immuno-staining, the monolayers were observed for fluorescent foci by microscopy after which the titers (in IU/ml) were calculated.

Results:

As can be seen from FIG. 32, the anti-rabies virus titre found in dogs that received the Nobivac rabies vaccine and the CpG ODN Thio-tcg-8-PTO (TCGTCGTCGTCGTCGTCGTCGTCG) [SEQ ID NO: 103] is three times the amount of that of the same rabies vaccine without this CpG ODN.

The invention claimed is:

1. An immunostimulatory non-methylated phosphorothioate (PTO) oligodeoxynucleotide consisting of the general formula selected from the group consisting of:
   (i) [tcgN1]$_n$, wherein N1=c or g and n≥6 and ≤100;
   (ii) [N1cgt]$_n$, wherein N1=g or c or a or t and n≥6 and ≤100;
   (iii) [gacgtt]$_n$, wherein n≥4 and ≤100;
   (iv) [gacgatcgtc]$_n$, [SEQ ID NO: 214] wherein n≥3 and ≤100;
   (v) [tcgtcgttttcg]$_n$, [SEQ ID NO: 215] wherein n≥3 and ≤100,
   (vi) [tcgtcgttgtcgttttgtcgtt]$_n$, [SEQ ID NO: 216] wherein n≥2 and ≤100;
   (vii) (t$_x$[ttcgtt]t$_y$)$_n$, wherein n≥5 and ≤100, x=0-5 and y=0-5;
   (viii) [ttcgtN$_1$]$_n$, wherein N$_1$=t or c and wherein n≥5 and ≤100;
   (ix) [N$_1$tcgtc]$_n$, wherein N$_1$=t or c and wherein n≥5 and ≤100;
   (x) [gN$_1$cgtt]$_n$, wherein n≥4 and ≤100 and N$_1$=a or t; and
   (xi) [acga]$_n$, and wherein n≥6 and ≤100.

2. The oligodeoxynucleotide claim 1, wherein said oligodeoxynucleotide is coupled to a carrier or hapten.

3. A vector comprising the oligodeoxynucleotide of claim 1.

4. A method of preventing or combating an infectious disease in a canine, by administering a vaccine to the canine in need thereof, wherein said vaccine comprises an immunological amount of an antigen component, a pharmaceutically acceptable carrier, and an immunostimulatory amount of a composition selected from the group consisting of an immunostimulatory non-methylated phosphorothioate (PTO) oligodeoxynucleotide consisting of the general formula [tcg]$_n$, the oligodeoxynucleotide consisting of the general formula [tcg]$_n$ coupled to a carrier or hapten, a vector comprising the oligodeoxynucleotide consisting of the general formula [tcg]$_n$, and a vector comprising the oligodeoxynucleotide consisting of the general formula [tcg]$_n$ coupled to a carrier or hapten; and wherein n≥6 and ≤100.

* * * * *

SEQUENCE LISTING

<160> NUMBER OF SEQ ID NOS: 217

<210> SEQ ID NO 1
<211> LENGTH: 3090
<212> TYPE: DNA
<213> ORGANISM: Bos taurus

<400> SEQUENCE: 1 atgggccct actgtgcccc gcaccccctt tctctcctgg tgcaggcggc ggcactggca    60

```
gcggccctgg ccgagggcac cctgcctgcc ttcctgccct gtgagctcca gccccatggt      120
caggtggact gcaactggct gttcctgaag tctgtgccgc acttttcggc tggagccccc      180
cgggccaatg tcaccagcct ctccttaatc tccaaccgca tccaccactt gcatgactct      240
gacttcgtcc acctgtccaa cctgcgggtc ctcaacctca gtggaactg cccgccggcc       300 ggcctcagcc ccatgcactt cccctgccgt atgaccatcg agcccaacac cttcctggct      360
gtgcccaccc tggaggagct gaacctgagc tacaacggca tcacgaccgt gcctgccctg      420
cccagttccc tcgtgtccct gtcgctgagc cacaccagca tcctggtgct aggccccacc      480
cacttcaccg gcctgcacgc cctgcgcttt ctgtacatgg acggcaactg ctactacatg      540 aaccctgcc cgcgggccct ggaggtggcc ccaggcgccc tcctcggcct gggcaacctc       600
acgcacctgt cgctcaagta caacaacctc acggaggtgc ccgccgcct gcccccagc       660 ctggacaccc tgctgctgtc ctacaaccac attgtcaccc tggcacccga ggacctggcc      720
aacctgactg ccctgcgcgt gcttgacgtg ggtgggaact ccgccgctg cgaccacgcc      780 cgcaacccct gcagggagtg cccaaagaac ttccccaagc tgcaccctga caccttcagt      840
cacctgagcc gcctcgaagg cctggtgttg aaggacagtt ctctctacaa actagagaaa      900
gattggttcc gcggcctggg caggctccaa gtgctcgacc tgagtgagaa cttcctctat      960
gactacatca ccaagaccac catcttcaac gacctgaccc agctgcgcag actcaacctg     1020
tccttcaatt accacaagaa ggtgtccttc gcccacctgc acctagcgtc ctcctttggg     1080
agtctggtgt ccctggagaa gctggacatg cacggcatct tcttccgctc cctcaccaac     1140
atcacgctcc agtcgctgac ccggctgccc aagctccaga gtctgcatct gcagctgaac     1200
ttcatcaacc aggcccagct cagcatcttt ggggccttcc cgagcctgct cttcgtggac     1260
ctgtcggaca accgcatcag cggagccgcg acgccagcgg ccgccctggg ggaggtggac     1320
agcagggtgg aagtctggcg attgcccagg ggcctcgctc caggcccgct ggacgccgtc     1380
agctcaaagg acttcatgcc aagctgcaac ctcaacttca ccttggacct gtcacggaac     1440
aacctggtga caatccagca agagatgttt acccgcctct cccgcctcca gtgcctgcgc     1500
ctgagccaca acagcatctc gcaggcggtt aatggctccc agttcgtgcc gctgaccagc     1560
ctgcgagtgc tcgacctgtc ccacaacaag ctggacctgt accatgggcg ctcattcacg     1620
gagctgccgc agctggaggc actggacctc agctacaaca gccagccctt cagcatgcag     1680
ggcgtgggcc acaacctcag cttcgtggcc cagctgcccc cctgcgcta cctcagcctt     1740 gcgcacaatg gcatccacag ccgcgtgtca cagaagctca gcagcgcctc gttgcgcgcc     1800
ctggacttca gcggcaactc cctgagccag atgtgggccg agggagacct ctatctctgc     1860
tttttcaaag gcttgaggaa cctggtccag ctggacctgt ccgagaacca tctgcacacc     1920
ctcctgcctc gtcacctgga caacctgccc aagagcctgc ggcagctgcg tctccgggac     1980
aataacctgg ccttcttcaa ctggagcagc ctgaccgtcc tgccccggct ggaagccctg     2040
gatctggcag gaaaccagct gaaggccctg agcaacggca gcctgccgcc tggcatccgg     2100
ctccagaagc tggacgtgag cagcaacagc atcggcttcg tgatccccgg cttcttcgtc     2160
cgcgcgactc ggctgataga gcttaacctc agcgccaatg ccctgaagac agtggatccc     2220
tcctggttcg gttccttagc agggaccctg aaaatcctag acgtgagcgc caacccgctc     2280
cactgcgcct gcggggcggc cttttgtgac ttcctgctgg agagacagga ggccgtgccc     2340
gggctgtcca ggcgcgtcac atgtggcagt ccgggccagc tccagggccg cagcatcttc     2400
```

```
acacaggacc tgcgcctctg cctggatgag accctctcct tggactgctt tggcctctca    2460
ctgctaatgg tggcgctggg cctggcagtg cccatgctgc accacctctg tggctgggac    2520
ctctggtact gcttccacct gtgtctggcc catttgcccc gacggcggcg gcagcggggc    2580
gaggacaccc tgctctatga tgccttcgtg gtcttcgaca aggtgcagag tgcagtggct    2640
gattgggtgt acaacgagct ccgcgtgcag ctggaggagc gccggggggcg ccgggcgctc    2700 cgcctctgcc tggaggagcg agactggctc cctggtaaga cgctcttcga gaacctgtgg    2760
gcctcggtct acagcagccg caagaccatg ttcgtgctgg accacacgga ccgggtcagc    2820
ggcctcctgc gcgccagctt cctgctggcc cagcagcgcc tgttggagga ccgcaaggac    2880
gtcgtagtgc tggtgatcct cgcccccgcc gcctatcggt cccgctacgt gcggctgcgc    2940
cagcgcctct gccgccagag cgtcctcctc tggccccacc agcccagtgg ccagggtagt    3000
ttctgggcca acctgggcat agccctgacc agggacaacc gtcacttcta taccggaaac    3060
ttctgccggg gccccacgac agccgaatag                                      3090
```

<210> SEQ ID NO 2
<211> LENGTH: 1029
<212> TYPE: PRT
<213> ORGANISM: Bos taurus

<400> SEQUENCE: 2

```
Met Gly Pro Tyr Cys Ala Pro His Pro Leu Ser Leu Leu Val Gln Ala
1               5                   10                  15

Ala Leu Ala Ala Ala Leu Ala Glu Gly Thr Leu Pro Ala Phe Leu
            20                  25                  30

Pro Cys Glu Leu Gln Pro His Gly Gln Val Asp Cys Asn Trp Leu Phe
        35                  40                  45

Leu Lys Ser Val Pro His Phe Ser Ala Gly Ala Pro Arg Ala Asn Val
    50                  55                  60

Thr Ser Leu Ser Leu Ile Ser Asn Arg Ile His His Leu His Asp Ser
65                  70                  75                  80

Asp Phe Val His Leu Ser Asn Leu Arg Val Leu Asn Leu Lys Trp Asn
                85                  90                  95

Cys Pro Pro Ala Gly Leu Ser Pro Met His Phe Pro Cys Arg Met Thr
            100                 105                 110

Ile Glu Pro Asn Thr Phe Leu Ala Val Pro Thr Leu Glu Glu Leu Asn
        115                 120                 125

Leu Ser Tyr Asn Gly Ile Thr Thr Val Pro Ala Leu Pro Ser Ser Leu
    130                 135                 140

Val Ser Leu Ser Leu Ser His Thr Ser Ile Leu Val Leu Gly Pro Thr
145                 150                 155                 160

His Phe Thr Gly Leu His Ala Leu Arg Phe Leu Tyr Met Asp Gly Asn
                165                 170                 175

Cys Tyr Tyr Met Asn Pro Cys Pro Arg Ala Leu Glu Val Ala Pro Gly
            180                 185                 190

Ala Leu Leu Gly Leu Gly Asn Leu Thr His Leu Ser Leu Lys Tyr Asn
        195                 200                 205

Asn Leu Thr Glu Val Pro Arg Arg Leu Pro Ser Leu Asp Thr Leu
    210                 215                 220

Leu Leu Ser Tyr Asn His Ile Val Thr Leu Ala Pro Glu Asp Leu Ala
225                 230                 235                 240

Asn Leu Thr Ala Leu Arg Val Leu Asp Val Gly Gly Asn Cys Arg Arg
                245                 250                 255
```

```
Cys Asp His Ala Arg Asn Pro Cys Arg Glu Cys Pro Lys Asn Phe Pro
            260                 265                 270

Lys Leu His Pro Asp Thr Phe Ser His Leu Ser Arg Leu Glu Gly Leu
            275                 280                 285

Val Leu Lys Asp Ser Ser Leu Tyr Lys Leu Glu Lys Asp Trp Phe Arg
            290                 295                 300

Gly Leu Gly Arg Leu Gln Val Leu Asp Leu Ser Glu Asn Phe Leu Tyr
305                 310                 315                 320

Asp Tyr Ile Thr Lys Thr Thr Ile Phe Asn Asp Leu Thr Gln Leu Arg
            325                 330                 335

Arg Leu Asn Leu Ser Phe Asn Tyr His Lys Val Ser Phe Ala His
            340                 345                 350

Leu His Leu Ala Ser Ser Phe Gly Ser Leu Val Ser Leu Glu Lys Leu
            355                 360                 365

Asp Met His Gly Ile Phe Phe Arg Ser Leu Thr Asn Ile Thr Leu Gln
            370                 375                 380

Ser Leu Thr Arg Leu Pro Lys Leu Gln Ser Leu His Leu Gln Leu Asn
385                 390                 395                 400

Phe Ile Asn Gln Ala Gln Leu Ser Ile Phe Gly Ala Phe Pro Ser Leu
            405                 410                 415

Leu Phe Val Asp Leu Ser Asp Asn Arg Ile Ser Gly Ala Ala Thr Pro
            420                 425                 430

Ala Ala Ala Leu Gly Glu Val Asp Ser Arg Val Glu Val Trp Arg Leu
            435                 440                 445

Pro Arg Gly Leu Ala Pro Gly Pro Leu Asp Ala Val Ser Ser Lys Asp
            450                 455                 460

Phe Met Pro Ser Cys Asn Leu Asn Phe Thr Leu Asp Leu Ser Arg Asn
465                 470                 475                 480

Asn Leu Val Thr Ile Gln Gln Glu Met Phe Thr Arg Leu Ser Arg Leu
            485                 490                 495

Gln Cys Leu Arg Leu Ser His Asn Ser Ile Ser Gln Ala Val Asn Gly
            500                 505                 510

Ser Gln Phe Val Pro Leu Thr Ser Leu Arg Val Leu Asp Leu Ser His
            515                 520                 525

Asn Lys Leu Asp Leu Tyr His Gly Arg Ser Phe Thr Glu Leu Pro Gln
            530                 535                 540

Leu Glu Ala Leu Asp Leu Ser Tyr Asn Ser Gln Pro Phe Ser Met Gln
545                 550                 555                 560

Gly Val Gly His Asn Leu Ser Phe Val Ala Gln Leu Pro Ser Leu Arg
            565                 570                 575

Tyr Leu Ser Leu Ala His Asn Gly Ile His Ser Arg Val Ser Gln Lys
            580                 585                 590

Leu Ser Ser Ala Ser Leu Arg Ala Leu Asp Phe Ser Gly Asn Ser Leu
            595                 600                 605

Ser Gln Met Trp Ala Glu Gly Asp Leu Tyr Leu Cys Phe Phe Lys Gly
            610                 615                 620

Leu Arg Asn Leu Val Gln Leu Asp Leu Ser Glu Asn His Leu His Thr
625                 630                 635                 640

Leu Leu Pro Arg His Leu Asp Asn Leu Pro Lys Ser Leu Arg Gln Leu
            645                 650                 655

Arg Leu Arg Asp Asn Asn Leu Ala Phe Phe Asn Trp Ser Ser Leu Thr
            660                 665                 670
```

-continued

Val Leu Pro Arg Leu Glu Ala Leu Asp Leu Ala Gly Asn Gln Leu Lys
            675                 680                 685

Ala Leu Ser Asn Gly Ser Leu Pro Gly Ile Arg Leu Gln Lys Leu
690                 695                 700

Asp Val Ser Ser Asn Ser Ile Gly Phe Val Ile Pro Gly Phe Phe Val
705                 710                 715                 720

Arg Ala Thr Arg Leu Ile Glu Leu Asn Leu Ser Ala Asn Ala Leu Lys
            725                 730                 735

Thr Val Asp Pro Ser Trp Phe Gly Ser Leu Ala Gly Thr Leu Lys Ile
            740                 745                 750

Leu Asp Val Ser Ala Asn Pro Leu His Cys Ala Cys Gly Ala Ala Phe
            755                 760                 765

Val Asp Phe Leu Leu Glu Arg Gln Glu Ala Val Pro Gly Leu Ser Arg
            770                 775                 780

Arg Val Thr Cys Gly Ser Pro Gly Gln Leu Gln Gly Arg Ser Ile Phe
785                 790                 795                 800

Thr Gln Asp Leu Arg Leu Cys Leu Asp Glu Thr Leu Ser Leu Asp Cys
            805                 810                 815

Phe Gly Leu Ser Leu Leu Met Val Ala Leu Gly Leu Ala Val Pro Met
            820                 825                 830

Leu His His Leu Cys Gly Trp Asp Leu Trp Tyr Cys Phe His Leu Cys
            835                 840                 845

Leu Ala His Leu Pro Arg Arg Arg Gln Arg Gly Glu Asp Thr Leu
            850                 855                 860

Leu Tyr Asp Ala Phe Val Val Phe Asp Lys Val Gln Ser Ala Val Ala
865                 870                 875                 880

Asp Trp Val Tyr Asn Glu Leu Arg Val Gln Leu Glu Glu Arg Gly
            885                 890                 895

Arg Arg Ala Leu Arg Leu Cys Leu Glu Glu Arg Asp Trp Leu Pro Gly
900                 905                 910

Lys Thr Leu Phe Glu Asn Leu Trp Ala Ser Val Tyr Ser Ser Arg Lys
            915                 920                 925

Thr Met Phe Val Leu Asp His Thr Asp Arg Val Ser Gly Leu Leu Arg
930                 935                 940

Ala Ser Phe Leu Leu Ala Gln Gln Arg Leu Leu Glu Asp Arg Lys Asp
945                 950                 955                 960

Val Val Val Leu Val Ile Leu Arg Pro Ala Ala Tyr Arg Ser Arg Tyr
                965                 970                 975

Val Arg Leu Arg Gln Arg Leu Cys Arg Gln Ser Val Leu Leu Trp Pro
            980                 985                 990

His Gln Pro Ser Gly Gln Gly Ser Phe Trp Ala Asn Leu Gly Ile Ala
            995                 1000                1005

Leu Thr Arg Asp Asn Arg His Phe Tyr Asn Arg Asn Phe Cys Arg
        1010                1015                1020

Gly Pro Thr Thr Ala Glu
1025

<210> SEQ ID NO 3
<211> LENGTH: 3093
<212> TYPE: DNA
<213> ORGANISM: Sus scrofa

<400> SEQUENCE: 3
atgggccccc gctgcaccct gcaccccctt tctctcctgg tgcaggtgac agcgctggct      60

-continued

```
gcggctctgg cccagggcag gctgcctgcc ttcctgccct gtgagctcca gccccacggc    120
ctggtgaact gcaactggct cttcctgaag tccgtgcccc acttctcggc ggcagcgccc    180
cgggccaacg tcaccagcct ctccttactc tccaaccgca tccaccacct gcacgactct    240
gacttcgtcc acctgtccag cctacgaact ctcaacctca gtggaactg cccgccggct    300 ggcctcagcc ccatgcactt ccctgccac atgaccatcg agcccaacac cttcctggcc    360
gtgcccaccc tggaggagct gaacctgagc tacaacagca tcgaccgt gcctgccctg    420 cccgactccc tcgtgtccct gtcgctgagc cgcaccaaca tcctggtgct agaccccacc    480
cacctcactg gcctacatgc cctgcgctac ctgtacatgg atggcaactg ctactacaag    540
aacccctgcc aggggggcgct ggaggtggtg ccgggtgccc tcctcggcct gggcaacctc    600
acacatctct cactcaagta caacaatctc acggaggtgc cccgcagcct gcccccagc    660 ctggagaccc tgctgttgtc ctacaaccac attgtcaccc tgacgcctga ggacctggcc    720
aatctgactg ccctgcgcgt gcttgatgtg gggggaact gccgccgctg tgaccatgcc    780
cgcaacccct gcagggagtg cccaaaggac caccccaagc tgcactctga caccttcagc    840
cacctgagcc gcctcgaagg cctggtgttg aaagacagtt ctctctacaa cctggacacc    900
aggtggttcc gaggcctgga caggctccaa gtgctggacc tgagtgagaa cttcctctac    960
gactgcatca ccaagaccac ggccttccag ggcctggccc gactgcgcag cctcaacctg   1020
tccttcaatt accacaagaa ggtgtccttt gccccactgc acctggcacc ctcctttggg   1080
cacctccggt ccctgaagga gctggacatg catggcatct tcttccgctc gctcagtgag   1140
accacgctcc aacctctggt ccaactgcct atgctccaga ccctgcgcct gcagatgaac   1200
ttcattaacc aggcccagct cagcatcttt gggggccttcc ctggcctgct gtacgtggac   1260
ctatcggaca accgcatcag cggagctgca aggccagtgg ccattactag ggaggtggat   1320
ggtagggaga gggtctggct gccttccagg aacctcgctc cacgtccact ggacactctc   1380
cgctcagagg acttcatgcc aaactgcaag gccttcagct tcaccttgga cctgtctcgg   1440
aacaacctgg tgacaatcca gtcggagatg tttgctcgcc tctcacgcct cgagtgcctg   1500
cgcctgagcc acaacagcat ctcccaggcg gtcaatggcc tcagtttgt gccgctgacc   1560 agcctgcggg tgctggacct gtcccacaac aagctggacc tgtatcacgg gcgctcgttc   1620
acggagctgc cgcgcctgga agcactggac ctcagctaca atagccagcc ctttaccatg   1680
cagggtgtgg ccacaacct cagcttcgtg gcccagctgc ccgccctgcg ctacctcagc   1740
ctggcgcaca tgacatcca tagccgagtg tcccagcagc tctgtagcgc ctcactgtgc   1800
gccctggact ttagcggcaa cgatctgagc cggatgtggg ctgagggaga cctctatctc   1860
cgcttcttcc aaggcctaag aagcctagtc tggctggacc tgtcccagaa ccacctgcac   1920
accctcctgc cacgtgccct ggacaacctc cccaaaagcc tgaagcatct gcatctccgt   1980
gacaataacc tggccttctt caactggagc agcctgaccc tcctgcccaa gctgaaacc   2040 ctggacttgg ctggaaaacca gctgaaggcc ctaagcaatg cagcctgcc atctggcacc   2100 cagctgcgga ggctggacct cagtggcaac agcatcggct tgtgaaccc tggcttcttt   2160 gccctggcca agcagttaga agagctcaac ctcagcgcca atgccctcaa gacagtggag   2220
ccctcctggt ttggctcgat ggtgggcaac ctgaaagtcc tagacgtgag cgccaaccct   2280
ctgcactgtg cctgtggggc gaccttcgtg ggcttcctgc tggaggtaca ggctgccgtg   2340
cctgggctgc cagccgcgt caagtgtggc agtccggggc agctccaggg ccatagcatc   2400
tttgcgcaag acctgcgcct ctgcctggat gagacccctct cgtggaactg ttttggcatc   2460
```

-continued

```
tcgctgctgg ccatggccct gggcctggtt gtgcccatgc tgcaccacct ctgcggctgg    2520
gacctctggt actgcttcca cctgtgcctg gcctggctgc cccaccgagg gcagcggcgg    2580
ggcgcagacg ccctgttcta tgatgccttc gtggtctttg acaaagctca gagtgctgtg    2640
gccgactggg tgtacaacga gctgcgggtg cagctggagg agcgccgtgg gcgccgcgca    2700
ctgcgcctgt gcctggagga gcgagactgg ttacctggca agacgctctt cgagaacctg    2760
tgggcctcag tctacagcag ccgcaagacc ctgtttgtgc tggcccacac ggaccgtgtc    2820
agcggcctct tgcgtgccag tttcctgctg gcccagcagc gcctgctgga ggaccgcaag    2880
gacgttgtag tgctggtgat cctgcgcccc gatgcctacc gctcccgcta cgtgcggctg    2940
cgccagcgcc tctgccgcca gagtgtcctc ctctggcccc accagcccg tgggcagggc     3000 agcttctggg cccagctggg cacagccctg accagggaca accaccactt ctataaccgg    3060
aacttctgcc ggggccccac gacagccgaa tag                                 3093
```

<210> SEQ ID NO 4
<211> LENGTH: 1030
<212> TYPE: PRT
<213> ORGANISM: Sus scrofa

<400> SEQUENCE: 4

```
Met Gly Pro Arg Cys Thr Leu His Pro Leu Ser Leu Leu Val Gln Val
1               5                   10                  15

Thr Ala Leu Ala Ala Ala Leu Ala Gln Gly Arg Leu Pro Ala Phe Leu
            20                  25                  30

Pro Cys Glu Leu Gln Pro His Gly Leu Val Asn Cys Asn Trp Leu Phe
        35                  40                  45

Leu Lys Ser Val Pro His Phe Ser Ala Ala Pro Arg Ala Asn Val
    50                  55                  60

Thr Ser Leu Ser Leu Leu Ser Asn Arg Ile His His Leu His Asp Ser
65                  70                  75                  80

Asp Phe Val His Leu Ser Ser Leu Arg Thr Leu Asn Leu Lys Trp Asn
                85                  90                  95

Cys Pro Pro Ala Gly Leu Ser Pro Met His Phe Pro Cys His Met Thr
            100                 105                 110

Ile Glu Pro Asn Thr Phe Leu Ala Val Pro Thr Leu Glu Glu Leu Asn
        115                 120                 125

Leu Ser Tyr Asn Ser Ile Thr Thr Val Pro Ala Leu Pro Asp Ser Leu
    130                 135                 140

Val Ser Leu Ser Leu Ser Arg Thr Asn Ile Leu Val Leu Asp Pro Thr
145                 150                 155                 160

His Leu Thr Gly Leu His Ala Leu Arg Tyr Leu Tyr Met Asp Gly Asn
                165                 170                 175

Cys Tyr Tyr Lys Asn Pro Cys Gln Gly Ala Leu Glu Val Val Pro Gly
            180                 185                 190

Ala Leu Leu Gly Leu Gly Asn Leu Thr His Leu Ser Leu Lys Tyr Asn
        195                 200                 205

Asn Leu Thr Glu Val Pro Arg Ser Leu Pro Pro Ser Leu Glu Thr Leu
    210                 215                 220

Leu Leu Ser Tyr Asn His Ile Val Thr Leu Thr Pro Glu Asp Leu Ala
225                 230                 235                 240

Asn Leu Thr Ala Leu Arg Val Leu Asp Val Gly Gly Asn Cys Arg Arg
                245                 250                 255
```

-continued

```
Cys Asp His Ala Arg Asn Pro Cys Arg Glu Cys Pro Lys Asp His Pro
            260                 265                 270

Lys Leu His Ser Asp Thr Phe Ser His Leu Ser Arg Leu Glu Gly Leu
        275                 280                 285

Val Leu Lys Asp Ser Ser Leu Tyr Asn Leu Asp Thr Arg Trp Phe Arg
    290                 295                 300

Gly Leu Asp Arg Leu Gln Val Leu Asp Leu Ser Glu Asn Phe Leu Tyr
305                 310                 315                 320

Asp Cys Ile Thr Lys Thr Thr Ala Phe Gln Gly Leu Ala Arg Leu Arg
                325                 330                 335

Ser Leu Asn Leu Ser Phe Asn Tyr His Lys Lys Val Ser Phe Ala His
            340                 345                 350

Leu His Leu Ala Pro Ser Phe Gly His Leu Arg Ser Leu Lys Glu Leu
        355                 360                 365

Asp Met His Gly Ile Phe Phe Arg Ser Leu Ser Glu Thr Thr Leu Gln
    370                 375                 380

Pro Leu Val Gln Leu Pro Met Leu Gln Thr Leu Arg Leu Gln Met Asn
385                 390                 395                 400

Phe Ile Asn Gln Ala Gln Leu Ser Ile Phe Gly Ala Phe Pro Gly Leu
                405                 410                 415

Leu Tyr Val Asp Leu Ser Asp Asn Arg Ile Ser Gly Ala Ala Arg Pro
            420                 425                 430

Val Ala Ile Thr Arg Glu Val Asp Gly Arg Glu Arg Val Trp Leu Pro
        435                 440                 445

Ser Arg Asn Leu Ala Pro Arg Pro Leu Asp Thr Leu Arg Ser Glu Asp
    450                 455                 460

Phe Met Pro Asn Cys Lys Ala Phe Ser Phe Thr Leu Asp Leu Ser Arg
465                 470                 475                 480

Asn Asn Leu Val Thr Ile Gln Ser Glu Met Phe Ala Arg Leu Ser Arg
                485                 490                 495

Leu Glu Cys Leu Arg Leu Ser His Asn Ser Ile Ser Gln Ala Val Asn
            500                 505                 510

Gly Ser Gln Phe Val Pro Leu Thr Ser Leu Arg Val Leu Asp Leu Ser
        515                 520                 525

His Asn Lys Leu Asp Leu Tyr His Gly Arg Ser Phe Thr Glu Leu Pro
    530                 535                 540

Arg Leu Glu Ala Leu Asp Leu Ser Tyr Asn Ser Gln Pro Phe Thr Met
545                 550                 555                 560

Gln Gly Val Gly His Asn Leu Ser Phe Val Ala Gln Leu Pro Ala Leu
                565                 570                 575

Arg Tyr Leu Ser Leu Ala His Asn Asp Ile His Ser Arg Val Ser Gln
            580                 585                 590

Gln Leu Cys Ser Ala Ser Leu Cys Ala Leu Asp Phe Ser Gly Asn Asp
        595                 600                 605

Leu Ser Arg Met Trp Ala Glu Gly Asp Leu Tyr Leu Arg Phe Phe Gln
    610                 615                 620

Gly Leu Arg Ser Leu Val Trp Leu Asp Leu Ser Gln Asn His Leu His
625                 630                 635                 640

Thr Leu Leu Pro Arg Ala Leu Asp Asn Leu Pro Lys Ser Leu Lys His
                645                 650                 655

Leu His Leu Arg Asp Asn Asn Leu Ala Phe Phe Asn Trp Ser Ser Leu
            660                 665                 670

Thr Leu Leu Pro Lys Leu Glu Thr Leu Asp Leu Ala Gly Asn Gln Leu
```

675                 680                 685
Lys Ala Leu Ser Asn Gly Ser Leu Pro Ser Gly Thr Gln Leu Arg Arg
    690                 695                 700

Leu Asp Leu Ser Gly Asn Ser Ile Gly Phe Val Asn Pro Gly Phe Phe
705                 710                 715                 720

Ala Leu Ala Lys Gln Leu Glu Glu Leu Asn Leu Ser Ala Asn Ala Leu
                725                 730                 735

Lys Thr Val Glu Pro Ser Trp Phe Gly Ser Met Val Gly Asn Leu Lys
            740                 745                 750

Val Leu Asp Val Ser Ala Asn Pro Leu His Cys Ala Cys Gly Ala Thr
        755                 760                 765

Phe Val Gly Phe Leu Leu Glu Val Gln Ala Ala Val Pro Gly Leu Pro
    770                 775                 780

Ser Arg Val Lys Cys Gly Ser Pro Gly Gln Leu Gln Gly His Ser Ile
785                 790                 795                 800

Phe Ala Gln Asp Leu Arg Leu Cys Leu Asp Glu Thr Leu Ser Trp Asn
                805                 810                 815

Cys Phe Gly Ile Ser Leu Leu Ala Met Ala Leu Gly Leu Val Val Pro
            820                 825                 830

Met Leu His His Leu Cys Gly Trp Asp Leu Trp Tyr Cys Phe His Leu
        835                 840                 845

Cys Leu Ala Trp Leu Pro His Arg Gly Gln Arg Gly Ala Asp Ala
    850                 855                 860

Leu Phe Tyr Asp Ala Phe Val Val Phe Asp Lys Ala Gln Ser Ala Val
865                 870                 875                 880

Ala Asp Trp Val Tyr Asn Glu Leu Arg Val Gln Leu Glu Glu Arg Arg
                885                 890                 895

Gly Arg Arg Ala Leu Arg Leu Cys Leu Glu Glu Arg Asp Trp Leu Pro
            900                 905                 910

Gly Lys Thr Leu Phe Glu Asn Leu Trp Ala Ser Val Tyr Ser Ser Arg
        915                 920                 925

Lys Thr Leu Phe Val Leu Ala His Thr Asp Arg Val Ser Gly Leu Leu
    930                 935                 940

Arg Ala Ser Phe Leu Leu Ala Gln Gln Arg Leu Leu Glu Asp Arg Lys
945                 950                 955                 960

Asp Val Val Val Leu Val Ile Leu Arg Pro Asp Ala Tyr Arg Ser Arg
                965                 970                 975

Tyr Val Arg Leu Arg Gln Arg Leu Cys Arg Gln Ser Val Leu Leu Trp
            980                 985                 990

Pro His Gln Pro Arg Gly Gln Gly Ser Phe Trp Ala Gln Leu Gly Thr
        995                 1000                1005

Ala Leu Thr Arg Asp Asn His His Phe Tyr Asn Arg Asn Phe Cys
    1010                1015                1020

Arg Gly Pro Thr Thr Ala Glu
1025                1030

<210> SEQ ID NO 5
<211> LENGTH: 3099
<212> TYPE: DNA
<213> ORGANISM: Canis familiaris

<400> SEQUENCE: 5
atgggcccct gccgtggcgc cctgcacccc ctgtctctcc tggtgcaggc tgccgcgcta    60
gccctggccc tggcccaggg caccctgcct gccttcctgc cctgtgagct ccagccccat   120

```
ggcctggtga actgcaactg gctgttcctc aagtccgtgc cccgcttctc ggcagctgca      180
ccccgcggta acgtcaccag cctttccttg tactccaacc gcatccacca cctccatgac      240
tatgactttg tccacttcgt ccacctgcgg cgtctcaatc tcaagtggaa ctgcccgccc      300
gccagcctca gccccatgca ctttccctgt cacatgacca ttgagcccaa caccttcctg      360
gctgtgccca ccctagagga cctgaatctg agctataaca gcatcacgac tgtgcccgcc      420
ctgcccagtt cgcttgtgtc cctgtccctg agccgcacca acatcctggt gctggaccct      480
gccaccctgg caggccttta tgccctgcgc ttcctgttcc tggatggcaa ctgctactac      540
aagaacccct gccagcaggc cctgcaggtg gccccaggtg ccctcctggg cctgggcaac      600
ctcacacacc tgtcactcaa gtacaacaac ctcaccgtgg tgccgcgggg cctgcccccc      660
agcctggagt acctgctctt gtcctacaac cacatcatca ccctggcacc tgaggacctg      720
gccaatctga ctgccctgcg tgtcctcgat gtgggtggga actgtcgccg ctgtgaccat      780
gcccgtaacc cctgcaggga gtgccccaag ggcttccccc agctgcaccc caacaccttc      840
ggccacctga ccacctcga aggcctggtg ttgagggaca gctctctcta cagcctggac      900
cccaggtggt ccatggcct gggcaacctc atggtgctgg acctgagtga gaacttcctg      960
tatgactgca tcaccaaaac caaagccttc tacggcctgg cccggctgcg cagactcaac      1020
ctgtccttca attatcataa gaaggtgtcc tttgcccacc tgcatctggc atcctccttc      1080
gggagcctac tgtccctgca ggagctggac atacatggca tcttcttccg ctcgctcagc      1140
gagaccacgc tccagtcgct ggcccacctg cccatgctcc agcgtctgca tctgcagttg      1200
aactttatca gccaggccca gctcagcatc ttcggcgcct ccctggcct gcggtacgtg      1260 gacttgtcag acaaccgcat cagtggagct gcagagcccg cggctgccac aggggaggta      1320
gaggcggact gtggggagag agtctggcca cagtcccggg accttgctct gggcacactg      1380
ggcacccccg gctcagaggc cttcatgccg agctgcagga ccctcaactt caccttggac      1440
ctgtctcgga caacctagt gactgttcag ccggagatgt ttgtccggct ggcgcgcctc      1500
cagtgcctgg gcctgagcca acagcatc tcgcaggcgg tcaatggctc gcagttcgtg      1560
cctctgagca acctgcgggt gctggacctg tcccataaca agctggacct gtaccacggg      1620
cgctcgttca cggagctgcc gcggctggag gccttggacc tcagctacaa cagccagccc      1680
ttcagcatgc ggggcgtggg ccacaatctc agctttgtgg cacagctgcc agccctgcgc      1740
tacctcagcc tggcgcacaa tggcatccac agccgcgtgt cccagcagct ccgcagcgcc      1800
tcgctccggg ccctggactt cagtggcaat accctgagcc agatgtgggc cgagggagac      1860
ctctatctcc gcttcttcca aggcctgaga gcctggttc agctggacct gtcccagaat      1920
cgcctgcata ccctcctgcc acgcaacctg gacaacctcc ccaagagcct gcggctcctg      1980
cggctccgtg acaattacct ggctttcttc aactggagca gcctggccct cctacccaag      2040
ctggaagccc tggacctggc gggaaaccag ctgaaggccc tgagcaatgg cagcttgccc      2100
aacggcaccc agctccagag gctggacctc agcggcaaca gcatcggctt cgtggtcccc      2160
ggcttttttg ccctggccgt gaggcttcga gagctcaacc tcagcgccaa cgccctcaag      2220
acggtggagc cctcctggtt tggttccctg cgggtgccc tgaaagtcct agacgtgacc      2280
gccaacccct gcattgcgc ttgcggcgca accttcgtgg acttcttgct ggaggtgcag      2340
gctgcggtgc ccgcctgcc tagccgtgtc aagtgcggca gcccgggcca gctccagggc      2400
cgcagcatct tcgcacagga cctgcgcctc tgcctggacg aagcgctctc ctgggtctgt      2460
```

-continued

```
ttcagcctct cgctgctggc tgtggccctg agcctggctg tgcccatgct gcaccagctc    2520
tgtggctggg acctctggta ctgcttccac ctgtgcctgg cctggctgcc cggcgggg      2580 cggcggcggg gtgtggatgc cctggcctac gacgccttcg tggtcttcga caaggcgcag    2640
agctcggtgg cggactgggt gtacaatgag ctgcgggtac agctagagga gcgccgtggg    2700
cgccgggcgc tacgcctgtg tctggaggaa cgtgactggg tacccggcaa aaccctcttc    2760
gagaacctct gggcctcagt ttacagcagc cgcaagacgc tgtttgtgct ggcccgcacg    2820
gacagagtca gcggcctcct gcgtgccagc ttcctgctgg cccaacagcg cctgctggag    2880
gaccgcaagg acgtcgtggt gctggtgatc ctgtgccccg acgccaccg ctcccgctat     2940 gtgcggctgc gccagcgcct ctgccgccag agtgtcctcc tctggcccca ccagcccagt    3000
ggccagcgca gcttctgggc ccagctgggc acggccctga ccagggacaa ccgccacttc    3060
tacaaccaga acttctgccg ggcccccacg acagcctga                           3099
```

<210> SEQ ID NO 6
<211> LENGTH: 1032
<212> TYPE: PRT
<213> ORGANISM: Canis familiaris

<400> SEQUENCE: 6

```
Met Gly Pro Cys Arg Gly Ala Leu His Pro Leu Ser Leu Leu Val Gln
1               5                   10                  15

Ala Ala Ala Leu Ala Leu Ala Leu Ala Gln Gly Thr Leu Pro Ala Phe
            20                  25                  30

Leu Pro Cys Glu Leu Gln Pro His Gly Leu Val Asn Cys Asn Trp Leu
        35                  40                  45

Phe Leu Lys Ser Val Pro Arg Phe Ser Ala Ala Pro Arg Gly Asn
    50                  55                  60

Val Thr Ser Leu Ser Leu Tyr Ser Asn Arg Ile His His Leu His Asp
65                  70                  75                  80

Tyr Asp Phe Val His Phe Val His Leu Arg Arg Leu Asn Leu Lys Trp
                85                  90                  95

Asn Cys Pro Pro Ala Ser Leu Ser Pro Met His Phe Pro Cys His Met
            100                 105                 110

Thr Ile Glu Pro Asn Thr Phe Leu Ala Val Pro Thr Leu Glu Asp Leu
        115                 120                 125

Asn Leu Ser Tyr Asn Ser Ile Thr Thr Val Pro Ala Leu Pro Ser Ser
    130                 135                 140

Leu Val Ser Leu Ser Leu Ser Arg Thr Asn Ile Leu Val Leu Asp Pro
145                 150                 155                 160

Ala Thr Leu Ala Gly Leu Tyr Ala Leu Arg Phe Leu Phe Leu Asp Gly
                165                 170                 175

Asn Cys Tyr Tyr Lys Asn Pro Cys Gln Gln Ala Leu Gln Val Ala Pro
            180                 185                 190

Gly Ala Leu Leu Gly Leu Gly Asn Leu Thr His Leu Ser Leu Lys Tyr
        195                 200                 205

Asn Asn Leu Thr Val Val Pro Arg Gly Leu Pro Ser Leu Glu Tyr
    210                 215                 220

Leu Leu Leu Ser Tyr Asn His Ile Ile Thr Leu Ala Pro Glu Asp Leu
225                 230                 235                 240

Ala Asn Leu Thr Ala Leu Arg Val Leu Asp Val Gly Gly Asn Cys Arg
                245                 250                 255

Arg Cys Asp His Ala Arg Asn Pro Cys Arg Glu Cys Pro Lys Gly Phe
```

-continued

```
                260                 265                 270
Pro Gln Leu His Pro Asn Thr Phe Gly His Leu Ser His Leu Glu Gly
            275                 280                 285

Leu Val Leu Arg Asp Ser Ser Leu Tyr Ser Leu Asp Pro Arg Trp Phe
            290                 295                 300

His Gly Leu Gly Asn Leu Met Val Leu Asp Leu Ser Glu Asn Phe Leu
305                 310                 315                 320

Tyr Asp Cys Ile Thr Lys Thr Lys Ala Phe Tyr Gly Leu Ala Arg Leu
            325                 330                 335

Arg Arg Leu Asn Leu Ser Phe Asn Tyr His Lys Lys Val Ser Phe Ala
            340                 345                 350

His Leu His Leu Ala Ser Ser Phe Gly Ser Leu Leu Ser Leu Gln Glu
            355                 360                 365

Leu Asp Ile His Gly Ile Phe Phe Arg Ser Leu Ser Glu Thr Thr Leu
            370                 375                 380

Gln Ser Leu Ala His Leu Pro Met Leu Gln Arg Leu His Leu Gln Leu
385                 390                 395                 400

Asn Phe Ile Ser Gln Ala Gln Leu Ser Ile Phe Gly Ala Phe Pro Gly
            405                 410                 415

Leu Arg Tyr Val Asp Leu Ser Asp Asn Arg Ile Ser Gly Ala Ala Glu
            420                 425                 430

Pro Ala Ala Ala Thr Gly Glu Val Glu Ala Asp Cys Gly Glu Arg Val
            435                 440                 445

Trp Pro Gln Ser Arg Asp Leu Ala Leu Gly Thr Leu Gly Thr Pro Gly
            450                 455                 460

Ser Glu Ala Phe Met Pro Ser Cys Arg Thr Leu Asn Phe Thr Leu Asp
465                 470                 475                 480

Leu Ser Arg Asn Asn Leu Val Thr Val Gln Pro Glu Met Phe Val Arg
            485                 490                 495

Leu Ala Arg Leu Gln Cys Leu Gly Leu Ser His Asn Ser Ile Ser Gln
            500                 505                 510

Ala Val Asn Gly Ser Gln Phe Val Pro Leu Ser Asn Leu Arg Val Leu
            515                 520                 525

Asp Leu Ser His Asn Lys Leu Asp Leu Tyr His Gly Arg Ser Phe Thr
            530                 535                 540

Glu Leu Pro Arg Leu Glu Ala Leu Asp Leu Ser Tyr Asn Ser Gln Pro
545                 550                 555                 560

Phe Ser Met Arg Gly Val Gly His Asn Leu Ser Phe Val Ala Gln Leu
            565                 570                 575

Pro Ala Leu Arg Tyr Leu Ser Leu Ala His Asn Gly Ile His Ser Arg
            580                 585                 590

Val Ser Gln Gln Leu Arg Ser Ala Ser Leu Arg Ala Leu Asp Phe Ser
            595                 600                 605

Gly Asn Thr Leu Ser Gln Met Trp Ala Glu Gly Asp Leu Tyr Leu Arg
            610                 615                 620

Phe Phe Gln Gly Leu Arg Ser Leu Val Gln Leu Asp Leu Ser Gln Asn
625                 630                 635                 640

Arg Leu His Thr Leu Leu Pro Arg Asn Leu Asp Asn Leu Pro Lys Ser
            645                 650                 655

Leu Arg Leu Leu Arg Leu Arg Asp Asn Tyr Leu Ala Phe Phe Asn Trp
            660                 665                 670

Ser Ser Leu Ala Leu Leu Pro Lys Leu Glu Ala Leu Asp Leu Ala Gly
            675                 680                 685
```

Asn Gln Leu Lys Ala Leu Ser Asn Gly Ser Leu Pro Asn Gly Thr Gln
        690                 695                 700

Leu Gln Arg Leu Asp Leu Ser Gly Asn Ser Ile Gly Phe Val Val Pro
705                 710                 715                 720

Gly Phe Phe Ala Leu Ala Val Arg Leu Arg Glu Leu Asn Leu Ser Ala
                725                 730                 735

Asn Ala Leu Lys Thr Val Glu Pro Ser Trp Phe Gly Ser Leu Ala Gly
            740                 745                 750

Ala Leu Lys Val Leu Asp Val Thr Ala Asn Pro Leu His Cys Ala Cys
        755                 760                 765

Gly Ala Thr Phe Val Asp Phe Leu Leu Glu Val Gln Ala Ala Val Pro
770                 775                 780

Gly Leu Pro Ser Arg Val Lys Cys Gly Ser Pro Gly Gln Leu Gln Gly
785                 790                 795                 800

Arg Ser Ile Phe Ala Gln Asp Leu Arg Leu Cys Leu Asp Glu Ala Leu
                805                 810                 815

Ser Trp Val Cys Phe Ser Leu Ser Leu Leu Ala Val Ala Leu Ser Leu
            820                 825                 830

Ala Val Pro Met Leu His Gln Leu Cys Gly Trp Asp Leu Trp Tyr Cys
        835                 840                 845

Phe His Leu Cys Leu Ala Trp Leu Pro Arg Arg Gly Arg Arg Gly
850                 855                 860

Val Asp Ala Leu Ala Tyr Asp Ala Phe Val Val Phe Asp Lys Ala Gln
865                 870                 875                 880

Ser Ser Val Ala Asp Trp Val Tyr Asn Glu Leu Arg Val Gln Leu Glu
                885                 890                 895

Glu Arg Arg Gly Arg Arg Ala Leu Arg Leu Cys Leu Glu Glu Arg Asp
            900                 905                 910

Trp Val Pro Gly Lys Thr Leu Phe Glu Asn Leu Trp Ala Ser Val Tyr
        915                 920                 925

Ser Ser Arg Lys Thr Leu Phe Val Leu Ala Arg Thr Asp Arg Val Ser
930                 935                 940

Gly Leu Leu Arg Ala Ser Phe Leu Leu Ala Gln Gln Arg Leu Leu Glu
945                 950                 955                 960

Asp Arg Lys Asp Val Val Val Leu Val Ile Leu Cys Pro Asp Ala His
                965                 970                 975

Arg Ser Arg Tyr Val Arg Leu Arg Gln Arg Leu Cys Arg Gln Ser Val
            980                 985                 990

Leu Leu Trp Pro His Gln Pro Ser Gly Gln Arg Ser Phe Trp Ala Gln
        995                 1000                1005

Leu Gly Thr Ala Leu Thr Arg Asp Asn Arg His Phe Tyr Asn Gln
    1010                1015                1020

Asn Phe Cys Arg Gly Pro Thr Thr Ala
1025                1030

<210> SEQ ID NO 7
<211> LENGTH: 2935
<212> TYPE: DNA
<213> ORGANISM: Gallus gallus

<400> SEQUENCE: 7
aagcttacca tgatggagac agcggagaag gcatggccca gcaccaggat gtgcccctcc      60
cactgctgtc cactctggct gctgctgctg gtgacagtga cactgatgcc gatggtgcac     120

```
ccgtatggct ttcgcaactg cattgaggat gtcaaggcac ctttgtactt ccgctgcatc    180
cagcgcttcc tgcagtcgcc ggccctggca gtgtctgacc tgccaccaca tgccatcgcg    240
ctcaatctgt catacaacaa aatgcgctgc ctgcagccct ctgcctttgc ccacctgaca    300
cagctgcata ccctggacct gacctacaac ctcctggaga ccctctcccc tggtgccttc    360
aatgggctgg gtgtgctggt ggtgctggac ctgtctcaca caagctgac cacacttgct    420 gaaggggtgt caacagctt gggcaacctg tcctcgctgc aggtacaaca taaccccctc    480
agcacggtgt caccaagtgc tctgctaccc ctggtcaacc tgcgccgcct gtctctacgg    540
ggcgggcggc tgaatgggtt gggggcagtg gcagtggcag tgcagggctt ggcacagctg    600
gagctgttgg acctatgtga aaacaacctg acaacgctgg ggccaggccc accgctaccc    660
gcctcgctgc tcaccctgca gctgtgcaac aactcgctga gggagttagc ggggggcagc    720
ccggagatgc tatggcacgt gaagatactc gacctctcct acaacagtat ctcacaggcg    780
gaggtcttca cccagctcca cctgcgcaac atcagcctgc tccacctgat cggcaacccc    840
ttggatgtct tccacctgtt ggacatctct gacatccaac ctcgcagcct ggatttctct    900
gggttggtgc tggggctca ggggctggat aaggtgtgcc tgaggctgca gggtccccag    960
gccttgcggc ggctgcagct acaacgcaac gggctgaagg tgctgcattg taatgcactg   1020
cagttgtgtc ctgtgctgag agagctggac ctgtcctgga ccggctaca gcacgtgggc   1080 tgtgccggcc ggctgctggg caagaagcag cgggagaagc tggaagtgct gacagtggaa   1140
cacaacctgc tgaagaaact gccgtcttgc ctgggggccc aggtgctgcc tcggctgtac   1200
aacatttcct tccgctttaa ccgcatcctg actgttgggc cccaagcctt tgcctacgcc   1260
ccggccctgc aggtgttgtg gctcaatatt aacagcctgg tgtggctgga caggcaggca   1320
ctgtggaggc tgcacaacct gacagagctg cgcctggaca caacctgct gaccgacctc   1380 tatcacaact ccttcattga cctccacaga ctgcgcaccc tcaacctgcg caacaaccgt   1440
gtctccgtcc tcttctctgg tgtcttccag gggctggctg agctgcagac gctggattta   1500 ggggcaaca acttgcgcca cctgactgca cagtcactgc aggggctgcc caaactgcgc   1560
aggctgtacc tggaccgcaa cagattgctg gaggtgagca gcactgtgtt cgccccagtg   1620
caggctaccc tgggggtgct ggacctgcgg gccaacaacc tgcagtacat ctcacagtgg   1680
ctgcgcaagc cgcccacctt ccgcaacctg agcagcctgt acgacctgaa gctgcaggcg   1740
cagcagccct atggactgaa gatgctgcct cactacttct tccagggctt ggtgaggctg   1800
cagcagctgc gcctgtcaca gaacatgctg cggtccatcc caccggatgt cttcgaggac   1860
ttgggccagc tgcgctccct ggcattggct gacagcagca atgggctgca tgacctgcct   1920
gacggcatct tcagaaacct gggcaacctg cggttcctgg acctggagaa tgcagggctg   1980
cactcgctca ctctggaagt cttcggcaat tcagccggc tgcaggtgct gcacttggcc   2040
agaaacgagc tgaagacctt caatgacagc gttgccagcc ggctgtcctc cttgcgctac   2100
ctggacctgc gcaagtgtcc gctcagctgc acctgtgaca catgtggct gcagggctgg   2160 ctgaacaaca gccgtgtgca ggttgtctac ccctacaact acacctgtgg ctcacagcac   2220
aatgcctaca tccacagctt tgacacacac gtctgcttcc tggacctggg gctctatctc   2280
tttgctggga ctgcaccggc agtgctgctg ctgctggtgg tgccggtggt gtaccaccgc   2340
gcctactgga ggctgaagta ccactggtac cttctgcggt gctgggtcaa ccagcggtgg   2400
cggcgggagg aaaagtgcta cctctatgac agctttgtgt cctacaattc agctgatgaa   2460
agttgggtgt tgcagaagct ggtgcctgag ctggagcacg gtgccttccg cctctgcttg   2520
```

```
caccaccgcg acttccagcc gggccgcagc atcattgaca acattgtgga tgctgtctac    2580
aacagccgga agacggtgtg cgtggtgagc cgcagctacc tgcgcagcga gtggtgctct    2640
ctagaggtgc agttggccag ctaccggctg ttggatgagc ggcgtgacat cctggtactg    2700
gtgctgctgg aggacgtggg tgatgctgag ctgtctgcct accaccgcat gcggcgggtg    2760
ctgctgcggc gcacctacct gcgctggcct cttgaccccg cagctcagcc gctcttttgg    2820
gcacggctga gagggcact gaggtgggga gaggaggag aggaggagga agaagaaggt     2880
ttgggtggag ggacgggaag gcccagggaa ggagacaaac agatgtagcg gccgc         2935
```

<210> SEQ ID NO 8
<211> LENGTH: 3093
<212> TYPE: DNA
<213> ORGANISM: Bos taurus

<400> SEQUENCE: 8

```
atgggcccct actgtgcccc gcacccccctt tctctcctgg tgcaggcggc ggcactggca      60
gcggccctgg ccgagggcac cctgcctgcc ttcctgccct gtgagctcca gccccatggt     120
caggtggact gcaactggct gttcctgaag tctgtgccgc acttttcggc tggagccccc     180
cgggccaatg tcaccagcct ctccttaatc tccaaccgca tccaccactt gcatgactct     240
gacttcgtcc acctgtccaa cctgcgggtc ctcaacctca gtggaactg cccgccggcc      300 ggcctcagcc ccatgcactt cccctgccgt atgaccatcg agcccaacac cttcctggct     360
gtgcccaccc tggaggagct gaacctgagc tacaacggca tcacgaccgt gcctgccctg     420
cccagttccc tcgtgtccct gtcgctgagc cacaccagca tcctggtgct aggccccacc     480
cacttcaccg gcctgcacgc cctgcgcttt ctgtacatgg acggcaactg ctactacatg     540 aaccccctgcc cgcgggccct ggaggtggcc ccaggcgccc cctcggcct gggcaacctc     600 acgcacctgt cgctcaagta caacaacctc acggaggtgc cccgccgcct gccccccagc     660
ctggacaccc tgctgctgtc ctacaaccac attgtcaccc tggcacccga ggacctggcc     720
aacctgactg ccctgcgcgt gcttgacgtg ggtgggaact gccgccgctg cgaccacgcc     780
cgcaacccct gcagggagtg cccaaagaac ttccccaagc tgcaccctga cacccttcagt    840 cacctgagcc gcctcgaagg cctggtgttg aaggacagtt ctctctacaa actagagaaa    900
gattggttcc gcggcctggg caggctccaa gtgctcgacc tgagtgagaa cttcctctat    960
gactacatca ccaagaccac catcttcaac gacctgaccc agctgcgcag actcaacctg    1020
tccttcaatt accacaagaa ggtgtccttc gcccacctgc acctagcgtc ctcctttggg    1080
agtctggtgt ccctggagaa gctggacatg cacggcatct tcttccgctc cctcaccaac    1140
atcacgctcc agtcgctgac ccggctgccc aagctccaga gtctgcatct gcagctgaac    1200
ttcatcaacc aggcccagct cagcatcttt gggccttcc cgagcctgct cttcgtggac    1260
ctgtcggaca accgcatcag cggagccgcg acgccagcgg ccgccctggg ggaggtggac    1320
agcagggtgg aagtctggcg attgcccagg ggcctcgctc caggcccgct ggacgccgtc    1380
agctcaaagg acttcatgcc aagctgcaac ctcaacttca ccttggacct gtcacggaac    1440
aacctggtga caatccagca agagatgttt acccgcctct cccgcctcca gtgcctgcgc    1500
ctgagccaca cagcatctc gcaggcggtt aatggctccc agttcgtgcc gctgaccagc    1560
ctgcgagtgc tcgacctgtc ccacaacaag ctggacctgt accatgggcg ctcattcacg    1620
gagctgccgc agctggaggc actggacctc agctacaaca gccagccctt cagcatgcag    1680
```

|         |            |            |            |            |      |
|---------|------------|------------|------------|------------|------|
| ggcgtgggcc | acaacctcag | cttcgtggcc | cagctgccct | ccctgcgcta | cctcagcctt | 1740 |
| gcgcacaatg | gcatccacag | ccgcgtgtca | cagaagctca | gcagcgcctc | gttgcgcgcc | 1800 |
| ctggacttca | gcggcaactc | cctgagccag | atgtgggccg | agggagacct | ctatctctgc | 1860 |
| tttttcaaag | gcttgaggaa | cctggtccag | ctggacctgt | ccgagaacca | tctgcacacc | 1920 |
| ctcctgcctc | gtcacctgga | caacctgccc | aagagcctgc | ggcagctgcg | tctccgggac | 1980 |
| aataaccctgg | ccttcttcaa | ctggagcagc | ctgaccgtcc | tgccccggct | ggaagccctg | 2040 |
| gatctggcag | gaaaccagct | gaaggccctg | agcaacggca | gctgccgcc | tggcatccgg | 2100 |
| ctccagaagc | tggacgtgag | cagcaacagc | atcggcttcg | tgatccccgg | cttcttcgtc | 2160 |
| cgcgcgactc | ggctgataga | gcttaacctc | agcgccaatg | ccctgaagac | agtggatccc | 2220 |
| tcctggttcg | gttccttagc | agggaccctg | aaaatcctag | acgtgagcgc | caacccgctc | 2280 |
| cactgcgcct | gcggggcggc | ctttgtggac | ttcctgctgg | agagacagga | ggccgtgccc | 2340 |
| gggctgtcca | ggcgcgtcac | atgtggcagt | ccgggccagc | tccagggccg | cagcatcttc | 2400 |
| acacaggacc | tgcgcctctg | cttcctggac | ctggggctct | atctctttgc | tgggactgca | 2460 |
| ccggcagtgc | tgctgctgct | ggtggtgccg | gtggtgtacc | accgcgccta | ctggaggctg | 2520 |
| aagtaccact | ggtaccttct | gcggtgctgg | gtcaaccagc | ggtggcggcg | ggaggaaaag | 2580 |
| tgctacctct | atgacagctt | tgtgtcctac | aattcagctg | atgaaagttg | ggtgttgcag | 2640 |
| aagctggtgc | ctgagctgga | gcacggtgcc | ttccgcctct | gcttgcacca | ccgcgacttc | 2700 |
| cagccgggcc | gcagcatcat | tgacaacatt | gtggatgctg | tctacaacag | ccggaagacg | 2760 |
| gtgtgcgtgg | tgagccgcag | ctacctgcgc | agcgagtggt | gctctctaga | ggtgcagttg | 2820 |
| gccagctacc | ggctgttgga | tgagcggcgt | gacatcctgg | tactggtgct | gctggaggac | 2880 |
| gtgggtgatg | ctgagctgtc | tgcctaccac | cgcatgcggc | gggtgctgct | gcggcgcacc | 2940 |
| tacctgcgct | ggcctcttga | ccccgcagct | cagccgctct | tttgggcacg | gctgaagagg | 3000 |
| gcactgaggt | ggggagaggg | aggagaggag | gaggaagaag | aaggtttggg | tggagggacg | 3060 |
| ggaaggccca | gggaaggaga | caaacagatg | tag |            |            | 3093 |

```
<210> SEQ ID NO 9
<211> LENGTH: 1030
<212> TYPE: PRT
<213> ORGANISM: Bos taurus

<400> SEQUENCE: 9

Met Gly Pro Tyr Cys Ala Pro His Pro Leu Ser Leu Leu Val Gln Ala
1               5                   10                  15

Ala Ala Leu Ala Ala Ala Leu Ala Glu Gly Thr Leu Pro Ala Phe Leu
            20                  25                  30

Pro Cys Glu Leu Gln Pro His Gly Gln Val Asp Cys Asn Trp Leu Phe
        35                  40                  45

Leu Lys Ser Val Pro His Phe Ser Ala Gly Ala Pro Arg Ala Asn Val
    50                  55                  60

Thr Ser Leu Ser Leu Ile Ser Asn Arg Ile His His Leu His Asp Ser
65                  70                  75                  80

Asp Phe Val His Leu Ser Asn Leu Arg Val Leu Asn Leu Lys Trp Asn
                85                  90                  95

Cys Pro Pro Ala Gly Leu Ser Pro Met His Phe Pro Cys Arg Met Thr
            100                 105                 110

Ile Glu Pro Asn Thr Phe Leu Ala Val Pro Thr Leu Glu Glu Leu Asn
        115                 120                 125
```

```
Leu Ser Tyr Asn Gly Ile Thr Thr Val Pro Ala Leu Pro Ser Ser Leu
130                 135                 140

Val Ser Leu Ser Leu Ser His Thr Ser Ile Leu Val Leu Gly Pro Thr
145                 150                 155                 160

His Phe Thr Gly Leu His Ala Leu Arg Phe Leu Tyr Met Asp Gly Asn
                165                 170                 175

Cys Tyr Tyr Met Asn Pro Cys Pro Arg Ala Leu Glu Val Ala Pro Gly
                180                 185                 190

Ala Leu Leu Gly Leu Gly Asn Leu Thr His Leu Ser Leu Lys Tyr Asn
            195                 200                 205

Asn Leu Thr Glu Val Pro Arg Arg Leu Pro Pro Ser Leu Asp Thr Leu
        210                 215                 220

Leu Leu Ser Tyr Asn His Ile Val Thr Leu Ala Pro Glu Asp Leu Ala
225                 230                 235                 240

Asn Leu Thr Ala Leu Arg Val Leu Asp Val Gly Gly Asn Cys Arg Arg
                245                 250                 255

Cys Asp His Ala Arg Asn Pro Cys Arg Glu Cys Pro Lys Asn Phe Pro
                260                 265                 270

Lys Leu His Pro Asp Thr Phe Ser His Leu Ser Arg Leu Glu Gly Leu
            275                 280                 285

Val Leu Lys Asp Ser Ser Leu Tyr Lys Leu Glu Lys Asp Trp Phe Arg
        290                 295                 300

Gly Leu Gly Arg Leu Gln Val Leu Asp Leu Ser Glu Asn Phe Leu Tyr
305                 310                 315                 320

Asp Tyr Ile Thr Lys Thr Thr Ile Phe Asn Asp Leu Thr Gln Leu Arg
                325                 330                 335

Arg Leu Asn Leu Ser Phe Asn Tyr His Lys Lys Val Ser Phe Ala His
            340                 345                 350

Leu His Leu Ala Ser Ser Phe Gly Ser Leu Val Ser Leu Glu Lys Leu
        355                 360                 365

Asp Met His Gly Ile Phe Phe Arg Ser Leu Thr Asn Ile Thr Leu Gln
370                 375                 380

Ser Leu Thr Arg Leu Pro Lys Leu Gln Ser Leu His Leu Gln Leu Asn
385                 390                 395                 400

Phe Ile Asn Gln Ala Gln Leu Ser Ile Phe Gly Ala Phe Pro Ser Leu
                405                 410                 415

Leu Phe Val Asp Leu Ser Asp Asn Arg Ile Ser Gly Ala Ala Thr Pro
            420                 425                 430

Ala Ala Ala Leu Gly Glu Val Asp Ser Arg Val Glu Val Trp Arg Leu
        435                 440                 445

Pro Arg Gly Leu Ala Pro Gly Pro Leu Asp Ala Val Ser Ser Lys Asp
450                 455                 460

Phe Met Pro Ser Cys Asn Leu Asn Phe Thr Leu Asp Leu Ser Arg Asn
465                 470                 475                 480

Asn Leu Val Thr Ile Gln Gln Glu Met Phe Thr Arg Leu Ser Arg Leu
                485                 490                 495

Gln Cys Leu Arg Leu Ser His Asn Ser Ile Ser Gln Ala Val Asn Gly
            500                 505                 510

Ser Gln Phe Val Pro Leu Thr Ser Leu Arg Val Leu Asp Leu Ser His
        515                 520                 525

Asn Lys Leu Asp Leu Tyr His Gly Arg Ser Phe Thr Glu Leu Pro Gln
530                 535                 540
```

```
Leu Glu Ala Leu Asp Leu Ser Tyr Asn Ser Gln Pro Phe Ser Met Gln
545                 550                 555                 560

Gly Val Gly His Asn Leu Ser Phe Val Ala Gln Leu Pro Ser Leu Arg
            565                 570                 575

Tyr Leu Ser Leu Ala His Asn Gly Ile His Ser Arg Val Ser Gln Lys
        580                 585                 590

Leu Ser Ser Ala Ser Leu Arg Ala Leu Asp Phe Ser Gly Asn Ser Leu
    595                 600                 605

Ser Gln Met Trp Ala Glu Gly Asp Leu Tyr Leu Cys Phe Phe Lys Gly
610                 615                 620

Leu Arg Asn Leu Val Gln Leu Asp Leu Ser Glu Asn His Leu His Thr
625                 630                 635                 640

Leu Leu Pro Arg His Leu Asp Asn Leu Pro Lys Ser Leu Arg Gln Leu
            645                 650                 655

Arg Leu Arg Asp Asn Asn Leu Ala Phe Phe Asn Trp Ser Ser Leu Thr
        660                 665                 670

Val Leu Pro Arg Leu Glu Ala Leu Asp Leu Ala Gly Asn Gln Leu Lys
    675                 680                 685

Ala Leu Ser Asn Gly Ser Leu Pro Pro Gly Ile Arg Leu Gln Lys Leu
690                 695                 700

Asp Val Ser Ser Asn Ser Ile Gly Phe Val Ile Pro Gly Phe Phe Val
705                 710                 715                 720

Arg Ala Thr Arg Leu Ile Glu Leu Asn Leu Ser Ala Asn Ala Leu Lys
            725                 730                 735

Thr Val Asp Pro Ser Trp Phe Gly Ser Leu Ala Gly Thr Leu Lys Ile
        740                 745                 750

Leu Asp Val Ser Ala Asn Pro Leu His Cys Ala Cys Gly Ala Ala Phe
    755                 760                 765

Val Asp Phe Leu Leu Glu Arg Gln Glu Ala Val Pro Gly Leu Ser Arg
770                 775                 780

Arg Val Thr Cys Gly Ser Pro Gly Gln Leu Gln Gly Arg Ser Ile Phe
785                 790                 795                 800

Thr Gln Asp Leu Arg Leu Cys Phe Leu Asp Leu Gly Leu Tyr Leu Phe
            805                 810                 815

Ala Gly Thr Ala Pro Ala Val Leu Leu Leu Val Val Pro Val Val
        820                 825                 830

Tyr His Arg Ala Tyr Trp Arg Leu Lys Tyr His Trp Tyr Leu Leu Arg
    835                 840                 845

Cys Trp Val Asn Gln Arg Trp Arg Arg Glu Glu Lys Cys Tyr Leu Tyr
850                 855                 860

Asp Ser Phe Val Ser Tyr Asn Ser Ala Asp Glu Ser Trp Val Leu Gln
865                 870                 875                 880

Lys Leu Val Pro Glu Leu Glu His Gly Ala Phe Arg Leu Cys Leu His
            885                 890                 895

His Arg Asp Phe Gln Pro Gly Arg Ser Ile Ile Asp Asn Ile Val Asp
        900                 905                 910

Ala Val Tyr Asn Ser Arg Lys Thr Val Cys Val Val Ser Arg Ser Tyr
    915                 920                 925

Leu Arg Ser Glu Trp Cys Ser Leu Glu Val Gln Leu Ala Ser Tyr Arg
930                 935                 940

Leu Leu Asp Glu Arg Arg Asp Ile Leu Val Leu Val Leu Leu Glu Asp
945                 950                 955                 960

Val Gly Asp Ala Glu Leu Ser Ala Tyr His Arg Met Arg Arg Val Leu
```

```
            965                970                975
Leu Arg Arg Thr Tyr Leu Arg Trp Pro Leu Asp Pro Ala Ala Gln Pro
            980                985                990

Leu Phe Trp Ala Arg Leu Lys Arg  Ala Leu Arg Trp Gly  Glu Gly Gly
         995                1000               1005

Glu Glu  Glu Glu Glu Glu Gly  Leu Gly Gly Gly Thr  Gly Arg Pro
    1010              1015               1020

Arg Glu  Gly Asp Lys Gln Met
1025             1030

<210> SEQ ID NO 10
<211> LENGTH: 3096
<212> TYPE: DNA
<213> ORGANISM: Sus scrofa

<400> SEQUENCE: 10
atgggccccc gctgcaccct gcacccccctt tctctcctgg tgcaggtgac agcgctggct      60
gcggctctgg cccagggcag gctgcctgcc ttcctgccct gtgagctcca gcccacggc      120 ctggtgaact gcaactggct cttcctgaag tccgtgcccc acttctcggc ggcagcgccc     180
cgggccaacg tcaccagcct ctccttactc tccaaccgca tccaccacct gcacgactct     240
gacttcgtcc acctgtccag cctacgaact ctcaacctca gtggaactg cccgccggct     300 ggcctcagcc ccatgcactt ccctgccac atgaccatcg agcccaacac cttcctggcc     360
gtgcccaccc tggaggagct gaacctgagc tacaacagca tcacgaccgt gcctgccctg     420
cccgactccc tcgtgtccct gtcgctgagc cgcaccaaca tcctggtgct agaccccacc     480
cacctcactg gcctacatgc cctgcgctac ctgtacatgg atggcaactg ctactacaag     540 aaccctgcc aggggcgct ggaggtggtg ccgggtgccc tcctcggcct gggcaacctc     600
acacatctct cactcaagta caacaatctc acggaggtgc ccgcagcct gccccccagc     660 ctggagaccc tgctgttgtc ctacaaccac attgtcaccc tgacgcctga ggacctggcc     720
aatctgactg ccctgcgcgt gcttgatgtg gggggaact gccgccgctg tgaccatgcc     780
cgcaacccct gcagggagtg cccaaaggac caccccaagc tgcactctga caccttcagc     840
cacctgagcc gcctcgaagg cctggtgttg aaagacagtt ctctctacaa cctggacacc     900
aggtggttcc gaggcctgga caggctccaa gtgctggacc tgagtgagaa cttcctctac     960
gactgcatca ccaagaccac ggccttccag ggcctggccc gactgcgcag cctcaacctg    1020
tccttcaatt accacaagaa ggtgtccttt gcccacctgc acctggcacc ctcctttggg    1080
cacctccggt ccctgaagga gctggacatg catggcatct tcttccgctc gctcagtgag    1140
accacgctcc aacctctggt ccaactgcct atgctccaga ccctgcgcct gcagatgaac    1200
ttcattaacc aggcccagct cagcatcttt ggggccttcc ctggcctgct gtacgtggac    1260
ctatcggaca accgcatcag cggagctgca aggccagtgg ccattactag ggaggtggat    1320
ggtagggaga gggtctggct gccttccagg aacctcgctc acgtccact ggacactctc    1380 cgctcagagg acttcatgcc aaactgcaag gccttcagct tcaccttgga cctgtctcgg    1440
aacaacctgg tgacaatcca gtcggagatg tttgctcgcc tctcacgcct cgagtgcctg    1500
cgcctgagcc acaacagcat ctcccaggcg gtcaatggct ctcagtttgt gccgctgacc    1560
agcctgcggg tgctggacct gtcccacaac aagctggacc tgtatacgg gcgctcgttc    1620 acggagctgc cgcgcctgga agcactggac ctcagctaca atagccagcc ctttaccatg    1680
cagggtgtgg ccacaacct cagcttcgtg gcccagctgc ccgccctgcg ctacctcagc    1740
```

```
ctggcgcaca atgacatcca tagccgagtg tcccagcagc tctgtagcgc ctcactgtgc    1800
gccctggact ttagcggcaa cgatctgagc cggatgtggg ctgagggaga cctctatctc    1860
cgcttcttcc aaggcctaag aagcctagtc tggctggacc tgtcccagaa ccacctgcac    1920
accctcctgc cacgtgccct ggacaacctc cccaaaagcc tgaagcatct gcatctccgt    1980
gacaataacc tggccttctt caactggagc agcctgaccc tcctgcccaa gctggaaacc    2040
ctggacttgg ctgaaaacca gctgaaggcc ctaagcaatg cagcctgcc atctggcacc     2100 cagctgcgga ggctggacct cagtggcaac agcatcggct tgtgaaccc tggcttcttt     2160 gccctggcca agcagttaga agagctcaac ctcagcgcca atgccctcaa gacagtggag    2220
ccctcctggt ttggctcgat ggtgggcaac ctgaaagtcc tagacgtgag cgccaaccct    2280
ctgcactgtg cctgtggggc gaccttcgtg ggcttcctgc tggaggtaca ggctgccgtg    2340
cctgggctgc ccagccgcgt caagtgtggc agtccggggc agctccaggg ccatagcatc    2400
tttgcgcaag acctgcgcct ctgcttcctg gacctgggc tctatctctt tgctgggact     2460
gcaccggcag tgctgctgct gctggtggtg ccggtggtgt accaccgcgc ctactggagg    2520
ctgaagtacc actggtacct tctgcggtgc tgggtcaacc agcggtggcg gcggaggaa     2580 aagtgctacc tctatgacag ctttgtgtcc tacaattcag ctgatgaaag ttgggtgttg    2640
cagaagctgg tgcctgagct ggagcacggt gccttccgcc tctgcttgca ccaccgcgac    2700
ttccagccgg gccgcagcat cattgacaac attgtggatg ctgtctacaa cagccggaag    2760
acggtgtgcg tggtgagccg cagctacctg cgcagcgagt ggtgctctct agaggtgcag    2820
ttggccagct accggctgtt ggatgagcgg cgtgacatcc tggtactggt gctgctggag    2880
gacgtgggtg atgctgagct gtctgcctac caccgcatgc ggcgggtgct gctgcggcgc    2940
acctacctgc gctggcctct tgaccccgca gctcagccgc tcttttgggc acggctgaag    3000
agggcactga ggtggggaga gggaggagag gaggaggaag aagaaggttt gggtggaggg    3060
acgggaaggc ccagggaagg agacaaacag atgtag                              3096
```

<210> SEQ ID NO 11
<211> LENGTH: 1031
<212> TYPE: PRT
<213> ORGANISM: Sus scrofa

<400> SEQUENCE: 11

```
Met Gly Pro Arg Cys Thr Leu His Pro Leu Ser Leu Val Gln Val
1               5                   10                  15

Thr Ala Leu Ala Ala Leu Ala Gln Gly Arg Leu Pro Ala Phe Leu
                20                  25                  30

Pro Cys Glu Leu Gln Pro His Gly Leu Val Asn Cys Asn Trp Leu Phe
            35                  40                  45

Leu Lys Ser Val Pro His Phe Ser Ala Ala Pro Arg Ala Asn Val
        50                  55                  60

Thr Ser Leu Ser Leu Leu Ser Asn Arg Ile His Leu His Asp Ser
65                  70                  75                  80

Asp Phe Val His Leu Ser Ser Leu Arg Thr Leu Asn Leu Lys Trp Asn
                85                  90                  95

Cys Pro Pro Ala Gly Leu Ser Pro Met His Phe Pro Cys His Met Thr
            100                 105                 110

Ile Glu Pro Asn Thr Phe Leu Ala Val Pro Thr Leu Glu Glu Leu Asn
        115                 120                 125
```

-continued

```
Leu Ser Tyr Asn Ser Ile Thr Thr Val Pro Ala Leu Pro Asp Ser Leu
130                 135                 140

Val Ser Leu Ser Leu Ser Arg Thr Asn Ile Leu Val Leu Asp Pro Thr
145                 150                 155                 160

His Leu Thr Gly Leu His Ala Leu Arg Tyr Leu Tyr Met Asp Gly Asn
                165                 170                 175

Cys Tyr Tyr Lys Asn Pro Cys Gln Gly Ala Leu Glu Val Val Pro Gly
                180                 185                 190

Ala Leu Leu Gly Leu Gly Asn Leu Thr His Leu Ser Leu Lys Tyr Asn
                195                 200                 205

Asn Leu Thr Glu Val Pro Arg Ser Leu Pro Pro Ser Leu Glu Thr Leu
210                 215                 220

Leu Leu Ser Tyr Asn His Ile Val Thr Leu Thr Pro Glu Asp Leu Ala
225                 230                 235                 240

Asn Leu Thr Ala Leu Arg Val Leu Asp Val Gly Gly Asn Cys Arg Arg
                245                 250                 255

Cys Asp His Ala Arg Asn Pro Cys Arg Glu Cys Pro Lys Asp His Pro
                260                 265                 270

Lys Leu His Ser Asp Thr Phe Ser His Leu Ser Arg Leu Glu Gly Leu
                275                 280                 285

Val Leu Lys Asp Ser Ser Leu Tyr Asn Leu Asp Thr Arg Trp Phe Arg
290                 295                 300

Gly Leu Asp Arg Leu Gln Val Leu Asp Leu Ser Glu Asn Phe Leu Tyr
305                 310                 315                 320

Asp Cys Ile Thr Lys Thr Thr Ala Phe Gln Gly Leu Ala Arg Leu Arg
                325                 330                 335

Ser Leu Asn Leu Ser Phe Asn Tyr His Lys Lys Val Ser Phe Ala His
                340                 345                 350

Leu His Leu Ala Pro Ser Phe Gly His Leu Arg Ser Leu Lys Glu Leu
                355                 360                 365

Asp Met His Gly Ile Phe Phe Arg Ser Leu Ser Glu Thr Thr Leu Gln
                370                 375                 380

Pro Leu Val Gln Leu Pro Met Leu Gln Thr Leu Arg Leu Gln Met Asn
385                 390                 395                 400

Phe Ile Asn Gln Ala Gln Leu Ser Ile Phe Gly Ala Phe Pro Gly Leu
                405                 410                 415

Leu Tyr Val Asp Leu Ser Asp Asn Arg Ile Ser Gly Ala Ala Arg Pro
                420                 425                 430

Val Ala Ile Thr Arg Glu Val Asp Gly Arg Glu Arg Val Trp Leu Pro
                435                 440                 445

Ser Arg Asn Leu Ala Pro Arg Pro Leu Asp Thr Leu Arg Ser Glu Asp
450                 455                 460

Phe Met Pro Asn Cys Lys Ala Phe Ser Phe Thr Leu Asp Leu Ser Arg
465                 470                 475                 480

Asn Asn Leu Val Thr Ile Gln Ser Glu Met Phe Ala Arg Leu Ser Arg
                485                 490                 495

Leu Glu Cys Leu Arg Leu Ser His Asn Ser Ile Ser Gln Ala Val Asn
                500                 505                 510

Gly Ser Gln Phe Val Pro Leu Thr Ser Leu Arg Val Leu Asp Leu Ser
                515                 520                 525

His Asn Lys Leu Asp Leu Tyr His Gly Arg Ser Phe Thr Glu Leu Pro
                530                 535                 540

Arg Leu Glu Ala Leu Asp Leu Ser Tyr Asn Ser Gln Pro Phe Thr Met
```

-continued

```
545                 550                 555                 560
Gln Gly Val Gly His Asn Leu Ser Phe Val Ala Gln Leu Pro Ala Leu
                565                 570                 575
Arg Tyr Leu Ser Leu Ala His Asn Asp Ile His Ser Arg Val Ser Gln
                580                 585                 590
Gln Leu Cys Ser Ala Ser Leu Cys Ala Leu Asp Phe Ser Gly Asn Asp
                595                 600                 605
Leu Ser Arg Met Trp Ala Glu Gly Asp Leu Tyr Leu Arg Phe Phe Gln
                610                 615                 620
Gly Leu Arg Ser Leu Val Trp Leu Asp Leu Ser Gln Asn His Leu His
625                 630                 635                 640
Thr Leu Leu Pro Arg Ala Leu Asp Asn Leu Pro Lys Ser Leu Lys His
                645                 650                 655
Leu His Leu Arg Asp Asn Asn Leu Ala Phe Phe Asn Trp Ser Ser Leu
                660                 665                 670
Thr Leu Leu Pro Lys Leu Glu Thr Leu Asp Leu Ala Gly Asn Gln Leu
                675                 680                 685
Lys Ala Leu Ser Asn Gly Ser Leu Pro Ser Gly Thr Gln Leu Arg Arg
                690                 695                 700
Leu Asp Leu Ser Gly Asn Ser Ile Gly Phe Val Asn Pro Gly Phe Phe
705                 710                 715                 720
Ala Leu Ala Lys Gln Leu Glu Glu Leu Asn Leu Ser Asn Ala Leu
                725                 730                 735
Lys Thr Val Glu Pro Ser Trp Phe Gly Ser Met Val Gly Asn Leu Lys
                740                 745                 750
Val Leu Asp Val Ser Ala Asn Pro Leu His Cys Ala Cys Gly Ala Thr
                755                 760                 765
Phe Val Gly Phe Leu Leu Glu Val Gln Ala Ala Val Pro Gly Leu Pro
                770                 775                 780
Ser Arg Val Lys Cys Gly Ser Pro Gly Gln Leu Gln Gly His Ser Ile
785                 790                 795                 800
Phe Ala Gln Asp Leu Arg Leu Cys Phe Leu Asp Leu Gly Leu Tyr Leu
                805                 810                 815
Phe Ala Gly Thr Ala Pro Ala Val Leu Leu Leu Val Val Pro Val
                820                 825                 830
Val Tyr His Arg Ala Tyr Trp Arg Leu Lys Tyr His Trp Tyr Leu Leu
                835                 840                 845
Arg Cys Trp Val Asn Gln Arg Trp Arg Glu Glu Lys Cys Tyr Leu
850                 855                 860
Tyr Asp Ser Phe Val Ser Tyr Asn Ser Ala Asp Glu Ser Trp Val Leu
865                 870                 875                 880
Gln Lys Leu Val Pro Glu Leu Glu His Gly Ala Phe Arg Leu Cys Leu
                885                 890                 895
His His Arg Asp Phe Gln Pro Gly Arg Ser Ile Ile Asp Asn Ile Val
                900                 905                 910
Asp Ala Val Tyr Asn Ser Arg Lys Thr Val Cys Val Val Ser Arg Ser
                915                 920                 925
Tyr Leu Arg Ser Glu Trp Cys Ser Leu Glu Val Gln Leu Ala Ser Tyr
                930                 935                 940
Arg Leu Leu Asp Glu Arg Asp Ile Leu Val Leu Val Leu Leu Glu
945                 950                 955                 960
Asp Val Gly Asp Ala Glu Leu Ser Ala Tyr His Arg Met Arg Arg Val
                965                 970                 975
```

Leu Leu Arg Arg Thr Tyr Leu Arg Trp Pro Leu Asp Pro Ala Ala Gln
         980                 985                 990

Pro Leu Phe Trp Ala Arg Leu Lys  Arg Ala Leu Arg Trp Gly Glu Gly
         995                 1000                1005

Gly Glu  Glu  Glu  Glu  Glu  Glu  Gly Leu Gly Gly Gly  Thr Gly Arg
         1010           1015               1020

Pro Arg  Glu Gly Asp Lys Gln  Met
1025              1030

<210> SEQ ID NO 12
<211> LENGTH: 3105
<212> TYPE: DNA
<213> ORGANISM: Canis familiaris

<400> SEQUENCE: 12

| | | | | | | |
|---|---|---|---|---|---|---|
| atgggcccct | gccgtggcgc | cctgcacccc | ctgtctctcc | tggtgcaggc | tgccgcgcta | 60 |
| gccctggccc | tggcccaggg | caccctgcct | gccttcctgc | cctgtgagct | ccagccccat | 120 |
| ggcctggtga | actgcaactg | gctgttcctc | aagtccgtgc | cccgcttctc | ggcagctgca | 180 |
| ccccgcggta | acgtcaccag | cctttccttg | tactccaacc | gcatccacca | cctccatgac | 240 |
| tatgactttg | tccacttcgt | ccacctgcgg | cgtctcaatc | tcaagtggaa | ctgcccgccc | 300 |
| gccagcctca | gccccatgca | ctttccctgt | cacatgacca | ttgagcccaa | caccttcctg | 360 |
| gctgtgccca | ccctagagga | cctgaatctg | agctataaca | gcatcacgac | tgtgcccgcc | 420 |
| ctgcccagtt | cgcttgtgtc | cctgtccctg | agccgcacca | acatcctggt | gctggaccct | 480 |
| gccaccctgg | caggcctttta | tgccctgcgc | ttcctgttcc | tggatggcaa | ctgctactac | 540 |
| aagaacccct | gccagcaggc | cctgcaggtg | gccccaggtg | ccctcctggg | cctgggcaac | 600 |
| ctcacacacc | tgtcactcaa | gtacaacaac | ctcaccgtgg | tgccgcgggg | cctgcccccc | 660 |
| agcctggagt | acctgctctt | gtcctacaac | cacatcatca | ccctggcacc | tgaggacctg | 720 |
| gccaatctga | ctgccctgcg | tgtcctcgat | gtgggtggga | actgtcgccg | ctgtgaccat | 780 |
| gcccgtaacc | cctgcaggga | gtgccccaag | ggcttccccc | agctgcaccc | caacaccttc | 840 |
| ggccacctga | gccacctcga | aggcctggtg | ttgagggaca | gctctctcta | cagcctggac | 900 |
| cccaggtggt | tccatggcct | gggcaacctc | atggtgctgg | acctgagtga | gaacttcctg | 960 |
| tatgactgca | tcaccaaaac | caaagccttc | tacggcctgg | cccggctgcg | cagactcaac | 1020 |
| ctgtccttca | attatcataa | gaaggtgtcc | tttgcccacc | tgcatctggc | atcctccttc | 1080 |
| gggagcctac | tgtccctgca | ggagctggac | atacatggca | tcttcttccg | ctcgctcagc | 1140 |
| gagaccacgc | tccagtcgct | ggcccacctg | cccatgctcc | agcgtctgca | tctgcagttg | 1200 |
| aactttatca | gccaggccca | gctcagcatc | ttcggcgcct | tccctggcct | gcggtacgtg | 1260 |
| gacttgtcag | acaaccgcat | cagtggagct | gcagagcccg | cggctgccac | aggggaggta | 1320 |
| gaggcggact | gtgggagag | agtctggcca | cagtcccggg | accttgctct | gggcacactg | 1380 |
| ggcaccccccg | gctcagaggc | cttcatgccg | agctgcagga | ccctcaactt | caccttggac | 1440 |
| ctgtctcgga | caacctagt | gactgttcag | ccagagatgt | ttgtccggct | ggcgcgcctc | 1500 |
| cagtgcctgg | gcctgagcca | caacagcatc | tcgcaggcgg | tcaatggctc | gcagttcgtg | 1560 |
| cctctgagca | acctgcgggt | gctggacctg | tcccataaca | agctggacct | gtaccacggg | 1620 |
| cgctcgttca | cggagctgcc | gcggctggag | gccttggacc | tcagctacaa | cagccagccc | 1680 |
| ttcagcatgc | ggggcgtggg | ccacaatctc | agctttgtgg | cacagctgcc | agccctgcgc | 1740 |

-continued

```
tacctcagcc tggcgcacaa tggcatccac agccgcgtgt cccagcagct ccgcagcgcc   1800
tcgctccggg ccctggactt cagtggcaat accctgagcc agatgtgggc cgagggagac   1860
ctctatctcc gcttcttcca aggcctgaga agcctggttc agctggacct gtcccagaat   1920
cgcctgcata ccctcctgcc acgcaacctg acaacctcc ccaagagcct gcggctcctg   1980
cggctccgtg acaattacct ggctttcttc aactggagca gcctggccct cctacccaag   2040
ctggaagccc tggacctggc gggaaaccag ctgaaggccc tgagcaatgg cagcttgccc   2100
aacggcaccc agctccagag gctggacctc agcggcaaca gcatcggctt cgtggtcccc   2160
ggcttttttg ccctggccgt gaggcttcga gagctcaacc tcagcgccaa cgccctcaag   2220
acggtggagc cctcctggtt tggttccctg gcgggtgccc tgaaagtcct agacgtgacc   2280 gccaaccct tgcattgcgc ttgcggcgca accttcgtgg acttcttgct ggaggtgcag   2340
gctgcggtgc ccggcctgcc tagccgtgtc aagtgcggca gcccgggcca gctccagggc   2400
cgcagcatct tcgcacagga cctgcgcctc tgcttcctgg acctggggct ctatctcttt   2460
gctgggactg caccggcagt gctgctgctg ctggtggtgc cggtggtgta ccaccgcgcc   2520
tactggaggc tgaagtacca ctggtacctt ctgcggtgct gggtcaacca gcggtggcgg   2580
cgggaggaaa agtgctacct ctatgacagc tttgtgtcct acaattcagc tgatgaaagt   2640
tgggtgttgc agaagctggt gcctgagctg gagcacggtg ccttccgcct ctgcttgcac   2700
caccgcgact tccagccggg ccgcagcatc attgacaaca ttgtggatgc tgtctacaac   2760
agccggaaga cggtgtgcgt ggtaagccgc agctacctgc gcagcgagtg gtgctctcta   2820
gaggtgcagt tggccagcta ccggctgttg gatgagcggc gtgacatcct ggtactggtg   2880
ctgctggagg acgtgggtga tgctgagctg tctgcctacc accgcatgcg gcgggtgctg   2940
ctgcggcgca cctacctgcg ctggcctctt gaccccgcag ctcagccgct cttttgggca   3000
cggctgaaga gggcactgag gtggggagag ggaggagagg aggaggaaga agaaggtttg   3060
ggtggaggga cgggaaggcc cagggaagga gacaaacaga tgtag             3105
```

<210> SEQ ID NO 13
<211> LENGTH: 1034
<212> TYPE: PRT
<213> ORGANISM: Canis familiaris

<400> SEQUENCE: 13

```
Met Gly Pro Cys Arg Gly Ala Leu His Pro Leu Ser Leu Leu Val Gln
1               5                   10                  15

Ala Ala Ala Leu Ala Leu Ala Leu Ala Gln Gly Thr Leu Pro Ala Phe
            20                  25                  30

Leu Pro Cys Glu Leu Gln Pro His Gly Leu Val Asn Cys Asn Trp Leu
        35                  40                  45

Phe Leu Lys Ser Val Pro Arg Phe Ser Ala Ala Pro Arg Gly Asn
    50                  55                  60

Val Thr Ser Leu Ser Leu Tyr Ser Asn Arg Ile His His Leu His Asp
65                  70                  75                  80

Tyr Asp Phe Val His Phe Val His Leu Arg Arg Leu Asn Leu Lys Trp
                85                  90                  95

Asn Cys Pro Pro Ala Ser Leu Ser Pro Met His Phe Pro Cys His Met
            100                 105                 110

Thr Ile Glu Pro Asn Thr Phe Leu Ala Val Pro Thr Leu Glu Asp Leu
        115                 120                 125

Asn Leu Ser Tyr Asn Ser Ile Thr Thr Val Pro Ala Leu Pro Ser Ser
```

```
            130                 135                 140
Leu Val Ser Leu Ser Leu Ser Arg Thr Asn Ile Leu Val Leu Asp Pro
145                 150                 155                 160

Ala Thr Leu Ala Gly Leu Tyr Ala Leu Arg Phe Leu Phe Leu Asp Gly
                165                 170                 175

Asn Cys Tyr Tyr Lys Asn Pro Cys Gln Gln Ala Leu Gln Val Ala Pro
                180                 185                 190

Gly Ala Leu Leu Gly Leu Gly Asn Leu Thr His Leu Ser Leu Lys Tyr
                195                 200                 205

Asn Asn Leu Thr Val Val Pro Arg Gly Leu Pro Pro Ser Leu Glu Tyr
210                 215                 220

Leu Leu Leu Ser Tyr Asn His Ile Ile Thr Leu Ala Pro Glu Asp Leu
225                 230                 235                 240

Ala Asn Leu Thr Ala Leu Arg Val Leu Asp Val Gly Gly Asn Cys Arg
                245                 250                 255

Arg Cys Asp His Ala Arg Asn Pro Cys Arg Glu Cys Pro Lys Gly Phe
                260                 265                 270

Pro Gln Leu His Pro Asn Thr Phe Gly His Leu Ser His Leu Glu Gly
                275                 280                 285

Leu Val Leu Arg Asp Ser Ser Leu Tyr Ser Leu Asp Pro Arg Trp Phe
                295                 300
290

His Gly Leu Gly Asn Leu Met Val Leu Asp Leu Ser Glu Asn Phe Leu
305                 310                 315                 320

Tyr Asp Cys Ile Thr Lys Thr Lys Ala Phe Tyr Gly Leu Ala Arg Leu
                325                 330                 335

Arg Arg Leu Asn Leu Ser Phe Asn Tyr His Lys Lys Val Ser Phe Ala
                340                 345                 350

His Leu His Leu Ala Ser Ser Phe Gly Ser Leu Leu Ser Leu Gln Glu
                355                 360                 365

Leu Asp Ile His Gly Ile Phe Phe Arg Ser Leu Ser Glu Thr Thr Leu
                375                 380
370

Gln Ser Leu Ala His Leu Pro Met Leu Gln Arg Leu His Leu Gln Leu
385                 390                 395                 400

Asn Phe Ile Ser Gln Ala Gln Leu Ser Ile Phe Gly Ala Phe Pro Gly
                405                 410                 415

Leu Arg Tyr Val Asp Leu Ser Asp Asn Arg Ile Ser Gly Ala Ala Glu
                420                 425                 430

Pro Ala Ala Ala Thr Gly Glu Val Glu Ala Asp Cys Gly Glu Arg Val
                435                 440                 445

Trp Pro Gln Ser Arg Asp Leu Ala Leu Gly Thr Leu Gly Thr Pro Gly
450                 455                 460

Ser Glu Ala Phe Met Pro Ser Cys Arg Thr Leu Asn Phe Thr Leu Asp
465                 470                 475                 480

Leu Ser Arg Asn Asn Leu Val Thr Val Gln Pro Glu Met Phe Val Arg
                485                 490                 495

Leu Ala Arg Leu Gln Cys Leu Gly Leu Ser His Asn Ser Ile Ser Gln
                500                 505                 510

Ala Val Asn Gly Ser Gln Phe Val Pro Leu Ser Asn Leu Arg Val Leu
                515                 520                 525

Asp Leu Ser His Asn Lys Leu Asp Leu Tyr His Gly Arg Ser Phe Thr
                535                 540
530

Glu Leu Pro Arg Leu Glu Ala Leu Asp Leu Ser Tyr Asn Ser Gln Pro
545                 550                 555                 560
```

```
Phe Ser Met Arg Gly Val Gly His Asn Leu Ser Phe Val Ala Gln Leu
                565                 570                 575

Pro Ala Leu Arg Tyr Leu Ser Leu Ala His Asn Gly Ile His Ser Arg
                580                 585                 590

Val Ser Gln Gln Leu Arg Ser Ala Ser Leu Arg Ala Leu Asp Phe Ser
                595                 600                 605

Gly Asn Thr Leu Ser Gln Met Trp Ala Glu Gly Asp Leu Tyr Leu Arg
                610                 615                 620

Phe Phe Gln Gly Leu Arg Ser Leu Val Gln Leu Asp Leu Ser Gln Asn
625                 630                 635                 640

Arg Leu His Thr Leu Leu Pro Arg Asn Leu Asp Asn Leu Pro Lys Ser
                645                 650                 655

Leu Arg Leu Leu Arg Leu Arg Asp Asn Tyr Leu Ala Phe Phe Asn Trp
                660                 665                 670

Ser Ser Leu Ala Leu Leu Pro Lys Leu Glu Ala Leu Asp Leu Ala Gly
                675                 680                 685

Asn Gln Leu Lys Ala Leu Ser Asn Gly Ser Leu Pro Asn Gly Thr Gln
                690                 695                 700

Leu Gln Arg Leu Asp Leu Ser Gly Asn Ser Ile Gly Phe Val Val Pro
705                 710                 715                 720

Gly Phe Phe Ala Leu Ala Val Arg Leu Arg Glu Leu Asn Leu Ser Ala
                725                 730                 735

Asn Ala Leu Lys Thr Val Glu Pro Ser Trp Phe Gly Ser Leu Ala Gly
                740                 745                 750

Ala Leu Lys Val Leu Asp Val Thr Ala Asn Pro Leu His Cys Ala Cys
                755                 760                 765

Gly Ala Thr Phe Val Asp Phe Leu Leu Glu Val Gln Ala Ala Val Pro
                770                 775                 780

Gly Leu Pro Ser Arg Val Lys Cys Gly Ser Pro Gly Gln Leu Gln Gly
785                 790                 795                 800

Arg Ser Ile Phe Ala Gln Asp Leu Arg Leu Cys Phe Leu Asp Leu Gly
                805                 810                 815

Leu Tyr Leu Phe Ala Gly Thr Ala Pro Ala Val Leu Leu Leu Leu Val
                820                 825                 830

Val Pro Val Val Tyr His Arg Ala Tyr Trp Arg Leu Lys Tyr His Trp
                835                 840                 845

Tyr Leu Leu Arg Cys Trp Val Asn Gln Arg Trp Arg Arg Glu Glu Lys
                850                 855                 860

Cys Tyr Leu Tyr Asp Ser Phe Val Ser Tyr Asn Ser Ala Asp Glu Ser
865                 870                 875                 880

Trp Val Leu Gln Lys Leu Val Pro Glu Leu Glu His Gly Ala Phe Arg
                885                 890                 895

Leu Cys Leu His His Arg Asp Phe Gln Pro Gly Arg Ser Ile Ile Asp
                900                 905                 910

Asn Ile Val Asp Ala Val Tyr Asn Ser Arg Lys Thr Val Cys Val Val
                915                 920                 925

Ser Arg Ser Tyr Leu Arg Ser Glu Trp Cys Ser Leu Glu Val Gln Leu
                930                 935                 940

Ala Ser Tyr Arg Leu Leu Asp Glu Arg Arg Asp Ile Leu Val Leu Val
945                 950                 955                 960

Leu Leu Glu Asp Val Gly Asp Ala Glu Leu Ser Ala Tyr His Arg Met
                965                 970                 975
```

Arg Arg Val Leu Leu Arg Arg Thr Tyr Leu Arg Trp Pro Leu Asp Pro
            980                 985                 990

Ala Ala Gln Pro Leu Phe Trp Ala Arg Leu Lys Arg Ala Leu Arg Trp
        995                 1000                1005

Gly Glu Gly Gly Glu Glu Glu Glu Glu Gly Leu Gly Gly Gly
    1010                1015                1020

Thr Gly Arg Pro Arg Glu Gly Asp Lys Gln Met
1025                1030

<210> SEQ ID NO 14
<211> LENGTH: 31
<212> TYPE: DNA
<213> ORGANISM: Artificial sequence
<220> FEATURE:
<223> OTHER INFORMATION: primer

<400> SEQUENCE: 14
gggtaccatg ggcccctact gtgccccgca c         31

<210> SEQ ID NO 15
<211> LENGTH: 31
<212> TYPE: DNA
<213> ORGANISM: Artificial sequence
<220> FEATURE:
<223> OTHER INFORMATION: primer

<400> SEQUENCE: 15
gtctagagtc tgtgctattc ggctgtcgtg g         31

<210> SEQ ID NO 16
<211> LENGTH: 37
<212> TYPE: DNA
<213> ORGANISM: Artificial sequence
<220> FEATURE:
<223> OTHER INFORMATION: primer

<400> SEQUENCE: 16
gaagcttacc atgggccccc gctgcaccct gcacccc    37

<210> SEQ ID NO 17
<211> LENGTH: 36
<212> TYPE: DNA
<213> ORGANISM: Artificial sequence
<220> FEATURE:
<223> OTHER INFORMATION: primer

<400> SEQUENCE: 17
ggcggccgct tacatgccag gctgggggt ggggtg      36

<210> SEQ ID NO 18
<211> LENGTH: 30
<212> TYPE: DNA
<213> ORGANISM: Artificial sequence
<220> FEATURE:
<223> OTHER INFORMATION: primer

<400> SEQUENCE: 18
ggtgacaatc cagtcggaga tgtttgctcg            30

<210> SEQ ID NO 19
<211> LENGTH: 29
<212> TYPE: DNA
<213> ORGANISM: Artificial sequence
<220> FEATURE:
<223> OTHER INFORMATION: primer

<400> SEQUENCE: 19
ggtccagctt gttgtgggac aggtccagc                                    29

<210> SEQ ID NO 20
<211> LENGTH: 36
<212> TYPE: DNA
<213> ORGANISM: Artificial sequence
<220> FEATURE:
<223> OTHER INFORMATION: primer

<400> SEQUENCE: 20
gaagcttacc atgggcccct gccgtggcgc cctgca                            36

<210> SEQ ID NO 21
<211> LENGTH: 36
<212> TYPE: DNA
<213> ORGANISM: Artificial sequence
<220> FEATURE:
<223> OTHER INFORMATION: primer

<400> SEQUENCE: 21
gtctagatga tcaggctgtc gtggggcccc ggcaga                            36

<210> SEQ ID NO 22
<211> LENGTH: 27
<212> TYPE: DNA
<213> ORGANISM: Artificial sequence
<220> FEATURE:
<223> OTHER INFORMATION: primer

<400> SEQUENCE: 22
tcaccttgga cctgtctcgg aacaacc                                      27

<210> SEQ ID NO 23
<211> LENGTH: 26
<212> TYPE: DNA
<213> ORGANISM: Artificial sequence
<220> FEATURE:
<223> OTHER INFORMATION: primer

<400> SEQUENCE: 23
acaggtccag cttgttatgg gacagg                                       26

<210> SEQ ID NO 24
<211> LENGTH: 29
<212> TYPE: DNA
<213> ORGANISM: Artificial sequence
<220> FEATURE:
<223> OTHER INFORMATION: primer

<400> SEQUENCE: 24
gcggatatca ccatgggccc ctactgtgc                                    29

<210> SEQ ID NO 25
<211> LENGTH: 42
<212> TYPE: DNA
<213> ORGANISM: Artificial sequence
<220> FEATURE:
<223> OTHER INFORMATION: primer

<400> SEQUENCE: 25
atagagcccc aggtccagga agcagaggcg caggtcctgt gt                     42

<210> SEQ ID NO 26

<210> SEQ ID NO 26
<211> LENGTH: 42
<212> TYPE: DNA
<213> ORGANISM: Artificial sequence
<220> FEATURE:
<223> OTHER INFORMATION: primer

<400> SEQUENCE: 26
acacaggacc tgcgcctctg cttcctggac ctggggctct at        42

<210> SEQ ID NO 27
<211> LENGTH: 29
<212> TYPE: DNA
<213> ORGANISM: Artificial sequence
<220> FEATURE:
<223> OTHER INFORMATION: primer

<400> SEQUENCE: 27
gcggaattcc tacatctgtt tgtctccctt        29

<210> SEQ ID NO 28
<211> LENGTH: 48
<212> TYPE: DNA
<213> ORGANISM: Artificial sequence
<220> FEATURE:
<223> OTHER INFORMATION: primer

<400> SEQUENCE: 28
ccaagaccac catcttcaac gacctgaccc agctgcgcag actcaacc        48

<210> SEQ ID NO 29
<211> LENGTH: 48
<212> TYPE: DNA
<213> ORGANISM: Artificial sequence
<220> FEATURE:
<223> OTHER INFORMATION: primer

<400> SEQUENCE: 29
ggttgagtct gcgcagctgg gtcaggtcgt tgaagatggt ggtcttgg        48

<210> SEQ ID NO 30
<211> LENGTH: 30
<212> TYPE: DNA
<213> ORGANISM: Artificial sequence
<220> FEATURE:
<223> OTHER INFORMATION: primer

<400> SEQUENCE: 30
gcggaattcc accatgggcc cccgctgcac        30

<210> SEQ ID NO 31
<211> LENGTH: 42
<212> TYPE: DNA
<213> ORGANISM: Artificial sequence
<220> FEATURE:
<223> OTHER INFORMATION: primer

<400> SEQUENCE: 31
atagagcccc aggtccagga agcagaggcg caggtcttgc gc        42

<210> SEQ ID NO 32
<211> LENGTH: 42
<212> TYPE: DNA
<213> ORGANISM: Artificial sequence
<220> FEATURE:
<223> OTHER INFORMATION: primer

<400> SEQUENCE: 32
gcgcaagacc tgcgcctctg cttcctggac ctggggctct at                               42

<210> SEQ ID NO 33
<211> LENGTH: 31
<212> TYPE: DNA
<213> ORGANISM: Artificial sequence
<220> FEATURE:
<223> OTHER INFORMATION: primer

<400> SEQUENCE: 33
gcggcggccg cctacatctg tttgtctcct t                                           31

<210> SEQ ID NO 34
<211> LENGTH: 30
<212> TYPE: DNA
<213> ORGANISM: Artificial sequence
<220> FEATURE:
<223> OTHER INFORMATION: primer

<400> SEQUENCE: 34
gcggaattcc accatgggcc cctgccgtgg                                             30

<210> SEQ ID NO 35
<211> LENGTH: 42
<212> TYPE: DNA
<213> ORGANISM: Artificial sequence
<220> FEATURE:
<223> OTHER INFORMATION: primer

<400> SEQUENCE: 35
atagagcccc aggtccagga agcagaggcg caggtcctgt gc                               42

<210> SEQ ID NO 36
<211> LENGTH: 42
<212> TYPE: DNA
<213> ORGANISM: Artificial sequence
<220> FEATURE:
<223> OTHER INFORMATION: primer

<400> SEQUENCE: 36
gcacaggacc tgcgcctctg cttcctggac ctggggctct at                               42

<210> SEQ ID NO 37
<211> LENGTH: 31
<212> TYPE: DNA
<213> ORGANISM: Artificial sequence
<220> FEATURE:
<223> OTHER INFORMATION: primer

<400> SEQUENCE: 37
gcggcggccg cctacatctg tttgtctcct t                                           31

<210> SEQ ID NO 38
<211> LENGTH: 37
<212> TYPE: DNA
<213> ORGANISM: Artificial sequence
<220> FEATURE:
<223> OTHER INFORMATION: primer

<400> SEQUENCE: 38
gcaggctgcc gcgctagccc tggccctggc ccagggc                                     37

<210> SEQ ID NO 39
<211> LENGTH: 37
<212> TYPE: DNA

```
<213> ORGANISM: Artificial sequence
<220> FEATURE:
<223> OTHER INFORMATION: primer

<400> SEQUENCE: 39
gccctgggcc agggccaggg ctagcgcggc agcctgc                              37

<210> SEQ ID NO 40
<211> LENGTH: 24
<212> TYPE: DNA
<213> ORGANISM: Artificial sequence
<220> FEATURE:
<223> OTHER INFORMATION: artificial DNA

<400> SEQUENCE: 40
tcgtcgtttt gtcgttttgt cgtt                                            24

<210> SEQ ID NO 41
<211> LENGTH: 22
<212> TYPE: DNA
<213> ORGANISM: Artificial sequence
<220> FEATURE:
<223> OTHER INFORMATION: artificial DNA

<400> SEQUENCE: 41
tcgtcgttgt cgttttgtcg tt                                              22

<210> SEQ ID NO 42
<211> LENGTH: 24
<212> TYPE: DNA
<213> ORGANISM: Artificial sequence
<220> FEATURE:
<223> OTHER INFORMATION: artificial DNA

<400> SEQUENCE: 42
tcgtcgtttt gtcgttttgt cgtt                                            24

<210> SEQ ID NO 43
<211> LENGTH: 22
<212> TYPE: DNA
<213> ORGANISM: Artificial sequence
<220> FEATURE:
<223> OTHER INFORMATION: Artificial DNA

<400> SEQUENCE: 43
tcgtcgttgt cgttttgtcg tt                                              22

<210> SEQ ID NO 44
<211> LENGTH: 12
<212> TYPE: DNA
<213> ORGANISM: Artificial sequence
<220> FEATURE:
<223> OTHER INFORMATION: Artificial DNA

<400> SEQUENCE: 44
gtcgtcgtcg tc                                                         12

<210> SEQ ID NO 45
<211> LENGTH: 15
<212> TYPE: DNA
<213> ORGANISM: Artificial sequence
<220> FEATURE:
<223> OTHER INFORMATION: Artificial DNA

<400> SEQUENCE: 45
gtcgtcgtcg tcgtc                                                      15
```

<210> SEQ ID NO 46
<211> LENGTH: 18
<212> TYPE: DNA
<213> ORGANISM: Artificial sequence
<220> FEATURE:
<223> OTHER INFORMATION: test DNA

<400> SEQUENCE: 46
gtcgtcgtcg tcgtcgtc                                                 18

<210> SEQ ID NO 47
<211> LENGTH: 21
<212> TYPE: DNA
<213> ORGANISM: Artificial sequence
<220> FEATURE:
<223> OTHER INFORMATION: Artificial DNA

<400> SEQUENCE: 47
gtcgtcgtcg tcgtcgtcgt c                                             21

<210> SEQ ID NO 48
<211> LENGTH: 24
<212> TYPE: DNA
<213> ORGANISM: Artificial sequence
<220> FEATURE:
<223> OTHER INFORMATION: test DNA

<400> SEQUENCE: 48
gtcgtcgtcg tcgtcgtcgt cgtc                                          24

<210> SEQ ID NO 49
<211> LENGTH: 30
<212> TYPE: DNA
<213> ORGANISM: Artificial sequence
<220> FEATURE:
<223> OTHER INFORMATION: Artificial DNA

<400> SEQUENCE: 49
gtcgtcgtcg tcgtcgtcgt cgtcgtcgtc                                    30

<210> SEQ ID NO 50
<211> LENGTH: 20
<212> TYPE: DNA
<213> ORGANISM: Artificial sequence
<220> FEATURE:
<223> OTHER INFORMATION: test DNA

<400> SEQUENCE: 50
tccatgacgt tcctgatgct                                               20

<210> SEQ ID NO 51
<211> LENGTH: 20
<212> TYPE: DNA
<213> ORGANISM: Artificial sequence
<220> FEATURE:
<223> OTHER INFORMATION: test DNA

<400> SEQUENCE: 51
gggggacgat cgtcggggggg                                              20

<210> SEQ ID NO 52
<211> LENGTH: 22
<212> TYPE: DNA
<213> ORGANISM: Artificial sequence
<220> FEATURE:

```
<223> OTHER INFORMATION: test DNA

<400> SEQUENCE: 52
tcgtcgtttt cggcgcgcgc cg                                                  22

<210> SEQ ID NO 53
<211> LENGTH: 24
<212> TYPE: DNA
<213> ORGANISM: Artificial sequence
<220> FEATURE:
<223> OTHER INFORMATION: test DNA

<400> SEQUENCE: 53
tcgtcgtttt gtcgttttgt cgtt                                                24

<210> SEQ ID NO 54
<211> LENGTH: 20
<212> TYPE: DNA
<213> ORGANISM: Artificial sequence
<220> FEATURE:
<223> OTHER INFORMATION: Artificial DNA

<400> SEQUENCE: 54
tccatgacgt tcctgatgct                                                     20

<210> SEQ ID NO 55
<211> LENGTH: 24
<212> TYPE: DNA
<213> ORGANISM: Artificial sequence
<220> FEATURE:
<223> OTHER INFORMATION: test DNA

<400> SEQUENCE: 55
gacgttgacg ttgacgttga cgtt                                                24

<210> SEQ ID NO 56
<211> LENGTH: 32
<212> TYPE: DNA
<213> ORGANISM: Artificial sequence
<220> FEATURE:
<223> OTHER INFORMATION: test DNA

<400> SEQUENCE: 56
tgacgttctg acgttctgac gttctgacgt tc                                       32

<210> SEQ ID NO 57
<211> LENGTH: 20
<212> TYPE: DNA
<213> ORGANISM: Artificial sequence
<220> FEATURE:
<223> OTHER INFORMATION: test DNA

<400> SEQUENCE: 57
gggggacgat cgtcgggggg                                                     20

<210> SEQ ID NO 58
<211> LENGTH: 20
<212> TYPE: DNA
<213> ORGANISM: Artificial sequence
<220> FEATURE:
<223> OTHER INFORMATION: test DNA

<400> SEQUENCE: 58
gacgatcgtc gacgatcgtc                                                     20
```

```
<210> SEQ ID NO 59
<211> LENGTH: 30
<212> TYPE: DNA
<213> ORGANISM: Artificial sequence
<220> FEATURE:
<223> OTHER INFORMATION: Artificial DNA

<400> SEQUENCE: 59
gacgatcgtc gacgatcgtc gacgatcgtc                                        30

<210> SEQ ID NO 60
<211> LENGTH: 22
<212> TYPE: DNA
<213> ORGANISM: Artificial sequence
<220> FEATURE:
<223> OTHER INFORMATION: test DNA

<400> SEQUENCE: 60
tcgtcgtttt cggcgcgcgc cg                                                22

<210> SEQ ID NO 61
<211> LENGTH: 24
<212> TYPE: DNA
<213> ORGANISM: Artificial sequence
<220> FEATURE:
<223> OTHER INFORMATION: Artificial DNA

<400> SEQUENCE: 61
tcgtcgtttt cgtcgtcgtt ttcg                                              24

<210> SEQ ID NO 62
<211> LENGTH: 36
<212> TYPE: DNA
<213> ORGANISM: Artificial sequence
<220> FEATURE:
<223> OTHER INFORMATION: test DNA

<400> SEQUENCE: 62
tcgtcgtttt cgtcgtcgtt ttcgtcgtcg ttttcg                                 36

<210> SEQ ID NO 63
<211> LENGTH: 24
<212> TYPE: DNA
<213> ORGANISM: Artificial sequence
<220> FEATURE:
<223> OTHER INFORMATION: test DNA

<400> SEQUENCE: 63
tcgtcgtttt gtcgttttgt cgtt                                              24

<210> SEQ ID NO 64
<211> LENGTH: 22
<212> TYPE: DNA
<213> ORGANISM: Artificial sequence
<220> FEATURE:
<223> OTHER INFORMATION: test DNA

<400> SEQUENCE: 64
tcgtcgttgt cgttttgtcg tt                                                22

<210> SEQ ID NO 65
<211> LENGTH: 28
<212> TYPE: DNA
<213> ORGANISM: Artificial sequence
<220> FEATURE:
<223> OTHER INFORMATION: test DNA
```

<400> SEQUENCE: 65
tcgtcgttgt cgttttgtcg ttgtcgtt                                28

<210> SEQ ID NO 66
<211> LENGTH: 28
<212> TYPE: DNA
<213> ORGANISM: artificial sequence
<220> FEATURE:
<223> OTHER INFORMATION: test DNA

<400> SEQUENCE: 66
tcgtcgtcgt cgttgtcgtt ttgtcgtt                                28

<210> SEQ ID NO 67
<211> LENGTH: 34
<212> TYPE: DNA
<213> ORGANISM: artificial sequence
<220> FEATURE:
<223> OTHER INFORMATION: test DNA

<400> SEQUENCE: 67
tcgtcgtcgt cgttgtcgtt ttgtcgttgt cgtt                         34

<210> SEQ ID NO 68
<211> LENGTH: 44
<212> TYPE: DNA
<213> ORGANISM: Artificial sequence
<220> FEATURE:
<223> OTHER INFORMATION: test DNA

<400> SEQUENCE: 68
tcgtcgttgt cgttttgtcg tttcgtcgtt gtcgttttgt cgtt              44

<210> SEQ ID NO 69
<211> LENGTH: 24
<212> TYPE: DNA
<213> ORGANISM: Artificial sequence
<220> FEATURE:
<223> OTHER INFORMATION: test DNA

<400> SEQUENCE: 69
tcgtcgtttt gtcgttttgt cgtt                                    24

<210> SEQ ID NO 70
<211> LENGTH: 24
<212> TYPE: DNA
<213> ORGANISM: Artificial sequence
<220> FEATURE:
<223> OTHER INFORMATION: Artificial DNA

<400> SEQUENCE: 70
gtcgtcgtcg tcgtcgtcgt cgtc                                    24

<210> SEQ ID NO 71
<211> LENGTH: 24
<212> TYPE: DNA
<213> ORGANISM: Artificial sequence
<220> FEATURE:
<223> OTHER INFORMATION: test DNA

<400> SEQUENCE: 71
gtcgtcgtcg tcgtcgtcgt cgtc                                    24

<210> SEQ ID NO 72
<211> LENGTH: 24

-continued

<212> TYPE: DNA
<213> ORGANISM: Artificial sequence
<220> FEATURE:
<223> OTHER INFORMATION: test DNA

<400> SEQUENCE: 72
gtcgtcgtcg tcgtcgtcgt cgtc        24

<210> SEQ ID NO 73
<211> LENGTH: 18
<212> TYPE: DNA
<213> ORGANISM: Artificial sequence
<220> FEATURE:
<223> OTHER INFORMATION: test DNA

<400> SEQUENCE: 73
ttcgtcttcg tcttcgtc        18

<210> SEQ ID NO 74
<211> LENGTH: 30
<212> TYPE: DNA
<213> ORGANISM: Artificial sequence
<220> FEATURE:
<223> OTHER INFORMATION: test DNA

<400> SEQUENCE: 74
ttcgtcttcg tcttcgtctt cgtcttcgtc        30

<210> SEQ ID NO 75
<211> LENGTH: 18
<212> TYPE: DNA
<213> ORGANISM: Artificial sequence
<220> FEATURE:
<223> OTHER INFORMATION: test DNA

<400> SEQUENCE: 75
gtcgttgtcg ttgtcgtt        18

<210> SEQ ID NO 76
<211> LENGTH: 22
<212> TYPE: DNA
<213> ORGANISM: Artificial sequence
<220> FEATURE:
<223> OTHER INFORMATION: test DNA

<400> SEQUENCE: 76
tcgacgtttg acgtttgacg tt        22

<210> SEQ ID NO 77
<211> LENGTH: 24
<212> TYPE: DNA
<213> ORGANISM: Artificial sequence
<220> FEATURE:
<223> OTHER INFORMATION: test DNA

<400> SEQUENCE: 77
tcgtcgtttt gtcgttttgt cgtt        24

<210> SEQ ID NO 78
<211> LENGTH: 24
<212> TYPE: DNA
<213> ORGANISM: Artificial sequence
<220> FEATURE:
<223> OTHER INFORMATION: test DNA

<400> SEQUENCE: 78

```
ttcgttttcg ttttcgtttt cgtt                                          24
```

<210> SEQ ID NO 79
<211> LENGTH: 30
<212> TYPE: DNA
<213> ORGANISM: Artificial sequence
<220> FEATURE:
<223> OTHER INFORMATION: test DNA

<400> SEQUENCE: 79

```
ttcgttttcg ttttcgtttt cgttttcgtt                                    30
```

<210> SEQ ID NO 80
<211> LENGTH: 24
<212> TYPE: DNA
<213> ORGANISM: Artificial sequence
<220> FEATURE:
<223> OTHER INFORMATION: test DNA

<400> SEQUENCE: 80

```
tttcgttttt tcgtttttc gttt                                           24
```

<210> SEQ ID NO 81
<211> LENGTH: 32
<212> TYPE: DNA
<213> ORGANISM: Artificial sequence
<220> FEATURE:
<223> OTHER INFORMATION: test DNA

<400> SEQUENCE: 81

```
tttcgttttt tcgttttttc gtttttttcgt tt                                32
```

<210> SEQ ID NO 82
<211> LENGTH: 30
<212> TYPE: DNA
<213> ORGANISM: Artificial sequence
<220> FEATURE:
<223> OTHER INFORMATION: test DNA

<400> SEQUENCE: 82

```
ttttcgtttt tttcgtttt ttttcgtttt                                     30
```

<210> SEQ ID NO 83
<211> LENGTH: 24
<212> TYPE: DNA
<213> ORGANISM: Artificial sequence
<220> FEATURE:
<223> OTHER INFORMATION: test DNA

<400> SEQUENCE: 83

```
tcgtcgtttt gtcgttttgt cgtt                                          24
```

<210> SEQ ID NO 84
<211> LENGTH: 24
<212> TYPE: DNA
<213> ORGANISM: Artificial sequence
<220> FEATURE:
<223> OTHER INFORMATION: primer

<400> SEQUENCE: 84

```
ttcgttttcg ttttcgtttt cgtt                                          24
```

<210> SEQ ID NO 85
<211> LENGTH: 24
<212> TYPE: DNA
<213> ORGANISM: Artificial sequence

```
<220> FEATURE:
<223> OTHER INFORMATION: test DNA

<400> SEQUENCE: 85
ttcgtcttcg tcttcgtctt cgtc                                          24

<210> SEQ ID NO 86
<211> LENGTH: 24
<212> TYPE: DNA
<213> ORGANISM: Artificial sequence
<220> FEATURE:
<223> OTHER INFORMATION: test DNA

<400> SEQUENCE: 86
ctcgtcctcg tcctcgtcct cgtc                                          24

<210> SEQ ID NO 87
<211> LENGTH: 24
<212> TYPE: DNA
<213> ORGANISM: Artificial sequence
<220> FEATURE:
<223> OTHER INFORMATION: test DNA

<400> SEQUENCE: 87
ttcgccttcg ccttcgcctt cgcc                                          24

<210> SEQ ID NO 88
<211> LENGTH: 30
<212> TYPE: DNA
<213> ORGANISM: Artificial sequence
<220> FEATURE:
<223> OTHER INFORMATION: test DNA

<400> SEQUENCE: 88
ttcgttttcg ttttcgtttt cgttttcgtt                                    30

<210> SEQ ID NO 89
<211> LENGTH: 30
<212> TYPE: DNA
<213> ORGANISM: Artificial sequence
<220> FEATURE:
<223> OTHER INFORMATION: test DNA

<400> SEQUENCE: 89
ttcgtcttcg tcttcgtctt cgtcttcgtc                                    30

<210> SEQ ID NO 90
<211> LENGTH: 30
<212> TYPE: DNA
<213> ORGANISM: Artificial sequence
<220> FEATURE:
<223> OTHER INFORMATION: test DNA

<400> SEQUENCE: 90
ctcgtcctcg tcctcgtcct cgtcctcgtc                                    30

<210> SEQ ID NO 91
<211> LENGTH: 30
<212> TYPE: DNA
<213> ORGANISM: Artificial sequence
<220> FEATURE:
<223> OTHER INFORMATION: test DNA

<400> SEQUENCE: 91
ttcgccttcg ccttcgcctt cgccttcgcc                                    30
```

```
<210> SEQ ID NO 92
<211> LENGTH: 22
<212> TYPE: DNA
<213> ORGANISM: Artificial sequence
<220> FEATURE:
<223> OTHER INFORMATION: test DNA

<400> SEQUENCE: 92
tcgacgtttg acgtttgacg tt                                          22

<210> SEQ ID NO 93
<211> LENGTH: 24
<212> TYPE: DNA
<213> ORGANISM: Artificial sequence
<220> FEATURE:
<223> OTHER INFORMATION: test DNA

<400> SEQUENCE: 93
tcgtcgtttt gtcgttttgt cgtt                                        24

<210> SEQ ID NO 94
<211> LENGTH: 18
<212> TYPE: DNA
<213> ORGANISM: Artificial sequence
<220> FEATURE:
<223> OTHER INFORMATION: test DNA

<400> SEQUENCE: 94
gacgttgacg ttgacgtt                                               18

<210> SEQ ID NO 95
<211> LENGTH: 24
<212> TYPE: DNA
<213> ORGANISM: Artificial sequence
<220> FEATURE:
<223> OTHER INFORMATION: test DNA

<400> SEQUENCE: 95
gacgttgacg ttgacgttga cgtt                                        24

<210> SEQ ID NO 96
<211> LENGTH: 30
<212> TYPE: DNA
<213> ORGANISM: Artificial sequence
<220> FEATURE:
<223> OTHER INFORMATION: test DNA

<400> SEQUENCE: 96
gacgttgacg ttgacgttga cgttgacgtt                                  30

<210> SEQ ID NO 97
<211> LENGTH: 18
<212> TYPE: DNA
<213> ORGANISM: Artificial sequence
<220> FEATURE:
<223> OTHER INFORMATION: test DNA

<400> SEQUENCE: 97
gtcgttgtcg ttgtcgtt                                               18

<210> SEQ ID NO 98
<211> LENGTH: 24
<212> TYPE: DNA
<213> ORGANISM: Artificial sequence
<220> FEATURE:
<223> OTHER INFORMATION: test DNA
```

<400> SEQUENCE: 98
gtcgttgtcg ttgtcgttgt cgtt                                          24

<210> SEQ ID NO 99
<211> LENGTH: 30
<212> TYPE: DNA
<213> ORGANISM: Artificial sequence
<220> FEATURE:
<223> OTHER INFORMATION: test DNA

<400> SEQUENCE: 99
gtcgttgtcg ttgtcgttgt cgttgtcgtt                                    30

<210> SEQ ID NO 100
<211> LENGTH: 20
<212> TYPE: DNA
<213> ORGANISM: Artificial sequence
<220> FEATURE:
<223> OTHER INFORMATION: test DNA

<400> SEQUENCE: 100
gggggacgat cgtcgggggg                                               20

<210> SEQ ID NO 101
<211> LENGTH: 24
<212> TYPE: DNA
<213> ORGANISM: Artificial sequence
<220> FEATURE:
<223> OTHER INFORMATION: test DNA

<400> SEQUENCE: 101
tcgtcgtttt gtcgttttgt cgtt                                          24

<210> SEQ ID NO 102
<211> LENGTH: 24
<212> TYPE: DNA
<213> ORGANISM: Artificial sequence
<220> FEATURE:
<223> OTHER INFORMATION: test DNA

<400> SEQUENCE: 102
acgacgacga cgacgacgac gacg                                          24

<210> SEQ ID NO 103
<211> LENGTH: 24
<212> TYPE: DNA
<213> ORGANISM: Artificial sequence
<220> FEATURE:
<223> OTHER INFORMATION: test DNA

<400> SEQUENCE: 103
tcgtcgtcgt cgtcgtcgtc gtcg                                          24

<210> SEQ ID NO 104
<211> LENGTH: 24
<212> TYPE: DNA
<213> ORGANISM: Artificial sequence
<220> FEATURE:
<223> OTHER INFORMATION: test DNA

<400> SEQUENCE: 104
tcgttcgttc gttcgttcgt tcgt                                          24

<210> SEQ ID NO 105

```
<211> LENGTH: 24
<212> TYPE: DNA
<213> ORGANISM: Artificial sequence
<220> FEATURE:
<223> OTHER INFORMATION: test DNA

<400> SEQUENCE: 105
tcgctcgctc gctcgctcgc tcgc                                              24

<210> SEQ ID NO 106
<211> LENGTH: 24
<212> TYPE: DNA
<213> ORGANISM: Artificial sequence
<220> FEATURE:
<223> OTHER INFORMATION: test DNA

<400> SEQUENCE: 106
tcgatcgatc gatcgatcga tcga                                              24

<210> SEQ ID NO 107
<211> LENGTH: 24
<212> TYPE: DNA
<213> ORGANISM: Artificial sequence
<220> FEATURE:
<223> OTHER INFORMATION: test DNA

<400> SEQUENCE: 107
tcggtcggtc ggtcggtcgg tcgg                                              24

<210> SEQ ID NO 108
<211> LENGTH: 24
<212> TYPE: DNA
<213> ORGANISM: Artificial sequence
<220> FEATURE:
<223> OTHER INFORMATION: test DNA

<400> SEQUENCE: 108
ccgtccgtcc gtccgtccgt ccgt                                              24

<210> SEQ ID NO 109
<211> LENGTH: 24
<212> TYPE: DNA
<213> ORGANISM: Artificial sequence
<220> FEATURE:
<223> OTHER INFORMATION: test DNA

<400> SEQUENCE: 109
acgtacgtac gtacgtacgt acgt                                              24

<210> SEQ ID NO 110
<211> LENGTH: 24
<212> TYPE: DNA
<213> ORGANISM: Artificial sequence
<220> FEATURE:
<223> OTHER INFORMATION: test DNA

<400> SEQUENCE: 110
gcgtgcgtgc gtgcgtgcgt gcgt                                              24

<210> SEQ ID NO 111
<211> LENGTH: 24
<212> TYPE: DNA
<213> ORGANISM: Artificial sequence
<220> FEATURE:
<223> OTHER INFORMATION: test DNA

<400> SEQUENCE: 111
```
acgaacgaac gaacgaacga acga 24

<210> SEQ ID NO 112
<211> LENGTH: 24
<212> TYPE: DNA
<213> ORGANISM: Artificial sequence
<220> FEATURE:
<223> OTHER INFORMATION: test DNA

<400> SEQUENCE: 112
ccgcccgccc gcccgcccgc ccgc 24

<210> SEQ ID NO 113
<211> LENGTH: 24
<212> TYPE: DNA
<213> ORGANISM: Artificial sequence
<220> FEATURE:
<223> OTHER INFORMATION: test DNA

<400> SEQUENCE: 113
gcgcgcgcgc gcgcgcgcgc gcgc 24

<210> SEQ ID NO 114
<211> LENGTH: 24
<212> TYPE: DNA
<213> ORGANISM: Artificial sequence
<220> FEATURE:
<223> OTHER INFORMATION: test DNA

<400> SEQUENCE: 114
gcgggcgggc gggcgggcgg gcgg 24

<210> SEQ ID NO 115
<211> LENGTH: 24
<212> TYPE: DNA
<213> ORGANISM: Artificial sequence
<220> FEATURE:
<223> OTHER INFORMATION: test DNA

<400> SEQUENCE: 115
gtcgtcgtcg tcgtcgtcgt cgtc 24

<210> SEQ ID NO 116
<211> LENGTH: 24
<212> TYPE: DNA
<213> ORGANISM: Artificial sequence
<220> FEATURE:
<223> OTHER INFORMATION: test DNA

<400> SEQUENCE: 116
gtcgttgtcg ttgtcgttgt cgtt 24

<210> SEQ ID NO 117
<211> LENGTH: 24
<212> TYPE: DNA
<213> ORGANISM: Artificial sequence
<220> FEATURE:
<223> OTHER INFORMATION: test DNA

<400> SEQUENCE: 117
gacgttgacg ttgacgttga cgtt 24

<210> SEQ ID NO 118
<211> LENGTH: 24
<212> TYPE: DNA

```
<213> ORGANISM: Artificial sequence
<220> FEATURE:
<223> OTHER INFORMATION: test DNA

<400> SEQUENCE: 118
gtcgttgtcg acgtcgttgt cgac                                          24

<210> SEQ ID NO 119
<211> LENGTH: 24
<212> TYPE: DNA
<213> ORGANISM: Artificial sequence
<220> FEATURE:
<223> OTHER INFORMATION: test DNA

<400> SEQUENCE: 119
gacgttgtcg ttgacgttgt cgtt                                          24

<210> SEQ ID NO 120
<211> LENGTH: 24
<212> TYPE: DNA
<213> ORGANISM: Artificial sequence
<220> FEATURE:
<223> OTHER INFORMATION: test DNA

<400> SEQUENCE: 120
tcgtgtcgtt tcgtgtcgtt tcgt                                          24

<210> SEQ ID NO 121
<211> LENGTH: 24
<212> TYPE: DNA
<213> ORGANISM: Artificial sequence
<220> FEATURE:
<223> OTHER INFORMATION: test DNA

<400> SEQUENCE: 121
tcgtgacgtt tcgtgacgtt tcgt                                          24

<210> SEQ ID NO 122
<211> LENGTH: 26
<212> TYPE: DNA
<213> ORGANISM: Artificial sequence
<220> FEATURE:
<223> OTHER INFORMATION: test DNA

<400> SEQUENCE: 122
gtcgtttcgt gtcgtttcgt gtcgtt                                        26

<210> SEQ ID NO 123
<211> LENGTH: 26
<212> TYPE: DNA
<213> ORGANISM: Artificial sequence
<220> FEATURE:
<223> OTHER INFORMATION: test DNA

<400> SEQUENCE: 123
gacgtttcgt gacgtttcgt gacgtt                                        26

<210> SEQ ID NO 124
<211> LENGTH: 24
<212> TYPE: DNA
<213> ORGANISM: Artificial sequence
<220> FEATURE:
<223> OTHER INFORMATION: test DNA

<400> SEQUENCE: 124
gtcgttgtcg tcgtcgttgt cgtc                                          24
```

<210> SEQ ID NO 125
<211> LENGTH: 24
<212> TYPE: DNA
<213> ORGANISM: Artificial sequence
<220> FEATURE:
<223> OTHER INFORMATION: test DNA

<400> SEQUENCE: 125
gacgttgtcg tcgacgttgt cgtc                                    24

<210> SEQ ID NO 126
<211> LENGTH: 24
<212> TYPE: DNA
<213> ORGANISM: Artificial sequence
<220> FEATURE:
<223> OTHER INFORMATION: test DNA

<400> SEQUENCE: 126
tcgtcgtttt gtcgttttgt cgtt                                    24

<210> SEQ ID NO 127
<211> LENGTH: 12
<212> TYPE: DNA
<213> ORGANISM: Artificial sequence
<220> FEATURE:
<223> OTHER INFORMATION: test DNA

<400> SEQUENCE: 127
gtcgtcgtcg tc                                                 12

<210> SEQ ID NO 128
<211> LENGTH: 15
<212> TYPE: DNA
<213> ORGANISM: Artificial sequence
<220> FEATURE:
<223> OTHER INFORMATION: test DNA

<400> SEQUENCE: 128
gtcgtcgtcg tcgtc                                              15

<210> SEQ ID NO 129
<211> LENGTH: 18
<212> TYPE: DNA
<213> ORGANISM: Artificial sequence
<220> FEATURE:
<223> OTHER INFORMATION: test DNA

<400> SEQUENCE: 129
gtcgtcgtcg tcgtcgtc                                           18

<210> SEQ ID NO 130
<211> LENGTH: 21
<212> TYPE: DNA
<213> ORGANISM: Artificial sequence
<220> FEATURE:
<223> OTHER INFORMATION: test DNA

<400> SEQUENCE: 130
gtcgtcgtcg tcgtcgtcgt c                                       21

<210> SEQ ID NO 131
<211> LENGTH: 24
<212> TYPE: DNA
<213> ORGANISM: Artificial sequence
<220> FEATURE:

<223> OTHER INFORMATION: test DNA

<400> SEQUENCE: 131
gtcgtcgtcg tcgtcgtcgt cgtc                                    24

<210> SEQ ID NO 132
<211> LENGTH: 30
<212> TYPE: DNA
<213> ORGANISM: Artificial sequence
<220> FEATURE:
<223> OTHER INFORMATION: test DNA

<400> SEQUENCE: 132
gtcgtcgtcg tcgtcgtcgt cgtcgtcgtc                              30

<210> SEQ ID NO 133
<211> LENGTH: 24
<212> TYPE: DNA
<213> ORGANISM: Artificial sequence
<220> FEATURE:
<223> OTHER INFORMATION: test DNA

<400> SEQUENCE: 133
gtcgtcgtcg tcgtcgtcgt cgtc                                    24

<210> SEQ ID NO 134
<211> LENGTH: 24
<212> TYPE: DNA
<213> ORGANISM: Artificial sequence
<220> FEATURE:
<223> OTHER INFORMATION: test DNA

<400> SEQUENCE: 134
gtcgtcgtcg tcgtcgtcgt cgtc                                    24

<210> SEQ ID NO 135
<211> LENGTH: 24
<212> TYPE: DNA
<213> ORGANISM: Artificial sequence
<220> FEATURE:
<223> OTHER INFORMATION: test DNA

<400> SEQUENCE: 135
gtcgtcgtcg tcgtcgtcgt cgtc                                    24

<210> SEQ ID NO 136
<211> LENGTH: 18
<212> TYPE: DNA
<213> ORGANISM: Artificial sequence
<220> FEATURE:
<223> OTHER INFORMATION: test DNA

<400> SEQUENCE: 136
ttcgtcttcg tcttcgtc                                           18

<210> SEQ ID NO 137
<211> LENGTH: 30
<212> TYPE: DNA
<213> ORGANISM: Artificial sequence
<220> FEATURE:
<223> OTHER INFORMATION: test DNA

<400> SEQUENCE: 137
ttcgtcttcg tcttcgtctt cgtcttcgtc                              30

```
<210> SEQ ID NO 138
<211> LENGTH: 24
<212> TYPE: DNA
<213> ORGANISM: Artificial sequence
<220> FEATURE:
<223> OTHER INFORMATION: test DNA

<400> SEQUENCE: 138
tcgtcgtttt gtcgttttgt cgtt                                          24

<210> SEQ ID NO 139
<211> LENGTH: 24
<212> TYPE: DNA
<213> ORGANISM: Artificial sequence
<220> FEATURE:
<223> OTHER INFORMATION: test DNA

<400> SEQUENCE: 139
ttcgttttcg ttttcgtttt cgtt                                          24

<210> SEQ ID NO 140
<211> LENGTH: 30
<212> TYPE: DNA
<213> ORGANISM: Artificial sequence
<220> FEATURE:
<223> OTHER INFORMATION: test DNA

<400> SEQUENCE: 140
ttcgttttcg ttttcgtttt cgttttcgtt                                    30

<210> SEQ ID NO 141
<211> LENGTH: 24
<212> TYPE: DNA
<213> ORGANISM: Artificial sequence
<220> FEATURE:
<223> OTHER INFORMATION: test DNA

<400> SEQUENCE: 141
tttcgttttt tcgttttttc gttt                                          24

<210> SEQ ID NO 142
<211> LENGTH: 32
<212> TYPE: DNA
<213> ORGANISM: Artificial sequence
<220> FEATURE:
<223> OTHER INFORMATION: test DNA

<400> SEQUENCE: 142
tttcgttttt tcgttttttc gtttttttcgt tt                                32

<210> SEQ ID NO 143
<211> LENGTH: 30
<212> TYPE: DNA
<213> ORGANISM: Artificial sequence
<220> FEATURE:
<223> OTHER INFORMATION: test DNA

<400> SEQUENCE: 143
ttttcgtttt ttttcgtttt ttttcgtttt                                    30

<210> SEQ ID NO 144
<211> LENGTH: 18
<212> TYPE: DNA
<213> ORGANISM: Artificial sequence
<220> FEATURE:
<223> OTHER INFORMATION: test DNA
```

```
<400> SEQUENCE: 144
gtcgttgtcg ttgtcgtt                                              18

<210> SEQ ID NO 145
<211> LENGTH: 22
<212> TYPE: DNA
<213> ORGANISM: Artificial sequence
<220> FEATURE:
<223> OTHER INFORMATION: test DNA

<400> SEQUENCE: 145
tcgacgtttg acgtttgacg tt                                         22

<210> SEQ ID NO 146
<211> LENGTH: 41
<212> TYPE: DNA
<213> ORGANISM: Artificial sequence
<220> FEATURE:
<223> OTHER INFORMATION: test DNA

<400> SEQUENCE: 146 gggggggttcg ttttcgtttt cgttttcgtt ttcgttgggg g                   41

<210> SEQ ID NO 147
<211> LENGTH: 24
<212> TYPE: DNA
<213> ORGANISM: Artificial sequence
<220> FEATURE:
<223> OTHER INFORMATION: test DNA

<400> SEQUENCE: 147
tcgtcgtttt gtcgttttgt cgtt                                       24

<210> SEQ ID NO 148
<211> LENGTH: 24
<212> TYPE: DNA
<213> ORGANISM: Artificial sequence
<220> FEATURE:
<223> OTHER INFORMATION: test DNA

<400> SEQUENCE: 148
acgacgacga cgacgacgac gacg                                       24

<210> SEQ ID NO 149
<211> LENGTH: 24
<212> TYPE: DNA
<213> ORGANISM: Artificial sequence
<220> FEATURE:
<223> OTHER INFORMATION: test DNA

<400> SEQUENCE: 149
tcgtcgtcgt cgtcgtcgtc gtcg                                       24

<210> SEQ ID NO 150
<211> LENGTH: 24
<212> TYPE: DNA
<213> ORGANISM: Artificial sequence
<220> FEATURE:
<223> OTHER INFORMATION: test DNA

<400> SEQUENCE: 150
tcgttcgttc gttcgttcgt tcgt                                       24

<210> SEQ ID NO 151
<211> LENGTH: 24
```

```
<212> TYPE: DNA
<213> ORGANISM: Artificial sequence
<220> FEATURE:
<223> OTHER INFORMATION: test DNA

<400> SEQUENCE: 151
tcgctcgctc gctcgctcgc tcgc                                        24

<210> SEQ ID NO 152
<211> LENGTH: 24
<212> TYPE: DNA
<213> ORGANISM: Artificial sequence
<220> FEATURE:
<223> OTHER INFORMATION: test DNA

<400> SEQUENCE: 152
tcgatcgatc gatcgatcga tcga                                        24

<210> SEQ ID NO 153
<211> LENGTH: 24
<212> TYPE: DNA
<213> ORGANISM: Artificial sequence
<220> FEATURE:
<223> OTHER INFORMATION: test DNA

<400> SEQUENCE: 153
tcggtcggtc ggtcggtcgg tcgg                                        24

<210> SEQ ID NO 154
<211> LENGTH: 24
<212> TYPE: DNA
<213> ORGANISM: Artificial sequence
<220> FEATURE:
<223> OTHER INFORMATION: test DNA

<400> SEQUENCE: 154
ccgtccgtcc gtccgtccgt ccgt                                        24

<210> SEQ ID NO 155
<211> LENGTH: 24
<212> TYPE: DNA
<213> ORGANISM: Artificial sequence
<220> FEATURE:
<223> OTHER INFORMATION: test DNA

<400> SEQUENCE: 155
acgtacgtac gtacgtacgt acgt                                        24

<210> SEQ ID NO 156
<211> LENGTH: 24
<212> TYPE: DNA
<213> ORGANISM: Artificial sequence
<220> FEATURE:
<223> OTHER INFORMATION: test DNA

<400> SEQUENCE: 156
gcgtgcgtgc gtgcgtgcgt gcgt                                        24

<210> SEQ ID NO 157
<211> LENGTH: 24
<212> TYPE: DNA
<213> ORGANISM: Artificial sequence
<220> FEATURE:
<223> OTHER INFORMATION: test DNA

<400> SEQUENCE: 157
```

-continued acgaacgaac gaacgaacga acga 24

<210> SEQ ID NO 158
<211> LENGTH: 24
<212> TYPE: DNA
<213> ORGANISM: Artificial sequence
<220> FEATURE:
<223> OTHER INFORMATION: test DNA

<400> SEQUENCE: 158
ccgcccgccc gcccgcccgc ccgc 24

<210> SEQ ID NO 159
<211> LENGTH: 24
<212> TYPE: DNA
<213> ORGANISM: Artificial sequence
<220> FEATURE:
<223> OTHER INFORMATION: test DNA

<400> SEQUENCE: 159
gcgcgcgcgc gcgcgcgcgc gcgc 24

<210> SEQ ID NO 160
<211> LENGTH: 24
<212> TYPE: DNA
<213> ORGANISM: Artificial sequence
<220> FEATURE:
<223> OTHER INFORMATION: test DNA

<400> SEQUENCE: 160
gcgggcgggc gggcgggcgg gcgg 24

<210> SEQ ID NO 161
<211> LENGTH: 24
<212> TYPE: DNA
<213> ORGANISM: Artificial sequence
<220> FEATURE:
<223> OTHER INFORMATION: test DNA

<400> SEQUENCE: 161
tcgtcgtttt gtcgttttgt cgtt 24

<210> SEQ ID NO 162
<211> LENGTH: 24
<212> TYPE: DNA
<213> ORGANISM: Artificial sequence
<220> FEATURE:
<223> OTHER INFORMATION: test DNA

<400> SEQUENCE: 162
tcgtcgtttt gtcgttttgt cgtt 24

<210> SEQ ID NO 163
<211> LENGTH: 20
<212> TYPE: DNA
<213> ORGANISM: Artificial sequence
<220> FEATURE:
<223> OTHER INFORMATION: test DNA

<400> SEQUENCE: 163
tccatgacgt tcctgatgct 20

<210> SEQ ID NO 164
<211> LENGTH: 24
<212> TYPE: DNA
<213> ORGANISM: Artificial sequence
<220> FEATURE:
<223> OTHER INFORMATION: test DNA

<400> SEQUENCE: 164
gacgttgacg ttgacgttga cgtt                                              24

<210> SEQ ID NO 165
<211> LENGTH: 32
<212> TYPE: DNA
<213> ORGANISM: Artificial sequence
<220> FEATURE:
<223> OTHER INFORMATION: test DNA

<400> SEQUENCE: 165
tgacgttctg acgttctgac gttctgacgt tc                                     32

<210> SEQ ID NO 166
<211> LENGTH: 20
<212> TYPE: DNA
<213> ORGANISM: Artificial sequence
<220> FEATURE:
<223> OTHER INFORMATION: test DNA

<400> SEQUENCE: 166
gggggacgat cgtcggggggg                                                  20

<210> SEQ ID NO 167
<211> LENGTH: 20
<212> TYPE: DNA
<213> ORGANISM: Artificial sequence
<220> FEATURE:
<223> OTHER INFORMATION: test DNA

<400> SEQUENCE: 167
gacgatcgtc gacgatcgtc                                                   20

<210> SEQ ID NO 168
<211> LENGTH: 30
<212> TYPE: DNA
<213> ORGANISM: Artificial sequence
<220> FEATURE:
<223> OTHER INFORMATION: test DNA

<400> SEQUENCE: 168
gacgatcgtc gacgatcgtc gacgatcgtc                                        30

<210> SEQ ID NO 169
<211> LENGTH: 22
<212> TYPE: DNA
<213> ORGANISM: Artificial sequence
<220> FEATURE:
<223> OTHER INFORMATION: primer

<400> SEQUENCE: 169
tcgtcgtttt cggcgcgcgc cg                                                22

<210> SEQ ID NO 170
<211> LENGTH: 24
<212> TYPE: DNA
<213> ORGANISM: Artificial sequence
<220> FEATURE:
<223> OTHER INFORMATION: primer

<400> SEQUENCE: 170
tcgtcgtttt cgtcgtcgtt ttcg                                              24

<210> SEQ ID NO 171
<211> LENGTH: 36
<212> TYPE: DNA
<213> ORGANISM: Artificial sequence
<220> FEATURE:
<223> OTHER INFORMATION: test DNA

<400> SEQUENCE: 171
tcgtcgtttt cgtcgtcgtt ttcgtcgtcg ttttcg                              36

<210> SEQ ID NO 172
<211> LENGTH: 24
<212> TYPE: DNA
<213> ORGANISM: Artificial sequence
<220> FEATURE:
<223> OTHER INFORMATION: test DNA

<400> SEQUENCE: 172
tcgtcgtttt gtcgttttgt cgtt                                           24

<210> SEQ ID NO 173
<211> LENGTH: 18
<212> TYPE: DNA
<213> ORGANISM: Artificial sequence
<220> FEATURE:
<223> OTHER INFORMATION: test DNA

<400> SEQUENCE: 173
gacgttgacg ttgacgtt                                                  18

<210> SEQ ID NO 174
<211> LENGTH: 24
<212> TYPE: DNA
<213> ORGANISM: Artificial sequence
<220> FEATURE:
<223> OTHER INFORMATION: test DNA

<400> SEQUENCE: 174
gacgttgacg ttgacgttga cgtt                                           24

<210> SEQ ID NO 175
<211> LENGTH: 30
<212> TYPE: DNA
<213> ORGANISM: Artificial sequence
<220> FEATURE:
<223> OTHER INFORMATION: test DNA

<400> SEQUENCE: 175
gacgttgacg ttgacgttga cgttgacgtt                                     30

<210> SEQ ID NO 176
<211> LENGTH: 18
<212> TYPE: DNA
<213> ORGANISM: Artificial sequence
<220> FEATURE:
<223> OTHER INFORMATION: test DNA

<400> SEQUENCE: 176
gtcgttgtcg ttgtcgtt                                                  18

<210> SEQ ID NO 177
<211> LENGTH: 24
<212> TYPE: DNA
<213> ORGANISM: Artificial sequence
<220> FEATURE:
<223> OTHER INFORMATION: test DNA -continued

```
<400> SEQUENCE: 177
gtcgttgtcg ttgtcgttgt cgtt                                              24

<210> SEQ ID NO 178
<211> LENGTH: 30
<212> TYPE: DNA
<213> ORGANISM: Artificial sequence
<220> FEATURE:
<223> OTHER INFORMATION: test DNA

<400> SEQUENCE: 178
gtcgttgtcg ttgtcgttgt cgttgtcgtt                                        30

<210> SEQ ID NO 179
<211> LENGTH: 41
<212> TYPE: DNA
<213> ORGANISM: Artificial sequence
<220> FEATURE:
<223> OTHER INFORMATION: test DNA

<400> SEQUENCE: 179
ggggggttcg ttttcgtttt cgttttcgtt ttcgttgggg g                           41

<210> SEQ ID NO 180
<211> LENGTH: 24
<212> TYPE: DNA
<213> ORGANISM: Artificial sequence
<220> FEATURE:
<223> OTHER INFORMATION: test DNA

<400> SEQUENCE: 180
tcgtcgtttt gtcgttttgt cgtt                                              24

<210> SEQ ID NO 181
<211> LENGTH: 22
<212> TYPE: DNA
<213> ORGANISM: Artificial sequence
<220> FEATURE:
<223> OTHER INFORMATION: test DNA

<400> SEQUENCE: 181
tcgtcgttgt cgttttgtcg tt                                                22

<210> SEQ ID NO 182
<211> LENGTH: 28
<212> TYPE: DNA
<213> ORGANISM: Artificial sequence
<220> FEATURE:
<223> OTHER INFORMATION: test DNA

<400> SEQUENCE: 182
tcgtcgttgt cgttttgtcg ttgtcgtt                                          28

<210> SEQ ID NO 183
<211> LENGTH: 28
<212> TYPE: DNA
<213> ORGANISM: Artificial sequence
<220> FEATURE:
<223> OTHER INFORMATION: test DNA

<400> SEQUENCE: 183
tcgtcgtcgt cgttgtcgtt ttgtcgtt                                          28

<210> SEQ ID NO 184
```

<211> LENGTH: 34
<212> TYPE: DNA
<213> ORGANISM: Artificial sequence
<220> FEATURE:
<223> OTHER INFORMATION: test DNA

<400> SEQUENCE: 184
tcgtcgtcgt cgttgtcgtt ttgtcgttgt cgtt                                    34

<210> SEQ ID NO 185
<211> LENGTH: 44
<212> TYPE: DNA
<213> ORGANISM: Artificial sequence
<220> FEATURE:
<223> OTHER INFORMATION: test DNA

<400> SEQUENCE: 185
tcgtcgttgt cgttttgtcg tttcgtcgtt gtcgttttgt cgtt                         44

<210> SEQ ID NO 186
<211> LENGTH: 24
<212> TYPE: DNA
<213> ORGANISM: Artificial sequence
<220> FEATURE:
<223> OTHER INFORMATION: test DNA

<400> SEQUENCE: 186
tcgtcgtttt gtcgttttgt cgtt                                               24

<210> SEQ ID NO 187
<211> LENGTH: 24
<212> TYPE: DNA
<213> ORGANISM: Artificial sequence
<220> FEATURE:
<223> OTHER INFORMATION: test DNA

<400> SEQUENCE: 187
ttcgttttcg ttttcgtttt cgtt                                               24

<210> SEQ ID NO 188
<211> LENGTH: 24
<212> TYPE: DNA
<213> ORGANISM: Artificial sequence
<220> FEATURE:
<223> OTHER INFORMATION: test DNA

<400> SEQUENCE: 188
ttcgtcttcg tcttcgtctt cgtc                                               24

<210> SEQ ID NO 189
<211> LENGTH: 24
<212> TYPE: DNA
<213> ORGANISM: Artificial sequence
<220> FEATURE:
<223> OTHER INFORMATION: test DNA

<400> SEQUENCE: 189
ctcgtcctcg tcctcgtcct cgtc                                               24

<210> SEQ ID NO 190
<211> LENGTH: 24
<212> TYPE: DNA
<213> ORGANISM: Artificial sequence
<220> FEATURE:
<223> OTHER INFORMATION: test DNA

<400> SEQUENCE: 190
ttcgccttcg ccttcgcctt cgcc                                          24

<210> SEQ ID NO 191
<211> LENGTH: 30
<212> TYPE: DNA
<213> ORGANISM: Artificial sequence
<220> FEATURE:
<223> OTHER INFORMATION: test DNA

<400> SEQUENCE: 191
ttcgttttcg ttttcgtttt cgtttcgtt                                     30

<210> SEQ ID NO 192
<211> LENGTH: 30
<212> TYPE: DNA
<213> ORGANISM: Artificial sequence
<220> FEATURE:
<223> OTHER INFORMATION: test DNA

<400> SEQUENCE: 192
ttcgtcttcg tcttcgtctt cgtcttcgtc                                    30

<210> SEQ ID NO 193
<211> LENGTH: 30
<212> TYPE: DNA
<213> ORGANISM: Artificial sequence
<220> FEATURE:
<223> OTHER INFORMATION: test DNA

<400> SEQUENCE: 193
ctcgtcctcg tcctcgtcct cgtcctcgtc                                    30

<210> SEQ ID NO 194
<211> LENGTH: 30
<212> TYPE: DNA
<213> ORGANISM: Artificial sequence
<220> FEATURE:
<223> OTHER INFORMATION: test DNA

<400> SEQUENCE: 194
ttcgccttcg ccttcgcctt cgccttcgcc                                    30

<210> SEQ ID NO 195
<211> LENGTH: 24
<212> TYPE: DNA
<213> ORGANISM: Artificial sequence
<220> FEATURE:
<223> OTHER INFORMATION: test DNA

<400> SEQUENCE: 195
gtcgtcgtcg tcgtcgtcgt cgtc                                          24

<210> SEQ ID NO 196
<211> LENGTH: 24
<212> TYPE: DNA
<213> ORGANISM: Artificial sequence
<220> FEATURE:
<223> OTHER INFORMATION: test DNA

<400> SEQUENCE: 196
gtcgttgtcg ttgtcgttgt cgtt                                          24

<210> SEQ ID NO 197
<211> LENGTH: 24
<212> TYPE: DNA

```
<213> ORGANISM: Artificial sequence
<220> FEATURE:
<223> OTHER INFORMATION: test DNA

<400> SEQUENCE: 197
gacgttgacg ttgacgttga cgtt                                              24

<210> SEQ ID NO 198
<211> LENGTH: 24
<212> TYPE: DNA
<213> ORGANISM: Artificial sequence
<220> FEATURE:
<223> OTHER INFORMATION: test DNA

<400> SEQUENCE: 198
gtcgttgtcg acgtcgttgt cgac                                              24

<210> SEQ ID NO 199
<211> LENGTH: 24
<212> TYPE: DNA
<213> ORGANISM: Artificial sequence
<220> FEATURE:
<223> OTHER INFORMATION: test DNA

<400> SEQUENCE: 199
gacgttgtcg ttgacgttgt cgtt                                              24

<210> SEQ ID NO 200
<211> LENGTH: 24
<212> TYPE: DNA
<213> ORGANISM: Artificial sequence
<220> FEATURE:
<223> OTHER INFORMATION: test DNA

<400> SEQUENCE: 200
tcgtgtcgtt tcgtgtcgtt tcgt                                              24

<210> SEQ ID NO 201
<211> LENGTH: 24
<212> TYPE: DNA
<213> ORGANISM: Artificial sequence
<220> FEATURE:
<223> OTHER INFORMATION: Artificial DNA

<400> SEQUENCE: 201
tcgtgacgtt tcgtgacgtt tcgt                                              24

<210> SEQ ID NO 202
<211> LENGTH: 26
<212> TYPE: DNA
<213> ORGANISM: Artificial sequence
<220> FEATURE:
<223> OTHER INFORMATION: Artificial DNA

<400> SEQUENCE: 202
gtcgtttcgt gtcgtttcgt gtcgtt                                            26

<210> SEQ ID NO 203
<211> LENGTH: 26
<212> TYPE: DNA
<213> ORGANISM: Artificial sequence
<220> FEATURE:
<223> OTHER INFORMATION: Artificial DNA

<400> SEQUENCE: 203
gacgtttcgt gacgtttcgt gacgtt                                            26
```

-continued

<210> SEQ ID NO 204
<211> LENGTH: 24
<212> TYPE: DNA
<213> ORGANISM: Artificial sequence
<220> FEATURE:
<223> OTHER INFORMATION: Artificial DNA

<400> SEQUENCE: 204
gtcgttgtcg tcgtcgttgt cgtc                                          24

<210> SEQ ID NO 205
<211> LENGTH: 24
<212> TYPE: DNA
<213> ORGANISM: Artificial sequence
<220> FEATURE:
<223> OTHER INFORMATION: artificial DNA

<400> SEQUENCE: 205
gacgttgtcg tcgacgttgt cgtc                                          24

<210> SEQ ID NO 206
<211> LENGTH: 24
<212> TYPE: DNA
<213> ORGANISM: Artificial sequence
<220> FEATURE:
<223> OTHER INFORMATION: test DNA

<400> SEQUENCE: 206
tcgtcgtcgt cgtcgtcgtc gtcg                                          24

<210> SEQ ID NO 207
<211> LENGTH: 3109
<212> TYPE: DNA
<213> ORGANISM: Bos taurus

<400> SEQUENCE: 207
ggtaccatgg gcccctactg tgccccgcac cccctttctc tcctggtgca ggcggcggca        60
ctggcagcgg ccctggccga gggcaccctg cctgccttcc tgccctgtga gctccagccc       120
catggtcagg tggactgcaa ctggctgttc ctgaagtctg tgccgcactt ttcggctgga       180
gccccccggg ccaatgtcac cagcctctcc ttaatctcca accgcatcca ccacttgcat       240
gactctgact tcgtccacct gtccaacctg cgggtcctca acctcaagtg gaactgcccg       300
ccggccggcc tcagccccat gcacttcccc tgccgtatga ccatcgagcc caacaccttc       360
ctggctgtgc ccaccctgga ggagctgaac ctgagctaca acggcatcac gaccgtgcct       420
gccctgccca gttccctcgt gtccctgtcg ctgagccaca ccagcatcct ggtgctaggc       480
cccacccact tcaccggcct gcacgccctg cgctttctgt acatggacgg caactgctac       540
tacatgaacc cctgcccgcg ggccctggag gtggcccag gcgccctcct cggcctgggc       600
aacctcacgc acctgtcgct caagtacaac aacctcacgg aggtgccccg ccgcctgccc       660
cccagcctgg acaccctgct gctgtcctac aaccacattg tcaccctggc acccgaggac       720
ctggccaacc tgactgccct gcgcgtgctt gacgtgggtg ggaactgccg ccgctgcgac       780
cacgcccgca cccctgcag ggagtgccca aagaacttcc ccaagctgca ccctgacacc       840
ttcagtcacc tgagccgcct cgaaggcctg gtgttgaagg acagttctct ctacaaacta       900
gagaaagatt ggttccgcgg cctgggcagg ctccaagtgc tcgacctgag tgagaacttc       960
ctctatgact acatcaccaa gaccaccatc ttcaacgacc tgacccagct gcgcagactc      1020

| | |
|---|---|
| aacctgtcct tcaattacca caagaaggtg tccttcgccc acctgcacct agcgtcctcc | 1080 |
| tttgggagtc tggtgtccct ggagaagctg gacatgcacg gcatcttctt ccgctccctc | 1140 |
| accaacatca cgctccagtc gctgacccgg ctgcccaagc tccagagtct gcatctgcag | 1200 |
| ctgaacttca tcaaccaggc ccagctcagc atctttgggg ccttcccgag cctgctcttc | 1260 |
| gtggacctgt cggacaaccg catcagcgga gccgcgacgc cagcggccgc cctggggag | 1320 |
| gtggacagca gggtggaagt ctggcgattg cccaggggcc tcgctccagg cccgctggac | 1380 |
| gccgtcagct caaaggactt catgccaagc tgcaacctca acttcacctt ggacctgtca | 1440 |
| cggaacaacc tggtgacaat ccagcaagag atgtttaccc gcctctcccg cctccagtgc | 1500 |
| ctgcgcctga gccacaacag catctcgcag gcggttaatg gctcccagtt cgtgccgctg | 1560 |
| accagcctgc gagtgctcga cctgtcccac aacaagctgg acctgtacca tgggcgctca | 1620 |
| ttcacggagc tgccgcagct ggaggcactg gacctcagct acaacagcca gcccttcagc | 1680 |
| atgcagggcg tgggccacaa cctcagcttc gtgcccagc tgccctccct gcgctacctc | 1740 |
| agccttgcgc acaatggcat ccacagccgc gtgtcacaga agctcagcag cgcctcgttg | 1800 |
| cgcgccctgg acttcagcgg caactccctg agccagatgt gggccgaggg agacctctat | 1860 |
| ctctgctttt tcaaaggctt gaggaacctg gtccagctgg acctgtccga gaaccatctg | 1920 |
| cacaccctcc tgcctcgtca cctggacaac ctgcccaaga gctgcggca gctgcgtctc | 1980 |
| cgggacaata acctggcctt cttcaactgg agcagcctga ccgtcctgcc ccggctggaa | 2040 |
| gccctggatc tggcaggaaa ccagctgaag gccctgagca acggcagcct gccgcctggc | 2100 |
| atccggctcc agaagctgga cgtgagcagc aacagcatcg gcttcgtgat ccccggcttc | 2160 |
| ttcgtccgcg cgactcggct gatagagctt aacctcagcg ccaatgccct gaagacagtg | 2220 |
| gatccctcct ggttcggttc cttagcaggg accctgaaaa tcctagacgt gagcgccaac | 2280 |
| ccgctccact gcgcctgcgg ggcggccttt gtggacttcc tgctggagag acaggaggcc | 2340 |
| gtgcccggc tgtccaggcg cgtcacatgt ggcagtccgg gccagctcca gggccgcagc | 2400 |
| atcttcacac aggacctgcg cctctgcctg gatgagaccc tctccttgga ctgctttggc | 2460 |
| ctctcactgc taatggtggc gctgggcctg gcagtgccca tgctgcacca cctctgtggc | 2520 |
| tgggacctct ggtactgctt ccacctgtgt ctggcccatt gccccgacg gcggcggcag | 2580 |
| cggggcgagg acaccctgct ctatgatgcc ttcgtggtct tcgacaaggt gcagagtgca | 2640 |
| gtggctgatt gggtgtacaa cgagctccgc gtgcagctgg aggagcgccg ggggcgccgg | 2700 |
| gcgctccgcc tctgcctgga ggagcgagac tggctccctg gtaagacgct cttcgagaac | 2760 |
| ctgtgggcct cggtctacag cagccgcaag accatgttcg tgctggacca cacggaccgg | 2820 |
| gtcagcggcc tcctgcgcgc cagcttcctg ctggcccagc agcgcctgtt ggaggaccgc | 2880 |
| aaggacgtcg tagtgctggt gatcctgcgc cccgccgcct atcggtcccg ctacgtgcgg | 2940 |
| ctgcgccagc gcctctgccg ccagagcgtc ctcctctggc cccaccagcc cagtggccag | 3000 |
| ggtagtttct gggccaacct gggcatagcc ctgaccaggg acaaccgtca cttctataac | 3060 |
| cggaacttct gccggggccc cacgacagcc gaatagcaca gactctaga | 3109 |

<210> SEQ ID NO 208
<211> LENGTH: 3233
<212> TYPE: DNA
<213> ORGANISM: Sus scrofa

<400> SEQUENCE: 208

| | |
|---|---|
| gaagcttacc atgggccccc gctgcaccct gcacccccctt tctctcctgg tgcaggtgac | 60 |

-continued

```
agcgctggct gcggctctgg cccagggcag gctgcctgcc ttcctgccct gtgagctcca      120
gccccacggc ctggtgaact gcaactggct cttcctgaag tccgtgcccc acttctcggc      180
ggcagcgccc cgggccaacg tcaccagcct ctccttactc tccaaccgca tccaccacct      240
gcacgactct gacttcgtcc acctgtccag cctacgaact ctcaacctca gtggaactg       300
cccgccggct ggcctcagcc ccatgcactt ccctgccac atgaccatcg agcccaacac       360
cttcctggcc gtgcccaccc tggaggagct gaacctgagc tacaacagca tcacgaccgt      420
gcctgccctg cccgactccc tcgtgtccct gtcgctgagc cgcaccaaca tcctggtgct      480
agaccccacc cacctcactg cctacatgc cctgcgctac ctgtacatgg atggcaactg       540
ctactacaag aaccctgcc aggggcgct ggaggtggtg ccgggtgccc tcctcggcct        600
gggcaacctc acacatctct cactcaagta caacaatctc acggaggtgc cccgcagcct     660
gcccccagc ctggagaccc tgctgttgtc ctacaaccac attgtcaccc tgacgcctga      720
ggacctggcc aatctgactg ccctgcgcgt gcttgatgtg gggggaact gccgccgctg       780
tgaccatgcc cgcaaccct gcagggagtg cccaaaggac caccccaagc tgcactctga      840
caccttcagc cacctgagcc gcctcgaagg cctggtgttg aaagacagtt ctctctacaa     900
cctggacacc aggtggttcc gaggcctgga caggctccaa gtgctggacc tgagtgagaa     960
cttcctctac gactgcatca ccaagaccac ggccttccag ggcctggccc gactgcgcag   1020
cctcaacctg tccttcaatt accacaagaa ggtgtccttt gcccacctgc acctggcacc   1080
ctcctttggg cacctccggt ccctgaagga gctggacatg catggcatct tcttccgctc   1140
gctcagtgag accacgctcc aacctctggt ccaactgcct atgctccaga ccctgcgcct   1200
gcagatgaac ttcattaacc aggcccagct cagcatcttt ggggccttcc ctggcctgct   1260
gtacgtggac ctatcggaca accgcatcag cggagctgca aggccagtgg ccattactag   1320
ggaggtggat ggtagggaga gggtctggct gccttccagg aacctcgctc cacgtccact   1380
ggacactctc cgctcagagg acttcatgcc aaactgcaag gccttcagct tcaccttgga   1440
cctgtctcgg aacaacctgg tgacaatcca gtcggagatg tttgctcgcc tctcacgcct   1500
cgagtgcctg cgcctgagcc acaacagcat ctcccaggcg gtcaatggct ctcagtttgt   1560
gccgctgacc agcctgcggg tgctggacct gtcccacaac aagctggacc tgtatcacgg   1620
gcgctcgttc acggagctgc cgcgcctgga agcactggac ctcagctaca atagccagcc   1680
ctttaccatg cagggtgtgg ccacaacct cagcttcgtg gcccagctgc ccgccctgcg   1740
ctacctcagc ctggcgcaca tgacatcca tagccgagtg tcccagcagc tctgtagcgc   1800
ctcactgtgc gccctggact ttagcggcaa cgatctgagc cggatgtggg ctgagggaga   1860
cctctatctc cgcttcttcc aaggcctaag aagcctagtc tggctggacc tgtcccagaa   1920
ccacctgcac accctcctgc cacgtgccct ggacaacctc cccaaaagcc tgaagcatct   1980
gcatctccgt gacaataacc tggccttctt caactggagc agcctgaccc tcctgcccaa   2040
gctggaaacc ctggacttgg ctggaaacca gctgaaggcc ctaagcaatg cagcctgcc   2100
atctggcacc cagctgcgga ggctggacct cagtggcaac agcatcggct tgtgaaccc    2160
tggcttcttt gccctggcca agcagttaga agagctcaac ctcagcgcca atgccctcaa   2220
gacagtggag ccctcctggt ttggctcgat ggtgggcaac ctgaaagtcc tagacgtgag   2280
cgccaaccct ctgcactgtg cctgggggc gaccttcgtg gcttcctgc tggaggtaca    2340
ggctgccgtg cctgggctgc ccagccgcgt caagtgtggc agtccggggc agctccaggg   2400
```

```
ccatagcatc tttgcgcaag acctgcgcct ctgcctggat gagaccctct cgtggaactg    2460
ttttggcatc tcgctgctgg ccatggccct gggcctggtt gtgcccatgc tgcaccacct    2520
ctgcggctgg gacctctggt actgcttcca cctgtgcctg gcctggctgc cccaccgagg    2580
gcagcggcgg ggcgcagacg ccctgttcta tgatgccttc gtggtctttg acaaagctca    2640
gagtgctgtg gccgactggg tgtacaacga gctgcgggtg cagctggagg agcgccgtgg    2700
gcgccgcgca ctgcgcctgt gcctggagga gcgagactgg ttacctggca agacgctctt    2760
cgagaacctg tgggcctcag tctacagcag ccgcaagacc ctgtttgtgc tggcccacac    2820
ggaccgtgtc agcggcctct tgcgtgccag tttcctgctg gcccagcagc gcctgctgga    2880
ggaccgcaag gacgttgtag tgctggtgat cctgcgcccc gatgcctacc gctcccgcta    2940
cgtgcggctg cgccagcgcc tctgccgcca gagtgtcctc ctctggcccc accagccccg    3000
tgggcagggc agcttctggg cccagctggg cacagccctg accagggaca accaccactt    3060
ctataaccgg aacttctgcc ggggcccac gacagccgaa tagcactgag tgacagccca    3120
gttgccccag ccccctgga tttgcctctc tgcctggggt gccccaacct gctttgctca    3180
gccacaccac tgctctgctc cctgttcccc accccacccc ccagcctggc atg            3233

<210> SEQ ID NO 209
<211> LENGTH: 3115
<212> TYPE: DNA
<213> ORGANISM: Canis familiaris

<400> SEQUENCE: 209
aagcttacca tgggcccctg ccgtggcgcc ctgcaccccc tgtctctcct ggtgcaggct      60
gccgcgctag ccctggccct ggcccagggc accctgcctg ccttcctgcc ctgtgagctc    120
cagccccatg gcctggtgaa ctgcaactgg ctgttcctca gtccgtgcc ccgcttctcg     180 gcagctgcac cccgcggtaa cgtcaccagc cttccttgt actccaaccg catccaccac    240
ctccatgact atgactttgt ccacttcgtc cacctgcggc gtctcaatct caagtggaac    300
tgcccgcccg ccagcctcag ccccatgcac tttccctgtc acatgaccat tgagcccaac    360
accttcctgg ctgtgcccac cctagaggac ctgaatctga gctataacag catcacgact    420 gtgccccgccc tgcccagttc gcttgtgtcc ctgtccctga gccgcaccaa catcctggtg    480
ctggaccctg ccaccctggc aggcctttat gccctgcgct tcctgttcct ggatggcaac    540
tgctactaca agaaccctg ccagcaggcc ctgcaggtgg cccaggtgc cctcctgggc    600 ctgggcaacc tcacacacct gtcactcaag tacaacaacc tcaccgtggt gccgcgggc    660 ctgccccca gcctggagta cctgctcttg tcctacaacc acatcatcac cctggcacct    720
gaggacctgg ccaatctgac tgccctgcgt gtcctcgatg tgggtgggaa ctgtcgccgc    780
tgtgaccatg cccgtaaccc ctgcagggag tgccccaagg gcttccccca gctgcacccc    840
aacaccttcg gccacctgag ccacctcgaa ggcctggtgt tgagggacag ctctctctac    900
agcctggacc ccaggtggtt ccatggcctg ggcaacctca tggtgctgga cctgagtgag    960
aacttcctgt atgactgcat caccaaaaacc aaagccttct acggcctggc ccggctgcgc   1020
agactcaacc tgtccttcaa ttatcataag aaggtgtcct tgcccacct gcatctggca   1080 tcctccttcg ggagcctact gtccctgcag gagctggaca tacatggcat cttcttccgc   1140
tcgctcagcg agaccacgct ccagtcgctg gcccacctgc ccatgctcca gtgtctgcat   1200
ctgcagttga acttatcag ccaggcccag ctcagcatct tcggcgcctt ccctggcctg   1260
cggtacgtgg acttgtcaga caaccgcatc agtggagctg cagagcccgc ggctgccaca   1320
```

```
ggggaggtag aggcggactg tggggagaga gtctggccac agtcccggga ccttgctctg   1380
ggcacactgg gcaccccggg ctcagaggcc ttcatgccga gctgcaggac cctcaacttc   1440
accttggacc tgtctcggaa caacctagtg actgttcagc cggagatgtt tgtccggctg   1500
gcgcgcctcc agtgcctggg cctgagccac aacagcatct cgcaggcggt caatggctcg   1560
cagttcgtgc ctctgagcaa cctgcgggtg ctggacctgt cccataacaa gctggacctg   1620
taccacgggc gctcgttcac ggagctgccg cggctggagg ccttggacct cagctacaac   1680
agccagccct tcagcatgcg gggcgtgggc cacaatctca gctttgtggc acagctgcca   1740
gccctgcgct acctcagcct ggcgcacaat ggcatccaca gccgcgtgtc ccagcagctc   1800
cgcagcgcct cgctccgggc cctggacttc agtggcaata ccctgagcca gatgtgggcc   1860
gagggagacc tctatctccg cttcttccaa ggcctgagaa gcctggttca gctggacctg   1920
tcccagaatc gcctgcatac cctcctgcca cgcaacctgg acaacctccc caagagcctg   1980 cggctccctgc ggctccgtga caattacctg gctttcttca actggagcag cctggccctc   2040
ctacccaagc tggaagccct ggacctggcg ggaaaccagc tgaaggccct gagcaatggc   2100
agcttgccca acggcaccca gctccagagg ctggacctca cgcgcaacag catcggcttc   2160
gtggtccccg gcttttttgc cctggccgtg aggcttcgag agctcaacct cagcgccaac   2220
gccctcaaga cggtggagcc ctcctggttt ggttccctgg cgggtgccct gaaagtccta   2280
gacgtgaccg ccaaccccct gcattgcgct tgcgcgcaa ccttcgtgga cttcttgctg   2340
gaggtgcagg ctgcggtgcc cggcctgcct agcgtgtca agtgcggcag cccgggccag   2400
ctccagggcc gcagcatctt cgcacaggac ctgcgcctct gcctggacga agcgctctcc   2460
tgggtctgtt tcagcctctc gctgctggct gtggccctga gctggctgt gcccatgctg   2520 caccagctct gtgctgggga cctctggtac tgcttccacc tgtgcctggc ctggctgccc   2580
cggcgggggc ggcggcgggg tgtggatgcc ctggcctacg acgccttcgt ggtcttcgac   2640
aaggcgcaga gctcggtggc ggactgggtg tacaatgagc tgcgggtaca gctagaggag   2700
cgccgtgggc gccgggcgct acgcctgtgt ctggaggaac gtgactgggt acccggcaaa   2760
accctcttcg agaacctctg gcctcagtt tacagcagcc gcaagacgct gtttgtgctg   2820
gcccgcacgg acagagtcag cggcctcctg cgtgccagct tcctgctggc caacagcgc   2880 ctgctggagg accgcaagga cgtcgtggtg ctggtgatcc tgtgccccga cgcccaccgc   2940
tcccgctatg tgcggctgcg ccagcgcctc tgccgccaga gtgtcctcct ctggccccac   3000
cagcccagtg gccagcgcag cttctgggcc cagctgggca cggccctgac cagggacaac   3060
cgccacttct acaaccagaa cttctgccgg ggccccacga cagcctgatc atcta         3115
```

<210> SEQ ID NO 210
<211> LENGTH: 2935
<212> TYPE: DNA
<213> ORGANISM: Gallus gallus

<400> SEQUENCE: 210

```
aagcttacca tgatggagac agcggagaag gcatggccca gcaccaggat gtgcccctcc     60
cactgctgtc cactctggct gctgctgctg gtgacagtga cactgatgcc gatggtgcac   120
ccgtatggct ttcgcaactg cattgaggat gtcaaggcac cttttgtactt ccgctgcatc   180 cagcgcttcc tgcagtcgcc ggccctggca gtgtctgacc tgccaccaca tgccatcgcg   240
ctcaatctgt catacaacaa aatgcgctgc ctgcagccct ctgcctttgc ccacctgaca   300
```

```
cagctgcata ccctggacct gacctacaac ctcctggaga ccctctcccc tggtgccttc    360
aatgggctgg gtgtgctggt ggtgctggac ctgtctcaca acaagctgac cacacttgct    420 gaagggtgt tcaacagctt gggcaacctg tcctcgctgc aggtacaaca taaccccctc     480
agcacggtgt caccaagtgc tctgctaccc ctggtcaacc tgcgccgcct gtctctacgg    540
ggcgggcggc tgaatgggtt gggggcagtg gcagtggcag tgcagggctt ggcacagctg    600
gagctgttgg acctatgtga aaacaacctg caacgctggg gccaggccc accgctaccc     660 gcctcgctgc tcaccctgca gctgtgcaac aactcgctga gggagttagc ggggggcagc    720
ccggagatgc tatggcacgt gaagatactc gacctctcct acaacagtat ctcacaggcg    780
gaggtcttca cccagctcca cctgcgcaac atcagcctgc tccacctgat cggcaacccc    840
ttggatgtct tccacctgtt ggacatctct gacatccaac ctcgcagcct ggatttctct    900
gggttggtgc tggggctca ggggctggat aaggtgtgcc tgaggctgca gggtccccag     960
gccttgcggc ggctgcagct acaacgcaac gggctgaagg tgctgcattg taatgcactg   1020
cagttgtgtc ctgtgctgag agagctggac ctgtcctgga accggctaca gcacgtgggc   1080
tgtgccggcc ggctgctggg caagaagcag cgggagaagc tggaagtgct gacagtggaa   1140
cacaacctgc tgaagaaact gccgtcttgc ctggggccc aggtgctgcc tcggctgtac    1200
aacatttcct tccgctttaa ccgcatcctg actgttgggc cccaagcctt tgcctacgcc   1260
ccggccctgc aggtgttgtg gctcaatatt aacagcctgg tgtggctgga caggcaggca   1320
ctgtggaggc tgcacaacct gacagagctg cgcctggaca acaacctgct gaccgacctc   1380
tatcacaact ccttcattga cctccacaga ctgcgcaccc tcaacctgcg caacaaccgt   1440
gtctccgtcc tcttctctgg tgtcttccag gggctggctg agctgcagac gctggattta   1500 ggggcaaca acttgcgcca cctgactgca cagtcactgc aggggctgcc caaactgcgc   1560
aggctgtacc tggaccgcaa cagattgctg gaggtgagca gcactgtgtt cgccccagtg   1620
caggctaccc tgggggtgct ggacctgcgg gccaacaacc tgcagtacat ctcacagtgg   1680
ctgcgcaagc cgccaccctt ccgcaacctg agcagcctgt acgacctgaa gctgcaggcg   1740
cagcagccct atggactgaa gatgctgcct cactacttct ccagggcctt ggtgaggctg   1800
cagcagctgt cgctgtcaca gaacatgctg cggtccatcc caccggatgt cttcgaggac   1860
ttgggccagc tgcgctccct ggcattggct gacagcagca atgggctgca tgacctgcct   1920
gacggcatct tcagaaacct gggcaacctg cggttcctgg acctggagaa tgcagggctg   1980
cactcgctca ctctggaagt cttcggcaat ctcagccggc tgcaggtgct gcacttggcc   2040
agaaacgagc tgaagaccttt caatgacagc gttgccagcc ggctgtcctc cttgcgctac   2100
ctggacctgc gcaagtgtcc gctcagctgc acctgtgaca acatgtggct gcagggctgg   2160
ctgaacaaca gccgtgtgca ggttgtctac ccctacaact acacctgtgg ctcacagcac   2220
aatgcctaca tccacagctt tgacacacac gtctgcttcc tggacctggg gctctatctc   2280
tttgctggga ctgcaccggc agtgctgctg ctgctggtgg tgccggtggt gtaccaccgc   2340
gcctactgga ggctgaagta ccactggtac cttctgcggt gctgggtcaa ccagcggtgg   2400
cggcgggagg aaaagtgcta cctctatgac agctttgtgt cctacaattc agctgatgaa   2460
agttgggtgt tgcagaagct ggtgcctgag ctggagcacg tgccttccg cctctgcttg   2520 caccaccgcg acttccagcc gggccgcagc atcattgaca acattgtgga tgctgtctac   2580
aacagccgga gacggtgtg cgtggtgagc cgcagctacc tgcgcagcga gtggtgctct   2640
ctagaggtgc agttggccag ctaccggctg ttggatgagc ggcgtgacat cctggtactg   2700
```

```
gtgctgctgg aggacgtggg tgatgctgag ctgtctgcct accaccgcat gcggcgggtg    2760
ctgctgcggc gcacctacct gcgctggcct cttgaccccg cagctcagcc gctcttttgg    2820
gcacggctga gagggcact gaggtgggga gagggaggag aggaggagga agaagaaggt    2880
ttgggtggag ggacgggaag gcccagggaa ggagacaaac agatgtagcg gccgc         2935

<210> SEQ ID NO 211
<211> LENGTH: 3108
<212> TYPE: DNA
<213> ORGANISM: Bos taurus

<400> SEQUENCE: 211
gatatcacca tgggcccta ctgtgccccg cacccccttt ctctcctggt gcaggcggcg       60
gcactggcag cggccctggc cgagggcacc ctgcctgcct tcctgccctg tgagctccag     120
ccccatggtc aggtggactg caactggctg ttcctgaagt ctgtgccgca cttttcggct     180 ggagccccc gggccaatgt caccagcctc tccttaatct ccaaccgcat ccaccacttg      240
catgactctg acttcgtcca cctgtccaac ctgcgggtcc tcaacctcaa gtggaactgc     300
ccgccggccg gcctcagccc catgcacttc ccctgccgta tgaccatcga gcccaacacc     360
ttcctggctg tgcccaccct ggaggagctg aacctgagct acaacggcat cacgaccgtg     420
cctgccctgc ccagttccct cgtgtccctg tcgctgagcc acaccagcat cctggtgcta     480
ggccccaccc acttcaccgg cctgcacgcc ctgcgctttc tgtacatgga cggcaactgc     540
tactacatga accctgcc gcgggccctg gaggtggccc caggcgccct cctcggcctg      600
ggcaacctca cgcacctgtc gctcaagtac aacaacctca cggaggtgcc ccgccgcctg     660
ccccccagcc tggacaccct gctgctgtcc tacaaccaca ttgtcaccct ggcacccgag     720
gacctggcca acctgactgc cctgcgcgtg cttgacgtgg gtgggaactg ccgccgctgc     780
gaccacgccc gcaacccctg cagggagtgc ccaaagaact tccccaagct gcaccctgac     840
accttcagtc acctgagccg cctcgaaggc ctggtgttga aggacagttc tctctacaaa     900
ctagagaaag attggttccg cggcctgggc aggctccaag tgctcgacct gagtgagaac     960
ttcctctatg actacatcac caagaccacc atcttcaacg acctgaccca gctgcgcaga    1020
ctcaacctgt ccttcaatta ccacaagaag gtgtccttcg cccacctgca cctagcgtcc    1080
tcctttggga gtcggtgtc cctggagaag ctggacatgc acggcatctt cttccgctcc    1140
ctcaccaaca tcacgctcca gtcgctgacc cggctgccca gctccagag tctgcatctg    1200 cagctgaact tcatcaacca ggcccagctc agcatctttg ggccttccc gagcctgctc    1260 ttcgtggacc tgtcggacaa ccgcatcagc ggagccgcga cgccagcggc cgccctgggg    1320
gaggtggaca gcagggtgga agtctggcga ttgcccaggg gcctcgctcc aggcccgctg    1380
gacgccgtca gctcaaagga cttcatgcca agctgcaacc tcaacttcac cttggacctg    1440
tcacggaaca acctggtgac aatccagcaa gagatgttta cccgcctctc ccgcctccag    1500
tgcctgcgcc tgagccacaa cagcatctcg caggcggtta atggctccca gttcgtgccg    1560
ctgaccagcc tgcgagtgct cgacctgtcc cacaacaagc tggacctgta ccatgggcgc    1620
tcattcacgg agctgccgca gctggaggca ctggacctcg ctacaacag ccagcccttc    1680 agcatgcagg gcgtgggcca caacctcagc ttcgtggccc agctgccctc cctgcgctac    1740
ctcagccttg cgcacaatgg catccacagc gcgtgtcac agaagctcag cagcgcctcg    1800 ttgcgcgcc tggacttcag cggcaactcc ctgagccaga tgtgggccga gggagacctc    1860
```

| | |
|---|---:|
| tatctctgct ttttcaaagg cttgaggaac ctggtccagc tggacctgtc cgagaaccat | 1920 |
| ctgcacaccc tcctgcctcg tcacctggac aacctgccca agagcctgcg gcagctgcgt | 1980 |
| ctccgggaca ataacctggc cttcttcaac tggagcagcc tgaccgtcct gccccggctg | 2040 |
| gaagccctgg atctgcagg aaaccagctg aaggccctga gcaacggcag cctgccgcct | 2100 |
| ggcatccggc tccagaagct ggacgtgagc agcaacagca tcggcttcgt gatccccggc | 2160 |
| ttcttcgtcc gcgcgactcg gctgatagag cttaacctca gcgccaatgc cctgaagaca | 2220 |
| gtggatccct cctggttcgg ttccttagca gggaccctga aaatcctaga cgtgagcgcc | 2280 |
| aacccgctcc actgcgcctg cggggcggcc tttgtggact tcctgctgga gagacaggag | 2340 |
| gccgtgcccg gctgtccag gcgcgtcaca tgtggcagtc cgggccagct ccagggccgc | 2400 |
| agcatcttca cacaggacct gcgcctctgc ttcctggacc tggggctcta tctctttgct | 2460 |
| gggactgcac cggcagtgct gctgctgctg gtggtgccgg tggtgtacca ccgcgcctac | 2520 |
| tggaggctga gtaccactg gtaccttctg cggtgctggg tcaaccagcg gtggcggcgg | 2580 |
| gaggaaaagt gctacctcta tgacagcttt gtgtcctaca attcagctga tgaaagttgg | 2640 |
| gtgttgcaga agctggtgcc tgagctggag cacggtgcct ccgcctctg cttgcaccac | 2700 |
| cgcgacttcc agccgggccg cagcatcatt gacaacattg tggatgctgt ctacaacagc | 2760 |
| cggaagacgg tgtgcgtggt gagccgcagc tacctgcgca gcgagtggtg ctctctagag | 2820 |
| gtgcagttgg ccagctaccg gctgttgat gagcggcgtg acatcctggt actggtgctg | 2880 |
| ctggaggacg tgggtgatgc tgagctgtct gcctaccacc gcatgcggcg ggtgctgctg | 2940 |
| cggcgcacct acctgcgctg gcctcttgac cccgcagctc agccgctctt ttgggcacgg | 3000 |
| ctgaagaggg cactgaggtg gggagaggga ggagaggagg aggaagaaga aggtttgggt | 3060 |
| ggagggacgg gaaggcccag ggaaggagac aaacagatgt aggaattc | 3108 |

<210> SEQ ID NO 212
<211> LENGTH: 3114
<212> TYPE: DNA
<213> ORGANISM: Sus scrofa

<400> SEQUENCE: 212

| | |
|---|---:|
| gaattccacc atgggccccc gctgcaccct gcacccectt tctctcctgg tgcaggtgac | 60 |
| agcgctggct gcggctctgg cccagggcag gctgcctgcc ttcctgccct gtgagctcca | 120 |
| gccccacggc ctggtgaact gcaactggct cttcctgaag tccgtgcccc acttctcggc | 180 |
| ggcagcgccc cgggccaacg tcaccagcct ctccttactc tccaaccgca tccaccacct | 240 |
| gcacgactct gacttcgtcc acctgtccag cctacgaact ctcaacctca gtggaactg | 300 |
| cccgccggct ggcctcagcc ccatgcactt ccectgccac atgaccatcg agcccaacac | 360 |
| cttcctggcc gtgcccaccc tggaggagct gaacctgagc tacaacagca tcacgaccgt | 420 |
| gcctgccctg cccgactccc tcgtgtccct gtcgctgagc cgcaccaaca tcctggtgct | 480 |
| agaccccacc cacctcactg gcctacatgc cctgcgctac ctgtacatgg atggcaactg | 540 |
| ctactacaag aaccectgcc aggggcgct ggaggtggtg ccgggtgccc tcctcggcct | 600 |
| gggcaacctc acacatctct cactcaagta caacaatctc acggaggtgc cccgcagcct | 660 |
| gccccccagc ctggagaccc tgctgttgtc ctacaaccac attgtcaccc tgacgcctga | 720 |
| ggacctggca aatctgactg ccctgcgcgt gcttgatgtg ggggggaact gccgccgctg | 780 |
| tgaccatgcc cgcaaccct gcaggagtg cccaaaggac cacccaagc tgcactctga | 840 |
| caccttcagc cacctgagcc gcctcgaagg cctggtgttg aaagacagtt ctctctacaa | 900 |

```
cctggacacc aggtggttcc gaggcctgga caggctccaa gtgctggacc tgagtgagaa    960
cttcctctac gactgcatca ccaagaccac ggccttccag ggcctggccc gactgcgcag   1020
cctcaacctg tccttcaatt accacaagaa ggtgtccttt gcccacctgc acctggcacc   1080
ctcctttggg cacctccggt ccctgaagga gctggacatg catggcatct tcttccgctc   1140
gctcagtgag accacgctcc aacctctggt ccaactgcct atgctccaga ccctgcgcct   1200
gcagatgaac ttcattaacc aggcccagct cagcatcttt ggggccttcc ctggcctgct   1260
gtacgtggac ctatcggaca accgcatcag cggagctgca aggccagtgg ccattactag   1320
ggaggtggat ggtagggaga gggtctggct gccttccagg aacctcgctc cacgtccact   1380
ggacactctc cgctcagagg acttcatgcc aaactgcaag gccttcagct tcaccttgga   1440
cctgtctcgg aacaacctgg tgacaatcca gtcggagatg tttgctcgcc tctcacgcct   1500
cgagtgcctg cgcctgagcc acaacagcat ctcccaggcg gtcaatggct ctcagtttgt   1560
gccgctgacc agcctgcggg tgctggacct gtcccacaac aagctggacc tgtatcacgg   1620
gcgctcgttc acggagctgc cgcgcctgga agcactggac ctcagctaca atagccagcc   1680
ctttaccatg cagggtgtgg ccacaacct cagcttcgtg gcccagctgc cgccctgcg   1740
ctacctcagc ctggcgcaca atgacatcca tagccgagtg tcccagcagc tctgtagcgc   1800
ctcactgtgc gccctggact ttagcggcaa cgatctgagc cggatgtggg ctgagggaga   1860
cctctatctc cgcttcttcc aaggcctaag aagcctagtc tggctggacc tgtcccagaa   1920
ccacctgcac accctcctgc cacgtgccct ggacaacctc cccaaaagcc tgaagcatct   1980
gcatctccgt gacaataacc tggccttctt caactggagc agcctgaccc tcctgcccaa   2040
gctggaaacc ctggacttgg ctggaaacca gctgaaggcc ctaagcaatg gcagcctgcc   2100
atctggcacc cagctgcgga ggctggacct cagtggcaac agcatcggct tgtgaaccc   2160
tggcttcttt gccctggcca agcagttaga agagctcaac ctcagcgcca atgccctcaa   2220
gacagtggag ccctcctggt ttggctcgat ggtgggcaac ctgaaagtcc tagacgtgag   2280
cgccaaccct ctgcactgtg cctgtgggc gaccttcgtg ggcttcctgc tggaggtaca   2340
ggctgccgtg cctgggctgc ccagccgcgt caagtgtgga agtccggggc agctccaggg   2400
ccatagcatc tttgcgcaag acctgcgcct ctgcttcctg gacctggggc tctatctctt   2460
tgctgggact gcaccggcag tgctgctgct gctggtggtg ccggtggtgt accaccgcgc   2520
ctactggagg ctgaagtacc actggtacct tctgcggtgc tgggtcaacc agcggtggcg   2580
gcgggaggaa aagtgctacc tctatgacag ctttgtgtcc tacaattcag ctgatgaaag   2640
ttgggtgttg cagaagctgg tgcctgagct ggagcacggt gccttccgcc tctgcttgca   2700
ccaccgcgac ttcagccgg ccgcagcat cattgacaac attgtggatg ctgtctacaa   2760
cagccggaag acggtgtgcg tggtgagccg cagctacctg cgcagcgagt ggtgctctct   2820
agaggtgcag ttggccagct accggctgtt ggatgagcgg cgtgacatcc tggtactggt   2880
gctgctggag gacgtgggtg atgctgagct gtctgcctac caccgcatgc ggcgggtgct   2940
gctgcggcgc acctacctgc gctggcctct tgacccgca gctcagccgc tcttttgggc   3000
acggctgaag agggcactga ggtggggaga gggaggagag gaggaggaag aagaaggttt   3060
gggtggaggg acgggaaggc ccagggaagg agacaaacag atgtaggcgg ccgc         3114
```

<210> SEQ ID NO 213
<211> LENGTH: 3122
<212> TYPE: DNA

<213> ORGANISM: Canis familiaris

<400> SEQUENCE: 213

```
gaatccacca tgggccoctg ccgtggcgcc ctgcaccccc tgtctctcct ggtgcaggct      60
gccgcgctag ccctggccct ggcccagggc accctgcctg ccttcctgcc ctgtgagctc     120
cagccccatg gcctggtgaa ctgcaactgg ctgttcctca agtccgtgcc ccgcttctcg     180
gcagctgcac cccgcggtaa cgtcaccagc ctttccttgt actccaaccg catccaccac     240
ctccatgact atgactttgt ccacttcgtc cacctgcggc gtctcaatct caagtggaac     300
tgcccgcccg ccagcctcag ccccatgcac tttccctgtc acatgaccat tgagcccaac     360
accttcctgg ctgtgcccac cctagaggac ctgaatctga gctataacag catcacgact     420
gtgcccgccc tgcccagttc gcttgtgtcc ctgtccctga gccgcaccaa catcctggtg     480
ctggaccctg ccaccctggc aggcctttat gccctgcgct tcctgttcct ggatggcaac     540
tgctactaca agaaccoctg ccagcaggcc ctgcaggtgg ccccaggtgc cctcctgggc     600
ctgggcaacc tcacacacct gtcactcaag tacaacaacc tcaccgtggt gccgcggggc     660
ctgcccccca gcctggagta cctgctcttg tcctacaacc acatcatcac cctggcacct     720
gaggacctgc caatctgac tgccctgcgt gtcctcgatg tgggtgggaa ctgtcgccgc     780
tgtgaccatg cccgtaaccc ctgcagggag tgccccaagg gcttccccca gctgcacccc     840
aacaccttcg gccacctgag ccacctcgaa ggcctggtgt tgaggacag ctctctctac     900
agcctggacc ccaggtggtt ccatggcctg gcaacctca tggtgctgga cctgagtgag     960
aacttcctgt atgactgcat caccaaaacc aaagccttct acggcctggc ccggctgcgc    1020
agactcaacc tgtccttcaa ttatcataag aaggtgtcct tgcccacct gcatctggca    1080
tcctccttcg ggagcctact gtccctgcag gagctggaca tacatggcat cttcttccgc    1140
tcgctcagcg agaccacgct ccagtcgctg gcccacctgc ccatgctcca gcgtctgcat    1200
ctgcagttga actttatcag ccaggcccag ctcagcatct tcggcgcctt ccctggcctg    1260
cggtacgtgg acttgtcaga caaccgcatc agtggagctg cagagcccgc ggctgccaca    1320
gggggaggtag aggcggactg tggggagaga gtctggccac agtcccggga ccttgctctg    1380
ggcacactgg gcacccccgg ctcagaggcc ttcatgccga gctgcaggac cctcaacttc    1440
accttggacc tgtctcggaa caacctagtg actgttcagc cagagatgtt tgtccggctg    1500
gcgcgcctcc agtgcctggg cctgagccac aacagcatct cgcaggcggt caatggctcg    1560
cagttcgtgc ctctgagcaa cctgcggtg ctggacctgt cccataacaa gctggacctg    1620
taccacgggc gctcgttcac ggagctgccg cggctggagg ccttggacct cagctacaac    1680
agccagccct tcagcatgcg gggcgtgggc cacaatctca gctttgtggc acagctgcca    1740
gccctgcgct acctcagcct ggcgcacaat ggcatccaca gccgcgtgtc ccagcagctc    1800
cgcagcgcct cgctccgggc cctggacttc agtggcaata ccctgagcca gatgtgggcc    1860
gagggagacc tctatctccg cttcttccaa ggcctgagaa gcctggttca gctggacctg    1920
tcccagaatc gcctgcatac cctcctgcca cgcaacctgg acaacctccc caagagcctg    1980
cggctcctgc ggctccgtga caattacctg gctttcttca actggagcag cctggccctc    2040
ctacccaagc tggaagccct ggacctggcg ggaaaccagc tgaaggccct gagcaatggc    2100
agcttgccca acggcacccca gctccagagg ctgaccctca gcggcaacag catcggcttc    2160
gtggtccccg gctttttgc cctggccgtg aggcttcgag agctcaacct cagcgccaac    2220
gccctcaaga cggtggagcc ctcctggttt ggttccctgg cgggtgccct gaaagtccta    2280
```

```
gacgtgaccg ccaaccccett gcattgcgct tgcggcgcaa ccttcgtgga cttcttgctg    2340
gaggtgcagg ctgcggtgcc cggcctgcct agccgtgtca agtgcggcag cccgggccag    2400
ctccagggcc gcagcatctt cgcacaggac ctgcgcctct gcttcctgga cctggggctc    2460
tatctctttg ctgggactgc accggcagtg ctgctgctgc tggtggtgcc ggtggtgtac    2520
caccgcgcct actggaggct gaagtaccac tggtaccttc tgcggtgctg ggtcaaccag    2580
cggtggcggc gggaggaaaa gtgctacctc tatgacagct ttgtgtccta caattcagct    2640
gatgaaagtt gggtgttgca agctggtg cctgagctgg agcacggtgc cttccgcctc    2700
tgcttgcacc accgcgactt ccagccgggc cgcagcatca ttgacaacat tgtggatgct    2760
gtctacaaca ccggaagac ggtgtgcgtg gtaagccgca gctacctgcg cagcgagtgg    2820
tgctctctag aggtgcagtt ggccagctac cggctgttgg atgagcggcg tgacatcctg    2880
gtactggtgc tgctggagga cgtgggtgat gctgagctgt ctgcctacca ccgcatgcgg    2940
cgggtgctgc tgcggcgcac ctacctgcgc tggcctcttg accccgcagc tcagccgctc    3000
ttttgggcac ggctgaagag ggcactgagg tggggagagg gagaggagga ggaggaagaa    3060
gaaggtttgg gtggagggac gggaaggccc agggaaggag acaaacagat gtaggcggcc    3120
gc                                                                   3122

<210> SEQ ID NO 214
<211> LENGTH: 10
<212> TYPE: DNA
<213> ORGANISM: artificial sequence
<220> FEATURE:
<223> OTHER INFORMATION: artificial DNA

<400> SEQUENCE: 214
gacgatcgtc                                                           10

<210> SEQ ID NO 215
<211> LENGTH: 12
<212> TYPE: DNA
<213> ORGANISM: artificial sequence
<220> FEATURE:
<223> OTHER INFORMATION: artificial DNA

<400> SEQUENCE: 215
tcgtcgtttt cg                                                        12

<210> SEQ ID NO 216
<211> LENGTH: 22
<212> TYPE: DNA
<213> ORGANISM: artificial sequence
<220> FEATURE:
<223> OTHER INFORMATION: artificial DNA

<400> SEQUENCE: 216
tcgtcgttgt cgttttgtcg tt                                             22

<210> SEQ ID NO 217
<211> LENGTH: 1034
<212> TYPE: PRT
<213> ORGANISM: Canis familiaris

<400> SEQUENCE: 217

Met Gly Pro Cys Arg Gly Ala Leu His Pro Leu Ser Leu Leu Val Gln
1               5                   10                  15

Ala Ala Ala Leu Ala Leu Ala Leu Ala Gln Gly Thr Leu Pro Ala Phe
```

```
                 20                  25                  30
Leu Pro Cys Glu Leu Gln Pro His Gly Leu Val Asn Cys Asn Trp Leu
             35                  40                  45
Phe Leu Lys Ser Val Pro Arg Phe Ser Ala Ala Pro Arg Gly Asn
 50                  55                  60
Val Thr Ser Leu Ser Leu Tyr Ser Asn Arg Ile His His Leu His Asp
 65                  70                  75                  80
Tyr Asp Phe Val His Phe Val His Leu Arg Arg Leu Asn Leu Lys Trp
                 85                  90                  95
Asn Cys Pro Pro Ala Ser Leu Ser Pro Met His Phe Pro Cys His Met
             100                 105                 110
Thr Ile Glu Pro Asn Thr Phe Leu Ala Val Pro Thr Leu Glu Asp Leu
             115                 120                 125
Asn Leu Ser Tyr Asn Ser Ile Thr Thr Val Pro Ala Leu Pro Ser Ser
             130                 135                 140
Leu Val Ser Leu Ser Leu Ser Arg Thr Asn Ile Leu Val Leu Asp Pro
145                 150                 155                 160
Ala Thr Leu Ala Gly Leu Tyr Ala Leu Arg Phe Leu Phe Leu Asp Gly
                 165                 170                 175
Asn Cys Tyr Tyr Lys Asn Pro Cys Gln Gln Ala Leu Gln Val Ala Pro
             180                 185                 190
Gly Ala Leu Leu Gly Leu Gly Asn Leu Thr His Leu Ser Leu Lys Tyr
             195                 200                 205
Asn Asn Leu Thr Val Val Pro Arg Gly Leu Pro Pro Ser Leu Glu Tyr
             210                 215                 220
Leu Leu Leu Ser Tyr Asn His Ile Ile Thr Leu Ala Pro Glu Asp Leu
225                 230                 235                 240
Ala Asn Leu Thr Ala Leu Arg Val Leu Asp Val Gly Gly Asn Cys Arg
                 245                 250                 255
Arg Cys Asp His Ala Arg Asn Pro Cys Arg Glu Cys Pro Lys Gly Phe
                 260                 265                 270
Pro Gln Leu His Pro Asn Thr Phe Gly His Leu Ser His Leu Glu Gly
             275                 280                 285
Leu Val Leu Arg Asp Ser Ser Leu Tyr Ser Leu Asp Pro Arg Trp Phe
             290                 295                 300
His Gly Leu Gly Asn Leu Met Val Leu Asp Leu Ser Glu Asn Phe Leu
305                 310                 315                 320
Tyr Asp Cys Ile Thr Lys Thr Lys Ala Phe Tyr Gly Leu Ala Arg Leu
                 325                 330                 335
Arg Arg Leu Asn Leu Ser Phe Asn Tyr His Lys Lys Val Ser Phe Ala
             340                 345                 350
His Leu His Leu Ala Ser Ser Phe Gly Ser Leu Leu Ser Leu Gln Glu
             355                 360                 365
Leu Asp Ile His Gly Ile Phe Phe Arg Ser Leu Ser Glu Thr Thr Leu
             370                 375                 380
Gln Ser Leu Ala His Leu Pro Met Leu Gln Arg Leu His Leu Gln Leu
385                 390                 395                 400
Asn Phe Ile Ser Gln Ala Gln Leu Ser Ile Phe Gly Ala Phe Pro Gly
                 405                 410                 415
Leu Arg Tyr Val Asp Leu Ser Asp Asn Arg Ile Ser Gly Ala Ala Glu
                 420                 425                 430
Pro Ala Ala Ala Thr Gly Glu Val Glu Ala Asp Cys Gly Glu Arg Val
             435                 440                 445
```

```
Trp Pro Gln Ser Arg Asp Leu Ala Leu Gly Thr Leu Gly Thr Pro Gly
    450                 455                 460

Ser Glu Ala Phe Met Pro Ser Cys Arg Thr Leu Asn Phe Thr Leu Asp
465                 470                 475                 480

Leu Ser Arg Asn Asn Leu Val Thr Val Gln Pro Glu Met Phe Val Arg
                485                 490                 495

Leu Ala Arg Leu Gln Cys Leu Gly Leu Ser His Asn Ser Ile Ser Gln
                500                 505                 510

Ala Val Asn Gly Ser Gln Phe Val Pro Leu Ser Asn Leu Arg Val Leu
            515                 520                 525

Asp Leu Ser His Asn Lys Leu Asp Leu Tyr His Gly Arg Ser Phe Thr
    530                 535                 540

Glu Leu Pro Arg Leu Glu Ala Leu Asp Leu Ser Tyr Asn Ser Gln Pro
545                 550                 555                 560

Phe Ser Met Arg Gly Val Gly His Asn Leu Ser Phe Val Ala Gln Leu
                565                 570                 575

Pro Ala Leu Arg Tyr Leu Ser Leu Ala His Asn Gly Ile His Ser Arg
                580                 585                 590

Val Ser Gln Gln Leu Arg Ser Ala Ser Leu Arg Ala Leu Asp Phe Ser
    595                 600                 605

Gly Asn Thr Leu Ser Gln Met Trp Ala Glu Gly Asp Leu Tyr Leu Arg
    610                 615                 620

Phe Phe Gln Gly Leu Arg Ser Leu Val Gln Leu Asp Leu Ser Gln Asn
625                 630                 635                 640

Arg Leu His Thr Leu Leu Pro Arg Asn Leu Asp Asn Leu Pro Lys Ser
                645                 650                 655

Leu Arg Leu Leu Arg Leu Arg Asp Asn Tyr Leu Ala Phe Phe Asn Trp
                660                 665                 670

Ser Ser Leu Ala Leu Leu Pro Lys Leu Glu Ala Leu Asp Leu Ala Gly
            675                 680                 685

Asn Gln Leu Lys Ala Leu Ser Asn Gly Ser Leu Pro Asn Gly Thr Gln
    690                 695                 700

Leu Gln Arg Leu Asp Leu Ser Gly Asn Ser Ile Gly Phe Val Val Pro
705                 710                 715                 720

Gly Phe Phe Ala Leu Ala Val Arg Leu Arg Glu Leu Asn Leu Ser Ala
                725                 730                 735

Asn Ala Leu Lys Thr Val Glu Pro Ser Trp Phe Gly Ser Leu Ala Gly
            740                 745                 750

Ala Leu Lys Val Leu Asp Val Thr Ala Asn Pro Leu His Cys Ala Cys
    755                 760                 765

Gly Ala Thr Phe Val Asp Phe Leu Leu Glu Val Gln Ala Ala Val Pro
    770                 775                 780

Gly Leu Pro Ser Arg Val Lys Cys Gly Ser Pro Gly Gln Leu Gln Gly
785                 790                 795                 800

Arg Ser Ile Phe Ala Gln Asp Leu Arg Leu Cys Phe Leu Asp Leu Gly
                805                 810                 815

Leu Tyr Leu Phe Ala Gly Thr Ala Pro Ala Val Leu Leu Leu Leu Val
                820                 825                 830

Val Pro Val Val Tyr His Arg Ala Tyr Trp Arg Leu Lys Tyr His Trp
            835                 840                 845

Tyr Leu Leu Arg Cys Trp Val Asn Gln Arg Trp Arg Arg Glu Glu Lys
    850                 855                 860
```

```
Cys Tyr Leu Tyr Asp Ser Phe Val Ser Tyr Asn Ser Ala Asp Glu Ser
865                 870             875              880

Trp Val Leu Gln Lys Leu Val Pro Glu Leu Glu His Gly Ala Phe Arg
            885             890                     895

Leu Cys Leu His His Arg Asp Phe Gln Pro Gly Arg Ser Ile Ile Asp
                900             905             910

Asn Ile Val Asp Ala Val Tyr Asn Ser Arg Lys Thr Val Cys Val Val
            915             920             925

Ser Arg Ser Tyr Leu Arg Ser Glu Trp Cys Ser Leu Glu Val Gln Leu
    930             935                 940

Ala Ser Tyr Arg Leu Leu Asp Glu Arg Arg Asp Ile Leu Val Leu Val
945             950             955                     960

Leu Leu Glu Asp Val Gly Asp Ala Glu Leu Ser Ala Tyr His Arg Met
                965             970                 975

Arg Arg Val Leu Leu Arg Arg Thr Tyr Leu Arg Trp Pro Leu Asp Pro
            980             985                 990

Ala Ala Gln Pro Leu Phe Trp Ala  Arg Leu Lys Arg Ala  Leu Arg Trp
        995             1000                  1005

Gly Glu  Gly Gly Glu Glu Glu  Glu Glu Glu Gly Leu  Gly Gly Gly
    1010             1015                 1020

Thr Gly  Arg Pro Arg Glu Gly  Asp Lys Gln Met
1025              1030
```